United States Patent
Raghavan et al.

(10) Patent No.: US 9,365,574 B2
(45) Date of Patent: Jun. 14, 2016

(54) SOLUBLE GUANYLATE CYCLASE ACTIVATORS

(75) Inventors: Subharekha Raghavan, Teaneck, NJ (US); John E. Stelmach, Westfield, NJ (US); Cameron J. Smith, Lawrenceville, NJ (US); Hong Li, Edison, NJ (US); Alan Whitehead, Scotch Plains, NJ (US); Sherman T. Waddell, Westfield, NJ (US); Yi-Heng Chen, Whippany, NJ (US); Shouwu Miao, Edison, NJ (US); Olga A. Ornoski, Teaneck, NJ (US); Joie Garfunkle, Metuchen, NJ (US); Xibin Liao, Edison, NJ (US); Jiang Chang, Westfield, NJ (US); Xiaoqing Han, Edison, NJ (US); Jian Guo, Scotch Plains, NJ (US); Jonathan A. Groeper, Metuchen, NJ (US); Linda L. Brockunier, Orange, NJ (US); Keith Rosauer, New Hampton, IA (US); Emma R. Parmee, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 324 days.

(21) Appl. No.: 13/699,046

(22) PCT Filed: May 24, 2011

(86) PCT No.: PCT/US2011/037718
§ 371 (c)(1),
(2), (4) Date: Nov. 20, 2012

(87) PCT Pub. No.: WO2011/149921
PCT Pub. Date: Dec. 1, 2011

(65) Prior Publication Data
US 2013/0072492 A1     Mar. 21, 2013

Related U.S. Application Data

(60) Provisional application No. 61/349,065, filed on May 27, 2010.

(51) Int. Cl.
| | |
|---|---|
| *C07D 487/04* | (2006.01) |
| *C07D 519/00* | (2006.01) |
| *A61K 31/519* | (2006.01) |
| *A61P 29/00* | (2006.01) |
| *A61P 9/12* | (2006.01) |
| *A61P 3/10* | (2006.01) |
| *A61P 9/10* | (2006.01) |
| *A61P 11/06* | (2006.01) |
| *A61P 15/10* | (2006.01) |
| *A61P 9/04* | (2006.01) |
| *A61P 13/12* | (2006.01) |
| *A61P 1/16* | (2006.01) |

(52) U.S. Cl.
CPC ............ *C07D 487/04* (2013.01); *A61K 31/519* (2013.01); *C07D 519/00* (2013.01)

(58) Field of Classification Search
CPC ... C07D 487/04; C07D 519/00; A61K 31/519
USPC ........................................ 544/280; 514/265.1
See application file for complete search history.

(56) References Cited

U.S. PATENT DOCUMENTS

| | | | |
|---|---|---|---|
| 5,585,381 | A | 12/1996 | Yanaka et al. |
| 6,162,819 | A | 12/2000 | Schindler et al. |
| 6,166,027 | A | 12/2000 | Straub et al. |
| 6,613,772 | B1 | 9/2003 | Schindler et al. |
| 6,693,102 | B2 | 2/2004 | Stasch et al. |
| 6,743,798 | B1 | 6/2004 | Straub et al. |
| 6,844,347 | B1 | 1/2005 | Schnidler et al. |

(Continued)

FOREIGN PATENT DOCUMENTS

| | | |
|---|---|---|
| CA | 2743864 A1 | 6/2010 |
| DE | 19744027 A1 | 10/1997 |

(Continued)

OTHER PUBLICATIONS

Search Report and Written Opinion for PCT/US09/064570 filed on Nov. 1, 2009; mailed on Jan. 27, 2010; 7 pages.

(Continued)

*Primary Examiner* — Susanna Moore
(74) *Attorney, Agent, or Firm* — Eric A. Meade; Anna L. Cocuzzo

(57) ABSTRACT

A compound of Formula (I): or a pharmaceutically acceptable salt thereof, are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, or a pharmaceutically acceptable salt thereof, for their use in the therapy and prophylaxis of the abovementioned diseases and for preparing pharmaceuticals for this purpose, and to pharmaceutical preparations which comprise compounds of Formula (I) or a pharmaceutically acceptable salt thereof.

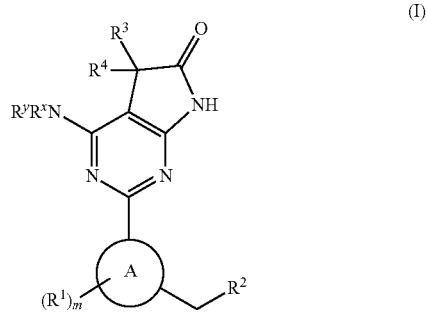

17 Claims, No Drawings

(56) References Cited

U.S. PATENT DOCUMENTS

| | | |
|---|---|---|
| 6,897,232 B2 | 5/2005 | Schindler et al. |
| 6,903,089 B1 | 6/2005 | Stasch et al. |
| 7,045,526 B2 | 5/2006 | Schindler et al. |
| 7,115,599 B2 | 10/2006 | Stasch et al. |
| 7,173,037 B2 | 2/2007 | Alonso-Alija et al. |
| 7,300,950 B2 | 11/2007 | Schindler et al. |
| 7,666,867 B2 | 2/2010 | Makriyannis et al. |
| 7,674,825 B2 | 3/2010 | Alonso-Alija et al. |
| 8,114,400 B2 | 2/2012 | Schirok et al. |
| 8,222,262 B2 | 7/2012 | Eriksen et al. |
| 8,309,551 B2 | 11/2012 | Schirok et al. |
| 2001/0044445 A1 | 11/2001 | Barnaung et al. |
| 2003/0105336 A1 | 6/2003 | Schindler et al. |
| 2004/0048866 A1 | 3/2004 | Kolas et al. |
| 2004/0053915 A1 | 3/2004 | Geiss et al. |
| 2004/0121994 A1 | 6/2004 | Anderson et al. |
| 2005/0143405 A1 | 6/2005 | Boehringer et al. |
| 2005/0147600 A1 | 7/2005 | Acton et al. |
| 2005/0176799 A1 | 8/2005 | Schindler et al. |
| 2005/0222170 A1 | 10/2005 | Weigand et al. |
| 2006/0014915 A1 | 1/2006 | Ahn et al. |
| 2006/0014951 A1 | 1/2006 | Feurer et al. |
| 2006/0052397 A1 | 3/2006 | Alonso-Alija et al. |
| 2006/0106041 A1 | 5/2006 | Kuo et al. |
| 2008/0188666 A1 | 8/2008 | Berger et al. |
| 2010/0029653 A1 | 2/2010 | Schirok et al. |
| 2010/0075964 A1 | 3/2010 | Busch et al. |
| 2010/0331295 A1 | 12/2010 | Busch et al. |
| 2011/0130445 A1 | 6/2011 | Lampe et al. |
| 2012/0022084 A1 | 1/2012 | Follmann et al. |
| 2013/0065884 A1 | 3/2013 | No et al. |
| 2013/0172372 A1 | 7/2013 | Follmann et al. |

FOREIGN PATENT DOCUMENTS

| | | |
|---|---|---|
| EP | 908456 B1 | 9/1998 |
| EP | 1339717 B1 | 9/2001 |
| EP | 1390365 B1 | 4/2002 |
| EP | 1509228 B1 | 5/2003 |
| GB | 876526 | 9/1961 |
| WO | 0027394 A1 | 5/2000 |
| WO | 0183490 A1 | 11/2001 |
| WO | WO0242299 A1 | 5/2002 |
| WO | 02074753 A2 | 9/2002 |
| WO | 02074753 A3 | 9/2002 |
| WO | WO03095451 A1 | 11/2003 |
| WO | 2004047730 A2 | 6/2004 |
| WO | WO2005046725 A1 | 5/2005 |
| WO | 2006134459 A1 | 12/2006 |
| WO | 2006134468 A1 | 12/2006 |
| WO | WO2007003435 A2 | 1/2007 |
| WO | WO2007009607 A1 | 1/2007 |
| WO | 2008031513 A1 | 3/2008 |
| WO | WO2008031513 A1 | 3/2008 |
| WO | 2008045484 A1 | 4/2008 |
| WO | 2008061657 A1 | 5/2008 |
| WO | 2009068652 A1 | 6/2009 |
| WO | 2010015652 A3 | 2/2010 |
| WO | WO2010065275 A1 | 6/2010 |

OTHER PUBLICATIONS

Search Report and Written Opinion for PCT/US10/024853 filed on Feb. 22, 2010; mailed on Aug. 18, 2010; 8 pages.

Search Report and Written Opinion for PCT/US11/037718 filed on May 24, 2011; mailed on Aug. 25, 2011; 6 pages.

Search Report and Written Opinion for PCT/US11/057419 filed on Oct. 24, 2011; mailed on Mar. 23, 2012; 6 pages.

Hering, K.W., et. al., "The design and synthesis of YC-1 analogues as probes for soluble guanylate cyclase"; Bioorg. Med. Chem. Lett, 2006, vol. 16, pp. 618-621.

Hoenicka, M.J., "Purified soluble guanylyl cyclase expressed in baculovirus/sf9 system:stimulation by YC-1, nitric oxide and carbon monoxide"; J. Mol. Med., 1999, vol. 77, pp. 14-23.

Mulsch, A., et. al., "Effect of YC-1, an NO-independent, super-oxide sensitive stimulator of soluble guanylyl cyclase, on smooth muscle responsiveness to nitrovasodilators", British Journal of Pharmacology, 1997, vol. 120, pp. 681-689.

Stasch, et. al., "Pharmacological actions of a novel NO-independent guanylyl cyclase stimulator, BAY 41-8543: in vitro studies", British Journal of Pharmacology, vol. 135, 2002, pp. 333-343.

Stasch, J. P., et. al., "NO-independent regulatory site on soluble guanylate cyclase"; Nature, vol. 410, 2001, pp. 212-215.

Stasch, J.P., et. al., "Cardiovascular actions of a novel NO-independent guanylyl cyclase stimulator, BAY 41-8543: in vivo studies", British Journal of Pharmacology, vol. 135, 2002, pp. 344-355.

Straub, A., et. al., "Metabolites of Orally Active NO-independent Pyrazolopyridine Stimulators of Soluble Guanylate Cyclase", Bioorg. Med. Chem., vol. 10, 2002, pp. 1711-1717.

Straub, A., et. al., "NO Independent stimulators of Soluble Guanylate Cyclase"; Bioorg. Med.Chem.Lett, vol. 11, 2001, pp. 781-784.

Mittendorf, J. et al. "Discovery of Riociguat (BAY 63-2521): A Potent, Oral Stimulator of Soluble Guanylate Cyclase for the treatment of Pulmonary Hypertension"; ChemMedChem, 4, 2009, pp. 853-865.

Grimminger, F. et al. "First acute haemodynamic study of soluble guanylate cyclase stimulator riociguat in Pulmonary Hypertension", European Respiratory Journal, 33, 2009, pp. 785-792.

Wu et al., "YC-1 inhibited human platelet aggregation through NO-independent activation of soluble guyanylate cyclase", Brit. J. Pharmacol. 1995, 116, pp. 1973-1978.

Yu et al., "Mechanism of anti-proliferation caused by YC-1, an indazole derivative, in cultured rat A10 vascular smooth muscle cells", Biochem. J., 1995, 306, pp. 787-792.

Ko et al., "YC-1 a novel activator of platelet guanylate cyclase", Blood, 1994, 84, pp. 4226-4233.

Yu et al., "Vasorelaxant effect of isoliquiritigenin, a novel soluble guanylate cyclase activator, in rat aorta", Brit. J. Pharmacol., 1995,114, pp. 1587-1594.

Pettibone et al., "A structurally novel stimulator of guanylate cyclase with long-lasting hypotensive activity in the dog", Eur. J. Pharmacol., 1985, 116, pp. 307-312.

Ignarro et al., "Regulation of Cytosolic Guanylyl Cyclase by Porphirins and Metalloporphyrins", Adv. Pharmacol. 1994, 26, pp. 35-65.

D.L. Vesely, et al., "Phencyclidine Stimulates Guanylate Cyclase Activity", Biochem. Biophys. Res. Comm., 1979, 88, pp. 1244-1248.

D.L. Vesely, et al., "B complex vitamins activate rat guanylate cyclase and increase cyclic GMP levels", Eur. J. Clin. Invest., 1985, 15, pp. 258-262.

Martin, F., et al., "Structure of Cinaciguat (bay 58-2667) bound to Nostoc H-Nox Domain reveals insights into Heme-mimetic activation of the Soluble Guanylyl Cyclase", Journal of Biological Chemistry, vol. 285, No. 29, pp. 22651-22657, (2010).

Fukagawa, et al, Japanese Abstract for JP 07104421; 1993.

Matsumoto, et al., Japanese Abstract for JP 09043786; 1995.

Nagaoka, et al., Japanese Abstract for JP 05027380; 1991.

Hirano, et al., Japanese Abstract for JP 04285955; 1991.

SOLUBLE GUANYLATE CYCLASE ACTIVATORS

RELATED APPLICATIONS

This application is a U.S. National Phase application under 35 U.S.C. §371 from International Application No. PCT/US2011/037718, filed May 24 2011, which claims the benefit of U.S. Provisional Application No. 61/349,065, filed May 27, 2010.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are composed of an $\alpha$ and a $\beta$ subunit each. Several subunit subtypes have been described which differ from one another with respect to sequence, tissue-specific distribution and expression in different development stages. The subtypes $\alpha_1$ and $\beta_1$ are mainly expressed in brain and lung, while $\ominus_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase and are valuable pharmaceutically active compounds for the therapy and prophylaxis of diseases, for example for cardiovascular diseases such as hypertension, heart failure, pulmonary hypertension, angina pectoris, diabetes, cardiac insufficiency, thromboses or atherosclerosis. The compounds of Formula I

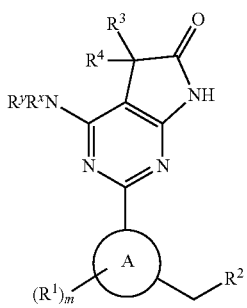

are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, to their use for the therapy and prophylaxis of the above-mentioned diseases and for preparing pharmaceuticals for this purpose, and to pharmaceutical preparations which comprise compounds of Formula I.

DETAILED DESCRIPTION OF THE INVENTION AND PREFERRED EMBODIMENTS

The invention concerns compounds of Formula I which activate soluble guanylate cyclase:

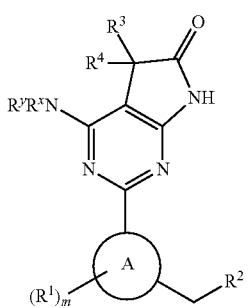

or a pharmaceutically acceptable salt thereof, wherein

is a heteroaryl selected from

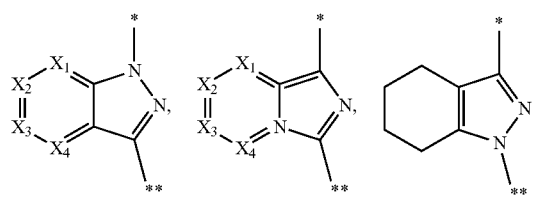

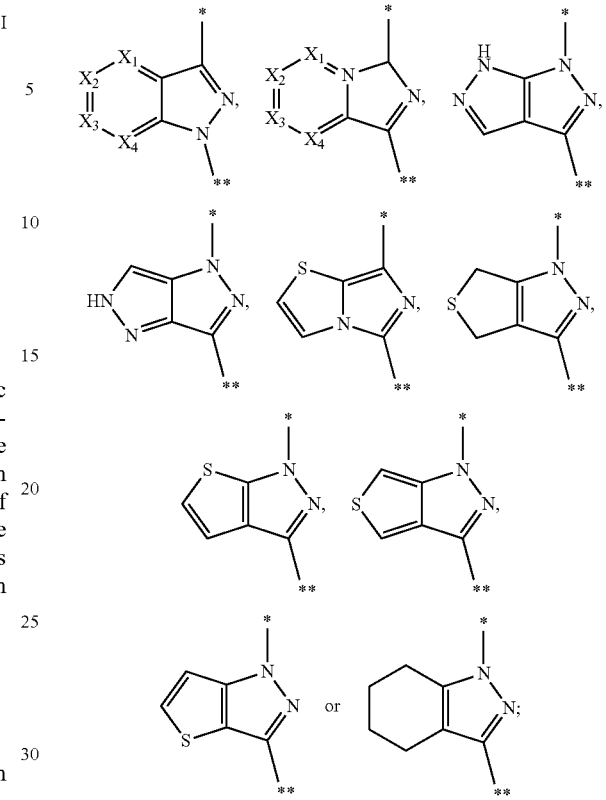

where * indicates attachment to the pyrimidinyl ring and ** indicates attachment to the —$CH_2$—$R^2$ of structural Formula I;

Each $X^1$, $X^2$, $X^3$ and $X^4$ is independently N or CH, provided that no more than two of $X^1$, $X^2$, $X^3$ and $X^4$ is N;

Each $R^x$ and $R^y$ are independently H, $C_{3-10}$ cycloalkyl, or —$C_1$-$C_6$ alkyl;

Each $R^1$ is independently —H, halo, OR, —$C_1$-$C_6$ alkyl, aryl, heterocyclyl, heteroaryl, —$C_{3-10}$ cycloalkyl, —CN, —$NR^aC(O)R^b$, or —$C(O)NR^aR^b$, said aryl, heteroaryl, and cycloalkyl optionally being substituted with one to three substituents selected from halo, —$C_1$-$C_6$ alkyl, —OR, —CN, and —$CF_3$;

$R^2$ is —$(CR^d_2)_tC_1$-$C_6$ alkyl, —$C_2$-$C_6$ alkenyl, —$C_2$-$C_6$ alkynyl, —$(CR^d_2)_tOR$, —$(CR^d_2)_tSR$, —$(CR^d_2)_tCF_3$, —$(CR^d_2)_t$ $C_{3-10}$cycloalkyl, —$(CR^d_2)_t$-aryl, —$(CR^d_2)_t$-heterocyclyl or —$(CR^d_2)_t$heteroaryl, said alkyl, cycloalkyl, aryl, heterocyclyl and heteroaryl being optionally substituted with one to three substituents selected from halo, —$C_1$-$C_6$ alkyl, —$CF_3$, —CN or —OR;

$R^3$ is —$(CR^d_2)_t$-aryl, —$(CR^d_2)_t$-heteroaryl, —$(CR^d_2)_t$-heterocyclyl, —$(CR^d_2)_tC_{3-10}$cycloalkyl, —$(CR^d_2)_tCN$, —$(CR^d_2)_t$—$C(O)NR^aR^b$, —$(CR^d_2)_t$—$NR^aC(O)R^b$, —$(CR^d_2)_t$—$C(S)NR^aR^b$, —$(CR^d_2)_t$—$C(O)OR^a$, —$(CR^d_2)_t$—$NR^aC(O)NR^b$, —$(CR^d_2)_t$—$NR^aC(O)OR^a$, —$(CR^d_2)_t$—$NR^aR^b$, or —$OR^a$, said, aryl, heteroaryl or heterocyclyl are optionally substituted with from one to three substituents selected from $R^5$;

$R^4$ is —$C_1$-$C_6$ alkyl, $C_{3-10}$cycloalkyl, halo or $CF_3$;

Each $R^5$ is independently halo, OR, CN, —$(CR^d_2)_tCF_3$, $S(O)_p$ $R^c$, —$(CR^d_2)_tC_{3-10}$cycloalkyl, or —$C_1$-$C_6$ alkyl, said alkyl and cycloalkyl being optionally substituted with one to three substituents selected from halo or OR;

Each $R^6$ is independently halo, —$C_1$-$C_6$ alkyl, OR, CN, $CF_3$, aryl or heteroaryl, where said alkyl, aryl or heteroaryl are optionally substituted with halo, $C_1$-$C_6$ alkyl or $CF_3$;

Each R is independently —H, —$C_1$-$C_6$ alkyl, —$CF_3$, or aryl;

Each $R^a$ and $R^b$ are independently —H, —$C_1$-$C_6$ alkyl, aryl, heteroaryl, heterocyclyl, or —$(CH_2)_{0-3}$-$C_{3-10}$ cycloalkyl, wherein said alkyl, heteroaryl, heterocyclyl, and cycloalkyl are optionally substituted with one to three substituents selected from $R^6$;

optionally, when $R^a$ and $R^b$ are —$C_1$-$C_6$ alkyl and are attached to the same nitrogen atom, $R^a$ and $R^b$ may be cyclized to form a $C_3$-$C_6$ cycloalkyl ring;

Each $R^c$ is independently —$C_1$-$C_6$ alkyl, —$CF_3$, or aryl;

Each $R^d$ is independently H, halo, —$CF_3$ or —$C_1$-$C_6$ alkyl;

m is an integer selected from 1, 2, or 3;

p is an integer independently selected from 0, 1 or 2; and t is an integer independently selected from 0, 1, 2, 3, or 4.

In a further embodiment, the invention is directed to compound of Formula I having structural Formula IA:

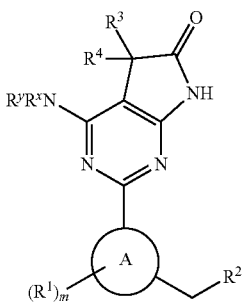

IA or a pharmaceutically acceptable salt thereof, wherein

is a heteroaryl selected from

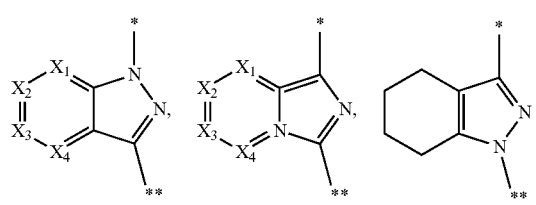

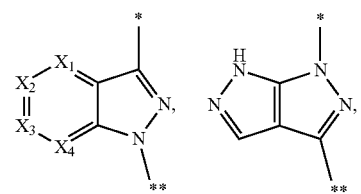

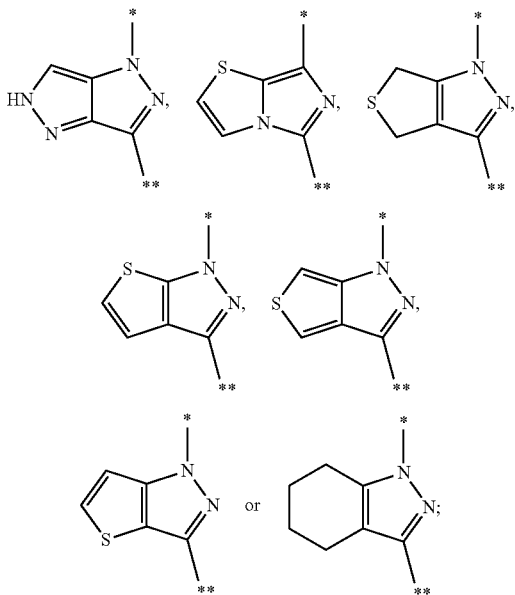

where * indicates attachment to the pyrmidinyl ring and ** indicates attachment to the —$CH_2$—$R^2$ of structural Formula I;

Each $X^1$, $X^2$, $X^3$ and $X^4$ are independently N or CH, provided that no more than two of $X^1$, $X^2$, $X^3$ and $X^4$ is N;

Each R is independently —H, —$C_1$-$C_6$ alkyl, —$CF_3$, or aryl;

Each $R^a$ and $R^b$ are independently —H, —$C_1$-$C_6$ alkyl, aryl, heteroaryl, heterocyclyl, or —$C_3$-$C_{10}$ cycloalkyl, wherein said alkyl, heteroaryl, heterocyclyl, and cycloalkyl are optionally substituted with one to three substituents selected $R^6$;

optionally, when $R^a$ and $R^b$ are —$C_1$-$C_6$ alkyl and are attached to the same nitrogen atom, $R^a$ and $R^b$ may be cyclized to form a $C_3$-$C_6$ cycloalkyl ring;

Each $R^c$ is independently —$C_1$-$C_6$ alkyl, —$CF_3$, or aryl;

Each $R^d$ is independently H, halo, —$CF_3$ or —$C_1$-$C_6$ alkyl;

Each $R^1$ is independently —H, halo, aryl, heterocyclyl, heteroaryl, —$C_{3-10}$ cycloalkyl, —CN, —$NR^aC(O)R^b$, or —$C(O)NR^aR^b$, said aryl, heteroaryl, and cycloalkyl optionally being substituted with one to three substituents selected from halo, —$C_1$-$C_6$ alkyl, —OR, —CN, and —$CF_3$;

$R^2$ is —$C_1$-$C_6$ alkyl, —$C_2$-$C_6$ alkenyl, —$C_2$-$C_6$ alkynyl, —$(CR^d_2)_t$OR, —$(CR^d_2)_t$SR, —$(CR^d_2)_t$CF_3$, —$(CR^d_2)_t$ $C_{3-10}$cycloalkyl, —$(CR^d_2)_t$-aryl, —$(CR^d_2)_t$-heterocyclyl or —$(CR^d_2)_t$heteroaryl, said alkyl, cycloalkyl, aryl, heterocyclyl and hetetoaryl being optionally substituted with one to three substituents selected from halo, —$C_1$-$C_6$ alkyl, —$CF_3$, —CN and —OR;

$R^3$ is aryl, heteroaryl, heterocyclyl, CN, —$C(O)NR^aR^b$, —$NR^aC(O)R^b$, —$C(S)NR^aR^b$, —$C(O)OR^a$, —$NR^aC(O)NR^b$, —$NR^aC(O)OR^a$, —$NR^aR^b$, or —$OR^a$, said, aryl, heteroaryl or heterocyclyl are optionally substituted with from one to three substituents selected $R^5$;

$R^4$ is —$C_1$-$C_6$ alkyl, halo or $CF_3$;

Each $R^5$ is independently halo, OR, CN, $S(O)_pR^c$, or —$C_1$-$C_6$ alkyl, said alkyl being optionally substituted with one to three substituents selected from halo or OR;

Each $R^6$ is independently halo, —$C_1$-$C_6$ alkyl, OR, CN, $CF_3$, aryl or heteroaryl, where said alkyl, aryl or heteroaryl are optionally substituted with halo, $C_1$-$C_6$ alkyl or $CF_3$;

m is an integer selected from 1, 2, or 3;

p is an integer independently selected from 0, 1 or 2; and t is an integer independently selected from 0, 1, 2, 3, or 4.

In a further embodiment, the invention is directed to compounds of Formula I having structural Formula IA:

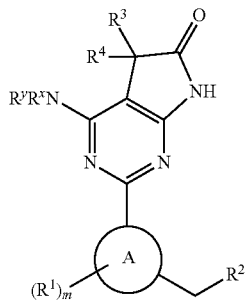

or a pharmaceutically acceptable salt thereof, wherein

is a heteroaryl selected from

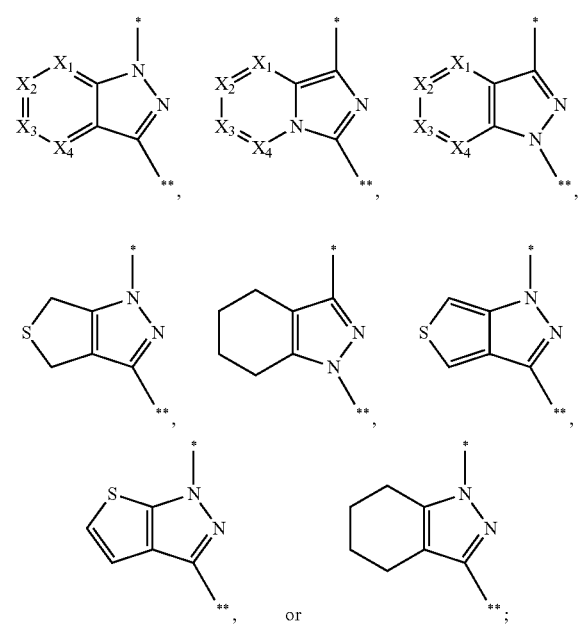

where * indicates attachment to the pyrimidinyl ring and ** indicates attachment to the —CH$_2$—R$^2$ of structural Formula I;

Each X$^1$, X$^2$, X$^3$ and X$^4$ are independently N or CH, provided that no more than two of X$^1$, X$^2$, X$^3$ and X$^4$ is N; and all other substituents and variables are as previously defined in Formula IA.

In another embodiment of Formula I and IA,

is a heteroaryl selected from

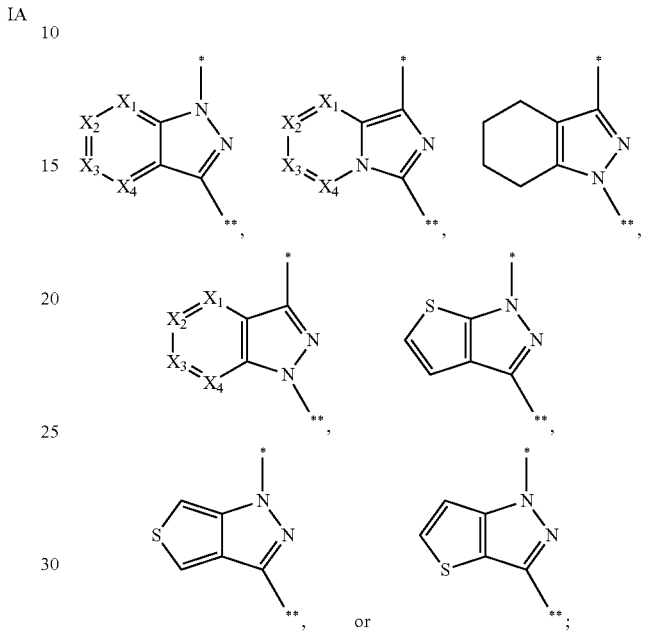

where * indicates attachment to the pyrmidinyl ring and ** indicates attachment to the —CH$_2$—R$^2$ of structural Formula I;

X$^1$, X$^2$, X$^3$ and X$^4$ are independently selected from N or CH, provided that no more than one of X$^1$, X$^2$, X$^3$ and X$^4$ is N; and all other variables are as previously defined in Formula IA.

In an embodiment of Formula I and IA, R$^3$ is aryl, heteroaryl, heterocyclyl, CN, —C(O)NR$^a$R$^b$, —NR$^a$C(O)R$^b$, —C(O)OR$^a$, or —OR$^a$, said aryl, heteroaryl or heterocyclyl are optionally substituted with from one to three substituents selected from halo, OR, CN, S(O)$_p$R$^c$, or —C$_1$-C$_6$ alkyl, said alkyl being optionally substituted with one to three substituents selected from halo or OR; and all other variables are as previously defined in Formula I.

In an embodiment of Formula I and IA, R$^4$ is —C$_1$-C$_6$ alkyl; and all other variables are as previously defined in Formula IA.

In a further embodiment, the invention is directed to compounds of Formula I having structural Formula II:

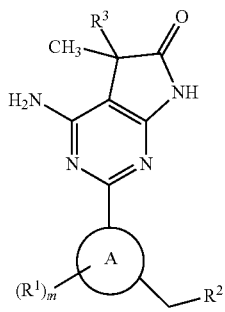

or a pharmaceutically acceptable salt thereof,
wherein

is a heteroaryl selected from

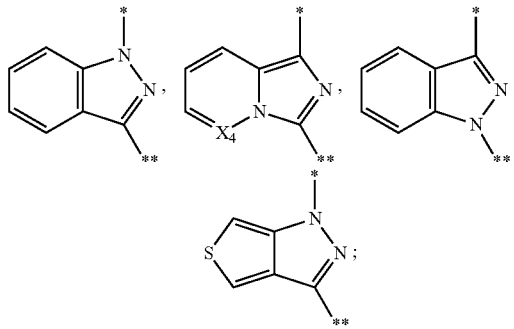

where * indicates attachment to the pyrmidinyl ring and ** indicates attachment to the —CH₂—R² of structural Formula II;
X⁴ is CH or N;
Each R is independently —H, —C₁-C₆ alkyl, —CF₃, or aryl;
Each Rᵃ is independently —H or —C₁-C₆ alkyl;
Each Rᵇ is independently —H, —C₁-C₆ alkyl or —C₃₋₁₀ cycloalkyl, wherein said alkyl and cycloalkyl are optionally substituted with one to three substituents selected R⁶;
Each Rᶜ is independently —C₁-C₆ alkyl, —CF₃, or aryl;
Each Rᵈ is independently H, halo, —CF₃ or —C₁-C₆ alkyl;
Each R¹ is independently —H, CN, halo or —C₁-C₆ alkyl, said alkyl optionally being substituted with one to three substituents selected from halo, —C₁-C₆ alkyl, and —CF₃;
R² is —C₁-C₆ alkyl, —(CRᵈ₂)ₜCF₃, —(CRᵈ₂)ₜ—C₃₋₁₀cycloalkyl, or —(CRᵈ₂)ₜaryl, said alkyl, cycloalkyl and aryl being optionally substituted with one to three substituents selected from halo, —C₁-C₆ alkyl and —CF₃;
R³ is aryl, heteroaryl, heterocyclyl, CN, —C(O)NRᵃRᵇ, —NRᵃC(O)Rᵇ, —C(O)ORᵃ, or —ORᵃ, said aryl, heteroaryl or heterocyclyl are optionally substituted with from one to three substituent selected R⁵;
Each R⁵ is independently halo, OR CN, S(O)ₚRᶜ, or —C₁-C₆ alkyl, said alkyl being optionally substituted with one to three substituents selected from halo or OR;
Each R⁶ is independently halo, —C₁-C₆ alkyl, OR, CN, CF₃, aryl or heteroaryl, where said alkyl, aryl or heteroaryl are optionally substituted with halo, C₁-C₆ alkyl or CF₃;
m is an integer selected from 1, 2, or 3;
p is an integer independently selected from 0, 1 or 2; and
t is an integer independently selected from 0, 1, 2, 3, or 4.

In a further embodiment, the invention is directed to compounds of Formula I having structural Formula III:

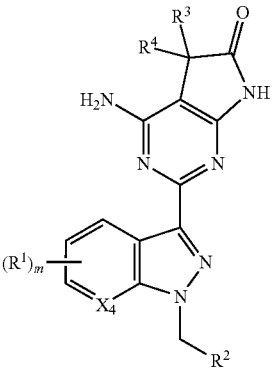

or a pharmaceutically acceptable salt thereof,
wherein
X⁴ is CH or N;
Each R is independently —H, —C₁-C₆ alkyl, —CF₃, or aryl;
Each Rᵃ is independently —H or —C₁-C₆ alkyl;
Each Rᵇ is independently —H, —C₁-C₆ alkyl, —C₃₋₁₀ cycloalkyl or heteroaryl, wherein said alkyl, cycloalkyl and heteroaryl are optionally substituted with one to three substituents selected R⁶;
Each Rᶜ is independently —C₁-C₆ alkyl, —CF₃, or aryl;
Each Rᵈ is independently H, halo, —CF₃ or —C₁-C₆ alkyl;
Each R¹ is independently —H, OR, CN, halo or —C₁-C₆ alkyl, said alkyl optionally being substituted with one to three substituents selected from halo, —C₁-C₆ alkyl, and —CF₃;
R² is —(CRᵈ₂)ₜC₁-C₆ alkyl, —(CRᵈ₂)ₜ—CF₃, —(CRᵈ₂)ₜ—C₃₋₁₀cycloalkyl, or —(CRᵈ₂)ₜaryl, said alkyl, cycloalkyl and aryl being optionally substituted with one to three substituents selected from halo, —C₁-C₆ alkyl and —CF₃;
R³ is aryl, heteroaryl, heterocyclyl, CN, —C(O)NRᵃRᵇ, —NRᵃC(O)Rᵇ, —C(O)ORᵃ, or —ORᵃ, said alkyl, aryl, heteroaryl or heterocyclyl are optionally substituted with from one to three substituent selected R⁵;
R⁴ is —CH₃ or C₃₋₁₀cycloalkyl;
Each R⁵ is independently halo, OR, CN, S(O)ₚRᶜ, or —C₁-C₆ alkyl, said alkyl being optionally substituted with one to three substituents selected from halo, —C₃₋₁₀cycloalkyl or OR;
Each R⁶ is independently halo, —C₁-C₆ alkyl, OR, CN, CF₃, aryl or heteroaryl, where said alkyl, aryl or heteroaryl are optionally substituted with halo, C₁-C₆ alkyl or CF₃;
m is an integer selected from 1, 2, or 3;
p is an integer independently selected from 0, 1 or 2; and
t is an integer independently selected from 0, 1, 2, 3, or 4,
In another embodiment, compounds of the invention are

| Example | IUPAC NAME |
| --- | --- |
| 1 | 4-amino-2-[5-chloro-3-(3,3,3-trifluoropropyl)-1H-indazol-1-yl]-5-methyl-5-phenyl-5,7-dihydro-6H-pyrrolo[2,3-d]pyrimidin-6-one |
| 2 | 4-amino-2-[5-chloro-3-(3,3,4,4,4-pentafluorobutyl)-1H-indazol-1-yl]-5-methyl-5-phenyl-5,7-dihydro-6H-pyrrolo[2,3-d]pyrimidin-6-one |
| 3 | 4-amino-2-[5-chloro-3-(2,3,6-trifluorobenzyl)-1H-indazol-1-yl]-5-methyl-5-phenyl-5,7-dihydro-6H-pyrrolo[2,3-d]pyrimidin-6-one |
| 4 | 4-amino-2-[5-chloro-3-(3,3,4,4,4-pentafluorobutyl)-1H-indazol-1-yl]-5-methyl-5-(3-methyl-1,2,4-oxadiazol-5-yl)-5,7-dihydro-6H-pyrrolo[2,3-d]pyrimidin-6-one |
| 5 | 4-amino-2-[3-(2-fluorobenzyl)-1H-indazol-1-yl]-5-methyl-5-phenyl-5,7-dihydro-6H-pyrrolo[2,3-d]pyrimidin-6-one |

-continued

| Example | IUPAC NAME |
|---|---|
| 6 | 4-amino-2-[5-chloro-3-(2-fluorobenzyl)-1H-indazol-1-yl]-5-methyl-5-phenyl-5,7-dihydro-6H-pyrrolo[2,3-d]pyrimidin-6-one |
| 7 | 4-amino-2-[5-chloro-3-(2-fluorobenzyl)-1H-indazol-1-yl]-5-methyl-5-(pyridin-3-yl)-5,7-dihydro-6H-pyrrolo[2,3-d]pyrimidin-6-one |
| 8 | 4-amino-2-[5-chloro-3-(2-fluorobenzyl)-1H-indazol-1-yl]-5-methyl-5-(pyridin-4-yl)-5,7-dihydro-6H-pyrrolo[2,3-d]pyrimidin-6-one |
| 9 | 4-amino-2-[5-chloro-3-(2,3-difluorobenzyl)-1H-indazol-1-yl]-5-methyl-5-phenyl-5,7-dihydro-6H-pyrrolo[2,3-d]pyrimidin-6-one |
| 10 | 4-amino-2-[5-chloro-3-(2,3-difluorobenzyl)-1H-indazol-1-yl]-5-methyl-5-(pyridin-3-yl)-5,7-dihydro-6H-pyrrolo[2,3-d]pyrimidin-6-one |
| 11 | 4-amino-2-[5-chloro-3-(2,3-difluorobenzyl)-1H-indazol-1-yl]-5-methyl-5-(pyridin-4-yl)-5,7-dihydro-6H-pyrrolo[2,3-d]pyrimidin-6-one |
| 12 | 4-amino-5-methyl-5-phenyl-2-[3-(2,3,6-trifluorobenzyl)-1H-indazol-1-yl]-5,7-dihydro-6H-pyrrolo[2,3-d]pyrimidin-6-one |
| 13 | 4-amino-2-[5-chloro-3-(2-phenylethyl)-1H-indazol-1-yl]-5-methyl-5-phenyl-5,7-dihydro-6H-pyrrolo[2,3-d]pyrimidin-6-one |
| 14 | 4-amino-5-methyl-5-phenyl-2-[3-(3,3,3-trifluoropropyl)-1H-indazol-1-yl]-5,7-dihydro-6H-pyrrolo[2,3-d]pyrimidin-6-one |
| 15 | 4-amino-2-[5-fluoro-3-(3,3,3-trifluoropropyl)-1H-indazol-1-yl]-5-methyl-5-phenyl-5,7-dihydro-6H-pyrrolo[2,3-d]pyrimidin-6-one |
| 16 | 4-amino-2-[5-chloro-3-(3,3,3-trifluoropropyl)-1H-indazol-1-yl]-5-(4-fluorophenyl)-5-methyl-5,7-dihydro-6H-pyrrolo[2,3-d]pyrimidin-6-one |
| 17 | 4-amino-2-[5-chloro-3-(3,3,3-trifluoropropyl)-1H-indazol-1-yl]-5-methyl-5-(pyridin-2-yl)-5,7-dihydro-6H-pyrrolo[2,3-d]pyrimidin-6-one |
| 18 | 4-amino-2-[5-chloro-3-(3,3,3-trifluoropropyl)-1H-indazol-1-yl]-5-methyl-5-(pyridin-3-yl)-5,7-dihydro-6H-pyrrolo[2,3-d]pyrimidin-6-one |
| 19 | 4-amino-2-[5-chloro-3-(3,3,3-trifluoropropyl)-1H-indazol-1-yl]-5-methyl-5-(pyridin-4-yl)-5,7-dihydro-6H-pyrrolo[2,3-d]pyrimidin-6-one |
| 20 | 4-amino-2-[5-chloro-3-(3,3,3-trifluoropropyl)-1H-indazol-1-yl]-5-methyl-5-(pyrazin-2-yl)-5,7-dihydro-6H-pyrrolo[2,3-d]pyrimidin-6-one |
| 21 | 4-amino-2-[5-chloro-3-(3,3,3-trifluoro-2-methylpropyl)-1H-indazol-1-yl]-5-methyl-5-phenyl-5,7-dihydro-6H-pyrrolo[2,3-d]pyrimidin-6-one |
| 22 | 4-amino-5-methyl-2-[3-(3,3,4,4,4-pentafluorobutyl)-1H-indazol-1-yl]-5-phenyl-5,7-dihydro-6H-pyrrolo[2,3-d]pyrimidin-6-one |
| 23 | 4-amino-5-(2-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one |
| 24 | 4-amino-5-(3-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one |
| 25 | 4-amino-5-(4-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one |
| 26 | 4-amino-2-[5-fluoro-3-(3,3,4,4,4-pentafluorobutyl)-1H-indazol-1-yl]-5-methyl-5-phenyl-5,7-dihydro-6H-pyrrolo[2,3-d]pyrimidin-6-one |
| 27 | 4-amino-2-[5-fluoro-3-(3,3,4,4,4-pentafluorobutyl)-1H-indazol-1-yl]-5-(2-fluorophenyl)-5-methyl-5,7-dihydro-6H-pyrrolo[2,3-d]pyrimidin-6-one |
| 28 | 4-amino-2-[5-chloro-3-(3,3,4,4,4-pentafluorobutyl)-1H-indazol-1-yl]-5-(2-fluorophenyl)-5-methyl-5,7-dihydro-6H-pyrrolo[2,3-d]pyrimidin-6-one |
| 29 | 4-amino-2-[5-chloro-3-(3,3,4,4,4-pentafluorobutyl)-1H-indazol-1-yl]-5-(3-fluorophenyl)-5-methyl-5,7-dihydro-6H-pyrrolo[2,3-d]pyrimidin-6-one |
| 30 | 4-amino-2-[5-chloro-3-(3,3,4,4,4-pentafluorobutyl)-1H-indazol-1-yl]-5-(4-fluorophenyl)-5-methyl-5,7-dihydro-6H-pyrrolo[2,3-d]pyrimidin-6-one |
| 31 | 4-amino-2-[5-chloro-3-(3,3,4,4,4-pentafluorobutyl)-1H-indazol-1-yl]-5-(3,5-difluorophenyl)-5-methyl-5,7-dihydro-6H-pyrrolo[2,3-d]pyrimidin-6-one |
| 32 | 4-amino-5-(4-chlorophenyl)-5-methyl-2-[3-(3,3,4,4,4-pentafluorobutyl)-1H-indazol-1-yl]-5,7-dihydro-6H-pyrrolo[2,3-d]pyrimidin-6-one |
| 33 | 4-amino-2-[5-chloro-3-(3,3,4,4,4-pentafluorobutyl)-1H-indazol-1-yl]-5-(4-chlorophenyl)-5-methyl-5,7-dihydro-6H-pyrrolo[2,3-d]pyrimidin-6-one |
| 34 | 4-amino-5-(4-bromophenyl)-2-[5-chloro-3-(3,3,4,4,4-pentafluorobutyl)-1H-indazol-1-yl]-5-methyl-5,7-dihydro-6H-pyrrolo[2,3-d]pyrimidin-6-one |
| 35 | 4-{4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidin-5-yl}benzonitrile |
| 36 | 4-amino-5-(4-hydroxyphenyl)-5-methyl-2-[3-(3,3,4,4,4-pentafluorobutyl)-1H-indazol-1-yl]-5,7-dihydro-6H-pyrrolo[2,3-d]pyrimidin-6-one |
| 37 | 4-amino-2-[5-chloro-3-(3,3,4,4,4-pentafluorobutyl)-1H-indazol-1-yl]-5-methyl-5-[4-(methylsulfonyl)phenyl]-5,7-dihydro-6H-pyrrolo[2,3-d]pyrimidin-6-one |
| 38 | 4-amino-5-methyl-2-[3-(3,3,4,4,4-pentafluorobutyl)-1H-indazol-1-yl]-5-(pyridin-2-yl)-5,7-dihydro-6H-pyrrolo[2,3-d]pyrimidin-6-one |
| 39 | 4-amino-2-[5-fluoro-3-(3,3,4,4,4-pentafluorobutyl)-1H-indazol-1-yl]-5-methyl-5-(pyridin-2-yl)-5,7-dihydro-6H-pyrrolo[2,3-d]pyrimidin-6-one |
| 40 | 4-amino-2-[5-chloro-3-(3,3,4,4,4-pentafluorobutyl)-1H-indazol-1-yl]-5-methyl-5-(pyridin-2-yl)-5,7-dihydro-6H-pyrrolo[2,3-d]pyrimidin-6-one |
| 41 | 4-amino-2-[5-chloro-3-(3,3,4,4,4-pentafluorobutyl)-1H-indazol-1-yl]-5-(5-fluoropyridin-2-yl)-5-methyl-5,7-dihydro-6H-pyrrolo[2,3-d]pyrimidin-6-one |
| 42 | 4-amino-5-(5-chloropyridin-2-yl)-5-methyl-2-[3-(3,3,4,4,4-pentafluorobutyl)-1H-indazol-1-yl]-5,7-dihydro-6H-pyrrolo[2,3-d]pyrimidin-6-one |

-continued

| Example | IUPAC NAME |
|---|---|
| 43 | 4-amino-2-[5-chloro-3-(3,3,4,4,4-pentafluorobutyl)-1H-indazol-1-yl]-5-(5-chloropyridin-2-yl)-5-methyl-5,7-dihydro-6H-pyrrolo[2,3-d]pyrimidin-6-one |
| 44 | 4-amino-2-[5-chloro-3-(3,3,4,4,4-pentafluorobutyl)-1H-indazol-1-yl]-5-methyl-5-(pyrazin-2-yl)-5,7-dihydro-6H-pyrrolo[2,3-d]pyrimidin-6-one |
| 45 | 4-amino-2-[5-chloro-3-(3,3,4,4,4-pentafluorobutyl)-1H-indazol-1-yl]-5-methyl-5-(5-methyl-1,2,4-oxadiazol-3-yl)-5,7-dihydro-6H-pyrrolo[2,3-d]pyrimidin-6-one |
| 46 | 4-amino-2-[5-fluoro-3-(3,3,4,4,4-pentafluorobutyl)-1H-indazol-1-yl]-5-methyl-5-(3-methyl-1,2,4-oxadiazol-5-yl)-5,7-dihydro-6H-pyrrolo[2,3-d]pyrimidin-6-one |
| 47 | 4-amino-2-[5-chloro-3-(4,4,5,5,5-pentafluoropentyl)-1H-indazol-1-yl]-5-methyl-5-phenyl-5,7-dihydro-6H-pyrrolo[2,3-d]pyrimidin-6-one |
| 48 | 4-amino-2-[5-chloro-3-(3,3,4,4,5,5,5-heptafluoropentyl)-1H-indazol-1-yl]-5-methyl-5-phenyl-5,7-dihydro-6H-pyrrolo[2,3-d]pyrimidin-6-one |
| 49 | methyl 4-amino-2-[5-chloro-3-(3,3,3-trifluoropropyl)-1H-indazol-1-yl]-5-methyl-6-oxo-6,7-dihydro-5H-pyrrolo[2,3-d]pyrimidine-5-carboxylate |
| 50 | ethyl 4-amino-2-[5-chloro-3-(3,3,3-trifluoropropyl)-1H-indazol-1-yl]-5-methyl-6-oxo-6,7-dihydro-5H-pyrrolo[2,3-d]pyrimidine-5-carboxylate |
| 51 | methyl 4-amino-2-[5-fluoro-3-(3,3,4,4,4-pentafluorobutyl)-1H-indazol-1-yl]-5-methyl-6-oxo-6,7-dihydro-5H-pyrrolo[2,3-d]pyrimidine-5-carboxylate |
| 52 | methyl 4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carboxylate |
| 53 | 4-amino-2-[5-chloro-3-(3,3,3-trifluoropropyl)-1H-thieno[2,3-c]pyrazol-1-yl]-5-methyl-5-phenyl-5,7-dihydro-6H-pyrrolo[2,3-d]pyrimidin-6-one |
| 54 | 4-amino-5-methyl-5-phenyl-2-[3-(2,3,6-trifluorobenzyl)-1H-thieno[3,4-c]pyrazol-1-yl]-5,7-dihydro-6H-pyrrolo[2,3-d]pyrimidin-6-one |
| 55 | 4-amino-2-[3-(2,3-difluorobenzyl)-1H-pyrazolo[4,3-b]pyridin-1-yl]-5-methyl-5-phenyl-5,7-dihydro-6H-pyrrolo[2,3-d]pyrimidin-6-one |
| 56 | 4-amino-5-methyl-5-phenyl-2-[3-(3,3,3-trifluoropropyl)-1H-pyrazolo[4,3-b]pyridin-1-yl]-5,7-dihydro-6H-pyrrolo[2,3-d]pyrimidin-6-one |
| 57 | 4-amino-5-methyl-2-[3-(3,3,4,4,4-pentafluorobutyl)-1H-pyrazolo[4,3-b]pyridin-1-yl]-5-phenyl-5,7-dihydro-6H-pyrrolo[2,3-d]pyrimidin-6-one |
| 58 | 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one |
| 59 | 4-amino-2-[6-chloro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one |
| 60 | 4-amino-5-methyl-5-phenyl-2-[1-(2,2,2-trifluoroethyl)-1H-indazol-3-yl]-5,7-dihydro-6H-pyrrolo[2,3-d]pyrimidin-6-one |
| 61 | 4-amino-2-[1-(2-methoxyethyl)-1H-indazol-3-yl]-5-methyl-5-phenyl-5,7-dihydro-6H-pyrrolo[2,3-d]pyrimidin-6-one |
| 62 | 4-amino-2-[1-(ethoxymethyl)-1H-indazol-3-yl]-5-methyl-5-phenyl-5,7-dihydro-6H-pyrrolo[2,3-d]pyrimidin-6-one |
| 63 | 4-amino-5-methyl-2-[1-(2,2,3,3,3-pentafluoropropyl)-1H-indazol-3-yl]-5-phenyl-5,7-dihydro-6H-pyrrolo[2,3-d]pyrimidin-6-one |
| 64 | 4-amino-2-{1-[(2,2-difluorocyclopropyl)methyl]-1H-indazol-3-yl}-5-methyl-5-phenyl-5,7-dihydro-6H-pyrrolo[2,3-d]pyrimidin-6-one |
| 65 | 4-amino-5-methyl-5-phenyl-2-[1-(3,3,3-trifluoropropyl)-1H-indazol-3-yl]-5,7-dihydro-6H-pyrrolo[2,3-d]pyrimidin-6-one |
| 66 | 4-amino-2-[6-chloro-1-(3,3,3-trifluoropropyl)-1H-indazol-3-yl]-5-methyl-5-phenyl-5,7-dihydro-6H-pyrrolo[2,3-d]pyrimidin-6-one |
| 67 | 4-amino-2-[6-chloro-1-(3,3,3-trifluoropropyl)-1H-indazol-3-yl]-5-methyl-5-(3-methyl-1,2,4-oxadiazol-5-yl)-5,7-dihydro-6H-pyrrolo[2,3-d]pyrimidin-6-one |
| 68 | methyl 4-amino-2-[6-chloro-1-(3,3,3-trifluoropropyl)-1H-indazol-3-yl]-5-methyl-6-oxo-6,7-dihydro-5H-pyrrolo[2,3-d]pyrimidine-5-carboxylate |
| 69 | 4-amino-5-methyl-2-[1-(3,3,4,4,4-pentafluorobutyl)-1H-indazol-3-yl]-5-phenyl-5,7-dihydro-6H-pyrrolo[2,3-d]pyrimidin-6-one |
| 70 | 4-amino-2-[6-fluoro-1-(3,3,4,4,4-pentafluorobutyl)-1H-indazol-3-yl]-5-methyl-5-phenyl-5,7-dihydro-6H-pyrrolo[2,3-d]pyrimidin-6-one |
| 71 | 4-amino-2-[6-bromo-1-(3,3,4,4,4-pentafluorobutyl)-1H-indazol-3-yl]-5-methyl-5-phenyl-5,7-dihydro-6H-pyrrolo[2,3-d]pyrimidin-6-one |
| 72 | 4-amino-5-(2-fluorophenyl)-5-methyl-2-[1-(3,3,4,4,4-pentafluorobutyl)-1H-indazol-3-yl]-5,7-dihydro-6H-pyrrolo[2,3-d]pyrimidin-6-one |
| 73 | 4-amino-2-[6-fluoro-1-(3,3,4,4,4-pentafluorobutyl)-1H-indazol-3-yl]-5-(2-fluorophenyl)-5-methyl-5,7-dihydro-6H-pyrrolo[2,3-d]pyrimidin-6-one |
| 74 | 4-amino-2-[6-chloro-1-(3,3,4,4,4-pentafluorobutyl)-1H-indazol-3-yl]-5-(2-fluorophenyl)-5-methyl-5,7-dihydro-6H-pyrrolo[2,3-d]pyrimidin-6-one |
| 75 | 4-amino-5-(4-chlorophenyl)-5-methyl-2-[1-(3,3,4,4,4-pentafluorobutyl)-1H-indazol-3-yl]-5,7-dihydro-6H-pyrrolo[2,3-d]pyrimidin-6-one |
| 76 | 4-amino-2-[6-chloro-1-(3,3,4,4,4-pentafluorobutyl)-1H-indazol-3-yl]-5-(4-chlorophenyl)-5-methyl-5,7-dihydro-6H-pyrrolo[2,3-d]pyrimidin-6-one |
| 77 | 4-amino-5-(4-bromophenyl)-2-[6-chloro-1-(3,3,4,4,4-pentafluorobutyl)-1H-indazol-3-yl]-5-methyl-5,7-dihydro-6H-pyrrolo[2,3-d]pyrimidin-6-one |
| 78 | 4-amino-2-[6-chloro-1-(3,3,4,4,4-pentafluorobutyl)-1H-indazol-3-yl]-5-methyl-5-[4-(methylsulfonyl)phenyl]-5,7-dihydro-6H-pyrrolo[2,3-d]pyrimidin-6-one |

| Example | IUPAC NAME |
|---|---|
| 79 | 4-amino-5-methyl-2-[1-(3,3,4,4,4-pentafluorobutyl)-1H-indazol-3-yl]-5-(pyridin-2-yl)-5,7-dihydro-6H-pyrrolo[2,3-d]pyrimidin-6-one |
| 80 | 4-amino-2-[6-chloro-1-(3,3,4,4,4-pentafluorobutyl)-1H-indazol-3-yl]-5-methyl-5-(pyridin-2-yl)-5,7-dihydro-6H-pyrrolo[2,3-d]pyrimidin-6-one |
| 81 | 4-amino-2-[6-chloro-1-(3,3,4,4,4-pentafluorobutyl)-1H-indazol-3-yl]-5-methyl-5-(pyrimidin-2-yl)-5,7-dihydro-6H-pyrrolo[2,3-d]pyrimidin-6-one |
| 82 | 4-amino-2-[6-chloro-1-(3,3,4,4,4-pentafluorobutyl)-1H-indazol-3-yl]-5-methyl-5-(5-methyl-1,3-oxazol-2-yl)-5,7-dihydro-6H-pyrrolo[2,3-d]pyrimidin-6-one |
| 83 | 4-amino-2-[6-fluoro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one |
| 84 | 4-amino-5-methyl-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one |
| 85 | 4-amino-2-[5-chloro-3-(3,3,4,4,4-pentafluorobutyl)-1H-indazol-1-yl]-5-methyl-5-(5-methyl-1,3,4-thiadiazol-2-yl)-5,7-dihydro-6H-pyrrolo[2,3-d]pyrimidin-6-one |
| 86 | 4-amino-2-[5-chloro-3-(3,3,4,4,4-pentafluorobutyl)-1H-indazol-1-yl]-5-methyl-5-(5-methyl-1,3,4-oxadiazol-2-yl)-5,7-dihydro-6H-pyrrolo[2,3-d]pyrimidin-6-one |
| 87 | 4-amino-5-methyl-6-oxo-2-[3-(3,3,4,4,4-pentafluorobutyl)-1H-indazol-1-yl]-6,7-dihydro-5H-pyrrolo[2,3-d]pyrimidine-5-carboxamide |
| 88 | 4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carboxamide |
| 89 | 4-amino-2-[5-fluoro-3-(3,3,4,4,4-pentafluorobutyl)-1H-indazol-1-yl]-N,5-dimethyl-6-oxo-6,7-dihydro-5H-pyrrolo[2,3-d]pyrimidine-5-carboxamide |
| 90 | 4-amino-2-[5-chloro-3-(3,3,4,4,4-pentafluorobutyl)-1H-indazol-1-yl]-N,5-dimethyl-6-oxo-6,7-dihydro-5H-pyrrolo[2,3-d]pyrimidine-5-carboxamide |
| 91 | 4-amino-2-[5-chloro-3-(3,3,4,4,4-pentafluorobutyl)-1H-indazol-1-yl]-N-ethyl-5-memyl-6-oxo-6,7-dihydro-5H-pyrrolo[2,3-d]pyrimidine-5-carboxamide |
| 92 | 4-amino-2-[5-chloro-3-(3,3,4,4,4-pentafluorobutyl)-1H-indazol-1-yl]-5-methyl-N-[(1-methyl-1H-pyrazol-3-yl)methyl]-6-oxo-6,7-dihydro-5H-pyrrolo[2,3-d]pyrimidine-5-carboxamide |
| 93 | 4-amino-5-methyl-5-(4-methyl-5-oxo-4,5-dihydro-1,3,4-oxadiazol-2-yl)-2-[3-(3,3,4,4,4-pentafluorobutyl)-1H-indazol-1-yl]-5,7-dihydro-6H-pyrrolo[2,3-d]pyrimidin-6-one |
| 94 | 4-amino-2-[5-chloro-3-(3,3,4,4,4-pentafluorobutyl)-1H-indazol-1-yl]-5-methyl-5-(1,3,4-thiadiazol-2-yl)-5,7-dihydro-6H-pyrrolo[2,3-d]pyrimidin-6-one |
| 95 | 4-amino-2-[6-chloro-1-(3,3,4,4,4-pentafluorobutyl)-1H-indazol-3-yl]-N,5-dimethyl-6-oxo-6,7-dihydro-5H-pyrrolo[2,3-d]pyrimidine-5-carboxamide |
| 96 | 4-amino-2-[6-chloro-1-(3,3,4,4,4-pentafluorobutyl)-1H-indazol-3-yl]-5-methyl-5-(4-methyl-5-oxo-4,5-dihydro-1,3,4-oxadiazol-2-yl)-5,7-dihydro-6H-pyrrolo[2,3-d]pyrimidin-6-one |
| 97 | 4-amino-2-[6-chloro-1-(3,3,4,4,4-pentafluorobutyl)-1H-indazol-3-yl]-5-methyl-5-(5-methyl-1,3,4-thiadiazol-2-yl)-5,7-dihydro-6H-pyrrolo[2,3-d]pyrimidin-6-one |
| 98 | 4-amino-2-[6-chloro-1-(3,3,4,4,4-pentafluorobutyl)-1H-indazol-3-yl]-5-methyl-5-(5-methyl-1,3,4-oxadiazol-2-yl)-5,7-dihydro-6H-pyrrolo[2,3-d]pyrimidin-6-one |
| 99 | 4-amino-5-methyl-5-phenyl-2-[3-(2,3,6-trifluorobenzyl)-4,6-dihydro-1H-thieno[3,4-c]pyrazol-1-yl]-5,7-dihydro-6H-pyrrolo[2,3-d]pyrimidin-6-one |
| 100 | 4-amino-5-methyl-2-[1-(3,3,4,4,4-pentafluorobutyl)-4,5,6,7-tetrahydro-1H-indazol-3-yl]-5-phenyl-5,7-dihydro-6H-pyrrolo[2,3-d]pyrimidin-6-one |
| 101 | 4-amino-5-(2-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one |
| 102 | 4-amino-5-(3-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one |
| 103 | 4-amino-5-(4-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one |
| 104 | 4-amino-5-methyl-5-phenyl-2-[1-(3,3,3-trifluoropropyl)-4,5,6,7-tetrahydro-1H-indazol-3-yl]-5,7-dihydro-6H-pyrrolo[2,3-d]pyrimidin-6-one |
| 105 | 4-amino-2-[6-chloro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one |
| 106 | 4-amino-2-[6-fluoro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one |
| 107 | 4-amino-5-methyl-2-[7-(3,3,4,4,4-pentafluorobutyl)imidazo[1,5-b]pyridazin-5-yl]-5-phenyl-5,7-dihydro-6H-pyrrolo[2,3-d]pyrimidin-6-one |
| 108 | 4-amino-5-methyl-5-(3-methyl-1,2,4-oxadiazol-5-yl)-2-[3-(3,3,4,4,4-pentafluorobutyl)imidazo[1,5-a]pyridin-1-yl]-5,7-dihydro-6H-pyrrolo[2,3-d]pyrimidin-6-one |

| Example | IUPAC NAME |
|---|---|
| 109 | 4-amino-2-[6-fluoro-3-(3,3,4,4,4-pentafluorobutyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one |
| 110 | 4-amino-2-[6-chloro-3-(3,3,4,4,4-pentafluorobutyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one |
| 111 | 4-amino-2-[6-chloro-3-(3,3,4,4,4-pentafluorobutyl)imidazo[1,5-a]pyridin-1-yl]-5-methyl-5-(5-methyl-1,3-oxazol-2-yl)-5,7-dihydro-6-pyrrolo[2,3-d]pyrimidin-6-one |
| 112 | 4-amino-2-[6-chloro-3-(3,3,4,4,4-pentafluorobutyl)imidazo[1,5-a]pyridin-1-yl]-5-methyl-5-(2-methyl-1,3-oxazol-4-yl)-5,7-dihydro-6H-pyrrolo[2,3-d]pyrimidin-6-one |
| 113 | 4-amino-2-[3-(2-fluorobenzyl)imidazo[1,5-a]pyridin-1-yl]-5-methyl-5-phenyl-5,7-dihydro-6H-pyrrolo[2,3-d]pyrimidin-6-one |
| 114 | 4-amino-2-[3-(2-fluorobenzyl)imidazo[1,5-a]pyridin-1-yl]-5-methyl-5-(pyridin-4-yl)-5,7-dihydro-6H-pyrrolo[2,3-d]pyrimidin-6-one |
| 115 | 4-amino-2-[6-chloro-3-(2-fluorobenzyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one |
| 116 | 4-amino-2-[3-(2,3-difluorobenzyl)imidazo[1,5-a]pyridin-1-yl]-5-methyl-5-phenyl-5,7-dihydro-6H-pyrrolo[2,3-d]pyrimidin-6-one |
| 117 | 4-amino-2-[3-(2,3-difluorobenzyl)-6-fluoroimidazo[1,5-a]pyridin-1-yl]-5-methyl-5-phenyl-5,7-dihydro-6H-pyrrolo[2,3-d]pyrimidin-6-one |
| 118 | 4-amino-2-[3-(2,3-difluorobenzyl)imidazo[1,5-a]pyridin-1-yl]-5-(4-fluorophenyl)-5-methyl-5,7-dihydro-6H-pyrrolo[2,3-d]pyrimidin-6-one |
| 119 | 4-amino-2-[3-(2,3-difluorobenzyl)-6-fluoroimidazo[1,5-a]pyridin-1-yl]-5-(4-fluorophenyl)-5-methyl-5,7-dihydro-6H-pyrrolo[2,3-d]pyrimidin-6-one |
| 120 | 4-amino-2-[3-(2,3-difluorobenzyl)imidazo[1,5-a]pyridin-1-yl]-5-methyl-5-(pyrazin-2-yl)-5,7-dihydro-6H-pyrrolo[2,3-d]pyrimidin-6-one |
| 121 | 4-amino-2-[3-(2,3-difluorobenzyl)-6-fluoroimidazo[1,5-a]pyridin-1-yl]-5-methyl-5-(pyrazin-2-yl)-5,7-dihydro-6H-pyrrolo[2,3-d]pyrimidin-6-one |
| 122 | 4-amino-5-methyl-5-phenyl-2-[3-(2,3,6-trifluorobenzyl)imidazo[1,5-a]pyridin-1-yl]-5,7-dihydro-6H-pyrrolo[2,3-d]pyrimidin-6-one |
| 123 | 4-amino-2-[6-fluoro-3-(2,3,6-trifluorobenzyl)imidazo[1,5-a]pyridin-1-yl]-5-methyl-5-phenyl-5,7-dihydro-6H-pyrrolo[2,3-d]pyrimidin-6-one |
| 124 | 4-amino-2-[6-chloro-3-(2,3,6-trifluorobenzyl)imidazo[1,5-a]pyridin-1-yl]-5-methyl-5-phenyl-5,7-dihydro-6H-pyrrolo[2,3-d]pyrimidin-6-one |
| 125 | 4-amino-2-[6-fluoro-3-(3,3,3-trifluoropropyl)imidazo[1,5-a]pyridin-1-yl]-5-methyl-5-phenyl-5,7-dihydro-6H-pyrrolo[2,3-d]pyrimidin-6-one |
| 126 | 4-amino-2-[6-chloro-3-(3,3,3-trifluoropropyl)imidazo[1,5-a]pyridin-1-yl]-5-methyl-5-phenyl-5,7-dihydro-6H-pyrrolo[2,3-d]pyrimidin-6-one |
| 127 | 4-amino-5-methyl-5-phenyl-2-[3-(4,4,4-trifluorobutyl)imidazo[1,5-a]pyridin-1-yl]-5,7-dihydro-6H-pyrrolo[2,3-d]pyrimidin-6-one |
| 128 | 4-amino-2-[6-fluoro-3-(4,4,4-trifluorobutyl)imidazo[1,5-a]pyridin-1-yl]-5-methyl-5-phenyl-5,7-dihydro-6H-pyrrolo[2,3-d]pyrimidin-6-one |
| 129 | 4-amino-2-[6-chloro-3-(4,4,4-trifluorobutyl)imidazo[1,5-a]pyridin-1-yl]-5-methyl-5-phenyl-5,7-dihydro-6H-pyrrolo[2,3-d]pyrimidin-6-one |
| 130 | 4-amino-2-[6-chloro-3-(4,4,4-trifluorobutyl)imidazo[1,5-a]pyridin-1-yl]-5-(4-fluorophenyl)-5-methyl-5,7-dihydro-6H-pyrrolo[2,3-d]pyrimidin-6-one |
| 131 | 4-amino-2-[6-chloro-3-(4,4,4-trifluorobutyl)imidazo[1,5-a]pyridin-1-yl]-5-methyl-5-(pyridin-2-yl)-5,7-dihydro-6H-pyrrolo[2,3-d]pyrimidin-6-one |
| 132 | 4-amino-2-[6-chloro-3-(4,4,4-trifluorobutyl)imidazo[1,5-a]pyridin-1-yl]-5-(5-fluoropyridin-2-yl)-5-methyl-5,7-dihydro-6H-pyrrolo[2,3-d]pyrimidin-6-one |
| 133 | 4-amino-2-[6-chloro-3-(4,4,4-trifluorobutyl)imidazo[1,5-a]pyridin-1-yl]-5-methyl-5-(pyrazin-2-yl)-5,7-dihydro-6H-pyrrolo[2,3-d]pyrimidin-6-one |
| 134 | 4-amino-5-methyl-2-[3-(3,3,4,4,4-pentafluorobutyl)imidazo[1,5-a]pyridin-1-yl]-5-phenyl-5,7-dihydro-6H-pyrrolo[2,3-d]pyrimidin-6-one |
| 135 | 4-amino-2-[6-fluoro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one |
| 136 | 4-amino-2-[6-chloro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one |
| 137 | 4-amino-5-(2-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 138 | 4-amino-5-(3-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 139 | 4-amino-5-(4-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 140 | 4-amino-5-(3,5-difluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 141 | 4-amino-5-(5-chloropyridin-2-yl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one |

| Example | IUPAC NAME |
|---|---|
| 142 | 4-amino-2-[6-fluoro-3-(3,3,4,4,4-pentafluorobutyl)imidazo[1,5-a]pyridin-1-yl]-5-(2-fluorophenyl)-5-methyl-5,7-dihydro-6H-pyrrolo[2,3-d]pyrimidin-6-one |
| 143 | 4-amino-2-[6-fluoro-3-(3,3,4,4,4-pentafluorobutyl)imidazo[1,5-a]pyridin-1-yl]-5-(3-fluorophenyl)-5-methyl-5,7-dihydro-6H-pyrrolo[2,3-d]pyrimidin-6-one |
| 144 | 4-amino-5-(3,5-difluorophenyl)-2-[6-fluoro-3-(3,3,4,4,4-pentafluorobutyl)imidazo[1,5-a]pyridin-1-yl]-5-methyl-5,7-dihydro-6H-pyrrolo[2,3-d]pyrimidin-6-one |
| 145 | 4-amino-2-[6-fluoro-3-(3,3,4,4,4-pentafluorobutyl)imidazo[1,5-a]pyridin-1-yl]-5-methyl-5-(pyridin-2-yl)-5,7-dihydro-6H-pyrrolo[2,3-d]pyrimidin-6-one |
| 146 | 4-amino-2-[6-fluoro-3-(3,3,4,4,4-pentafluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one |
| 147 | ethyl 4-amino-2-[6-fluoro-3-(3,3,4,4,4-pentafluorobutyl)imidazo[1,5-a]pyridin-1-yl]-5-methyl-6-oxo-6,7-dihydro-5H-pyrrolo[2,3-d]pyrimidine-5-carboxylate |
| 148 | 4-amino-2-[6-chloro-3-(3,3,4,4,4-pentafluorobutyl)imidazo[1,5-a]pyridin-1-yl]-5-(2-fluorophenyl)-5-methyl-5,7-dihydro-6H-pyrrolo[2,3-d]pyrimidin-6-one |
| 149 | 4-amino-2-[6-chloro-3-(3,3,4,4,4-pentafluorobutyl)imidazo[1,5-a]pyridin-1-yl]-5-(3-fluorophenyl)-5-methyl-5,7-dihydro-6H-pyrrolo[2,3-d]pyrimidin-6-one |
| 150 | 4-amino-2-[6-chloro-3-(3,3,4,4,4-pentafluorobutyl)imidazo[1,5-a]pyridin-1-yl]-5-(3,5-difluorophenyl)-5-methyl-5,7-dihydro-6H-pyrrolo[2,3-d]pyrimidin-6-one |
| 151 | 4-amino-2-[6-chloro-3-(3,3,4,4,4-pentafluorobutyl)imidazo[1,5-a]pyridin-1-yl]-5-(4-chlorophenyl)-5-methyl-5,7-dihydro-6H-pyrrolo[2,3-d]pyrimidin-6-one |
| 152 | 4-amino-2-[6-chloro-3-(3,3,4,4,4-pentafluorobutyl)imidazo[1,5-a]pyridin-1-yl]-5-methyl-5-(pyridin-2-yl)-5,7-dihydro-6H-pyrrolo[2,3-d]pyrimidin-6-one |
| 153 | 4-amino-2-[6-chloro-3-(3,3,4,4,4-pentafluorobutyl)imidazo[1,5-a]pyridin-1-yl]-5-methyl-5-(5-fluoropyridin-2-yl)-5,7-dihydro-6H-pyrrolo[2,3-d]pyrimidin-6-one |
| 154 | 4-amino-2-[6-chloro-3-(3,3,4,4,4-pentafluorobutyl)imidazo[1,5-a]pyridin-1-yl]-5-methyl-5-(pyrazin-2-yl)-5,7-dihydro-6H-pyrrolo[2,3-d]pyrimidin-6-one |
| 155 | 4-amino-2-[6-chloro-3-(3,3,4,4,4-pentafluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one |
| 156 | 4-amino-2-[3-(2,3-difluorobenzyl)imidazo[1,5-a]pyrazin-1-yl]-5-methyl-5-phenyl-5,7-dihydro-6H-pyrrolo[2,3-d]pyrimidin-6-one |
| 157 | ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxylate |
| 158 | ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate |
| 159 | 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide |
| 160 | 4-amino-2-[6-chloro-1-(3,3,4,4,4-pentafluorobutyl)-1H-indazol-3-yl]-N-cyclopropyl-5-methyl-6-oxo-6,7-dihydro-5H-pyrrolo[2,3-d]pyrimidine-5-carboxamide |
| 161 | 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 162 | 4-amino-5-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 163 | 4-amino-5-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbonitrile |
| 164 | 4-amino-N-cyclopropyl-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 165 | 4-amino-2-[6-chloro-1-(3,3,4,4,4-pentafluorobutyl)-1H-indazol-3-yl]-5-methyl-6-oxo-N-phenyl-6,7-dihydro-5H-pyrrolo[2,3-d]pyrimidine-5-carboxamide |
| 166 | ethyl (4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)carbamate |
| 167 | 4-amino-2-[6-chloro-1-(3,3,4,4,4-pentafluorobutyl)-1H-indazol-3-yl]-5-(4,5-dimethyl-1,3-thiazol-2-yl)-5-methyl-5,7-dihydro-6H-pyrrolo[2,3-d]pyrimidin-6-one |
| 168 | 4-amino-5-methyl-2-[1-(3,3,4,4,4-pentafluorobutyl)-1H-pyrazolo[3,4-b]pyridin-3-yl]-5-(1,3,4-thiadiazol-2-yl)-5,7-dihydro-6H-pyrrolo[2,3-d]pyrimidin-6-one |
| 169 | 4-amino-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |

-continued

| Example | IUPAC NAME |
|---|---|
| 170 | 4-amino-5-methyl-2-[1-(3,3,4,4,4-pentafluorobutyl)-1H-pyrazolo[3,4-b]pyridin-3-yl]-5-pyrimidin-2-yl-5,7-dihydro-6H-pyrrolo[2,3-d]pyrimidin-6-one |
| 171 | 4-amino-2-[6-chloro-1-(3,3,4,4,4-pentafluorobutyl)-1H-indazol-3-yl]-5-methyl-5-[5-oxo-4-(propan-2-yl)-4,5-dihydro-1,3,4-oxadiazol-2-yl]-5,7-dihydro-6H-pyrrolo[2,3-d]pyrimidin-6-one |
| 172 | 4-amino-2-[6-chloro-1-(3,3,4,4,4-pentafluorobutyl)-1H-indazol-3-yl]-5-methyl-5-[4-(propan-2-yl)-5-thioxo-4,5-dihydro-1,3,4-oxadiazol-2-yl]-5,7-dihydro-6H-pyrrolo[2,3-d]pyrimidin-6-one |
| 173 | 4-amino-5-(1-ethyl-1H-1,2,3-triazol-4-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 174 | 4-amino-5-[(cyclopropylmethyl)amino]-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 175 | {4-amino-2-[6-chloro-1-(3,3,4,4,4-pentafluorobutyl)-1H-indazol-3-yl]-5-methyl-6-oxo-6,7-dihydro-5h-pyrrolo[2,3-d]pyrimidin-5-yl}acetonitrile |
| 176 | 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide |
| 177 | 4-amino-2-(6-cyano-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide |
| 178 | 4-amino-N-cyclopropyl-2-(6-methoxy-1-(3,3,4,4,,4-pentafluorobutyl)-1H-pyrazolo[3,4-b]pyridin-3-yl)-5-methyl-6-oxo-6,7-dihydro-5H-pyrrolo[2,3-d]pyrimidine-5-carboxamide |
| 179 | 4-amino-N-cyclopropyl-5-methyl-2-(6-methyl-1-(3,3,4,4,4-pentafluorobutyl)-1H-pyrazolo[3,4-b]pyridin-3-yl)-6-oxo-6,7-dihydro-5H-pyrrolo[2,3-d]pyrimidine-5-carboxamide |
| 180 | 4-amino-5-[1-(cyclopropylmethyl)-1H-1,2,3-triazol-4-yl]-5-methyl-2-[1-(3,3,3-trifluoropropyl)-1H-pyrazolo[3,4-b]pyridin-3-yl]-5,7-dihydro-6H-pyrrolo[2,3-d]pyrimidin-6-one |
| 181 | 4-amino-N-cyclopropyl-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide |
| 182 | 4-amino-5-methyl-6-oxo-N-(pyridin-3-yl)-2-[1-(3,3,3-trifluoropropyl)-1H-pyrazolo[3,4-b]pyridin-3-yl]-6,7-dihydro-5H-pyrrolo[2,3-d]pyrimidine-5-carboxamide |
| 183 | 4-amino-2-[6-chloro-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide |
| 184 | 4-amino-N-cyclopropyl-5-methyl-2-[6-methyl-1-(3,3,3-trifluoropropyl)-1H-pyrazolo[3,4-b]pyridin-3-yl]-6-oxo-6,7-dihydro-5H-pyrrolo[2,3-d]pyrimidine-5-carboxamide |
| 185 | 4-amino-N-cyclopropyl-2-[6-methoxy-1-(3,3,3-trifluoropropyl)-1H-pyrazolo[3,4-B]pyridin-3-yl]-5-methyl-6-oxo-6,7-dihydro-5H-pyrrolo[2,3-D]pyrimidine-5-carboxamide |
| 186 | 5-methyl-4-(methylamino)-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one |
| 187 | N-cyclopropyl-5-methyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 188 | 2-[6-chloro-1-(3,3,4,4,4-pentafluorobutyl)-1H-indazol-3-yl]-5-methyl-4-(methylamino)-5-phenyl-5,7-dihydro-6H-pyrrolo[2,3-d]pyrimidin-6-one |
| 189 | 5-methyl-4-(methylamino)-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 190 | 4-amino-5-methyl-2-[1-(3,3,4,4,4-pentafluorobutyl)imidazo[1,5-a]pyridin-3-yl]-5-phenyl-5,7-dihydro-6H-pyrrolo[2,3-d]pyrimidin-6-one |
| 191 | 4-amino-5-methyl-2-[8-(3,3,4,4,4-pentafluorobutyl)imidazo[1,5-a]pyrimidin-6-yl]-5-phenyl-5,7-dihydro-6H-pyrrolo[2,3-d]pyrimidin-6-one |
| 192 | 4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide |
| 193 | 4-amino-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide |
| 194 | 4-amino-N-cyclopropyl-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide |
| 195 | 4-amino-N-cyclopropyl-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide |
| 196 | 4-amino-2-[6-chloro-1-(3,3,4,4,4-pentafluorobutyl)-1H-indazol-3-yl]-N-cyclobutyl-5-methyl-6-oxo-6,7-dihydro-5H-pyrrolo[2,3-d]pyrimidine-5-carboxamide |
| 197 | 4-amino-5-methyl-N-(1-methylethyl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |

-continued

| Example | IUPAC NAME |
|---|---|
| 198 | 4-amino-2-[6-chloro-1-(3,3,3-trifluoropropyl)-1H-indazol-3-yl]-5-methyl-5-(5-methyl-1,3,4-oxadiazol-2-yl)-5,7-dihydro-6H-pyrrolo[2,3-d]pyrimidin-6-one |
| 199 | 4-amino-5-methyl-5-[4-(1-methylethyl)-5-oxo-4,5-dihydro-1,3,4-oxadiazol-2-yl]-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 200 | 4-amino-N-cyclopropyl-5-methyl-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide |
| 201 | 4,5-diamino-2-[6-chloro-1-(3,3,4,4,4-pentafluorobutyl)-1H-indazol-3-yl]-5-methyl-5,7-dihydro-6H-pyrrolo[2,3-d]pyrimidin-6-one |
| 202 | 4-amino-2-[6-chloro-1-(3,3,4,4,4-pentafluorobutyl)-1H-indazol-3-yl]-5-[(cyclopropylmethyl)amino]-5-methyl-5,7-dihydro-6H-pyrrolo[2,3-d]pyrimidin-6-one |
| 203 | 4-amino-5-methyl-2-[1-(3,3,4,4,4-pentafluorobutyl)-1H-pyrazolo[3,4-b]pyridin-3-yl]-5-[5-(trifluoromethyl)-1,3,4-oxadiazol-2-yl]-5,7-dihydro-6H-pyrrolo[2,3-d]pyrimidin-6-one |
| 204 | 4-amino-5-methyl-5-(1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 205 | 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbothioamide |
| 206 | 4-amino-5-(4,5-dimethyl-1,3-thiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 207 | 4-amino-5-methyl-2-[1-(3,3,4,4,4-pentafluorobutyl)-1H-pyrazolo[3,4-b]pyridin-3-yl]-5-[3-(trifluoromethyl)-1,2,4-oxadiazol-5-yl]-5,7-dihydro-6H-pyrrolo[2,3-d]pyrimidin-6-one |
| 208 | 2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-N-cyclopropylacetamide |
| 209 | 4-amino-5-methyl-6-oxo-N-pyridin-2-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide |
| 210 | 4-amino-5-methyl-N-(1-methyl-1H-pyrazol-3-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide |
| 211 | 4-amino-5-(5-ethyl-1,3,4-oxadiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 212 | 4-amino-5-[5-(difluoromethyl)-1,3,4-oxadiazol-2-yl]-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 213 | 4-amino-5-methyl-5-[5-(1-methylethyl)-1,3,4-oxadiazol-2-yl]-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 214 | 4-amino-2-[6-chloro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide |
| 215 | 4-amino-5-methyl-N-(1-methyl-1H-pyrazol-4-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide |
| 216 | 4-amino-5-methyl-2-[1-(3,3,4,4,4-pentafluorobutyl)-1H-pyrazolo[3,4-b]pyridin-3-yl]-5-[5-(2,2,2-trifluoroethyl)-1,3,4-oxadiazol-2-yl]-5,7-dihydro-6H-pyrrolo[2,3-d]pyrimidin-6-one |
| 217 | 4-amino-2-[6-chloro-1-(3,3,4,4,4-pentafluorobutyl)-1H-indazol-3-yl]-5-methyl-N-(1-methyl-1H-pyrazol-4-yl)-6-oxo-6,7-dihydro-5H-pyrrolo[2,3-d]pyrimidine-5-carboxamide |
| 218 | 4-amino-5-methyl-N-(1-methyl-1H-pyrazol-3-yl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 219 | 4-amino-5-ethynyl-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 220 | 4-amino-2-[6-methoxy-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide |
| 221 | 4-amino-2-[6-cyano-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide |
| 222 | 4-amino-N-cyclopropyl-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 223 | 4-amino-N-cyclopropyl-2-[6-cyclopropyl-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide |
| 224 | 4-amino-N-cyclopropyl-2-[6-cyclopropyl-1-(3,3,3-trifluoropropyl)-1H-pyrazolo[3,4-b]pyridin-3-yl]-5-methyl-6-oxo-6,7-dihydro-5H-pyrrolo[2,3-b]pyrimidine-5-carboxamide |

-continued

| Example | IUPAC NAME |
|---|---|
| 225 | 4-amino-5-(5-cyclopropyl-1,3,4-oxadiazol-2-yl)-5-methyl-2-[1-(4,4,4-trifluorobutyl)-1H-pyrazolo[3,4-b]pyridin-3-yl]-5,7-dihydro-6H-pyrrolo[2,3-d]pyrimidin-6-one |
| 226 | 4-amino-5-methyl-6-oxo-N-pyridin-2-yl-2-[1-(4,4,4-trifluorobuty])-1H-pyrazolo[3,4-b]pyridin-3-yl]-6,7-dihydro-5H-pyrrolo[2,3-d]pyrimidine-5-carboxamide |
| 227 | 4-amino-5-methyl-6-oxo-N-pyridin-3-yl-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 228 | 4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 229 | 4-amino-2-[6-chloro-1-(3,3,4,4,4-pentafluorobutyl)-1H-indazol-3-yl]-5-methy]-5-(1-methyl-1H-pyrazol-4-yl)-5,7-dihydro-6H-pyrrolo[2,3-d]pyrimidin-6-one |
| 230 | 4-amino-2-[6-chloro-1-(3,3,4,4,4-pentafluorobutyl)-1H-pyrazolo[3,4-b]pyridin-3-yl]-5-methyl-N-oxetan-3-yl-6-oxo-6,7-dihydro-5H-pyrrolo[2,3-d]pyrimidine-5-carboxamide |
| 231 | 4-amino-5-methyl-N-oxetan-3-yl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 232 | 4-amino-5-methyl-5-pyridin-2-yl-2-[1-(3,3,3-trifluoropropyl)-1H-pyrazolo[3,4-b]pyridin-3-yl]-5,7-dihydro-6H-pyrrolo[2,3-d]pyrimidin-6-one |
| 233 | 4-amino-5-methyl-6-oxo-N-pyridin-3-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide |
| 234 | 4-amino-5-methyl-6-oxo-2-[1-(3,3,4,4,4-pentafluorobutyl)-1H-pyrazolo[3,4-b]pyridin-3-yl]-N-pyridin-3-yl-6,7-dihydro-5H-pyrrolo[2,3-d]pyrimidine-5-carboxamide |
| 235 | 4-amino-5-methyl-6-oxo-2-[1-(3,3,4,4,4-pentafluorobutyl)-1H-pyrazolo[3,4-b]pyridin-3-yl]-N-(tetrahydrofuran-3-yl)-6,7-dihydro-5H-pyrrolo[2,3-d]pyrimidine-5-carboxamide |
| 236 | 4-amino-5-methyl-5-(1,3,4-thiadiazol-2-yl)-2-[1-(4,4,4-trifluorobutyl)-1H-pyrazolo[3,4-b]pyridin-3-yl]-5,7-dihydro-6H-pyrrolo[2,3-d]pyrimidin-6-one |
| 237 | 4-amino-N-cyclopropyl-5-methyl-6-oxo-2-[1-(3,3,4,4-tetrafluorobutyl)-1H-pyrazolo[3,4-b]pyridin-3-yl]-6,7-dihydro-5H-pyrrolo[2,3-d]pyrimidine-5-carboxamide |
| 238 | 4-amino-N-cyclopropyl-2-[1-(3,3-difluoropropyl)-1H-pyrazolo[3,4-b]pyridin-3-yl]-5-methyl-6-oxo-6,7-dihydro-5H-pyrrolo[2,3-d]pyrimidine-5-carboxamide |
| 239 | 4-amino-5-methyl-2-[6-methyl-1-(3,3,4,4,4-pentafluorobutyl)-1H-pyrazolo[3,4-b]pyridin-3-yl]-6-oxo-N-(tetrahydro-2H-pyran-4-yl)-6,7-dihydro-5H-pyrrolo[2,3-d]pyrimidine-5-carboxamide |
| 240 | 4-amino-N-cyclopropyl-2-[1-(3,3-difluorobutyl)-1H-pyrazolo[3,4-b]pyridin-3-yl]-5-methyl-6-oxo-6,7-dihydro-5H-pyrrolo[2,3-d]pyrimidine-5-carboxamide |
| 241 | 4-amino-5-ethyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 242 | 4-amino-N,5-dicyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 243 | 4-amino-5-cyclopentyl-N-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 244 | 4-amino-5-(1-methylethyl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 245 | 4-amino-N,5-dicyclopropyl-6-oxo-2-[1-(3,3,3-trifluoropropyl)-1H-pyrazolo[3,4-b]pyridin-3-yl]-6,7-dihydro-5-pyrrolo[2,3-d]pyrimidine-5-carboxamide |
| 246 | 4-amino-N,5-dicyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 247 | 4-amino-5-cyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 248 | 4-amino-2-[6-fluoro-3-(4,4,4-trifluorobutyl)imidazo[1,5-a]pyridin-1-yl]-5-methyl-5-[3-(trifluoromethyl)-1,2,4-oxadiazol-5-yl]-5,7-dihydro-6H-pyrrolo[2,3-d]pyrimidin-6-one |
| 249 | 4-amino-2-[6-chloro-3-(4,4,4-trifluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one |
| 250 | 4-amino-2-[6-chloro-3-(3,3,4,4,4-pentafluorobutyl)imidazo[1,5-a]pyridin-1-yl]-H-cyclopropyl-5-methyl-6-oxo-6,7-dihydro-5H-pyrrolo[2,3-d]pyrimidine-5-carboxamide |
| 251 | 4-amino-H-cyclopropyl-5-methyl-6-oxo-2-[7-(3,3,4,4,4-pentafluorobutyl)imidazo[1,5-b]pyridazin-3-yl]-6,7-dihydro-5H-pyrrolo[2,3-d]pyrimidine-5-carboxamide |

| Example | IUPAC NAME |
|---|---|
| 252 | 4-amino-H-cyclopropyl-2-[6-fluoro-3-(3,3,4,4,4-pentafluorobutyl)imidazo[1,5-a]pyridin-1-yl]-5-methyl-6-oxo-6,7-dihydro-5H-pyrrolo[2,3-d]pyrimidine-5-carboxamide |
| 253 | 4-amino-2-[6-fluoro-3-(3,3,4,4,4-pentafluorobutyl)imidazo[1,5-a]pyridin-1-yl]-5-methyl-6-oxo-H-pyridin-3-yl-6,7-dihydro-5H-pyrrolo[2,3-d]pyrimidine-5-carboxamide |
| 254 | 4-amino-5-methyl-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide |
| 255 | 4-amino-5-(5-cyclopropyl-1,3,4-oxadiazol-2-yl)-5-methyl-2-[7-(3,3,4,4,4-pentafluorobutyl)imidazo[1,5-b]pyridazin-5-yl]-5,7-dihydro-6H-pyrrolo[2,3-d]pyrimidin-6-one |
| 256 | 4-amino-H-cyclopropyl-5-methyl-6-oxo-2-[7-(3,3,3-trifluoropropyl)imidazo[1,5-b]pyridazin-5-yl]-6,7-dihydro-5H-pyrrolo[2,3-d]pyrimidine-5-carboxamide |
| 257 | 2-[6-chloro-1-(3,3,4,4,4-pentafluorobutyl)-1H-indazol-3-yl]-N-cyclopropyl-5-methyl-4-(methylamino)-6-oxo-6,7-dihydro-5H-pyrrolo[2,3-d]pyrimidine-5-carboxamide |
| 258 | 2-[6-chloro-1-(3,3,4,4,4-pentafluorobutyl)-1H-indazol-3-yl]-N,5-dimethyl-4-(methylamino)-6-oxo-6,7-dihydro-5H-pyrrolo[2,3-d]pyrimidine-5-carboxamide |
| 259 | N,5-dimethyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 260 | N-cyclopropyl-5-methyl-4-(methylamino)-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide |
| 261 | 5-(5-cyclopropyl-1,3,4-oxadiazol-2-yl)-5-methyl-4-(methylamino)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 262 | N,5-dicyclopropyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide |
| 263 | N-cyclopropyl-5-methyl-4-(methylamino)-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide |
| 264 | N-cyclopropyl-5-methyl-4-(methylamino)-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide |
| 265 | 4-amino-2-[5-chloro-3-(3,3,4,4,4-pentafluorobutyl)-1H-indazol-1-yl]-N,N,5-trimethyl-6-oxo-6,7-dihydro-5H-pyrrolo[2,3-d]pyrimidine-5-carboxamide |
| 266 | 4-amino-N-cyclopropyl-5-methyl-6-oxo-2-[3-(3,3,4,4,4-pentafluorobutyl)-1H-pyrazolo[4,3-b]pyridin-1-yl]-6,7-dihydro-5H-pyrrolo[2,3-d]pyrimidine-5-carboxamide |
| 267 | 4-amino-2-[5-chloro-1-(3,3,4,4,4-pentafluorobutyl)-1H-pyraxolo[3,4-b]pyridin-3-yl]-N-cyclopropyl-5-methyl-6-oxo-6,7-dihydro-5H-pyrrolo[2,3-d]pyrimidine-5-carboxamide |
| 268 | 4-amino-2-[5-chloro-1-(3,3,4,4,4-pentafluorobutyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide |
| 269 | 4-amino-2-[5-chloro-1-(3,3,4,4,4-pentafluorobutyl)-1H-pyrazolo[3,4-b]pyridin-3-yl]-5-methyl-5-(5-methyl-1,3,4-oxadiazol-2-yl)-5,7-dihydro-6H-pyrrolo[2,3-d]pyrimidin-6-one |
| 270 | 4-amino-5-methyl-6-oxo-2-[1-(3,3,4,4,4-pentafluorobutyl)imidazo[1,5-a]pyridin-3-yl]-6,7-dihydro-5H-pyrrolo[2,3-d]pyrimidine-5-carboxamide | or a pharmaceutically acceptable salt thereof.

In a further embodiment, a compound of the instant invention is:

| Example | IUPAC Name |
|---|---|
| 2 | 4-amino-2-[5-chloro-3-(3,3,4,4,4-pentafluorobutyl)-1H-indazol-1-yl]-5-methyl-5-phenyl-5,7-dihydro-6H-pyrrolo[2,3-d]pyrimidin-6-one |
| 26 | 4-amino-2-[5-fluoro-3-(3,3,4,4,4-pentafluorobutyl)-1H-indazol-1-yl]-5-methyl-5-phenyl-5,7-dihydro-6H-pyrrolo[2,3-d]pyrimidin-6-one |
| 58 | 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one |
| 59 | 4-amino-2-[6-chloro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one |
| 70 | 4-amino-2-[6-fluoro-1-(3,3,4,4,4-pentafluorobutyl)-1H-indazol-3-yl]-5-methyl-5-phenyl-5,7-dihydro-6H-pyrrolo[2,3-d]pyrimidin-6-one |

-continued

| Example | IUPAC Name |
|---|---|
| 105 | 4-amino-2-[6-chloro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one |
| 136 | 4-amino-2-[6-chloro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one |
| 159 | 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide |
| 160 | 4-amino-2-[6-chloro-1-(3,3,4,4,4-pentafluorobutyl)-1H-indazol-3-yl]-N-cyclopropyl-5-methyl-6-oxo-6,7-dihydro-5H-pyrrolo[2,3-d]pyrimidine-5-carboxamide |
| 162 | 4-amino-5-cyclopropyl-6-oxo-2-[1-(3,3,4,4,4-pentafluorobutyl)-1H-pyrazolo[3,4-b]pyridin-3-yl]-6,7-dihydro-5h-pyrrolo[2,3-d]pyrimidine-5-carboxamide |
| 168 | 4-amino-5-methyl-2-[1-(3,3,4,4,4-pentafluorobutyl)-1H-pyrazolo[3,4-b]pyridin-3-yl]-5-(1,3,4-thiadiazol-2-yl)-5,7-dihydro-6H-pyrrolo[2,3-d]pyrimidin-6-one |
| 169 | 4-amino-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 170 | 4-amino-5-methyl-2-[1-(3,3,4,4,4-pentafluorobutyl)-1H-pyrazolo[3,4-b]pyridin-3-yl]-5-pyrimidin-2-yl-5,7-dihydro-6H-pyrrolo[2,3-d]pyrimidin-6-one |
| 173 | 4-amino-5-(1-ethyl-1H-1,2,3-triazol-4-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one |
| 180 | 4-amino-5-[1-(cyclopropylmethyl)-1H-1,2,3-triazol-4-yl]-5-methyl-2-[1-(3,3,3-trifluoropropyl)-1H-pyrazolo[3,4-b]pyridin-3-yl]-5,7-dihydro-6H-pyrrolo[2,3-d]pyrimidin-6-one |
| 181 | 4-amino-N-cyclopropyl-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide |
| 182 | 4-amino-5-methyl-6-oxo-N-(pyridin-3-yl)-2-[1-(3,3,3-trifluoropropyl)-1H-pyrazolo[3,4-b]pyridin-3-yl]-6,7-dihydro-5H-pyrrolo[2,3-d]pyrimidine-5-carboxamide |
| 184 | 4-amino-N-cyclopropyl1-5-methyl-2-[6-methyl-1-(3,3,3-trifluoropropyl)-1H-pyrazolo[3,4-b]pyridin-3-yl]-6-oxo-6,7-dihydro-5H-pyrrolo[2,3-d]pyrimidine-5-carboxamide |
| 185 | 4-amino-N-cyclopropyl-2-[6-methoxy-1-(3,3,3-trifluoropropyl)-1H-pyrazolo[3,4-b]pyridin-3-yl]-5-methyl-6-oxo-6,7-dihydro-5H-pyrrolo[2,3-d]pyrimidine-5-carboxamide | or a pharmaceutically acceptable salt thereof.

In a further embodiment, a compound of the instant invention is:

| EXAMPLE NO. | IUPAC NAME |
|---|---|
| 159 | 4-amino-2-[6-chloro-1-(3,3,4,4,4-pentafluorobutyl)-1H-indazol-3-yl]-5-methyl-6-oxo-6,7-dihydro-5H-pyrrolo[2,3-D]pyrimidine-5-carboxamide |
| 160 | 4-amino-2-[6-chloro-1-(3,3,4,4,4-pentafluorobutyl)-1H-indazol-3-yl]-N-cyclopropyl-5-methyl-6-oxo-6,7-dihydro-5H-pyrrolo[2,3-D]pyrimidine-5-carboxamide |
| 162 | 4-amino-5-cyclopropyl-6-oxo-2-[1-(3,3,4,4,4-pentafluorobutyl)-1H-pyrazolo[3,4-B]pyridin-3-yl]-6,7-dihydro-5h-pyrrolo[2,3-D]pyrimidine-5-carboxamide |
| 168 | 4-amino-5-methyl-2-[1-(3,3,4,4,4-pentafluorobutyl)-1H-pyrazolo[3,4-B]pyridin-3-yl]-5-(1,3,4-thiadiazol-2-yl)-5,7-dihydro-6H-pyrrolo[2,3-D]pyrimidin-6-one |
| 169 | 4-amino-5-methyl-5-(5-methyl-1,3,4-oxadiazol-2-yl)-2-[1-(3,3,4,4,4-pentafluorobutyl)-1H-pyrazolo[3,4-B]pyridin-3-yl]-5,7-dihydro-6H-pyrrolo[2,3-D]pyrimidin-6-one |
| 170 | 4-amino-5-methyl-2-[1-(3,3,4,4,4-pentafluorobutyl)-1H-pyrazolo[3,4-B]pyridin-3-yl]-5-pyrimidin-2-yl-5,7-dihydro-6H-pyrrolo[2,3-D]pyrimidin-6-one |
| 173 | 4-amino-5-(1-ethyl-1H-1,2,3-triazol-4-yl)-5-methyl-2-[1-(3,3,4,4,4-pentafluorobutyl)-1H-pyrazolo[3,4-B]pyridin-3-yl]-5,7-dihydro-6H-pyrrolo[2,3-D]pyrimidin-6-one |
| 180 | 4-amino-5-[1-(cyclopropylmethyl)-1H-1,2,3-triazol-4-yl]-5-methyl-2-[1-(3,3,3-trifluoropropyl)-1H-pyrazolo[3,4-B]pyridin-3-yl]-5,7-dihydro-6H-pyrrolo[2,3-D]pyrimidin-6-one |

| EXAMPLE NO. | IUPAC NAME |
|---|---|
| 181 | 4-amino-N-cyclopropyl-5-methyl-6-oxo-2-[1-(3,3,3-trifluoropropyl)-1H-pyrazolo[3,4-B]pyridin-3-yl]-6,7-dihydro-5H-pyrrolo[2,3-D]pyrimidine-5-carboxamide |
| 182 | 4-amino-5-methyl-6-oxo-N-(pyridin-3-yl)-2-[1-(3,3,3-trifluoropropyl)-1H-pyrazolo[3,4-B]pyridin-3-yl]-6,7-dihydro-5H-pyrrolo[2,3-D]pyrimidine-5-carboxamide |
| 184 | 4-amino-N-cyclopropyl1-5-methyl-2-[6-methyl-1-(3,3,3-trifluoropropyl)-1H-pyrazolo[3,4-B]pyridin-3-yl]-6-oxo-6,7-dihydro-5H-pyrrolo[2,3-D]pyrimidine-5-carboxamide |
| 185 | 4-amino-N-cyclopropyl-2-[6-methoxy-1-(3,3,3-trifluoropropyl)-1H-pyrazolo[3,4-B]pyridin-3-yl]-5-methyl-6-oxo-6,7-dihydro-5H-pyrrolo[2,3-D]pyrimidine-5-carboxamide | or a pharmaceutically acceptable salt thereof $R^1$ can be attached to any available carbon atom on the

ring. An example of $R^1$ substitutions, for illustrative purposes, includes:

1) The structure

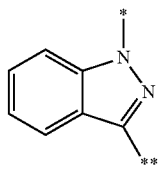

represents when

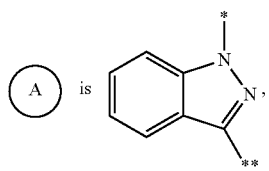

m is 1, 2 or 3 and $R^1$ is H;

2) The structure

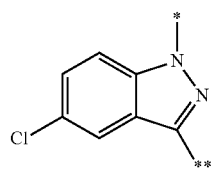

is an example of when

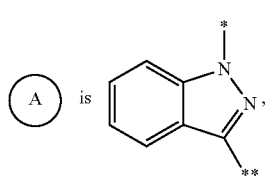

m is 1 and $R^1$ is Cl.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. In an embodiment, cycloalkyl is cyclopropyl. Commonly used abbreviations for alkyl groups are used throughout the specification, e.g. methyl may be represented by conventional abbreviations including "Me" or $CH_3$ or a symbol that is an) extended bond without defined terminal group, e.g. '⌇—', ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. In an embodiment, aryl is phenyl.

"Heteroaryl" unless otherwise indicated, means a mono- or bicyclic aromatic ring or ring system having 5 to 10 atoms and containing at least one heteroatom selected from O, S and N.

Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyrimidyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium. In an embodiment, heteroaryl is imidazolyl, indazolyl, oxadiazolyl, 1,3,4-oxadiazolyl-2(3H)-one, pyrimidinyl, pyridinyl, pyrazolyl, thiadiazolyl, triazolyl, tetrazolyl or thiazolyl.

"Heterocyclyl", unless otherwise indicated, means a 5- or 6-membered monocyclic saturated ring containing at least one heteroatom selected from N, S and O, in which the point of attachment may be carbon or nitrogen. Examples of "heterocyclyl" include, but are not limited to, pyrrolidinyl, piperidinyl, piperazinyl, morpholinyl, imidazolidinyl, 2,3-dihydrofuro(2,3-b)pyridyl, benzoxazinyl, oxetanyl, tetrahydrofuranyl or tetrahydropyranyl and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium. In an embodiment, heterocyclyl is oxetanyl, tetrahydrofuranyl or tetrahydropyranyl.

"Halogen (or halo)" unless otherwise indicated, includes fluorine (fluoro), chlorine (chloro), bromine (bromo) and iodine (iodo). In one embodiment, halo is fluoro (—F) or chloro (—Cl).

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

When any variable (e.g., $R^1$, $R^a$, etc.) occurs more than one time in any constituent or in Formula I or other generic Formulae herein, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

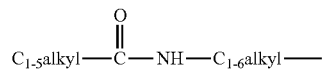

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Reference to the compounds of structural Formula I includes the compounds of other generic structural Formulae that fall within the scope of Formula I, including but not limited to Formulae IA, II and III.

Compounds of structural Formula I may contain one or more asymmetric centers and can thus occur as racemates and racemic mixtures, single enantiomers, diastereoisomeric mixtures and individual diastereoisomers. The present invention is meant to comprehend all such isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer or isomers of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol foul). are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

The present invention includes all stereoisomeric fauns of the compounds of Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of Formula I or at the stage of an intermediate during the synthesis.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mutate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts, Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, including but not limited to the ethyl acetate solvate, and in particular, the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts. The terms "physiologically acceptable salt(s)" and "pharmaceutically acceptable salt(s)" are intended to have the same meaning and are used interchangeably herein.

As appropriate, the following embodiments may apply to structural Formulae I, IA, II and/or III.

As illustrated by the examples herein,

represents an 8- or 9-membered bicyclic heteroaryl ring system, comprised of a 5-membered ring fused to a 5- or 6-membered ring so that the fused rings share two adjacent atoms. In particular, the 8- or 9-membered heteroaryl is composed of a first ring which is a 5-membered ring containing two nitrogens, fused to a second ring that optionally contains one or more heteroatoms (N, O or S). The two nitrogens of the first ring may be fully in the first ring, or one of the two nitrogens may be shared at a fusion point with the second ring. The 8- or 9-membered bicyclic heteroaryl is attached to the pyrmidinyl ring and the —CH$_2$—R$^2$ group of structural Formula I, IA or II via the first ring, and more specifically via each of the atoms in the first ring that are adjacent to each of the two atoms shared by both rings in the bicyclic heteroaryl.

In an embodiment,

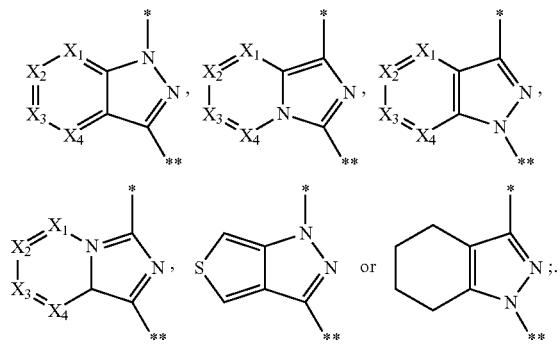

is

In another embodiment,

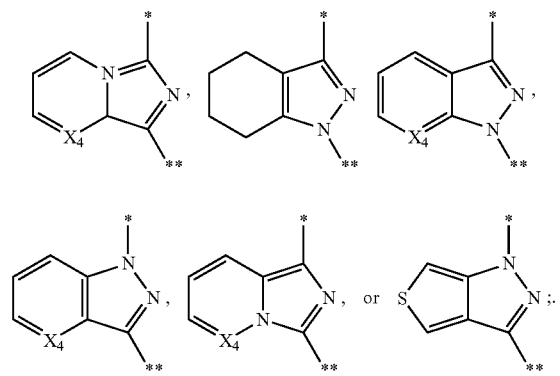

is

In another embodiment,

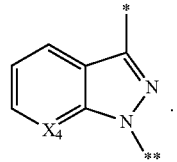

is

As used herein, * indicates attachment to the pyrmidinyl ring and ** indicates attachment to the —CH$_2$—R$^2$ of structural Formula I, IA or II.

In an embodiment, each R$^1$ is independently H, halo, aryl, OR, CN, heteroaryl, —C$_1$-C$_6$ alkyl, or —C$_{3-10}$cycloalkyl, said aryl, heteroaryl, alkyl and cycloalkyl optionally being substituted with one to three substituents selected from halo, —C$_1$-C$_6$ alkyl, —OR, oxo and —CF$_3$. In a further embodiment, each R$^1$ is independently H, halo or —C$_1$-C$_6$ alkyl, wherein said —C$_1$-C$_6$ alkyl is optionally substituted with one to three substituents selected from halo or —CF$_3$. In another embodiment, each R$^1$ is independently H, halo, CN, OCH$_3$ or CH$_3$.

In an embodiment, R$^2$ is —(CR$^d_2$)$_t$C$_1$-C$_6$ alkyl, —(CR$^d_2$)$_t$CF$_3$, —(CR$^d_2$)$_t$—C$_{3-10}$cycloalkyl, —(CR$^d_2$)$_t$heteroaryl, or —(CR$^d_2$)$_t$aryl, said alkyl, cycloalkyl, heteroaryl, and aryl being optionally substituted with one to three substituents selected from halo, —C$_1$-C$_6$ alkyl and —CF$_3$. In another embodiment, R$^2$ is —C$_1$-C$_6$ alkyl, —C$_{3-10}$cycloalkyl, aryl, heteroaryl, or —C(O)Oalkyl, said alkyl, cycloalkyl, aryl, and heteroaryl being optionally substituted with one to three substituents selected from halo, —C$_1$-C$_6$ alkyl, —CF$_3$, —CN and —OR. In another embodiment, R$^2$ is —(CR$^d_2$)$_t$C$_1$-C$_6$ alkyl, or —(CR$^d_2$)$_t$CF$_3$, said alkyl being optionally substituted with one to three substituents selected from halo, —C$_1$-C$_6$ alkyl and —CF$_3$. In another embodiment, R$^2$ is —C$_1$-C$_6$ alkyl or -aryl, said alkyl and aryl being optionally substituted with one to three substituents selected from halo, —C$_1$-C$_6$ alkyl and —CF$_3$. In another embodiment, R$^2$ is CH$_2$CF$_2$CF$_3$, CH$_2$CH$_2$CF$_3$, CH$_2$CF$_2$CHF$_2$, CH$_2$CF$_3$, or CH$_2$CHF$_2$. In an embodiment, R$^2$ is CH$_2$CF$_2$CF$_3$, or CH$_2$CF$_3$.

In an embodiment, R$^3$ is aryl, heteroaryl, CN, —C(O)NR$^a$R$^b$, —NR$^a$C(O)R$^b$, —C(O)OR$^a$, or —OR$^a$, said alkyl, aryl, heteroaryl or heterocyclyl are optionally substituted with from one to three substituent selected R$^5$. In another embodiment, R$^3$ is —C(O)NR$^a$R$^b$, aryl or heteroaryl, wherein said aryl and heteroaryl being optionally substituted with one to three substituents selected from halo, —C$_1$-C$_6$ alkyl and —CF$_3$. In an embodiment, R$^3$ is heteroaryl, —C(O)NR$^a$R$^b$, or —NR$^a$C(O)R$^b$. In another embodiment, R$^3$ is heteroaryl, where said heteroaryl is oxadizaolyl, thiadiazolyl, dihydro-oxadiazolyl, or triazolyl, or —C(O)NR$^a$R$^b$, where R$^a$ and R$^b$ are independently —H, —C$_1$-C$_6$ alkyl, heteroaryl, or —(CH$_2$)$_{0-3}$—C$_{3-10}$ cycloalkyl.

In an embodiment, R$^4$ is C$_1$-C$_6$ alkyl or C$_{3-10}$cycloalkyl. In a further embodiment, R$^4$ is methyl. In an embodiment, R$^4$ is methyl or cyclopropyl.

In an embodiment, R$^5$ is halo, —(CR$^d_2$)$_t$CF$_3$, —(CR$^d_2$)$_t$C$_{3-10}$cycloalkyl, or —C$_1$-C$_6$ alkyl, said alkyl and cycloalkyl being optionally substituted with one to three substituents independently selected from halo or OR.

In an embodiment, m is 1 or 2. More particularly, m is 1 and $R^1$ is H, Cl or F. In an embodiment, t is 0, 1, or 2.

The present invention also relates to processes for the preparation of the compounds of Formula I which are described in the following and by which the compounds of the invention are obtainable.

The compounds of Formula I according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula I can be examined, for example, in the activity assay described below.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula I are, for example, cardiovascular diseases, such as endothelial dysfunction, diastolic dysfunction, atherosclerosis, hypertension, heart failure, pulmonary hypertension, which includes pulmonary arterial hypertension (PAH), stable and unstable angina pectoris, thromboses, restenoses, myocardial infarction, strokes, cardiac insufficiency or pulmonary hypertonia, or, for example, erectile dysfunction, asthma bronchiale, chronic kidney insufficiency and diabetes. Compounds of Formula I can additionally be used in the therapy of cirrhosis of the liver and also for improving a restricted memory performance or ability to learn.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A subject of the present invention therefore also are the compounds of Formula I and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formula I and/or its pharmaceutically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of Formula I and/or their pharmaceutically acceptable salts. The preparation of the pharmaceutical preparations can be carried out in a manner known per se. For this purpose, one or more compounds of Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be adminstered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula I activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin H receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5 (S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

In one embodiment of the present invention, compounds with structure 1 may be prepared by the sequence depicted in Scheme 1. Ring structure Z represents a five or six membered aryl, heterocyclyl or heteroaryl ring. Reaction of compound 2 with the aminoguanidine hydrazone 3 in an alcohol solvent such as MeOH, n-BuOH or t-BuOH and a base such as NaOMe, NaOEt, t-BuOK, $K_2CO_3$ or $NaHCO_3$ at 90° C. to 150° C. gives the pyrimidine hydrazone 4. The reaction may also be carried out in the absence of a base. Additionally, the reaction may also be carried out on the corresponding ethyl or propyl ester of compound 2. Compound 1 is prepared by treating the pyrimidine hydrazone 4 with CuI and a ligand such as trans-N,N'-dimethylcyclohexane-1,2-diamine or N,N'-dimethylethylenediamine in a solvent such as DMF, DMA or NMP at ambient temperature to 160° C. The reaction may also be carried out in the absence of a ligand. The copper mediated cyclization of hydrazones to form indazoles may also be carried out using the conditions described by Liu, R. et al Synthetic Communications 2008, 32(2), 249. In addition to the bromide 4, the copper mediated cyclization shown in Scheme 1 may also be carried out on the corresponding chloride or iodide.

SCHEME 1

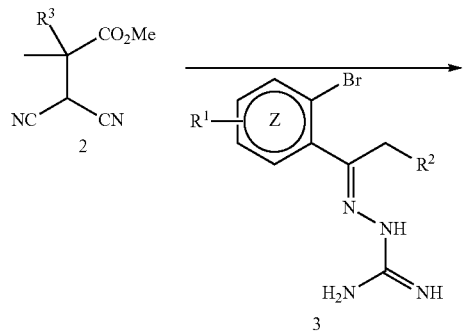

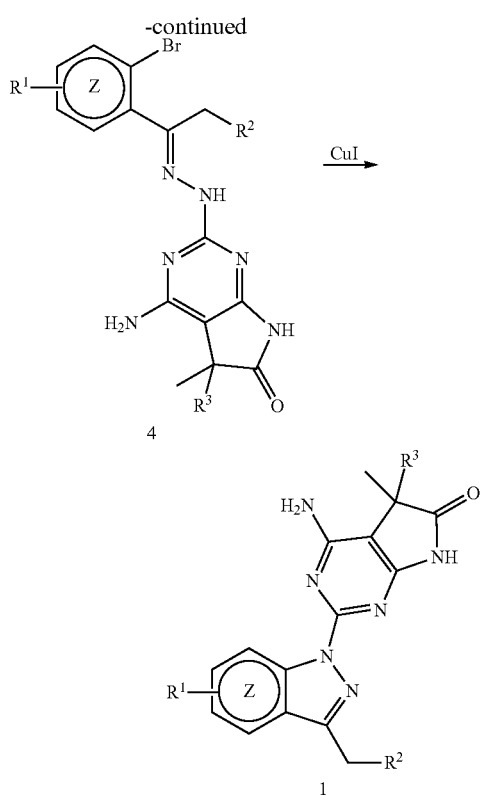

The preparation of compound 2 is outlined in Scheme 2. Deprotonation of ester 5 using a base such as LiHMDS, NaHMDS, NaH or LDA in a solvent such as THF or DMF followed by treatment with methyl iodide affords the ester 6. The esters 5 and 6 may be prepared from the corresponding carboxylic acid by treatment with trimethylsilyl diazomethane or methanol with catalytic sulfuric acid. The esters 5 and 6 may be prepared by the alpha arylation/heteroarylation of esters as described by Buchwald, S. L. et al Organic Letters 2009, 11(8), 1773; or by Shen, H. C. et al Organic Letters 2006, 8(7), 1447. Compounds 5 and 6, where $R^3$ is 5-membered ring heterocycle, may be prepared using methods familiar to those skilled in the art. For example, compound 5, where $R^3$ is a 2-methyl-1,3-oxazol-4-yl group, may be prepared by the condensation of methyl chloroacetoacetate and acetamide. Compound 6, where $R^3$ is a 3-methyl-1,2,4-oxadiazol-5-yl group, may be prepared from dimethyl methyl malonate using the procedure described by Du, W. et al Tetrahedron Letters 2006, 47(25), 4271. Compound 6, where $R^3$ is a 5-methyl-1,3-oxazol-2-yl group, may be prepared from dimethyl methyl malonate using the procedure described by Hashmi, A. S. K. et al Organic Letters 2004, 6(23), 4391. In another example, compound 6, where $R^3$ is a 5-methyl-1,2,4-oxadiazol-3-yl group, may be prepared by the reaction of methyl 2-methylcyanoacetate with hydroxylamine and acetic anhydride. The compound 7 is prepared by treating compound 6 with a brominating reagent such as NBS and AIBN in a solvent such as carbon tetrachloride at refluxing temperatures. Alternatively, the compound 7 may be prepared by reaction with NBS and magnesium perchlorate in acetonitrile solvent at room temperature as described by Yang, D. et al Journal of Organic Chemistry 2002, 67(21), 7429. Compound 7 may also be prepared by treating compound 6 with a base such as sodium hydride followed by treatment with NBS. Compound 2 is obtained from 7 by reaction with malononitrile and a base such as sodium hydride, t-BuOK, K$_2$CO$_3$ or DBU in a solvent such as THF or DMF at ambient temperature to 100° C. The synthetic sequence depicted in Scheme 2 may also used to prepare the corresponding ethyl or propyl ester of compound 2.

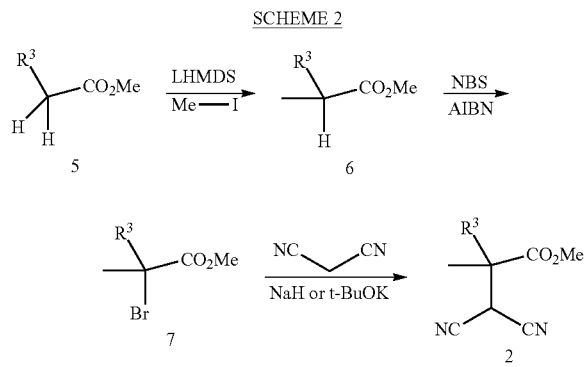

The preparation of the aminoguanidine hydrazone 3 is outlined in Scheme 3. Formation of the dianion of carboxylic acid 9 with a base such as NaHMDS followed by treatment with ester 8 gives the ketone 10. The ketone 10 may be prepared using numerous methods familiar to those skilled in the art. Compound 3 is prepared by treatment of the ketone 10 with aminoguanidine hydrochloride and boron trifluoride etherate in an alcohol solvent such as methanol at 100° C.

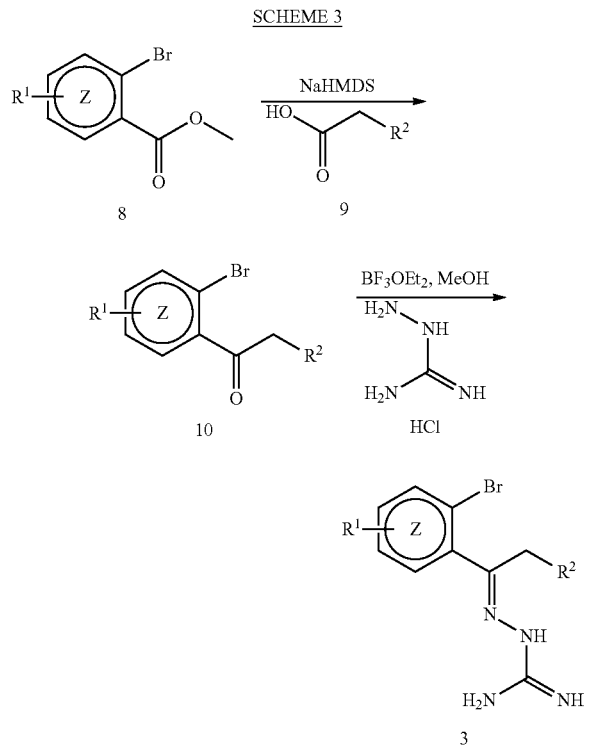

In one embodiment of the present invention compounds with the structure 17 are prepared as outlined in Scheme 4.

Reaction of fluoro aldehyde 11 with hydrazine at 100° C. in a solvent such as DMA affords the indazole 12. Alternatively, indazole 12 may prepared from a 2-methyl aniline using the procedure described by Ruchardt, C. et al *Synthesis* 1972, 7, 375. Treatment of 1.2 with an iodinating reagent such as NIS in a solvent such as DCM or acetonitrile at ambient temperature to 100° C. gives the compound 13. Reaction of 1.3 with zinc cyanide in the presence of a catalyst such as Pd$_2$(dba)$_3$ and DPPF in a solvent such as DMA at 120° C. affords compound 14. Alkylation of 14 with the halide R$^2$CH$_2$I using a base such as cesium carbonate, sodium hydride or K$_2$CO$_3$ in a solvent such as DMF, DMA or acetonitrile at ambient temperature to 100° C. gives the compound 15. Conversion of the nitrile 15 to the amidine 16 can be accomplished with a reagent such as amino(chloro)methylaluminum, prepared from trimethylaluminum and ammonium chloride, in a non-polar solvent such as toluene at 100° C. as described by Garigipati, R. S. et al *Tetrahedron Letters* 1990, 31(14), 1969. The reaction may also be carried out on the corresponding methyl ester of compound 15. Compound 16 can be converted to compound 17 as described in Scheme 1 (compound 3 to 4).

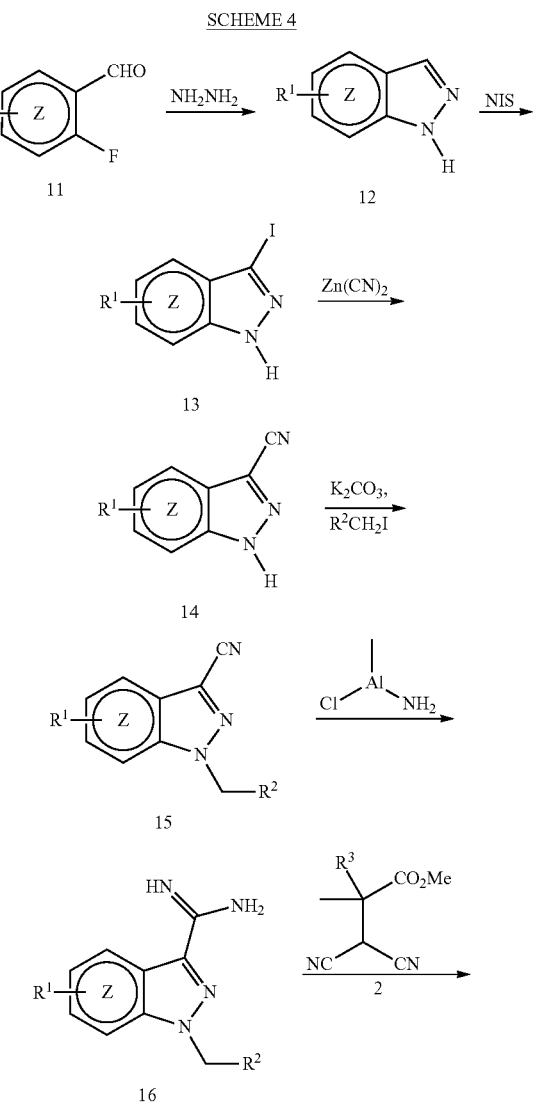

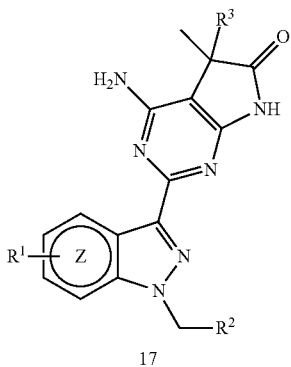

17

In one embodiment of the present invention compounds with structure 20 may be prepared by the sequence depicted in Scheme 5. Conversion of the nitrile 18 to the amidine 19 can be accomplished using the conditions described for the conversion of compound 15 to 16 in Scheme 4. Reaction of amidine 19 with the compound 2 as described in Scheme 1 (compound 3 to 4) affords 20.

organic base such as DIEA or TEA in a solvent like DCM to afford the amide 22. This can be converted to the imidazopyridine 23 with phosphorous oxychloride in a chlorinated solvent such DCE under refluxing conditions. Iodination of 23 to afford 24 can be accomplished with NIS in solvents like DCM or acetonitrile at ambient temperature or under reflux conditions. The nitrile 18 can be prepared by treatment of the iodide 24 with zinc cyanide in the presence of a suitable catalyst such as Pd(PPh$_3$)$_4$ or Pd$_2$(dba)$_3$ and ligand such as dppf in a polar solvent such as DMF.

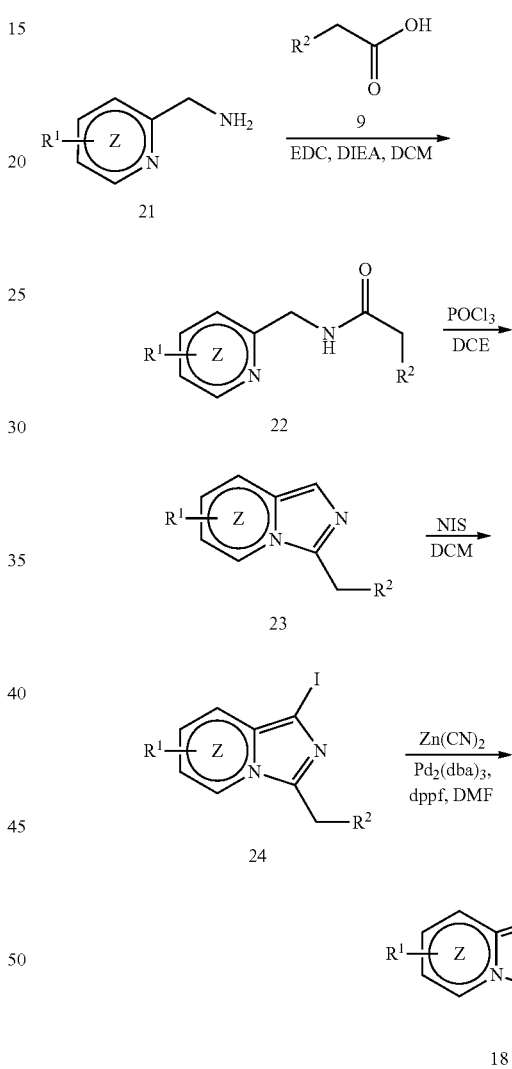

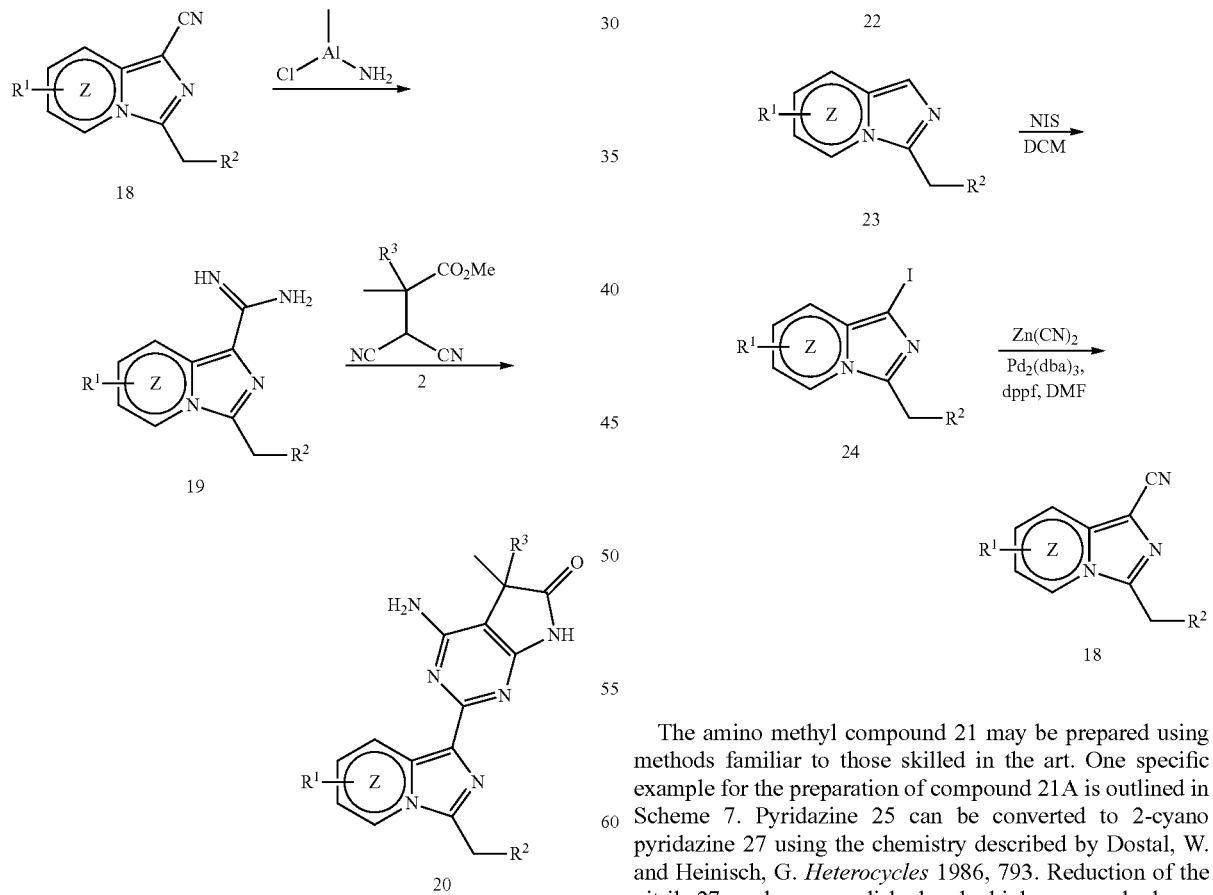

Scheme 6 outlines the preparation of nitrile intermediate 18. Amino methyl compound 21 can be coupled with the carboxylic acid 9 and a coupling reagent such as EDC and an The amino methyl compound 21 may be prepared using methods familiar to those skilled in the art. One specific example for the preparation of compound 21A is outlined in Scheme 7. Pyridazine 25 can be converted to 2-cyano pyridazine 27 using the chemistry described by Dostal, W. and Heinisch, G. *Heterocycles* 1986, 793. Reduction of the nitrile 27 can be accomplished under high pressure hydrogenation conditions using a suitable catalyst such as palladium on carbon in an alcoholic solvent such as methanol or ethanol and a suitable acid such as hydrochloric acid to afford the 2-amino methylpyridazine hydrochloride 21A.

SCHEME 7

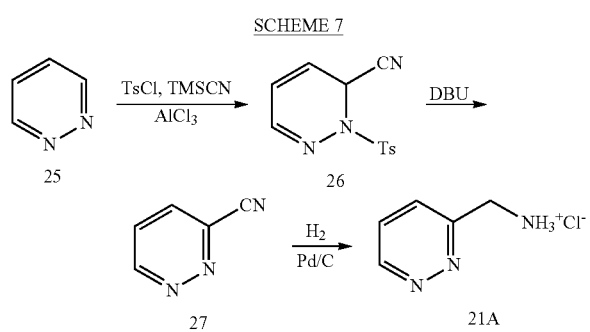

The amino methyl compounds 21B and 21C may be prepared as outlined in Scheme 8. Addition of diethyl acetamidomalonate to 2-chloro-5-nitropyridine affords compound 29. Reduction of 29 with hydrogen and palladium on carbon gives the amine 30. Sandmeyer reaction of 30 using the indicated conditions gives the halo (chloro or fluoro) pyridine 31. Saponification of 31 with base followed by treatment with hydrochloric acid gives amino methyl compounds 21B and 21C.

SCHEME 8

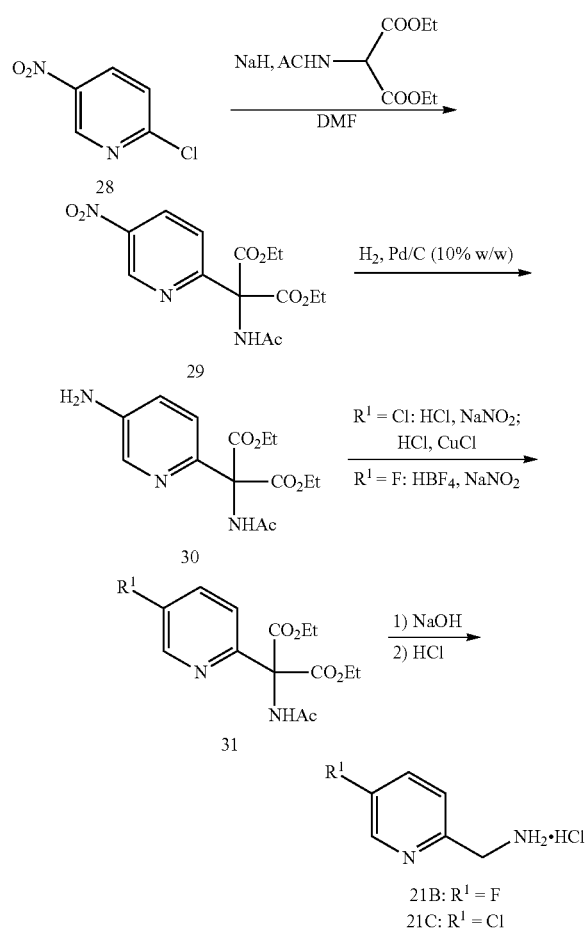

Compounds of the present invention may be prepared using methods familiar to those skilled in the art. One such method is the reduction of ring structure Z in compounds 1, 17 and 20 to the corresponding tetrahydro or dihydro compounds using hydrogen and a catalyst such as palladium or platinum. This reduction may also be carried out using a reducing agent such as triethylsilane and an acid such as TFA. Compounds 1, 17 and 20 bearing a halogen substituent may be converted to the corresponding cyanide as described in Scheme 4 (compound 13 to 14), or to a hydroxyl as described by Buchwald, S. L. et al *Journal of the American Chemical Society* 2006, 128 (33), 10694, or to another halogen as described by Arvela, R. K. et al *Synlett* 2003, 8, 1145. Halogen substituents on compounds 1, 17 and 20 may be converted to aryl or heteroaryl substituents by a Suzuki coupling using conditions described by Buchwald, S. L. et al *Journal of the American Chemical Society* 2007, 129 (11), 3358. Compounds 1, 17 and 20, where $R^3$ is an ester (represented as structure 32 in Scheme 9), may be converted to a $R^3$ 5-membered ring heterocycle using methods mentioned for compounds 5 and 6 in Scheme 2. Additional methods for this conversion are summarized in Scheme 9. The ester 32 can be converted to amide 33 by treatment with amines such as ammonia, hydrazine, or methyl hydrazine in an alcohol solvent such as methanol at ambient temperature to 50° C. Acylation of 33B with N-acetylimidazole gives an acyl hydrazine intermediate with can be converted to 34A by treatment with thionyl chloride or to 34B by treatment with Lawesson's reagent. Compound 35 is prepared by reacting 33C with carbonyl diimidazole.

SCHEME 9

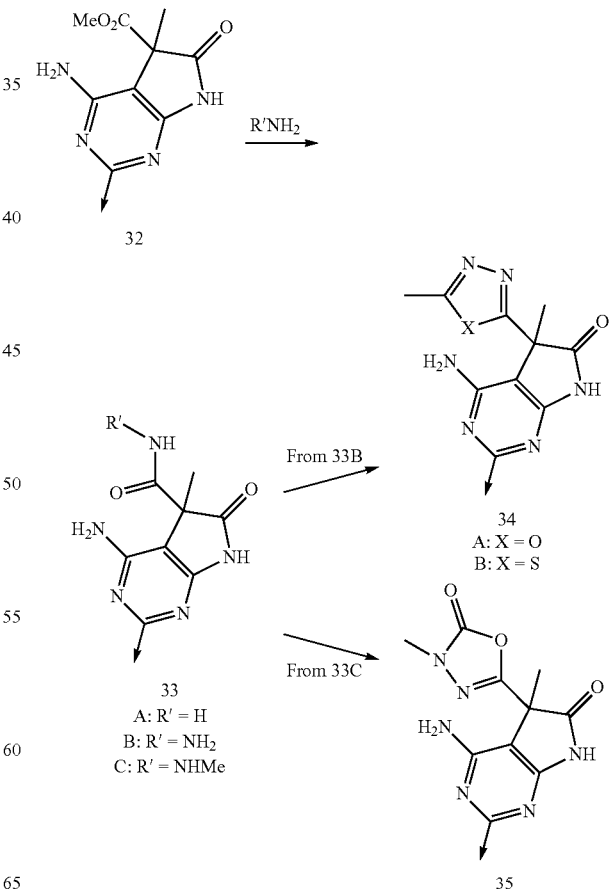

Compounds of the present invention possess an asymmetric center about the carbon bearing the $R^3$ substituent which can be either R or S configuration. These enantiomeric isomers may be separated or resolved using methods familiar to those skilled in the art. For example, the compounds of the present invention may be resolved to the pure isomers using chiral SFC chromatography. Alternatively, compound 2 may be resolved using a method such as chiral SFC chromatography. Use of the enantiomerically pure compound 2 as described in Schemes 1, 4 and 5 affords enantiomerically pure products 1, 17 and 20. Unless otherwise noted, the examples in the present invention are enantiomerically pure isomers (R or S). Data is given for the more active isomer.

In addition to the methods described in Scheme 2, compound 2 (depicted as the ethyl ester) may also be prepared as shown in Scheme 10. Reaction of alkyl, or aryl magnesium bromide with the dicyanopropenoate 36A (or 36B) and lithium chloride in a solvent such as THF affords compound 2. Cycloalkyl, heteroaryl, and alkynyl magnesium halides are also suitable reagents for this reaction. Compound 36A ($R^3$ is $CO_2Et$) can be prepared using the procedure described by Sentman et. al. *J. Org. Chem.* 1982, 47, 4577. Compound 36B ($R^4$ is Me) can be prepared using the procedure described by Hagiware et. al. *Synthesis* 1974, 9, 669.

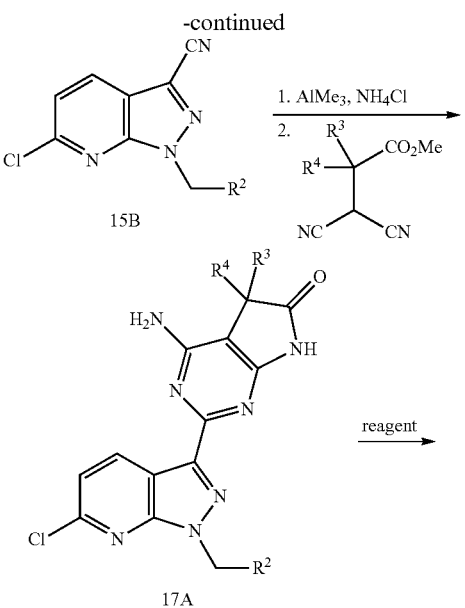

SCHEME 10

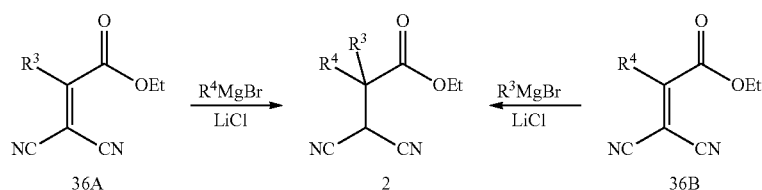

The $R^1$ substituent, if not present in starting material (e.g. compound 11 in Scheme 4), may be incorporated in a late intermediate using methods familiar to those skilled in the art. For example, the compound 14 ($R^1$ is H) can be converted to a bromide ($R^1$ is Br) by reaction with bromine and sulfuric acid. Another method is depicted in Scheme 11. Treatment of compound 15A with mCPBA in acetic acid solvent at 75° C. affords the N-oxide which is then reacted with phosphorous oxychloride at 75° C. to give compound 15B. Compound 15B can be converted to 17A using the procedures described in Scheme 4. The chloro substituent in compound 17A may be converted to a variety of groups using methods familiar to those skilled in the art. For example, the chloro substituent can be converted to methoxy, methyl and cyano substituents using the conditions summarized in Scheme 11 (compound 17B).

SCHEME 11

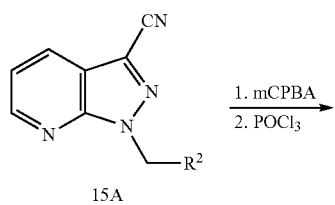

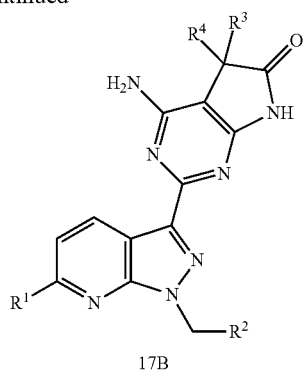

$R^1$ reagent
MeO: NaOMe, MeOH, 60° C.
Me: MeMgBr, Fe(acac)$_3$, THF, rt
CN: Zn(CN)$_2$, Pd$_2$(dba)$_3$, dppf, DMF, 130° C.

In one embodiment of the present invention compounds with structure 42 may be prepared as depicted in Scheme 12. Reaction of the ketone 37 with hydroxylamine gives an oxime which is subsequently reduced with zinc to afford amine compound 38. The ketone compound 37 may be prepared using numerous methods familiar to those skilled in the art. Treatment of compound 38 with methyl oxalyl chloride affords compound 39. Cyclization of compound 39 to compound 40 can be accomplished with phosphorous oxychloride at 120° C. Conversion of compound 40 to compound 42 is accomplished using the methods discussed in Schemes 4.

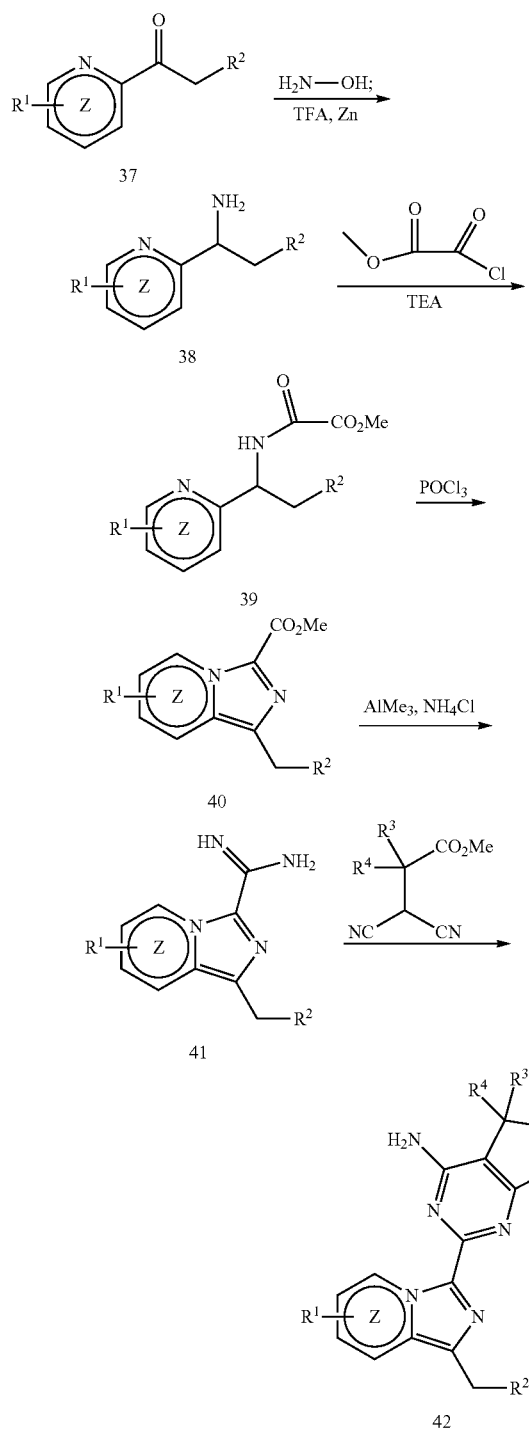

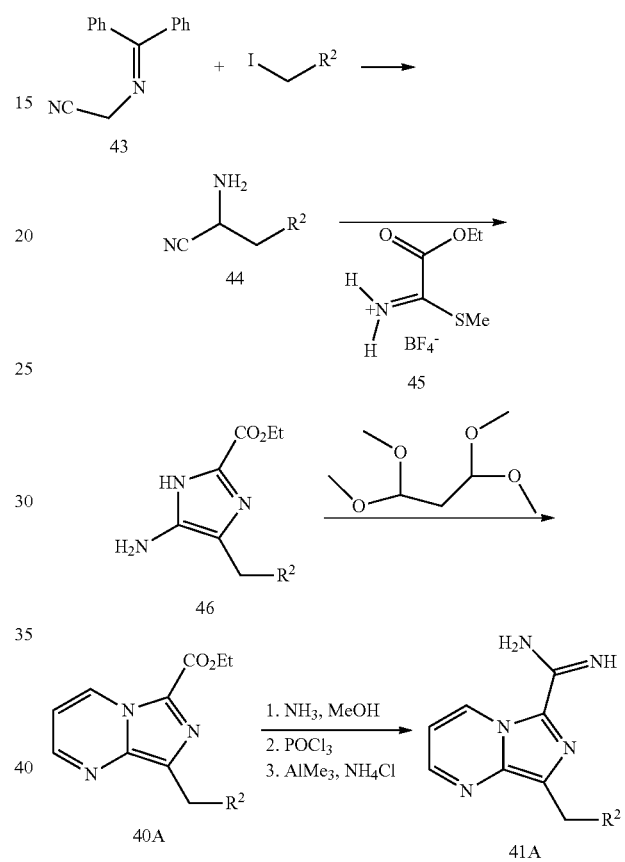

The preparation of compound 41A is outlined in Scheme 13. Alkylation of compound 43 using a base such as potassium hydroxide and a phase transfer catalyst such as benzyltriethylammonium chloride in dichloromethane solvent gives the amino nitrile compound 44. Reaction of compound 44 with compound 45 in a solvent such as 1,4-dioxane at ambient temperature affords compound 46. The compound 45 can be prepared by methylating ethyl thiooxamate with trimethyloxonium tetrafluoroborate. Conversion of compound 46 to compound 40A is achieved by heating with 1,1,3,3-tetramethoxypropane at 160° C. in an alcohol solvent such as ethanol. The compound 40A is then converted to the amidine 41A using the three step sequence depicted in Scheme 13.

Compounds possessing an alkyl amino pyrimidine substituent (i.e. compound 49) may be prepared as outlined in Scheme 14. Reaction of compound 47 with tert-butyl nitrite and copper (II) bromide at 65° C. in a solvent such as 1,2-dichloroethane affords the bromide 48. This can then be reacted with amines at elevated temperature (50° C. to 150° C.) to afford compound 49.

SCHEME 14

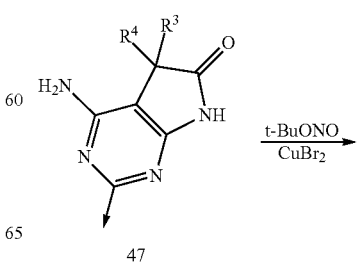

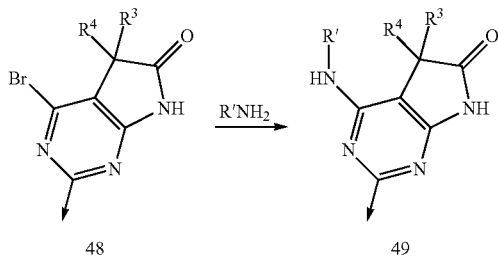

The ester 32 in Scheme 9 can be converted to alkyl amide 33 simply by heating with an amine. Aryl and heteroaryl amides can be prepared by treating compound 32 with an amine and a reagent such i-PrMgCl, i-PrMgCl with LiCl, or AlMe$_3$. Alternatively, amides may be prepared from acyl hydrazide 33B as depicted in Scheme 15. Treatment of 33B with sodium nitrite or an alkyl nitrite such as tert-butyl nitrite affords the acyl azide 50. This can then be reacted with an alkyl, aryl or heteroaryl amine at ambient temperature to afford amide 33. Alternatively, the acyl azide 50 undergoes the Curtius rearrangement at elevated temperature to give an isocyanate which can then react with an amine to give a urea or an alcohol such as tert-butanol to give the carbamate 51 as depicted in Scheme 15. Carbamate 51 may then be treated with an acid such as trifluoroacetic acid to give the primary amine which can then be used in a variety of reactions, such as a coupling with a carboxylic acid or a reductive amination to give compound 52, as the depicted in Scheme 15.

The amide 33A in Scheme 9 may be converted to number of substituents using methods familiar to those skilled in the art. In addition to the methods depicted in Scheme 9, compound 33A can be converted to the corresponding nitrile by treatment with a reagent such as phosphorous oxychloride. Alternatively, the amide 33A can be reacted with Lawesson's reagent to form a thioamide which can then be converted to a number of heterocycles such as a 1,3-thiazole. A 1,2,3-triazole can be prepared by the copper catalyzed reaction of alkyne 53 and an azide as depicted in Scheme 16. Alternatively, compound 56 can be prepared by the alkylation of the mono substituted lactam 55 as depicted in Scheme 16.

SCHEME 16

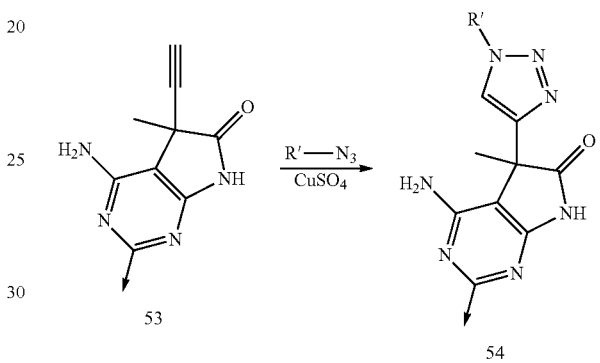

SCHEME 15

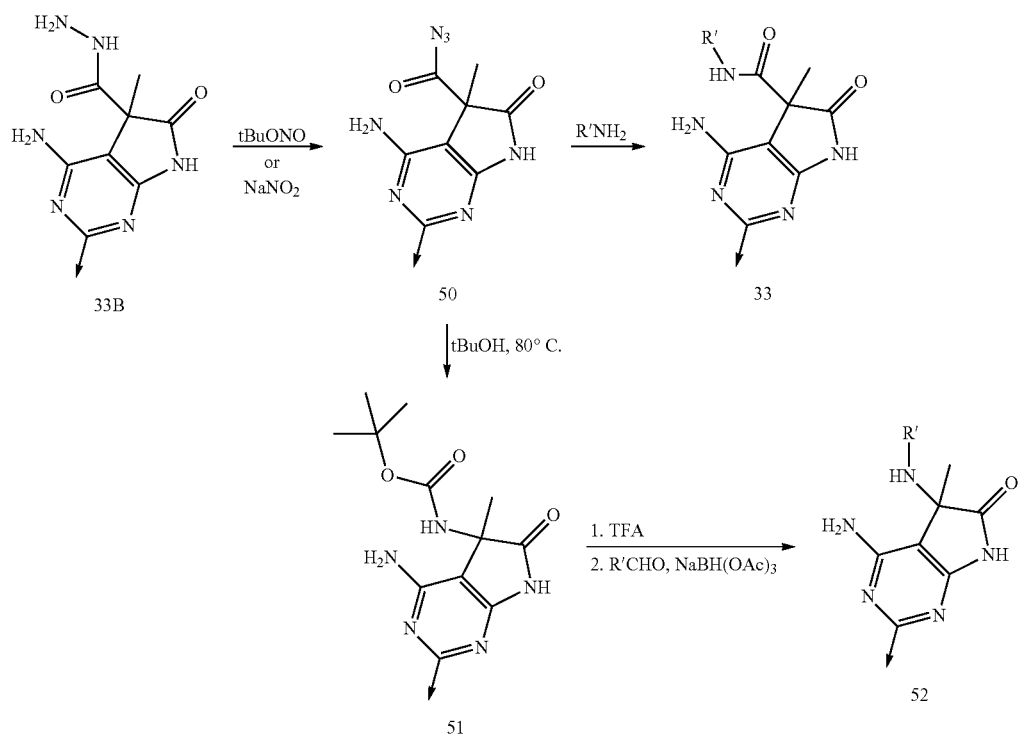

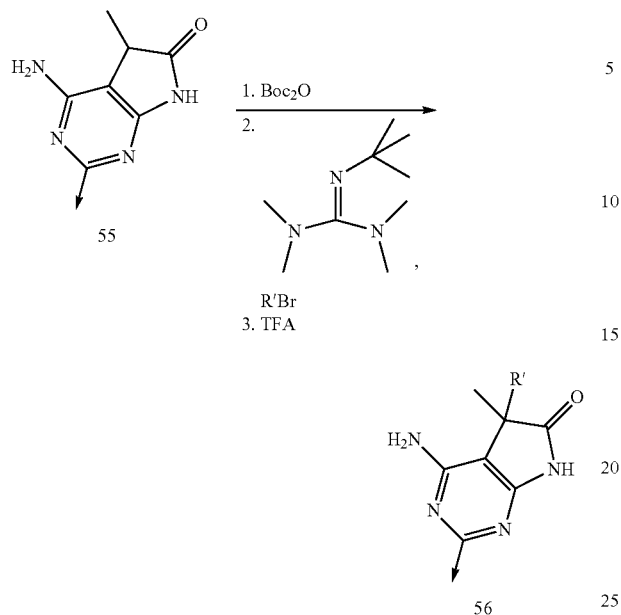

Throughout the synthetic schemes and examples, abbreviations are used with the following meanings unless otherwise indicated:

| | |
|---|---|
| aq, aq. = aqueous | AIBN = 2,2'-Azobisisobutyronitrile |
| Ar = aryl | AuCl$_3$ = gold trichloride |
| Ac = acetate | Bn = benzyl |
| BF$_3$OEt$_2$ = boron trifluoride diethyl etherate | t-BuOK = potassium tert-butoxide |
| Bu = butyl, t-Bu = tert-butyl | t-Boc$_2$O = di-tert-butyl dicarbonate |
| t-BuONO = tert-butyl nitrite | conc, conc. = concentrated |
| cPr = cyclopropyl | DBU = 1,8-Diazabicyclo[4.3.0]undec-7-ene |
| dppf = 1,1'-Bis(diphenylphosphino)ferrocene | dba = dibenzylideneacetone |
| DCE = 1,2-dichloroethane | DCM = dichloromethane |
| DIEA = diisopropylethylamine | DME = 1,2-dimethoxyethane |
| DMA, DMAC = dimethylacetamide | DMF = N,N-dimethylformamide |
| DMAP = 4-dimethylaminopyridine | DMSO = dimethylsulfoxide |
| Et = ethyl | EDC = 1-Ethyl-3-(3-dimethylaminopropyl)carbodiimidehydrochloride |
| EtOAc = ethyl acetate | EtOH = ethanol |
| eq. = equivalent(s) | Fe(acac)$_3$ = iron(III) acetylacetonate |
| HOAc = acetic acid | HPLC = High pressure liquid chromatography |
| h, hr = hour | HMPA = hexamethylphosphoramide |
| iPr = isopropyl | iPA = isopropyl alcohol |
| IPA, i-PrOH = isopropanol | LDA = lithium diisopropylamide |
| LAH = Lithium aluminum hydride | LiHMDS, LHMDS = lithium bis(trimethylsilyl)amide |
| Me = methyl | MeOH = methanol |
| min, min. = minute | Mp = melting point |
| mCPBA = 3-chloroperoxybenzoic acid | NMP = N-methylpyrrolidone |
| NaHMDS = sodium bis(trimethylsilyl)amide | NBS = N-bromo succinimide |
| NIS = N-iodosuccinimide | NMR = nuclear magnetic resonance |
| PDA = photodiode array | Pd/C = palladium on activated carbon |
| Pd$_2$(dba)$_3$ = tris(dibenzylideneacetone)dipalladium (0) | Ph = phenyl |
| Pd(PPH$_3$)$_4$ = tetrakis(triphenylphosphine)palladium (0) | Pr = propyl |
| iPrMgCl = isopropylmagnesium chloride | psig = pounds per square inch gauge |
| rt = retention time | PTFE = polytetrafluoroethylene |
| RT = room temperature | sat. = saturated |
| SFC = supercritical fluid chromatography | TEA = triethylamine |
| TFA = trifluoroacetic acid | THF = tetrahydrofuran |
| TLC = thin layer chromatography | prep TLC = preparative thin layer chromatography |
| TMSCN = trimethylsilyl cyanide | TsCl = 4-toluenesulfonyl chloride |

The following examples are provided to more fully illustrate the present invention, and shall not be construed as limiting the scope in any manner. Unless stated otherwise:

1) All operations were carried out at room or ambient temperature (RT), that is, at a temperature in the range 18-25° C.;
2) Reactions are generally done using commercially available anhydrous solvents under an inert atmosphere, either nitrogen or argon;
3) Microwave reactions were done using a Biotage Initiator™ or CEM Explorer® system;
4) Evaporation of solvent was carried out using a rotary evaporator under reduced pressure (4.5-30 mmHg) with a bath temperature of up to 50° C.;
5) The course of reactions was followed by thin layer chromatography (TLC) and/or tandem high performance liquid chromatography (HPLC) followed by electron spray mass spectroscopy (MS), herein termed LCMS, and any reaction times are given for illustration only;
6) The structure of all final compounds was assured by at least one of the following techniques: MS or proton nuclear magnetic resonance (1H NMR) spectrometry, and the purity was assured by at least one of the following techniques: TLC or HPLC;
7) $^1$H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens);

conventional abbreviations used for signal shape are: s. singlet; d. doublet (apparent); t. triplet (apparent); m. multiplet; br. broad; etc., 8) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection.

9) Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (typically 5% acetonitrile to 95% acetonitrile) or on a Shimadzu system using a Sunfire Prep C18 OBD 5 µM column (100×30 mm i.d.) eluting at 50 mL/min with a water/acetonitrile (0.1% TFA) gradient;

10) Purification of compounds by preparative thin layer chromatography (PTLC) was conducted on 20×20 cm glass plates coated with silica gel, commercially available from Analtech; or E. Merck.

11) Flash column chromatography was carried out on a glass silica gel column using Kieselgel 60, 0.063-0.200 mm (SiO$_2$), or on a Biotage SiO$_2$ cartridge system using the Biotage Horizon and Biotage SP-1 systems; or a Teledyne Isco SiO$_2$ cartridge using the CombiFlashRf system;

12) Chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), uM (micromolar), nM (nanomolar), ca (circa/about).

INTERMEDIATE 1

Methyl 3,3-Dicyano-2-Methyl-2-Phenylpropanoate

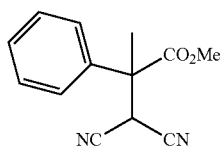 [SMILES: COC(=O)C(C)(c1ccccc1)C(C#N)C#N]

Step A: methyl 2-phenylpropanoate

Trimethylsilyl diazomethane (2.0M in hexanes, 40 mL, 80 mmol) was added dropwise to a solution of racemic 2-phenylpropionic acid (10.0 g, 66.6 mmol) in benzene (100 mL) and methanol (20 mL) cooled in an ice bath. After the addition was complete the reaction solution was stirred at room temperature for 2 hours. The solution was then concentrated to give the indicated product. m/z=165.1 (M+H).

Step B: methyl 2-bromo-2-phenylpropanoate

A carbon tetrachloride (150 mL) solution of the intermediate from Step A (10.39 g, 66.6 mmol), N-bromosuccinimide (14.22 g, 80 mmol) and AIBN (0.547 g, 3.33 mmol) was heated to reflux. After 4 hours the reaction solution was cooled to room temperature and the mixture filtered. The filtrate was concentrated and the residue purified by silica gel chromatography using a hexanes/EtOAc gradient to give the indicated product. $^1$H NMR (500 MHz, CHCl$_3$-d): δ 7.59-7.53 (m, 2H); 7.37-7.30 (m, 3H); 3.80 (s, 3H); 2.31 (s, 3H).

Step C: methyl 3,3-dicyano-2-methyl-2-phenylpropanoate

Malononitrile (4.29 g, 65 mmol) and potassium t-butoxide (7.29 g, 65 mmol) were added to a THF (100 mL) solution containing the intermediate from Step B (15.8 g, 65 mmol). The reaction solution was then placed in an 85° C. oil bath for 4 hours. The solution was then cooled to room temperature and partitioned between saturated aqueous ammonium chloride and ethyl acetate. The organic layer was washed with brine, dried over sodium sulfate, filtered and concentrated. The crude was purified by silica gel chromatography using a hexanes/EtOAc gradient to give the indicated racemic product. $^1$H NMR (500 MHz, CHCl$_3$-d): δ 7.44-7.42 (m, 3H); 7.38-7.36 (m, 2H); 4.50 (s, 1H); 3.80 (s, 3H); 2.00 (s 3H). The racemic material was resolved on a Berger SFC II preparative instrument using a ChiralPak AD-H, 250×30 mm I.D. column and a SFC CO$_2$/Methanol eluent.

INTERMEDIATE 2

Methyl 3,3-Dicyano-2-Methyl-2-(Pyridin-2-yl)Propanoate

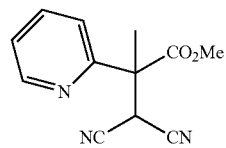

Step A: methyl 2-(pyridin-2-yl)propanoate

Methyl 2-pyridylacetate (6.81 mL, 50 mmol) was added dropwise to LHMDS (1.0M in THF, 50 mL) and THF (65 mL) cooled to 0° C. After 30 minutes iodomethane (3.97 g, 63.5 mmol) was added to the solution. After stirring for 1 hour at 0° C. the solution was concentrated and the residue was purified by silica gel chromatography using a hexanes/EtOAc gradient to give the indicated product. $^1$H NMR (400 MHz, CHCl$_3$-d): δ 8.56 (d, J=4.9 Hz, 1H); 7.66 (td, J=7.6, 1.8 Hz, 1H); 7.18 (dd, J=7.6, 4.9 Hz, 1H); 3.96 (q, J=7.2 Hz, 1H); 3.69 (s, 3H). 1.56 (d, J=7.2 Hz, 3H). m/z 166.5 (M+H).

Step B: methyl 2-bromo-2-(pyridin-2-yl)propanoate

Magnesium perchlorate (0.46 g, 2.08 mmol) was added to an acetonitrile (18 mL) solution containing the intermediate from Step A (1.04 g, 6.30 mmol). After stirring for 5 minutes N-bromosuccinimide (1.35 g, 7.55 mmol) was added and the reaction solution was stirred overnight. The solution was then partitioned between EtOAc and 1N NaHCO$_3$ aq. The organic layer was washed with brine, dried over MgSO$_4$, filtered and concentrated. The residue was purified by silica gel chromatography using a hexanes/EtOAc gradient to give the indicated product. $^1$H NMR (400 MHz, CH$_3$CN-d$_3$): δ 8.48 (d, J=4.8 Hz, 1H); 7.85-736 (m, 2H); 7.32-7.26 (m, 1H); 3.72 (s, 3H); 2.24 (s, 3H). m/z=244.4 (M+H).

Step C: methyl 3,3-dicyano-2-methyl-2-(pyridin-2-yl)propanoate

A DMF (7 mL) solution of malononitrile (0.413 g, 6.24 mmol) was added to a suspension of NaH (0.252 g, 6.30 mmol, 60%) in DMF (9 mL) cooled to 0° C. After 10 minutes a DMF (7 mL) solution of the intermediate from Step B (1.438 g, 5.89 mmol) was added. The reaction solution was then stirred overnight at room temperature. The solution was then partitioned between EtOAc and water. The organic layer was washed with brine, dried over $MgSO_4$, filtered and concentrated. The residue was purified by silica gel chromatography using a hexanes/EtOAc gradient to give the indicated product. $^1$H NMR (400 MHz, $CHCl_3$-d): δ 8.59 (d, J=4.8 Hz, 1H); 7.79 (td, J=7.7, 1.8 Hz, 1H); 7.50 (d, J=8.0 Hz, 1H); 7.32 (dd, J=7.6, 4.8 Hz, 1H); 5.25 (s, 1H); 3.77 (s, 3H); 2.01 (s, 3H). m/z=230.2 (M+H). The racemic material was resolved on a Berger SFC II preparative instrument using a ChiralCel IA-H, 250×30 mm I.D. column and a SFC $CO_2$/Methanol/MeCN eluent.

INTERMEDIATE 3

Methyl 3,3-Dicyano-2-Methyl-2-(Pyrazin-2-yl)Propanoate

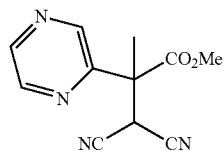 [SMILES: COC(=O)C(C)(c1cnccn1)C(C#N)C#N]

Step A: tert-butyl 2-(pyrazin-2-yl)propanoate

A solution of NaHMDS (1M in toluene, 349 mL, 349 mmol) was added over 5 minutes to a toluene (200 mL) solution containing chloropyrazine (20 g, 175 mmol) and t-butyl propionate (22.73 g, 175 mmol) cooled to 0° C. The solution was stirred at 0° C. for 2 hours and then at room temperature for 4 hours. The reaction was then quenched with saturated aqueous $NH_4Cl$. The mixture was extracted with ethyl acetate and the organic layer concentrated. The residue was purified by silica gel chromatography using a hexanes/EtOAc gradient to give the indicated product. m/z=209.3 (M+H).

Step B: methyl 2-(pyrazin-2-yl)propanoate

Trifluoroacetic acid (30 mL) was added to a DCM (100 mL) solution of the intermediate from Step A (30.1 g, 144 mmol). After 30 minutes of stirring at room temperature the solvent was concentrated to give 18 g of a red oil. m/z=153.2 (M+H). To this oil was added 50 mL of MeOH, 200 mL of benzene and trimethylsilyl diazomethane (2.0M in hexanes, 60 mL, 120 mmol). After stirring for 10 minutes the reaction was quenched with trifluoroacetic acid. The solution was concentrated and the residue purified by silica gel chromatography using a hexanes/EtOAc gradient to give the indicated product. m/z=167.1 (M+H).

Step C: methyl 2-bromo-2-(pyrazin-2-yl)propanoate

A carbon tetrachloride (150 mL) solution containing the intermediate from Step B (18 g, 108 mmol), N-bromosuccinimide (26.6 g, 150 mmol) and AIBN (0.5 g) was heated at reflux overnight. The solution was cooled to room temperature, filtered and concentrated. The residue was purified by silica gel chromatography using a hexanes/EtOAc gradient to give the indicated product. m/z=245.1 (M+H).

Step D: methyl 3,3-dicyano-2-methyl-2-(pyrazin-2-ylpropanoate

A DMF (15 mL) solution of sodium hydride (0.38 g, 9.4 mmol, 60%) was added to malononitrile (0.62 g, 9.4 mmol) in DMF (3 mL) at 0° C. After 10 minutes the intermediate from Step C (2.1 g, 8.6 mmol) was added. After stirring for 2 hours at room temperature the reaction was quenched with saturated aqueous $NH_4Cl$. The mixture was extracted with ethyl acetate and the organic layer concentrated. The residue was purified by silica gel chromatography using a hexanes/EtOAc gradient to give the indicated product. $^1$H NMR δ (ppm) ($CHCl_3$-d): 8.85 (1H, s), 8.65 (1H, d, J=2.6 Hz), 8.58 (1H, s), 5.12 (1H, s), 3.81 (3H, s), 2.09 (3H, s). m/z=231.0 (M+H).

INTERMEDIATE 4

Ethyl 3,3-Dicyano-2-Methyl-2-(5-Methyl-1,2,4-Oxadiazol-3-yl)Propanoate

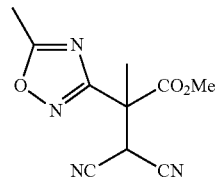 [SMILES: COC(=O)C(C)(c1noc(C)n1)C(C#N)C#N]

Step A: ethyl (3Z)-3-amino-3-(hydroxyimino)-2-methylpropanoate

Ethyl 2-methylcyanoacetate (5 g, 39 mmol) and hydroxylamine (2.6 g, 39 mmol) were dissolved in 50 mL of MeOH. The solution was heated at the 50° C. overnight. The solution was then concentrated and the residue purified by silica gel chromatography using a hexanes/EtOAc gradient to give the indicated product. $^1$H NMR δ (ppm) (DMSO-$d_6$): 9.05 (1H, s), 5.40 (2H, s), 4.06 (2H, dd, J=12.8, 7.0 Hz), 3.15 (1H, m), 1.24 (3H, d, J=7.2 Hz), 1.18 (3H, t, J=7.1 Hz). m/z=161.1 (M+H)

Step B: ethyl 2(5-methyl-1,2,4-oxadiazol-3-yl)propanoate

Acetic anhydride (4.6 mL, 49 mmol) was added to a pyridine (50 mL) solution of the intermediate from Step A (2.6 g, 16.2 mmol). The solution was heated at reflux for 1 hour and then at room temperature overnight. The solution was then concentrated to remove most of the pyridine. The concentrated solution was diluted with EtOAc and washed twice with water. The organic layer was concentrated and the residue purified by silica gel chromatography using a hexanes/EtOAc gradient to give the indicated product. $^1$H NMR δ

(ppm) (CHCl₃-d): 4.19 (2H, dd, J=72, 3.6 Hz), 3.94 (1H, m, J=7.3 Hz), 2.58 (3H, s), 1.60 (3H, t, 7.3 Hz), 1.25 (3H, t, J=7.1 Hz). m/z=185.1 (M+H).

Step C: ethyl 2-bromo-2-(5-methyl-1,2,4-oxadiazol-3-yl)propanoate

A carbon tetrachloride (30 mL) solution containing the intermediate from Step B (1.9 g, 10.3 mmol), N-bromosuccinimide (3.56 g, 20 mmol) and AIBN (0.1 g) was heated at reflux for 4 hours. The solution was cooled to room temperature, filtered and concentrated. The residue was purified by silica gel chromatography using a hexanes/EtOAc gradient to give the indicated product. m/z=263.0 (M+H).

Step D: ethyl 3,3-dicyano-2-methyl-2-(5-methyl-1,2,4-oxadiazol-3-yl)propanoate

DBU (2.56 mL, 8.1 mmol) was added dropwise to a −78° C. THF (20 mL) solution of malononitrile (1.12 g, 17 mmol) and the intermediate from Step C (1.49 g, 5.66 mmol). The reaction solution was stirred at −78° C. for 15 minutes and then at room temperature for 1 hour. The solution was then concentrated and the residue purified by silica gel chromatography using a hexanes/EtOAc gradient to give the indicated product. ¹H NMR δ (ppm) (CHCl₃-d): 4.79 (1H, s), 4.30 (2H, dd, J=7.1, 2.6 Hz), 2.64 (3H, s), 2.02 (3H, s), 1.31-1.25 (3H, m).

INTERMEDIATE 5

Methyl 3,3-Dicyano-2-Methyl-2-(3-Methyl-1,2,4-Oxadiazol-5-yl)Propanoate

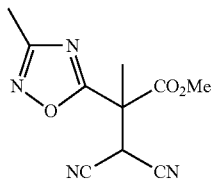 [SMILES: COC(=O)C(C)(c1nc(C)no1)C(C#N)C#N]

Step A: methyl 2-(3-methyl-1,2,4-oxadiazol-5-yl)propanoate

To a screw cap pressure vessel was added acetamide oxime (0.900 g, 12.2 mmol) and dimethyl methyl malonate (3.55 g, 24.3 mmol) and the resulting mixture was heated at 140° C. for 4 hours. The residue was purified by silica gel chromatography using a hexanes/EtOAc gradient to give the indicated product (colorless oil). ¹H NMR (CDCl₃, 500 MHz) δ 4.09 (1H, q, J=7.4 Hz), 3.76 (3H, s), 2.41 (3H, s), 1.79 (3H, d, J=7.4 Hz). m/z=171 (M+H).

Step B: methyl 2-bromo-2-(3-methyl-1,2,4-oxadiazol-5-yl)propanoate

The intermediate from Step A (0.765 g, 4.50 mmol), NBS (0.960 g, 5.39 mmol), and AIBN (0.037 g, 0.225 mmol) in 20 mL of CCl₄ was refluxed for 2 hours. The mixture was cooled to room temperature, filtered, and concentrated. The residue was purified by silica gel chromatography using a hexanes/EtOAc gradient to give the indicated product (pale yellow oil). ¹H NMR (CDCl₃, 500 MHz) δ 3.89 (3H, s), 2.47 (3H, s), 2.39 (3H, s). m/z=249 (M+H).

Step C: methyl 3,3-dicyano-2-methyl-2-(3-methyl-1,2,4-oxadiazol-5-yl)propanoate

To NaH (0.525 g, 13.1 mmol, 60%) in 10 mL of DMF at 0° C. was added dropwise malononitrile (0.867 g, 13.1 mmol) in 10 mL of DMF. After stirring at room temperature for 20 minutes, the intermediate from Step C (2.970 g, 11.92 mmol) in 5 mL of DMF was added. The resulting mixture was stirred for 3 hours. The solution was then quenched with saturated aqueous NH₄Cl solution. The mixture was extracted with EtOAc, dried with MgSO₄, and concentrated. The residue was purified by silica gel chromatography using a hexanes/EtOAc gradient to give the indicated product (colorless oil). ¹H NMR (CDCl₃, 500 MHz) δ 4.83 (1H, s), 3.91 (3H, s), 2.48 (3H, s), 2.10 (3H, s).

INTERMEDIATE 6

Methyl 3,3-Dicyano-2-Methyl-2-(5-Methyl-1,3-Oxazol-2-yl)Propanoate

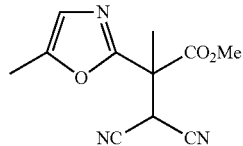 [SMILES: COC(=O)C(C)(c1ncc(C)o1)C(C#N)C#N]

Step A: methyl 2-methyl-3-oxo-3-(prop-2-yn-1-ylamino)propanoate

To a screw cap pressure vessel was added propargyl amine (3.05 g, 55.4 mmol) and dimethyl methyl malonate (8.10 g, 55.4 mmol). The mixture was heated at 90° C. overnight. The residue was purified by silica gel chromatography using a hexanes/EtOAc gradient to give the indicated compound (white solid). ¹H NMR (CDCl₃, 500 MHz) δ 6.82 (1H, s), 4.16-4.05 (2H, m), 3.81 (3H, s), 3.38 (1H, q, 5=7.3 Hz), 2.29-2.26 (1H, m), 1.51 (3H, d, J=7.5 Hz).

Step B: methyl 2-(5-methyl-1,3-oxazol-2-yl)propanoate

To the intermediate from Step A (1.46 g, 8.63 mmol) in 20 mL of CH₃CN at room temperature was added a solution of AuCl₃ (0.262 g, 0.863 mmol) in 5 mL of CH₃CN. The resulting mixture was stirred at 50° C. for 14 hours and concentrated. The residue was purified by silica gel chromatography using a hexanes/EtOAc gradient to give the indicated product (pale yellow oil). ¹H NMR (CDCl₃, 500 MHz) δ 6.78 (1H, s), 4.07 (1H, q, J=7.4 Hz), 3.79 (3H, s), 2.37 (3H, s), 1.67 (3H, d, J=7.5 Hz).

Step C: methyl 2-bromo-2-(5-methyl-1,3-oxazol-2-yl)propanoate

A mixture of the intermediate from Step B (0.322 g, 1.903 mmol), NBS (0.373 g, 2.09 mmol), and AIBN (0.016 g, 0.095 mmol) in 15 mL of CCl₄ was refluxed for 1 hour. The mixture was cooled to room temperature, filtered, and concentrated. The residue was purified by silica gel chromatography using a hexanes/EtOAc gradient to give a 7:1 mixture of the indicated product and methyl 2-bromo-2-[4-(bromomethyl)-1,3-oxazol-2-yl]propanoate (pale yellow oil). The mixture was used in the next step without further purification.

Step D: methyl 3,3-dicyano-2-methyl-2-(5-methyl-1,3-oxazol-2-yl)propanoate

To NaH (60%, 0.085 g, 2.1 mmol) in 5 mL of DMF at 0° C. was added dropwise malononitrile (0.141 g, 2.13 mmol) in 3 mL of DMF. After stirring at room temperature for 15 minutes, the intermediate from Step C in 5 mL of DMF was added. After stirring overnight the reaction mixture was quenched with saturated aqueous NH$_4$Cl. The solution was extracted with EtOAc, dried with MgSO$_4$, and concentrated. The residue was purified by silica gel chromatography using a hexanes/EtOAc gradient to give the indicated compound (a pale yellow oil). $^1$H NMR (CDCl$_3$, 500 MHz) δ 6.82 (1H, s), 4.86 (1H, s), 3.87 (3H, s), 2.38 (3H, s), 2.05 (3H, s).

INTERMEDIATE 7

Methyl 3,3-Dicyano-2-Methyl-2-(2-Methyl-1,3-Oxazol-4-yl)Propanoate

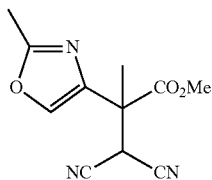 [SMILES: COC(=O)C(C)(c1coc(C)n1)C(C#N)C#N]

Step A: methyl (2-methyl-1,3-oxazol-4-yl)acetate

A mixture of acetamide (1.312 g, 22.21 mmol) and methyl chloroacetoacetate in 20 mL of 1,4-dioxane and 20 mL of toluene was heated at 120° C. for 4 hours. The solution was concentrated and the residue was purified by silica gel chromatography using a hexanes/EtOAc gradient to give the indicated compound (a pale yellow oil). $^1$H NMR (CDCl$_3$, 500 MHz) δ 7.58 (1H, s), 3.78 (3H, s), 3.64 (2H, s), 2.51 (3H, s).

Step B: methyl 2-(2-methyl-1,3-oxazol-4-yl)propanoate

To the intermediate from Step A (1.35 g, 8.71 mmol) and HMPA (6.24 g, 34.8 mmol) in 10 mL of THF at −78° C. was added dropwise a LDA solution (2.0 M, 5.22 mL, 10.5 mmol). The mixture was stirred at −78° C. for 30 min and MeI (1.48 g, 10.45 mmol) was added dropwise. The resulting mixture was slowly warmed to room temperature. The reaction was quenched with saturated aqueous NH$_4$Cl solution and extracted with EtOAc. The organic phase was washed with brine, dried with MgSO$_4$, and concentrated. The residue was purified by silica gel chromatography using a hexanes/EtOAc gradient to give the indicated compound (yellow oil). $^1$H NMR (CDCl$_3$, 500 MHz) δ 7.48 (1H, s), 3.77 (3H, s), 3.76 (1H, q, J=7.5 Hz), 2.49 (3H, s), 1.55 (3H, d, J=7.5 Hz).

Step C: methyl 2-bromo-2-(2-methyl-1,3-oxazol-4-yl)propanoate

A mixture of the intermediate from Step B (2.336 g, 13.81 mmol), NBS (2.458 g, 13.81 mmol), and AIBN (0.113 g, 0.690 mmol) in 50 mL of CCl$_4$ was refluxed for 1 hour. The mixture was cooled to room temperature, filtered, and concentrated. The residue was purified by silica gel chromatography using a hexanes/EtOAc gradient to give the indicated compound (yellow oil). $^1$H NMR (CDCl$_3$, 500 MHz) δ 7.72 (1H, s), 3.89 (3H, s), 2.50 (3H, s), 2.29 (3H, s).

Step D: methyl 3,3-dicyano-2-methyl-2-(2-methyl-1,3-oxazol-4-yl)propanoate

To NaH (60%, 0.293 g, 7.32 mmol) in 10 mL of DMF at room temperature was added dropwise malononitrile (0.483 g, 7.32 mmol) in 5 mL of DMF. After stirring at room temperature for 15 minutes, the intermediate from Step C (1.82 g, 7.32 mmol) in 10 mL of DMF was added. The resulting mixture was stirred for 2 hours and then quenched with water. The mixture was extracted with EtOAc, dried with MgSO$_4$, and concentrated. The residue was purified by silica gel chromatography using a hexanes/EtOAc gradient to give the indicated compound (a pale yellow oil). $^1$H NMR (CDCl$_3$, 500 MHz) δ 7.66 (1H, s), 4.88 (1H, s), 3.87 (3H, s), 2.49 (3H, s), 1.92 (3H, s). m/z=234 (M+H).

Using essentially the same procedures described in Intermediates 1 to 7, the following compounds in Table 1 were made.

TABLE 1

| INTER-MEDIATE | R$^3$ | R' | m/z (M + H) |
|---|---|---|---|
| 8 | 2-F Ph | Me | 247.1 |
| 9 | 3-F Ph | Me | not ionized |
| 10 | 4-F Ph | Me | 247.2 |
| 11 | 3,5-di-F Ph | Me | 265.0 |
| 12 | 4-Cl Ph | Me | not ionized |
| 13 | 4-Br Ph | Me | 307.1 |
| 14 | 4-MeSO$_2$ Ph | Me | 307.2 |
| 15 | 3-pyridyl | Et | 244.2 |
| 16 | 4-pyridyl | Et | 244.2 |
| 17 | pyrazinyl | Me | 231.2 |
| 18 | pyrimidinyl | Et | 245.1 |
| 19 | 5-F-pyridyl | Me | 248.0 |

TABLE 1-continued

R³-C(CO₂R')(H)-C(H)(CN)(CN)

| INTER-MEDIATE | R³ | R' | m/z (M + H) |
|---|---|---|---|
| 20 | 2-(5-chloropyridyl) | Me | 263.9 |
| 21 | CO₂Me | Me | not ionized |
| 22 | CO₂Et | Et | not ionized |
| 23 | 3-(trifluoromethyl)-1,2,4-oxadiazol-5-yl | Me | not ionized |
| 24 | H | Et | not ionized |

| Intermediate | Data |
|---|---|
| 11 | ¹H NMR (500 MHz, CHCl₃-d): δ 7.46-7.40 (m, 1H); 7.17-7.07 (m, 3H); 4.49 (s, 1H); 3.82 (s, 3H); 2.00 (s, 3H). |
| 12 | ¹H NMR (400 MHz, CH₃CN-d₃): δ 7.49-7.45 (m, 2H); 7.40-7.35 (m, 2H); 4.76 (s, 1H); 3.76 (s, 3H); 1.90 (s, 3H). |
| 13 | ¹H NMR (500 MHz, CH₃CN-d₃): δ 7.65 (d, J = 8.4 Hz, 2H); 7.35 (d, J = 8.5 Hz, 2H); 4.80 (s, 1H); 3.79 (s, 3H); 1.93 (s, 3H). |
| 21 | ¹H NMR (500 MHz, CHCl₃-d): δ 4.58 (s, 1H); 3.92 (s, 3H); 1.87 (s, 3H). |
| 22 | ¹H NMR (500 MHz, CHCl₃-d): δ 4.55 (1 H, s), 4.41-4.28 (4 H, m), 1.83 (3 H, s), 1.35 (6 H, t, J = 7.15 Hz). |
| 23 | ¹H NMR (500 MHz, CHCl₃-d): δ 4.84 (1H, s), 3.95 (3H, s), 2.18 (3H, s) |

INTERMEDIATE 25

Ethyl 2-(Dicyanomethyl)-2-Methylbut-3-Ynoate

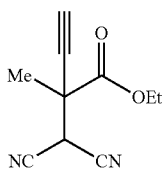

To a flask containing anhydrous LiCl (25.8 mg, 0.609 mmol) in THF (1 mL) was added a solution of ethynylmagnesium bromide (1.3 mL, 0.640 mmol, 0.5M in THF). The reaction was stirred at room temperature for 25 min. The resulting solution was then added dropwise to a THF (22.5 mL) solution of ethyl 3,3-dicyano-2-methylprop-2-enoate (0.609 mL, 0.609 mmol, 1M solution in benzene) cooled to −10 to −20° C. Ethyl 3,3-dicyano-2-methylprop-2-enoate was prepared according to the procedure described by Hagiware et. al. *Synthesis* 1974, 9, 669. The reaction was stirred for 10 min in the cooling bath then quenched with saturated aqueous NH₄Cl, and then diluted with water and EtOAc. The layers were separated and the organic layer was dried (sodium sulfate) and concentrated in vacuo. Purification by silica gel column chromatography using a hexanes/EtOAc gradient afforded the title product as a clear oil. ¹H NMR (500 MHz, CHCl₃-d): δ 4.34 (q, J=7.17 Hz, 2H); 4.31 (s, 1H); 2.66 (s, 1H); 1.80 (s, 3H); 1.35 (t, J=7.14 Hz, 3H).

INTERMEDIATE 26

Ethyl 3,3-Dicyano-2-Methyl-2-(1-Methyl-1H-Pyrazol-4-yl)Propanoate

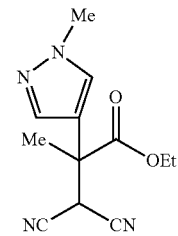

Isopropylmagnesium chloride LiCl complex (1627 μl, 2.115 mmol, 1.3 M in THF) was added to a THF solution of 4-iodo pyrazole (400 mg, 1.923 mmol) cooled to −30° C. The reaction was stirred for hours with the temperature maintained between −20 and −30° C. After two hours, ethyl 3,3-dicyano-2-methylprop-2-enoate (1442 μl, 1.442 mmol, 1 M solution in benzene) was quickly added and the reaction was warmed to room temperature and stirred for five minutes. The reaction was then quenched with saturated aqueous NH₄Cl and extracted between EtOAc. The organic layer was dried (sodium sulfate) and concentrated in vacuo. Purification by silica gel column chromatography using a hexanes/EtOAc gradient afforded the title product as a clear oil, ¹H NMR (500 MHz, CHCl₃-d): δ 7.44 (s, 1H); 7.42 (s, 1H); 4.44 (s, 1H); 4.28-4.19 (m, 2H); 3.86 (s, 3H); 1.84 (s, 3H); 1.25 (t, J=7.12 Hz, 3H).

INTERMEDIATE 27

Diethyl Cyclopropyl (Dicyanomethyl)Propanedioate

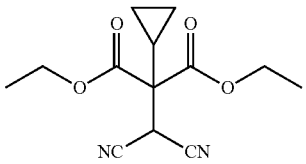 [SMILES: CCOC(=O)C(C(=O)OCC)(C(C#N)C#N)C1CC1]

A THF (45.0 ml) solution of diethyl(dicyanomethylidene)propanedioate (4.50 ml, 4.50 mmol, 1M solution in benzene) was cooled to 0° C. and cyclopropylmagnesium bromide (9.00 ml, 4.50 mmol) and lithium chloride (0.191 g, 4.50 mmol) were added. Diethyl(dicyanomethylidene)propanedioate was prepared analogous to the procedure by Sentman et. al. *J. Org. Chem.* 1982, 47, 4577. The reaction was stirred at 0° C. for 2 hours and then warmed to room temperature while stirring for an additional 2 h. The reaction was diluted with EtOAc and quenched with saturated aqueous NH₄Cl. The layers were separated and the organic layer dried (MgSO₄), filtered, and concentrated in vacuo. Purification by silica gel column chromatography using a hexanes/EtOAc gradient afforded the indicated product as a clear oil. ¹H NMR (500 MHz, CHCl₃-d): δ 4.41 (s, 1H); 4.38-4.26 (m, 4H); 1.52-1.45 (m, 1H); 1.33 (t, J=7.14 Hz, 6H); 0.86-0.79 (m, 2H); 0.71-0.66 (m, 2H).

Using essentially the same procedure described in Intermediate 27, the following compounds in Table IA were made.

TABLE 1A

| INTERMEDIATE | R⁴ | Data |
|---|---|---|
| 28 | Et | ¹H NMR (500 MHz, CHCl₃-d): δ 4.53-4.39 (m, 1 H); 4.36-4.26 (m, 4 H); 2.26 (q, J = 7.52 Hz, 2 H); 1.31 (t, J = 7.15 Hz, 6 H); 1.05 (t, J = 7.51 Hz, 3 H). |
| 29 | iPr | ¹H NMR (500 MHz, CHCl₃-d): δ 4.44 (s, 1 H); 4.36 (q, J = 7.15 Hz, 4 H); 2.79-2.68 (m, 1 H); 1.38-1.31 (m, 6 H); 1.15 (d, 6 H). |
| 30 | cyclopentylmethyl | ¹H NMR (500 MHz, CHCl₃-d): δ 4.40-4.26 (m, 5 H); 2.72-2.61 (m, 1 H); 1.86-1.92 (m, 2 H); 1.77-1.50 (m, 6 H); 1.36-1.30 (m, 6 H). |

EXAMPLE 1

4-Amino-2-[5-Chloro-3-(3,3,3-Trifluoropropyl)-1H-Indazol-1-yl]-5-Methyl-5-Phenyl-5,7-Dihydro-6H-Pyrrolo[2,3-D]Pyrimidin-6-One

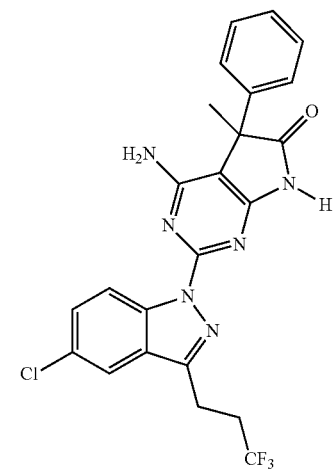 [SMILES: CC1(c2ccccc2)C(=O)Nc2nc(-n3nc(CCC(F)(F)F)c4cc(Cl)ccc43)nc(N)c21]

Step A: 1-(2-bromo-5-chlorophenyl)-4,4,4-trifluorobutan-1-one

A THF solution of sodium bis(trimethylsilyl)amide (1.0M, 194 mL, 194 mmol) was added dropwise to a –78° C. THF (400 mL) solution containing methyl 2-bromo-5-chlorobenzoate (16.10 g, 64.5 mmol) and 4,4,4-trifluorobutyric acid (9.17 g, 64.5 mmol). After stirring for 15 minutes at –78° C. the solution was warmed to 0° C. and stirred for an additional 2 hours. The reaction was quenched with an excess of aqueous 1N HCl (ca 400 mL) and stirred overnight at room temperature. The solution was concentrated to remove the majority of the THF. The solution was then diluted with EtOAc and washed with 1N NaHCO₃ (twice) and brine. The organic phase was then dried over anhydrous sodium sulfate, filtered and concentrated. The residue was purified by silica gel chromatography using a hexanes/EtOAc gradient to give the indicated compound (solid). ¹H NMR (500 MHz, CDCl₃): δ 7.58 (d, J=8.4 Hz, 1H); 7.41 (d, J=2.5 Hz, 1H); 7.33 (dd, J=8.5, 2.5 Hz, 1H); 3.22 (t, J=7.8 Hz, 2H); 2.68-2.56 (m, 2H).

Step B: (2E)-2-[1-(2-bromo-5-chlorophenyl)-4,4,4-trifluorobutylidene]hydrazinecarboximidamide To a screw cap pressure vessel was added the intermediate from Step A (3.22 g, 10.2 mmol), aminoguanidine hydrochloride (1.69 g, 15.3 mmol), methanol (25 mL) and boron trifluoride diethyl etherate (2.6 mL, 20.4 mmol). The reaction solution was heated at 100° C. for 70 minutes. The solution was concentrated and the residue partitioned between EtOAc and aqueous 1N NaOH. The organic phase was washed twice with aqueous 1N NaOH and brine (1×). The organic phase was dried over anhydrous magnesium sulfate, filtered and concentrated to give the indicated compound as a mixture of E, Z hydrazone isomers. ¹H NMR (400 MHz, CD₃CN): δ 7.54 (d, J=8.4 Hz, 1H); 7.24-7.17 (m, 1H); 7.10 (d, J=2.6 Hz, 1H); 2.68-2.51 (m, 4H). m/z 371 (M+H).

Step C: 4-amino-2-{(2E)-2-[1-(2-bromo-5-chlorophenyl)-4,4,4-trifluorobutylidene]hydrazinyl}-5-methyl-5-phenyl-5,7-dihydro-6H-pyrrolo[2,3-d]pyrimidin-6-one A methanol (4 mL) solution of the intermediate from Step B (50 mg, 0.135 mmol), racemic Intermediate 1 (61.4 mmol, 0.269 mmol), and sodium bicarbonate (11.3 mg, 0.135 mmol) was heated at 135° C. for 40 minutes in a microwave. The solution was concentrated and the residue partitioned between EtOAc and water. The organic phase was washed with brine, dried over anhydrous magnesium sulfate, filtered and concentrated to give the indicated compound which was used in the next step without further purification. m/z=567.2 (M+H).

Step D: 4-amino-2-[5-chloro-3-(3,3,3-trifluoropropyl)-1H-indazol-1-yl]-5-methyl-5-phenyl-5,7-dihydro-6H-pyrrolo[2,3-d]pyrimidin-6-one A DMF (3 mL) solution of the crude intermediate from Step C (77 mg, 0.135 mmol), copper (I) iodide (25.7 mg, 0.135 mmol), and N,N'-dimethylethylenediamine (14.3 mg, 0.162 mmol) was stirred at ambient temperature for 1 hour. The reaction mixture was diluted with EtOAc and washed with 10% aqueous $NH_4OH$ solution (2×), water (3×), and brine. The organic phase was JO dried over anhydrous magnesium sulfate, filtered and concentrated. The residue was purified by reverse phase HPLC using a water/acetonitrile (with 0.1% TFA) gradient. The isolated material was converted to the free base by suspending in EtOAc, washing with aqueous saturated $NaHCO_3$ solution (2×) and brine. The solution was dried over anhydrous $MgSO_4$, filtered, concentrated. The residue was purified by silica gel chromatography using a hexanes/EtOAc gradient to give the indicated compound as a racemic mixture. The enantiomers were separated on a ChiralPak IB column using 7% EtOH/heptane as eluent to give the indicated compound. Data is given for the faster eluting enantiomer. $^1$H NMR (500 MHz, DMSO-$d_6$): δ (ppm) 11.23 (1H, s), 8.86 (1H, d, J=9.1 Hz), 8.07 (1H, d, J=2.1 Hz), 7.52 (1H, dd, J=9.0, 2.1 Hz), 7.37-7.25 (5H, m), 6.75 (2H, s), 3.30-3.20 (2H, m), 2.88-2.76 (2H, m), 1.79 (3H, s). m/z=487.1 (M+H).

EXAMPLE 2

4-Amino-2-[5-Chloro-3-(3,3,4,4,4-Pentafluorobutyl)-1H-Indazol-1-yl]-5-Methyl-5-Phenyl-5,7-Dihydro-6H-Pyrrolo[2,3-D]Pyrimidin-6-One

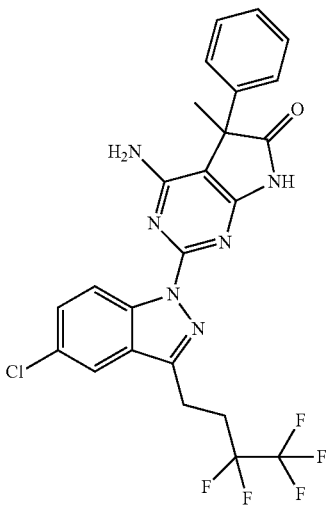 [SMILES: CC1(c2ccccc2)C(=O)Nc2nc(-n3nc(CCC(F)(F)C(F)(F)F)c4cc(Cl)ccc43)nc(N)c21]

Step A: 4,4,5,5,5-pentafluoropentanoic acid

To an aqueous solution of pentafluoropentanol (1M, 1.0 g, 5.61 mmol) was added tetraethylammonium hydrogen sulfate (10.21 mg, 0.045 mmol). The solution was heated to 70° C. and an aqueous solution of sodium permanganate monohydrate (1.5M, 1.257 g, 7.86 mmol) was added over 20 minutes. The reaction was stirred at 70° C. for an additional 4 hours. The reaction mixture was filtered through Celite™ (diatomaceous earth). The filter cake was washed with hot water (10 mL). The aqueous solution was acidified to a pH=1 with concentrated sulfuric acid (200 uL) and extracted with methyl tert-butyl ether (3×10 mL). The organic fractions were combined and dried over magnesium sulfate, filtered and concentrated. $^1$H NMR (500 MHz, $CH_3$ CN-$d_3$): δ 2.59 (t, J=7.5 Hz, 2H); 2.49-2.39 (m, 3H).

Step B: 1-(2-bromo-5-chlorophenyl)-4,4,5,5,5-pentafluoropentan-1-one

A THF solution of sodium bis(trimethylsilyl)amide (1.0M, 10 mL, 10 mmol) was added dropwise to a −78° C. THF (20 mL) solution containing methyl 2-bromo-5-chlorobenzoate (0.836 g, 3.35 mmol) and 3,3,4,4-pentafluoropentanoic acid (0.644 g, 3.35 mmol, intermediate from Step A). After stirring for 15 minutes at −78° C. the solution was warmed to 0° C. and stirred for an additional 2 hours. The reaction was quenched with an excess of aqueous 1N HCl(ca 20 mL) and stirred overnight at room temperature. The solution was concentrated to remove the majority of the THF. The solution was then diluted with EtOAc and washed with 1N $NaHCO_3$ (twice) and brine. The organic phase was then dried over anhydrous sodium sulfate, filtered and concentrated. The residue was purified by silica gel chromatography using a hexanes/EtOAc gradient to give the indicated compound (liquid). $^1$H NMR (500 MHz, $CH_3$ CN-$d_3$): δ 7.64 (d, J=8.6 Hz, 1H); 7.56 (d, J=2.6 Hz, 1H); 7.40 (dd, J=8.5, 2.7 Hz, 1H); 3.23 (t, J=7.3 Hz, 2H); 2.61-2.50 (m, 2H). m/z=365.1 (M+H).

Step C: (2E)-2-[1-(2-bromo-5-chlorophenyl)-4,4,5,5,5-pentafluoropentylidene]hydrazinecarboximidamide To a screw cap pressure vessel was added the intermediate from Step B (0.450 g, 1.2 mmol), aminoguanidine hydrochloride (0.456 g, 6.2 mmol), methanol (20 mL) and boron trifluoride diethyl etherate (0.94 mL, 7.4 mmol). The reaction solution was heated at 100° C. for 3 hours. The solution was concentrated and the residue partitioned between EtOAc and aqueous 1N NaOH. The organic phase was washed twice with aqueous 1N NaOH and brine (1×). The organic phase was dried over anhydrous magnesium sulfate, filtered and concentrated to give the indicated compound as a mixture of E,Z hyrazone isomers. $^1$H NMR (500 MHz, $CH_3OH$-$d_4$): δ 7.60 (d, J=8.6 Hz, 1H); 7.26-7.23 (m, 1H); 7.18 (d, J=2.5 Hz, 1H); 2.74 (s, 2H); 2.56 (s, 2H). m/z=421.2 (M+H).

Step D: 4-amino-2-{(2E)-2-[1-(2-bromo-5-chlorophenyl)-4,4,5,5,5-pentafluoropentylidene]hydrazinyl}-5-methyl-5-phenyl-5,7-dihydro-6H-pyrrolo[2,3-d]pyrimidin-6-one A methanol (2 mL) solution of the intermediate from Step C (50 mg, 0.12 mmol), Intermediate 1 (54 mg, 0.24 mmol, slower eluting enantiomer) and $NaHCO_3$ (10 mg, 0.12 mmol) were heated at 135° C. for 40 minutes in a microwave. The methanol was concentrated and the residue taken up in EtOAc. The solution was washed with water (2×), brine and dried over anhydrous sodium sulfate to give the indicated compound which was used without purification in the next step. m/z=617.2 (M+H).

Step E: 4-amino-2-[5-chloro-3-(3,3,4,4,4-pentafluorobutyl)-1H-indazol-1-yl]-5-methyl-5-phenyl-5,7-dihydro-6H-pyrrolo[2,3-d]pyrimidin-6-one A DMF (2 mL) solution of the crude intermediate from Step D (73 mg, 0.12 mmol), copper (I) iodide (23 mg, 0.12 mmol) and N,N'-dimethylaminocyclohexane (17 mg, 0.12 mmol) was stirred at room temperature for 30 minutes. The DMF reaction mixture was filtered and purified by reverse phase HPLC using a water/acetonitrile (with 0.1% TFA) gradient to give the indicated compound. $^1$H NMR (500 MHz, CH$_3$CN-d$_3$): δ 9.17 (s, 1H); 8.83-8.78 (m, 1H); 7.84 (d, T=3.7 Hz, 1H); 7.54-7.49 (m, 1H); 7.38-7.28 (m, 5H); 5.38 (s, 2H); 3.31-3.26 (m, 2H); 2.73-2.66 (m, 2H); 1.82 (s, 3H). m/z=537.2 (M+H).

EXAMPLE 3

4-Amino-2-[5-Chloro-3-(2,3,6-Trifluorobenzyl)-1H-Indazol-1-yl]-5-Methyl-5-Phenyl-5,7-Dihydro-6H-Pyrrolo[2,3-D]Pyrimidin-6-One

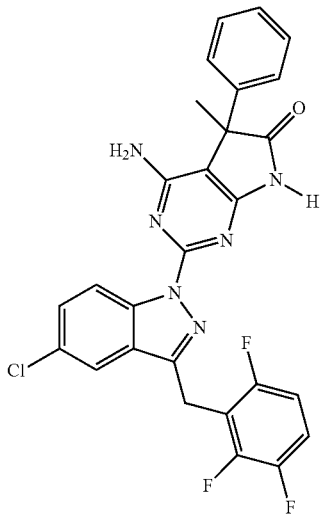 [SMILES: CC1(c2ccccc2)C(=O)Nc2nc(-n3nc(Cc4c(F)ccc(F)c4F)c4cc(Cl)ccc43)nc(N)c21]

Step A: 1-(2-bromo-5-chlorophenyl-2-(2,3,6-trifluorophenyl)ethanone

To a solution of 2,3,6 trifluorophenyl acetic acid (5 g, 26.3 mmol) and methyl 2-bromo-5-chloro benzoate in anhydrous THF (53 mL) cooled to −78° C. was slowly added NaHMDS (110 mL, 65.7 mmol, 0.6 M). The reaction was then warmed to 0° C. After stirring for 30 minutes the reaction was quenched by adding aqueous 1N HCl (100 mL). The resulting mixture was stirred vigorously at room temperature for 1 hour. The reaction mixture was concentrated to remove the excess organic solvents. The solution was extracted with EtOAc. The organic layer was washed with saturated sodium bicarbonate solution (2×), water and brine. The organic layer was then dried over sodium sulfate, filtered and concentrated to give the indicated product. $^1$H NMR (400 MHz, CD$_3$CN): δ 7.66-7.61 (m, 2H); 7.40 (dd, J=8.6, 2.6 Hz, 1H); 7.25 (m, 1H); 6.98 (m, 1H); 4.34 (s, 2H).

Step B: (2Z)-2-[1-(2-bromo-5-chlorophenyl)-2-(2,3,6-trifluorophenyl)ethylidene]hydrazinecarboximidamide To a screw cap pressure vessel was added the intermediate from Step A (800 mg, 2.20 mmol), aminoguanidine hydrochloride (280 mg, 2.53 mmol), methanol (20 mL) and boron trifluoride diethyl etherate (0.63 mL, 4.95 mmol). After stirring at 100° C. for 1 hour, boron trifluoride diethyl etherate (1 mL) and aminoguanidine hydrochloride (200 mg) were added and the reaction solution heated at 100° C. for 3 hours. The solution was concentrated and the residue partitioned between EtOAc and aqueous 1N NaOH. The organic phase was washed with aqueous 1N NaOH (2×), brine and dried over anhydrous sodium sulfate. The solution was then filtered and concentrated to give the indicated product. m/z=419 (M+H).

Step C: 4-amino-2-{(2Z)-2-[1-(2-bromo-5-chlorophenyl)-2-(2,3,6-trifluorophenyl)ethylidene]hydrazinyl}-5-methyl-5-phenyl-5,7-dihydro-6H-pyrrolo[2,3-d]pyrimidin-6-one A methanol (5 mL) solution of the intermediate from Step B (100 mg, 0.24 mmol), Intermediate 1 (109 mg, 0.48 mmol, slower eluting enantiomer), and sodium bicarbonate (20 mg, 0.24 mmol) was heated at 135° C. for 40 minutes in a microwave. The solution was concentrated and the residue partitioned between EtOAc and water. The organic phase was washed with brine, dried over anhydrous magnesium sulfate, filtered, and concentrated to give the indicated compound which was used in the next step without further purification. m/z=615.1 (M+H).

Step D: 4-amino-2-[5-chloro-3-(2,3,6-trifluorobenzyl)-1H-indazol-1-yl]-5-methyl-5-phenyl-5,7-dihydro-6H-pyrrolo[2,3-d]pyrimidin-6-one A DMF (5 mL) solution of the crude intermediate from Step C (ca 0.24 mmol), copper (I) iodide (45.3 mg, 0.24 mmol) and N,N'-dimethylethylenediamine (25.2 mg, 0.29 mmol) was stirred at ambient temperature for 1 hour. The reaction mixture was diluted with EtOAc and washed with 10% aqueous NH$_4$OH solution (2×), water (2×), 0.5 N HCl (1×), and brine. The organic phase was dried over anhydrous magnesium sulfate, filtered and concentrated. The residue was purified by preparative thin layer chromatography using 5% MeOH/CHCl$_3$ as eluent. The isolated material was purified again by silica gel column chromatography using a hexanes/EtOAc gradient to give the indicated compound. $^1$H NMR (500 MHz, DMSO-d$_6$): δ (ppm) 11.19 (1H, s), 8.86 (1H, d, J=9.0 Hz), 7.93 (1H, d, J=2.0 Hz), 7.55-7.43 (2H, m), 7.34-7.24 (5H, m), 7.20 (1H, t, J=9.7 Hz), 6.74 (2H, s), 4.46 (2H, s), 1.77 (3H, s). m/z=535.4 (M+H).

EXAMPLE 4

4-Amino-2-[5-Chloro-3-(3,3,4,4,4-Pentafluorobutyl)-1H-Indazol-1-yl]-5-Methyl-5-(3-Methyl-1,2,4-Oxadiazol-5-yl)-5,7-Dihydro-6H-Pyrrolo[2,3-D]Pyrimidin-6-One

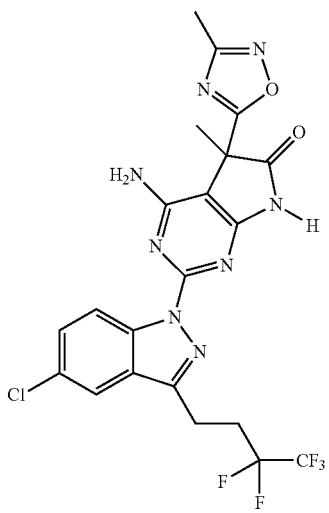 [SMILES: Cc1noc(C2(C)C(=O)Nc3nc(-n4nc(CCC(F)(F)C(F)(F)F)c5cc(Cl)ccc54)nc(N)c32)n1]

The indicated compound was prepared from the intermediate from Step C in Example 2 and Intermediate 5 using the procedure described in Example 2. The racemic compound was resolved by chiral SFC chromatography using an OJ column. Data is given for the more active isomer (slower eluting) compound. $^1$H NMR (DMSO-$d_6$, 500 MHz) δ 11.68 (1H, s), 8.83 (1H, d, J=9.0 Hz), 8.11 (1H, d, J=2.0 Hz), 7.55 (1H, dd, J=9.0, 2.0 Hz), 7.15 (2H, s), 3.32-3.29 (2H, m), 2.84-2.72 (2H, m), 2.33 (3H, s), 1.88 (3H, s). m/z=543 (M+H).

Using essentially the same procedures described in Examples 1 to 4, the following compounds in Table 2 and Table 3 were made.

TABLE 2

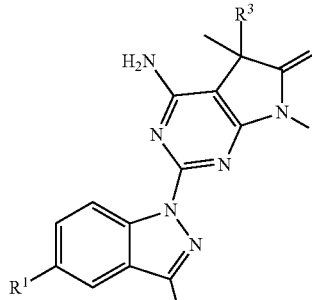

| EXAMPLE | R$^1$ | R$^2$ | R$^3$ | m/z (M + H) |
|---|---|---|---|---|
| 5 | H | 2-F Ph | Ph | 465.4 |
| 6 | Cl | 2-F Ph | Ph | 499.3 |
| 7 | Cl | 2-F Ph | 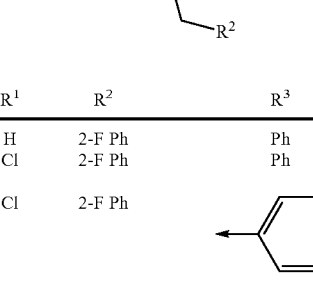 | 500.4 |
| 8 | Cl | 2-F Ph | 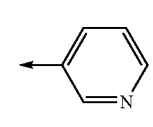 | 500.4 |
| 9 | Cl | 2,3-diF Ph | Ph | 517.3 |
| 10 | Cl | 2,3-diF Ph | 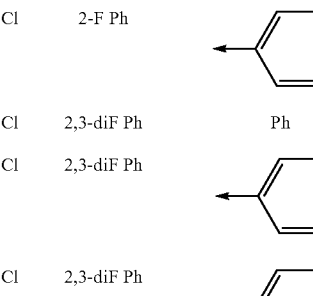 | 518.4 |
| 11 | Cl | 2,3-diF Ph | 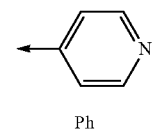 | 518.4 |
| 12 | H | 2,3,6-triF Ph | Ph | 501.3 |
| 13 | Cl | CH$_2$Ph | Ph | 495.4 |
| 14 | H | CH$_2$CF$_3$ | Ph | 453.4 |
| 15 | F | CH$_2$CF$_3$ | Ph | 471.3 |
| 16 | Cl | CH$_2$CF$_3$ | 4-F Ph | 505.3 |
| 17 | Cl | CH$_2$CF$_3$ | 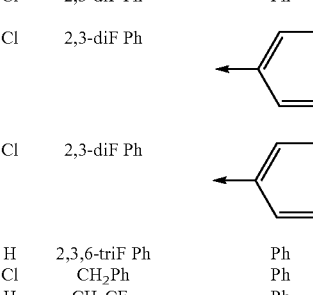 | 488.3 |
| 18 | Cl | CH$_2$CF$_3$ | 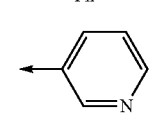 | 488.3 |
| 19 | Cl | CH$_2$CF$_3$ | 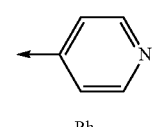 | 488.3 |

TABLE 2-continued

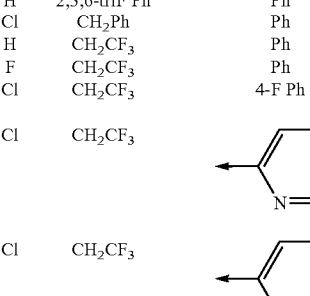

| EXAMPLE | R$^1$ | R$^2$ | R$^3$ | m/z (M + H) |
|---|---|---|---|---|
| 20 | Cl | CH$_2$CF$_3$ | 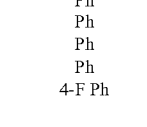 | 489.3 |
| 21 | Cl | CH(CH$_3$)CF$_3$ | Ph | 501.2 |
| 22 | H | CH$_2$CF$_2$CF$_3$ | Ph | 503.2 |
| 23 | H | CH$_2$CF$_2$CF$_3$ | 2-F Ph | 521.2 |
| 24 | H | CH$_2$CF$_2$CF$_3$ | 3-F Ph | 521.2 |
| 25 | H | CH$_2$CF$_2$CF$_3$ | 4-F Ph | 521.2 |
| 26 | F | CH$_2$CF$_2$CF$_3$ | Ph | 521.3 |
| 27 | F | CH$_2$CF$_2$CF$_3$ | 2-F Ph | 539.2 |
| 28 | Cl | CH$_2$CF$_2$CF$_3$ | 2-F Ph | 555.2 |
| 29 | Cl | CH$_2$CF$_2$CF$_3$ | 3-F Ph | 555.2 |
| 30 | Cl | CH$_2$CF$_2$CF$_3$ | 4-F Ph | 555.3 |
| 31 | Cl | CH$_2$CF$_2$CF$_3$ | 3,5-diF Ph | 573.2 |
| 32 | H | CH$_2$CF$_2$CF$_3$ | 4-Cl Ph | 537.3 |
| 33 | Cl | CH$_2$CF$_2$CF$_3$ | 4-Cl Ph | 571.1 |
| 34 | Cl | CH$_2$CF$_2$CF$_3$ | 4-Br Ph | 615.1 |
| 35 | Cl | CH$_2$CF$_2$CF$_3$ | 4-CN Ph | 562.2 |
| 36 | H | CH$_2$CF$_2$CF$_3$ | 4-OH Ph | 519.3 |
| 37 | Cl | CH$_2$CF$_2$CF$_3$ | 4-MeSO$_2$ Ph | 615.2 |
| 38 | H | CH$_2$CF$_2$CF$_3$ | 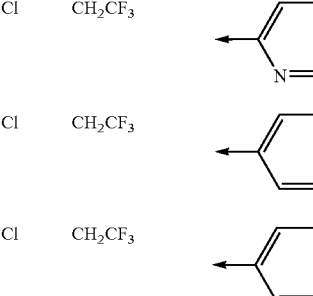 | 540.3 |
| 39 | F | CH$_2$CF$_2$CF$_3$ | 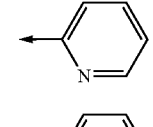 | 522.3 |
| 40 | Cl | CH$_2$CF$_2$CF$_3$ | 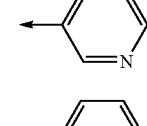 | 538.3 |
| 41 | Cl | CH$_2$CF$_2$CF$_3$ | 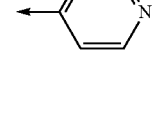 | 556.2 |
| 42 | H | CH$_2$CF$_2$CF$_3$ | 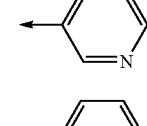 | 538.2 |
| 43 | Cl | CH$_2$CF$_2$CF$_3$ | 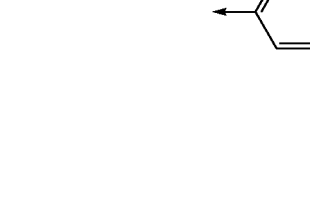 | 572.1 |
| 44 | Cl | CH$_2$CF$_2$CF$_3$ | 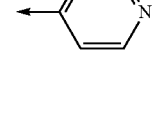 | 539.2 |

TABLE 2-continued

| EXAMPLE | R¹ | R² | R³ | m/z (M + H) |
|---|---|---|---|---|
| 45 | Cl | CH₂CF₂CF₃ | 5-methyl-1,2,4-oxadiazol-3-yl | 543 |
| 46 | F | CH₂CF₂CF₃ | 3-methyl-1,2,4-oxadiazol-5-yl | 527 |
| 47 | Cl | CH₂CH₂CF₂CF₃ | Ph | 550.9 |
| 48 | Cl | CH₂CF₂CF₂CF₃ | Ph | 587.3 |
| 49 | Cl | CH₂CF₃ | CO₂Me | 469.2 |
| 50 | Cl | CH₂CF₃ | CO₂Et | 483.2 |
| 51 | F | CH₂CF₂CF₃ | CO₂Me | 503.2 |
| 52 | Cl | CH₂CF₂CF₃ | CO₂Me | 519.1 |

TABLE 3

| EXAMPLE | A | R² | m/z (M + H) |
|---|---|---|---|
| 53 | 5-chloro-thieno[2,3-c]pyrazol-1-yl | CH₂CF₃ | 493.2 |
| 54 | thieno[3,4-c]pyrazol-1-yl | 2,3,6-tri-F Ph | 507.2 |
| 55 | pyrazolo[3,4-b]pyridin-1-yl | 2,3-diF Ph | 484.4 |
| 56 | pyrazolo[4,3-b]pyridin-1-yl | CH₂CF₃ | 454.4 |
| 57 | pyrazolo[4,3-b]pyridin-1-yl | CH₂CF₂CF₃ | 504.3 |

EXAMPLE 58

4-Amino-2-[6-Chloro-1-(3,3,4,4,4-Pentafluorobutyl)-1H-Indazol-3-yl]-5-Methyl-5-Phenyl-5,7-Dihydro-6H-Pyrrolo[2,3-D]Pyrimidin-6-One

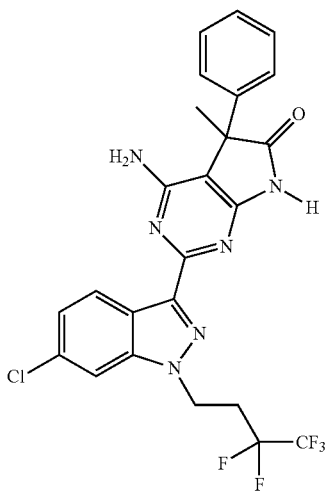 [SMILES: CC1(c2ccccc2)C(=O)Nc2nc(-c3nn(CCC(F)(F)C(F)(F)F)c4cc(Cl)ccc34)nc(N)c21]

Step A: 6-chloro-1H-indazole

Acetic anhydride (10.0 mL, 106 mmol) was added dropwise to a benzene solution (110 mL) containing 5-chloro-2-methylaniline (5.0 g, 35.3 mmol) and potassium acetate (3.8 g, 38.7 mmol) at room temperature. After 10 minutes the reaction mixture, which had formed a thick white suspension, was heated to 80° C. Tert-butyl nitrite (6.99 mL, 90%, 53.0 mmol) was added over 20 minutes. The reaction mixture was kept at 80° C. overnight. The reaction was then cooled to room temperature and concentrated. The residue was dissolved in MeOH and stirred for 10 minutes. The solution was concentrated and to the residue was added MeOH (175 mL), THF (30 mL), water (60 mL) and lithium hydroxide monohydrate (8 g, 195 mmol). The solution was then stirred overnight at room temperature. The solution was then concentrated and the residue partitioned between EtOAc and 0.5 M NaOH aq. The aqueous phase was extracted twice with EtOAc. The combined organics were washed with brine, dried over MgSO$_4$, filtered and concentrated to give the indicated product. The material was used in Step B without further purification. $^1$H NMR (400 MHz, CH$_3$CN-d$_3$): δ 11.20 (broad s, 1H); 8.01 (s, 1H); 7.75-7.70 (m, 1H); 7.60 (s, 1H); 7.13 (dd, J=8.6, 1.7 Hz, 1H). m/z=153.0 (M+H).

Step A alternative: 6-chloro-1H-indazole

A DMA (250 mL) solution containing 4-chloro-2-fluorobenzaldehyde (50 g, 315 mmol) and hydrazine monohydrate (230 mL, 4730 mmol) was stirred for 30 minutes at room temperature. The solution was then stirred at 100° C. for 17 hours. The reaction mixture, which was a thick white slurry, was cooled to room temperature. The solid was collected by filtration, washed with water and dried under vacuum to give the indicated product.

Step B: 6-chloro-3-iodo-1H-indazole

An acetonitrile solution (250 mL) containing the intermediate from Step A (6.14 g, 40.2 mmol) and NIS (9.33 g, 41.4 mmol) was heated at 60° C. for 3 hours. The reaction solution was cooled to room temperature and concentrated to approximately 70 mL volume. The reaction was then diluted with water (ca 400 mL). The suspension was stirred for 10 minutes and then filtered. The solid was air dried on the filter to give the indicated product. The material was used in Step C without further purification. $^1$H NMR (400 MHz, CH3CN-d$_3$): δ 1.52 (broad s, 1H); 7.62 (d, J=1.7 Hz, 1H); 7.44 (d, J=8.6 Hz, 1H); 7.21 (dd, J=8.6, 1.7 Hz, 1H). m/z=279.0 (M+H).

Step C: 6-chloro-1H-indazole-3-carbonitrile

A DMA (48 mL) solution containing the intermediate from Step B (4.0 g, 14.36 mmol), zinc powder (113 mg, 1.72 mmol), zinc cyanide (1.01 g, 8.86 mmol), 1,1'-bis(diphenylphosphino)ferrocene (318 mg, 0.58 mmol) and tris(dibenzylideneacetone)dipalladium (263 mg, 0.29 mmol) was heated at 120° C. for 45 minutes. The solution was cooled to room temperature and partitioned between EtOAc and 0.5M HCl aq. The organic phase was washed twice with 0.5M HCl aq and brine. The organic phase was then dried over MgSO$_4$, filtered and concentrated. The crude material was purified by silica gel chromatography using a hexanes/EtOAc gradient to give the indicated product. $^1$H NMR (400 MHz, CH$_3$ CN-d$_3$): δ 7.83 (d, J=8.7 Hz, 1H); 7.77 (d, J=1.7 Hz, 1H); 7.36 (dd, J=8.7, 1.7 Hz, 1H). m/z=178.1 (M+H).

Step D: 6-chloro-1-(3,3,4,4,4-pentafluorobutyl)-1H-indazole-3-carbonitrile

An acetonitrile solution (450 mL) containing the intermediate from Step C (30 g, 169 mmol), potassium carbonate (116.6 g, 844 mmol) and 1,1,1,2,2-pentafluoro-4-iodobutane (97.2 g, 354.7 mmol) was refluxed for 36 hours. The solution was cooled to room temperature and partitioned between EtOAc and water. The organic phase was concentrated and the crude material was filtered through a plug of silica gel using 10% EtOAc/heptanes as the eluent. The isolated material was subsequently recrystallized from heptanes to give the indicated product. $^1$H NMR (400 MHz, CH$_3$ CN-d$_3$): δ 7.87-7.80 (m, 2H); 7.40 (dd, J=8.7, 1.7 Hz, 1H); 4.77 (t, J=7.0 Hz, 2H); 2.95-2.78 (m, 2H). m/z=324.1 (M+H).

Step E: 6-chloro-1-(3,3,4,4,4-pentafluorobutyl)-1H-indazole-3-carboximidamide Trimethylaluminum (2.0M in toluene, 23.17 mL, 46.3 mmol) was added dropwise to a suspension of ammonium chloride (2.49 g, 46.5 mmol) in 69 mL toluene cooled to 0° C. The solution was then stirred at room temperature for 3 hours. This solution was then added to the intermediate from Step D (3.0 g, 9.27 mmol) and then heated at 110° C. for 6 hours. The solution was then cooled to room temperature and carefully poured to silica gel (ca 150 mL) and methanol (ca 250 mL). After stirring for 1.5 hours the suspension was filtered and the filtrate concentrated to give the indicated product which was used in the next step without further purification. $^1$H NMR (400 MHz, CH$_3$ CN-d$_3$): selected peaks δ 8.26 (d, J=8.7 Hz, 1H); 7.70 (d, J=1.7 Hz, 1H); 7.24 (dd, J=8.7, 1.8 Hz, 1H); 4.67 (t, J=7.1 Hz, 2H); 3.01-2.78 (m, 2H). m/z=341.1 (M+H).

81

Step F: 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one To a screw cap pressure tube was added the intermediate from Step E (230 mg, 0.675 mmol), Intermediate 1 (208 mg, 0.911 mmol, slower eluting enantiomer), sodium bicarbonate (68.1 mg, 0.810 mmol) and t-butanol (12 mL). The reaction solution was heated at 140° C. for 75 minutes. The solution was cooled to room temperature and concentrated. The residue was partitioned between EtOAc and 1N NaOH aq. The organic phase was washed with brine, dried over MgSO$_4$, filtered and concentrated. The residue was purified by silica gel chromatography using a hexanes/EtOAc gradient to give the indicated compound. $^1$H NMR (400 MHz, CH$_3$CN-d$_3$): δ 8.87 (s, 1H); 8.68 (d, J=8.7 Hz, 1H); 7.71 (d, J=1.7 Hz, 1H); 7.39-7.29 (m, 5H); 7.27 (dd, J=8.7, 1.7 Hz, 1H); 5.22 (s, 2H); 4.77 (t, J=7.1 Hz, 2H); 2.91-2.77 (m, 2H); 1.82 (s, 3H). m/z=537.2 (M+H).

EXAMPLE 59

4-Amino-2-[6-Chloro-1-(3,3,4,4,4-Pentafluorobutyl)-1H-Indazol-3-yl]-5-Methyl-5-(3-Methyl-1,2,4-Oxadiazol-5-yl)-5,7-Dihydro-6H-Pyrrolo[2,3-D]Pyrimidin-6-One

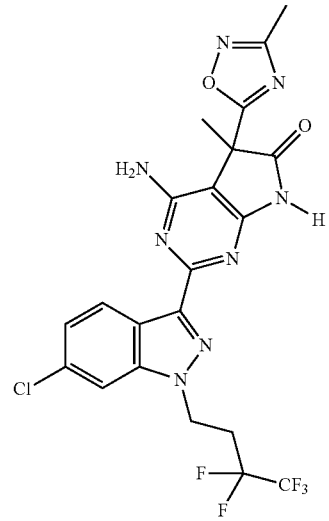 [SMILES: Cc1noc(C2(C)C(=O)Nc3nc(-c4nn(CCC(F)(F)C(F)(F)F)c5cc(Cl)ccc45)nc(N)c32)n1]

The indicated compound was prepared from the intermediate from Step E in Example 58 and Intermediate 5 using the procedure described in Example 58. The racemic material was resolved by chiral SFC chromatography to give the indicated compound. Data is given for the more active isomer (slower eluting using an OJ column), $^1$H NMR (DMSO-d$_6$, 500 MHz) δ 11.56 (1H, s) 8.68 (1H, d, J=8.7 Hz), 8.06 (1H, s), 7.30 (1H, dd, J=8.7, 1.7 Hz), 6.95 (2H, s), 4.85 (2H, t, J=6.9 Hz), 2.97-2.88 (2H, m), 2.34 (3H, s), 1.90 (3H, s). m/z=543 (M+H).

Using essentially the same procedures described in Examples 58 and 59, the following compounds in Table 4 were made, Data is given for the more active enantiomer except for Example 68 which is racemic.

TABLE 4

| EXAMPLE | R$^1$ | R$^2$ | R$^3$ | m/z (M + H) |
|---|---|---|---|---|
| 60 | H | CF$_3$ | Ph | 439.2 |
| 61 | H | CH$_2$OCH$_3$ | Ph | 415.2 |
| 62 | H | OCH$_2$CH$_3$ | Ph | 415.2 |
| 63 | H | CF$_2$CF$_3$ | Ph | 489.2 |
| 64 | H | (1,1-difluorocyclopropyl) | Ph | 447.2 |
| 65 | H | CH$_2$CF$_3$ | Ph | 453.3 |
| 66 | Cl | CH$_2$CF$_3$ | Ph | 487.3 |
| 67 | Cl | CH$_2$CF$_3$ | 3-methyl-1,2,4-oxadiazol-5-yl | 493 |
| 68 | Cl | CH$_2$CF$_3$ | CO$_2$Me | 469.2 |
| 69 | H | CH$_2$CF$_2$CF$_3$ | Ph | 503.3 |
| 70 | F | CH$_2$CF$_2$CF$_3$ | Ph | 521.2 |
| 71 | Br | CH$_2$CF$_2$CF$_3$ | Ph | 581.3 |
| 72 | H | CH$_2$CF$_2$CF$_3$ | 2-F Ph | 520.7 |
| 73 | F | CH$_2$CF$_2$CF$_3$ | 2-F Ph | 538.7 |
| 74 | Cl | CH$_2$CF$_2$CF$_3$ | 2-F Ph | 555.2 |
| 75 | H | CH$_2$CF$_2$CF$_3$ | 4-Cl Ph | 537.3 |
| 76 | Cl | CH$_2$CF$_2$CF$_3$ | 4-Cl Ph | 571.2 |
| 77 | Cl | CH$_2$CF$_2$CF$_3$ | 4-Br Ph | 615.0 |
| 78 | Cl | CH$_2$CF$_2$CF$_3$ | 4-MeSO$_2$ Ph | 615.2 |
| 79 | H | CH$_2$CF$_2$CF$_3$ | 2-pyridyl | 504.14 |
| 80 | Cl | CH$_2$CF$_2$CF$_3$ | 2-pyridyl | 538.3 |
| 81 | Cl | CH$_2$CF$_2$CF$_3$ | 2-pyrimidinyl | 539.2 |
| 82 | Cl | CH$_2$CF$_2$CF$_3$ | 5-methyloxazol-2-yl | 542 |
| 83 | F | CH$_2$CF$_2$CF$_3$ | 3-methyl-1,2,4-oxadiazol-5-yl | 527 |

TABLE 4-continued

| EXAMPLE | R¹ | R² | R³ | m/z (M + H) |
|---------|----|----|----|-------------|
| 84 | | | | 504.2 |

EXAMPLE 85

4-Amino-2-[5-Chloro-3-(3,3,4,4,4-Pentafluorobutyl)-1H-Indazol-1-yl]-5-Methyl-5-(5-Methyl-1,3,4-Thiadiazol-2-yl)-5,7-Dihydro-6H-Pyrrolo[2,3-D]Pyrimidin-6-One

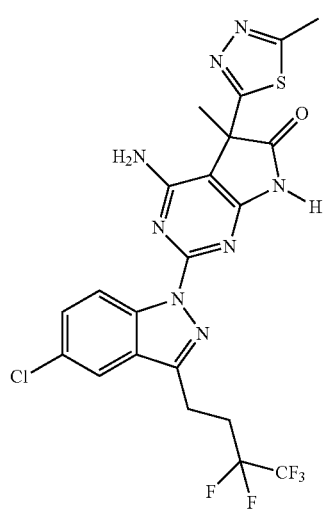 [SMILES: Cc1nnc(C2(C)C(=O)Nc3nc(-n4nc(CCC(F)(F)C(F)(F)F)c5cc(Cl)ccc54)nc(N)c32)s1]

Step A: 4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carbohydrazide To a methanol (0.5 mL) solution of Example 52 (255 mg, 0.491 mmol) in a screw-cap vial was added anhydrous hydrazine (5 mL, 159 mmol) and water (0.1 mL, 0.55 mmol). The resultant mixture was heated to 50° C. for 2 hours, then cooled and concentrated in vacuo. Excess hydrazine was azeotropically removed by treatment with MeOH and finally DCM to give the indicated product which was used in the next step without further purification. m/z=519.1 (M+H).

Step B: N-acetyl-4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carbohydrazide To a THF solution (3 mL) of the intermediate from Step A (100 mg, 0.193 mmol) was added 1-acetylimidazole (85 mg, 0.771 mmol). The resultant mixture was stirred at ambient temperature under a nitrogen atmosphere for 3 hours then purified by preparative TLC using 10% MeOH/ 1% NH₄OH I DCM as eluent to give the indicated product. m/z=561.1 (M+H).

Step C: 4-amino-2-[5-chloro-3-(3,3,4,4,4-pentafluorobutyl)-1H-indazol-1-yl]-5-methyl-5-(5-methyl-1,3,4-thiadiazol-2-yl)-5,7-dihydro-6H-pyrrolo[2,3-d]pyrimidin-6-one To a toluene solution (1 mL) of the intermediate from Step B (41.3 mg, 0.074 mmol) in a screw cap vial was added Lawesson's reagent (29.8 mg, 0.074 mmol). The resultant mixture was heated to 80° C. for 1.5 hours then diluted with EtOAc and washed with saturated aqueous NaHCO₃ and brine. The organic phase was dried over anhydrous MgSO₄, filtered, and concentrated in vacuo. The crude was purified by preparative TLC using 5% MeOH/0.5% NH₄OH/DCM as the eluent to give the indicated compound. $^1$H NMR (500 MHz, CH₃CN-d₃): δ 9.51 (s, 1H); 8.83 (d, J=9.0 Hz, 1H); 7.89 (d, J=2.0 Hz, 1H); 7.55 (dd, J=9.0, 2.0 Hz, 1H); 6.34 (s, 2H); 3.37-3.31 (m, 2H); 2.87-2.63 (m, 5H); 1.90 (s, 3H). m/z=559.1 (M+H).

EXAMPLE 86

4-Amino-2-[5-Chloro-3-(3,3,4,4,4-Pentafluorobutyl)-1H-Indazol-1-yl]-5-Methyl-5-(5-Methyl-1,3,4-Oxadiazol-2-yl)-5,7-Dihydro-6H-Pyrrolo[2,3-D]Pyrimidin-6-One

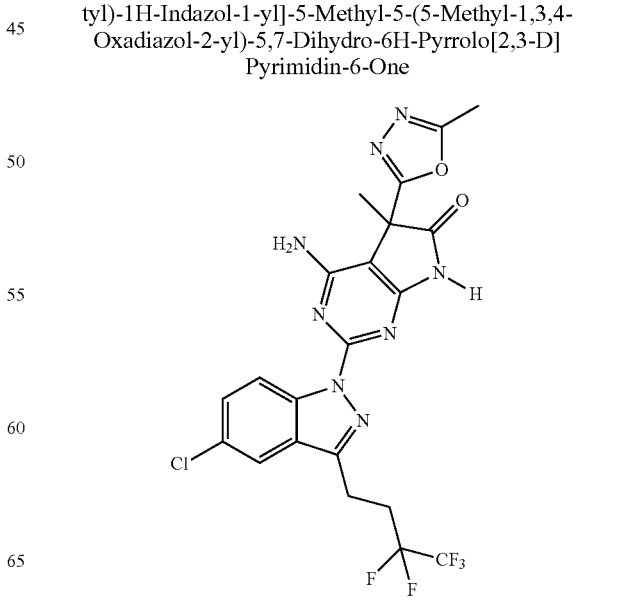

To the intermediate from Step B in Example 85 (50 mg, 0.089 mmol) was added thionyl chloride (0.1 mL, 1.37 mmol) and the resultant mixture heated at 75° C. for 1.5 hours. The solution was diluted with EtOAc, washed with 0.5 N NaOH (3×) and brine (1×). The organic layer was dried over anhydrous magnesium sulfate, filtered, and concentrated in vacuo. The crude was purified by preparative TLC using 5% MeOH/0.5% NH$_4$OH/DCM as the eluent to give the indicated compound. $^1$H NMR (500 MHz, CH$_3$CN-d$_3$): δ 9.43 (s, 1H); 8.79 (t, J=9.0 Hz, 1H); 7.89 (d, J=1.9 Hz, 1H); 7.57 (d, J=9.0 Hz, 1H); 5.81 (s, 2H); 3.32 (m, 2H); 2.76 (m, 2H); 2.49 (s, 3H); 1.92 (s, 3H). m/z=543.2 (M+H).

Using essentially the same procedures described in the previous Examples 85 and 86, the following compounds in Table 5 and Table 6 were made.

TABLE 5

| EXAMPLE | R$^1$ | R$^3$ | m/z (M + H) |
|---------|-------|-------|-------------|
| 87 | H | CONH$_2$ | 470.3 |
| 88 | Cl | CONH$_2$ | 504.1 |
| 89 | F | CONHMe | 502.2 |
| 90 | Cl | CONHMe | 518.1 |
| 91 | Cl | CONHEt | 532.2 |
| 92 | Cl | (acetamido-methyl-N-methylpyrazole) | 598.1 |
| 93 | H | (methyl-oxadiazolone) | 525.2 |
| 94 | Cl | (methyl-thiadiazole) | 545.1 |

TABLE 6

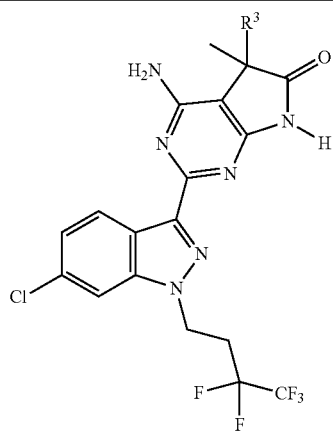

| EXAMPLE | R$^3$ | m/z (M + H) |
|---------|-------|-------------|
| 95 | CONHMe | 518.1 |
| 96 | (methyl-oxadiazolone) | 559.2 |
| 97 | (methyl-thiadiazole) | 559.2 |
| 98 | (methyl-oxadiazole) | 543.2 |

EXAMPLE 99

4-Amino-5-Methyl-5-Phenyl-2-[3-(2,3,6-Trifluorobenzyl)-4,6-Dihydro-1H-Thieno[3,4-C]Pyrazol-1-yl]-5,7-Dihydro-6H-Pyrrolo[2,3-D]Pyrimidin-6-One In a screw cap tube was added Example 54 (15 mg, 0.03 mmol, racemic), 1,2-dichloroethane (1 mL), triethylsilane (0.7 mL) and TFA (0.3 mL). The reaction mixture was heated at 75° C. for 3 hours. The reaction solution was then concentrated and partitioned between EtOAc and 1N NaOH aq. The organic phase was washed with brine and dried over $MgSO_4$. The crude was purified by reverse phase HPLC using a water/acetonitrile (with 0.1% TFA) gradient to give the indicated product. $^1$H NMR (400 MHz, $CH_3CN$-$d_3$): δ 9.16 (s, 1H); 7.37-7.27 (m, 5H); 7.25-7.15 (m, 1H); 6.99-6.92 (m, 1H); 5.31 (s, 2H); 4.32 (t, J=3.1 Hz, 2H); 3.99 (s, 2H); 3.63 (t, J=3.1 Hz, 2H); 1.77 (s, 3H). m/z=509.2 (M+H).

EXAMPLE 100

4-Amino-5-Methyl-2-[1-(3,3,4,4,4-Pentafluorobutyl)-4,5,6,7-Tetrahydro-1H-Indazol-3-yl]-5-Phenyl-5,7-Dihydro-6H-Pyrrolo[2,3-D]Pyrimidin-6-One

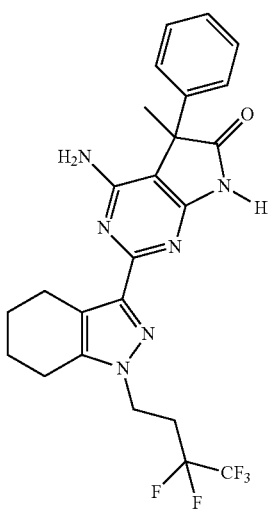 [SMILES: CC1(c2ccccc2)C(=O)Nc2nc(-c3nn(CCC(F)(F)C(F)(F)F)c4c3CCCC4)nc(N)c21]

To a 15 mL reaction vessel was added Example 69 (13.1 mg, 0.026 mmol), 5 mL of 4/1 MeOH/acetic acid and 20 mg of 20 wt. % palladium hydroxide on activated charcoal. The resultant mixture was heated to 65° C. under 40 psig for 18 hours. The reaction mixture was filtered through a PTFE filter disk and the filtrate concentrated in vacuo. The crude material was purified by reverse phase HPLC using a water/acetonitrile (with 0.1% TEA) gradient. The isolated material was converted to the free base by suspending in DCM and washing with saturated $NaHCO_3$ solution (2×) and brine (1×). The organic phase was dried over anhydrous magnesium sulfate, filtered, and concentrated in vacuo to give the indicated compound. $^1$H NMR (500 MHz, DMSO-$d_6$): δ 10.95 (s, 1H); 7.38-7.24 (m, 5H); 6.25 (s, 2H); 4.33 (t, J=7.1 Hz, 2H); 2.87-2.72 (m, 4H); 2.66 (t, J=6.3 Hz, 2H); 1.82-1.73 (m, 5H); 1.68 (d, J=7.5 Hz, 2H). m/z=507 (M+H).

Using essentially the same procedure described in Example 100, the following compounds in Table 7 were made.

TABLE 7

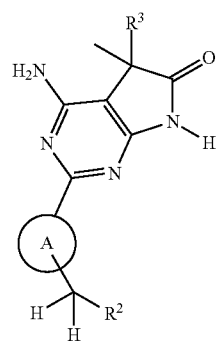

| EXAMPLE | A | $R^2$ | $R^3$ | m/z (M + H) |
|---|---|---|---|---|
| 101 | ![tetrahydroindazole] | $CH_2CF_2CF_3$ | 2-F Ph | 525.2 |
| 102 | ![tetrahydroindazole] | $CH_2CF_2CF_3$ | 3-F Ph | 525.2 |
| 103 | ![tetrahydroindazole] | $CH_2CF_2CF_3$ | 4-F Ph | 525.2 |
| 104 | ![tetrahydroindazole] | $CH_2CF_3$ | Ph | 457.3 |

EXAMPLE 105

4-Amino-2-[6-Chloro-3-(3,3,4,4,4-Pentafluorobutyl)
Imidazo[1,5-A]Pyridin-1-yl]-5-(4-Fluorophenyl)-5-
Methyl-5,7-Dihydro-6H-Pyrrolo[2,3-D]Pyrimidin-6-
One

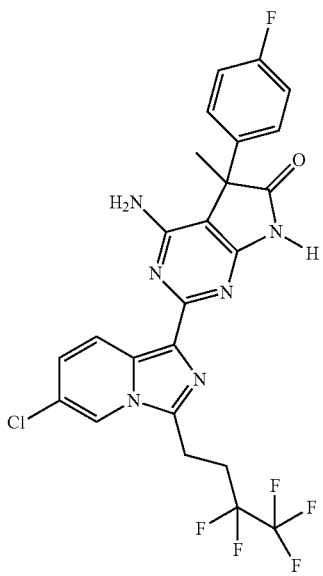 [SMILES: CC1(c2ccc(F)cc2)C(=O)Nc2nc(-c3nc(CCC(F)(F)C(F)(F)F)n4cc(Cl)ccc34)nc(N)c21]

Step A: diethyl(acetylamino)(5-nitropyridin-2-yl)
propanedioate

To a stirred slurry of sodium hydride (46 g, 1 mol, 50% oil dispersion) in dimethylformamide (500 mL, distilled from calcium oxide) was slowly added a solution of diethyl acetamidomalonate (217 g, 1 mol) in dimethylformamide (1200 mL). After the initial reaction, the slurry was heated to 45° C. for 1.5 hours and then 2-chloro-5-nitropyridine (159 g, 1 mol) in DMF (800 mL) was added. The mixture became dark brown during addition of the 2-chloro-5-nitropyridine. The mixture was stirred at 45° C. overnight. After cooling, the mixture was diluted with 1000 mL hydrochloric acid (0.2 N), and then extracted with dichloromethane (3×1200 mL). The combined organic phases were dried over anhydrous magnesium sulfate, filtered, and the solvent evaporated to give a dark brown oil. The oil was dry-loaded on silica gel and chromatographed on a dry-packed silica gel column. The column was eluted with petroleum ether-ethyl acetate (8:1 and then 5:1). Fractions containing the indicated compound were combined and concentrated to give pale yellow solid. Mp 82-83° C.

Step B: diethyl(acetylamino)(5-aminopyridin-2-yl)
propanedioate

A mixture of the intermediate from Step A (115 g, 0.33 mol) and 2.5 g Pd/C catalyst (10%) in 200 mL of methanol was hydrogenated at 60 prig overnight. The mixture was filtered through Celite™ (diatomaceous earth), and the filtrate was concentrated to give diethyl (5-amino-2-pyridyl)acetamidomalonate as an off-white solid. Mp: 154-155° C.

Step C: diethyl(acetylamino)(5-chloropyridin-2-yl)
propanedioate

A solution of diethyl (5-amino-2-pyridyl)acetamidomalonate (55 g, 0.17 mol, Step B) in 200 mL of 3.5 N hydrochloric acid was cooled to −10° C., and then treated dropwise with a solution of sodium nitrite (12.2 g, 0.17 mol) in 50 mL of water. When the addition was complete, the reaction mixture was stirred below 5° C. for 2 hour, and then added to a solution of cupric chloride (69 g, 0.51 mol) in 200 mL of concentrated hydrochloric acid. The mixture was stirred at ambient temperature for 2 hours, and then diluted with 300 mL of dichloromethane. The organic phases was separated, dried over $MgSO_4$, and filtered. The solvent was evaporated to afford a dark green solid. The crude product was purified by silica gel column chromatography (ethyl acetate/petroleum ether=1:5) to give the indicated compound as a pale yellow solid. Mp: 89-90° C.

Step D: 1-(5-chloropyridin-2-yl)methanamine

Diethyl (5-chloro-2-pyridyl)acetamidomalonate (70 g, 0.21 mol, Step C) was dissolved in 95% ethanol (200 mL). To the stirred solution (2° C.) was added sodium hydroxide solution (105 mL, 8 N). After 2 hours, the mixture was cooled to 5° C. and acidified to pH 2 with hydrochloric acid (6 N, ~40 mL). The ethanol was evaporated under reduced pressure to give a mixture containing some solid. The mixture, was treated with hydrochloric acid (5 N, 150 mL) and heated to 80° C. for 4 hours, and then maintained at room temperature overnight. Sodium hydroxide solution (4 N) was slowly added to the mixture to adjust pH 10. The mixture was extracted with DCM (4×200 mL), the organic phases were combined, dried over anhydrous $Na_2SO_4$, and filtered. The solvent was evaporated to give the indicated product as a pale yellow oil.

Step E: 1-(5-chloropyridin-2-yl)methanamine
hydrochloride

The compound 2-(aminomethyl)-5-chloropyridine (18 g, 0.13 mol, from Step D) was dissolved in dichloromethane (50 mL) and hydrochloric methanol solution (5 M, 50 mL) was added. After stirring for several min a white solid began to precipitate. The mixture was stirred for 1 h at 0-5° C., and the solid was collected by filtration and the filtrate was evaporated in vacuo to give some off-white solid. The combined solid was washed with a small amount of cold DCM. The product was dried in vacuo to yield the indicated compound as the hydrochloric salt. $^1$H-NMR (DMSO-$d_6$, 400 MHz) δ 8.70 (s, 3H), 8.62 (s, 1H), 8.0 (dd, J=2.5, 6 Hz, 1H), 7.60 (d, J=8.5 Hz, 1H), 4.15 (m, 2H).

Step F: N-[(5-chloropyridin-2-yl)methyl]-4,4,5,5,5-
pentafluoropentanamide

To a solution of 4,4,5,5,5-pentafluoropentanoic acid (6.44 g, 33.5 mmol) and the intermediate from Step E (5.0 g, 27.9 mmol) in DCM (100 mL) was added EDC (7.49 g, 39.1 mmol) followed by DIEA (24.4 mL, 140 mmol). After stirring the reaction at room temperature for 2 hours, it was diluted with DCM (100 mL), and washed with water (2×). The organic layer was washed with brine, dried over anhydrous sodium sulfate, filtered, and concentrated to give a colorless oil. m/z=316.8 (M+H).

Step G: 6-chloro-3-(3,3,4,4,4-pentafluorobutyl)imi-
dazo[1,5-A]pyridine

To a solution of the intermediate from Step F (7.1 g, 22.42 mmol) in 1,2-dichloroethane (30 mL) was added phosphorous oxychloride (10.45 mL, 112 mmol). The resulting mixture was refluxed for 18 hours. The reaction mixture was cooled to room temperature and concentrated. The residue was partitioned between water and ethyl acetate. The aqueous layer was neutralized with solid sodium bicarbonate and then extracted with ethyl acetate (3×). The organic layer was washed with brine, dried over anhydrous sodium sulfate, filtered, and concentrated. The residue was purified by silica gel chromatography using a hexanes/EtOAc gradient to give a light yellow solid. m/z=298.9 (M+H).

Step H: 6-chloro-1-iodo-3-(3,3,4,4,4-pentafluorobutyl)imidazo[1,5-A]pyridine

To a solution of the intermediate from Step G (3.64 g, 12.19 mmol) in anhydrous DCM (50 mL) was added NIS (5.48 g, 24.4 mmol). The reaction mixture was stirred at room temperature for 18 hours and concentrated. The residue was suspended in ethyl acetate and washed with saturated sodium thiosulfate (2×). The organic layer was washed with brine, dried over anhydrous sodium sulfate, filtered, and concentrated. The residue was purified by silica gel chromatography using a hexanes/EtOAc gradient to give a bright white solid. m/z=424.7 (M+H).

Step I: 6-chloro-3-(3,3,4,4,4-pentafluorobutyl)imidazo[1,5-A]pyridine-1-carbonitrile To a solution of the intermediate from Step H (4.32 g, 10.18 mmol) in DMF (50 mL) was added zinc cyanide (2.39 g, 20.35 mmol), $Pd_2 dba_3$ (0.47 g, 0.51 mmol), DPPF (0.564 g, 1.02 mmol), and water (2.5 mL). The resulting solution was heated at 120° C. for 18 hours. The reaction was cooled to room temperature, diluted with 15% $NH_4OH$ solution (10 mL) and extracted with ethyl acetate. The organic layer was washed with brine, dried over anhydrous sodium sulfate, filtered, and concentrated. m/z=323.9 (M+H).

Step J: 6-chloro-3-(3,3,4,4,4-pentafluorobutyl)imidazo[1,5-A]pyridine-1-carboximidamide Trimethyl aluminum (2.0 M toluene, 10 mL, 20 mmol) was added to ammonium chloride (1.07 g, 20 mmol) suspended in toluene (30 mL) at 0° C. The solution was then stirred at room temperature for 2 hours to give a 0.5 M amino(chloro)methylaluminum solution in toluene. To the intermediate from Step I (2 g, 6.33 mmol) in toluene (1 mL) was added amino(chloro)methylaluminum (40 mL of 0.5 M solution in toluene, 20 mmol). The resulting mixture was left stirring at 100° C. for 18 hours. The reaction mixture was cooled to room temperature and quenched with silica-gel and 1:1 methanol-chloroform (50 mL). The resulting slurry was stirred vigorously for 30 minutes. The reaction mixture was filtered through a silca gel pad (1") and washed with methanol. The filtrate was concentrated. The residue was suspended in water and extracted with 30% $IPA/CHCl_3$ (3×). The organic layer was concentrated in vacuo to yield a brown solid. m/z=340.8 (M+1).

Step K: 4-amino-2-[6-chloro-3-(3,3,4,4,4-pentafluorobutyl)imidazo[1,5-A]-pyridin-1-yl]-5-(4-fluorophenyl)-5-methyl-5,7-dihydro-6H-pyrrolo[2,3-d]pyrimidin-6-one A tert-butanol (3 mL) solution containing the intermediate from Step J (200 mg, 0.587 mmol), Intermediate 10 (173 mg, 0.704 mmol) and potassium tert-butoxide (40 mg, 035 mmol) was heated at 110° C. in a sealed tube for 40 minutes. The reaction was then purified by reverse phase HPLC using water/acetonitrile (0.1% TFA) to give the indicated product. $^1$H NMR δ (ppm) (500 MHz, DMSO-$d_6$): 11.04 (1H, s), 8.68 (2H, d, J=8.5 Hz), 7.28 (2H, dd, J=8.5, 5.4 Hz), 7.16 (2H, t, J=8.7 Hz), 7.04 (1H, d, J=9.8 Hz), 6.42 (2H, s), 3.34-3.29 (2H, m, overlapping with DMSO), 2.84 (2H, m), 1.76 (3H, s). m/z=555.1 (M+H).

EXAMPLE 106

4-Amino-2-[6-Fluoro-3-(3,3,4,4,4-Pentafluorobutyl) Imidazo[1,5-A]Pyridin-1-yl]-5-(4-Fluorophenyl)-5-Methyl-5,7-Dihydro-6H-Pyrrolo[2,3-D]Pyrimidin-6-One

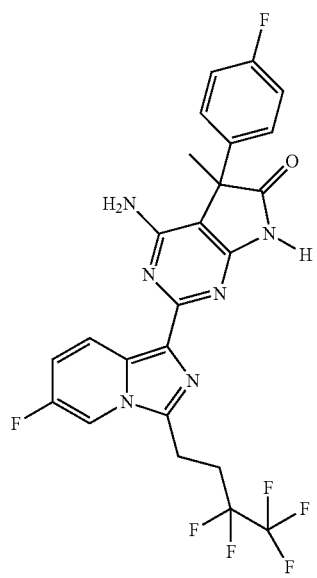 [SMILES: CC1(c2ccc(F)cc2)C(=O)Nc2nc(-c3nc(CCC(F)(F)C(F)(F)F)n4cc(F)ccc34)nc(N)c21]

Step A: diethyl(acetylamino)(5-fluoropyridin-2-yl) propanedioate

A stirred solution of the intermediate from Step B Example 105 (80 g, 0.25 mol) in 200 mL of 48% aqueous $HBF_4$ was cooled to −5° C. The solution of sodium nitrite (20.7 g, 0.3 mol) in 50 mL of water was added dropwise and kept the reaction mixture below 0° C. After addition, the solution was stirred for another 1 hour below 0° C., and then for 2 h at room temperature. The reaction mixture was extracted with dichloromethane (3×100 mL), and the combined organic phases were dried over anhydrous $MgSO_4$ and filtered. The filtrate was concentrated to give a brown yellow oil. The crude product was purified by silica gel chromatography using petroleum ether/EtOAc (5:1 to 3:1) to give the indicated compound as a pale yellow solid.

Step B: 1-(5-fluoropyridin-2-yl)methanamine

To a solution of diethyl (5-fluoro-2-pyridyl)acetamidomalonate from Step A (70 g, 0.21 mol) in 200 mL of 95% ethanol was added sodium hydroxide solution (105 mL, 8 N). After refluxing for 2 hours, the mixture was cooled to 5° C. and acidified to pH 2 with hydrochloric acid (6 N, ~40 mL). The ethanol in the solution was evaporated to give a mixture containing some solid, and then 150 mL of hydrochloric acid (5 N) was added. The mixture was heated to 80° C. for 4 hours, and then maintained at room temperature overnight. Sodium hydroxide solution (4 N) was slowly added to the mixture to adjust pH 10. The mixture was extracted with DCM (4×200 mL), and then the combined organic phases were dried over anhydrous Na$_2$SO$_4$ and filtered. The solvent was evaporated to give the indicated product as a pale yellow oil which decomposed on prolonged contact with air. $^1$H-NMR (CDCl$_3$, 400 MHz) δ 8.42 (s, 1H), 7.4 (m, 2H), 3.99 (s, 2H), 1.79 (m, 2H). m/z=127 (M+H).

Step C: 1-(5-fluoropyridin-2-yl)methanamine hydrochloride

The compound 2-(aminomethyl)-5-fluoropyridine from Step B (18 g, 0.14 mol) was dissolved in dichloromethane (50 mL) and hydrochloric methanol solution (5 M, 50 mL) was added. After stirring for several minutes a white solid began to precipitate. The mixture was stirred for 1 hour at 0-5° C., and the solid was collected by filtration and the filtrate was evaporated to give an off-white solid. The combined solid was washed with a small amount of cold DCM. The product was dried under reduced pressure to give the indicated compound as the dihydrochloride salt. $^1$H NMR (DMSO-d$_6$, 400 MHz) δ 8.70 (3H, s), 8.62 (1H, s), 7.8 (1H, m), 7.64 (1H, m), 4.13 (2H, m). m/z=127 (M+H).

Step D: 4-amino-2-[6-fluoro-3-(3,3,4,4,4-pentafluorobutyl)imidazo[1,5-A]pyridin-1-yl]-5-(4-fluorophenyl)-5-methyl-5,7-dihydro-6H-pyrrolo[2,3-d]pyrimidin-6-one The indicated compound was prepared from the amidine intermediate derived from Step C and Intermediate 10 using the procedure described in Example 105. $^1$H NMR δ (ppm) (500 MHz, DMSO-d$_6$): 11.01 (1H, s), 8.74 (1H, dd, J=10.0, 5.8 Hz), 8.62 (1H, d, J=4.9 Hz), 7.29 (2H, dd, J=8.5, 5.4 Hz), 7.18-7.11 (3H, m), 6.39 (2H, s), 3.34-3.29 (2H, m, overlapping with DMSO), 2.86-2.83 (2H, m), 1.76 (3H, s). MS m/z=539.1 (M+H).

EXAMPLE 107

4-Amino-5-Methyl-2-[7-(3,3,4,4,4-Pentafluorobutyl) Imidazo[1,5-B]Pyridazin-5-yl]-5-Phenyl-5,7-Dihydro-6H-Pyrrolo[2,3-D]Pyrimidin-6-One

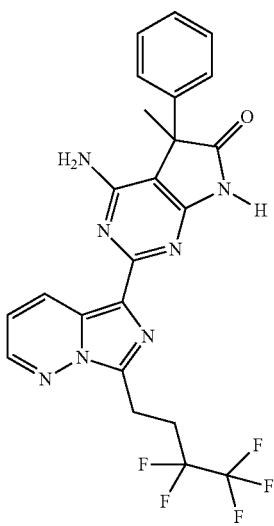 [SMILES: CC1(c2ccccc2)C(=O)Nc2nc(-c3nc(CCC(F)(F)C(F)(F)F)n4ncccc34)nc(N)c21]

Step A: 2-[(4-methylphenyl)sulfonyl]-2,3-dihydropyridazine-3-carbonitrile

To a solution of pyridazine (3.63 mL, 49.9 mmol) in DCM (60 mL) was added trimethylsilyl cyanide (11.99 mL, 90 mmol) and aluminum chloride (20 mg, 0.150 mmol). After stirring the reaction mixture at room temperature for 10 minutes, a solution of para-toluene sulfonyl chloride (16.38 mL, 86 mmol) in DCM (100 mL) was added dropwise via an addition funnel over 30 minutes. The resulting light orange solution was left stirring at room temperature overnight. The reaction mixture was concentrated to give a light brown solid. To this material was added EtOH (100 mL). A white precipitate formed which was filtered through a sintered funnel. The precipitate was washed with ethanol and collected. m/z=262 (M+H).

Step B: pyridazine-3-carbonitrile

To a solution of the intermediate from Step A (10 g, 38.3 mmol) in anhydrous THF (90 mL) was added DBU (7.21 mL, 47.8 mmol). The resulting solution was stirred at room temperature for 30 minutes. The reaction was quenched by the addition of saturated ammonium chloride solution (40 mL). The resulting mixture was diluted with water (30 mL) and extracted with ethyl acetate several times (until aqueous layer had no product). The organic layer was washed with brine, dried over anhydrous sodium sulfate, filtered and concentrated. The residue was purified by silica gel chromatography using a ethyl acetate hexanes gradient to afford a white solid. $^1$H NMR (500 MHz, CDCl$_3$) δ 9.4 (m, 1H), 7.9 (m, 1H), 7.7 (m, 1H). m/z=106 (M+H).

Step C: 1-(pyridazin-3-yl)methanamine hydrochloride

To a solution of the intermediate from Step B (5.96 g, 56.7 mmol) in MeOH (35 mL) was added 6N HCl (20.89 mL, 125 mmol) followed by Pd/C (0.905 g, 8.51 mmol). The reaction mixture was kept on Parr shaker for 2 hours at 40 psig hydrogen. The reaction mixture was filtered through Celite™ (diatomaceous earth) and washed with 600 mL of MeOH and the filtrate concentrated. The residue was azeotroped several times with toluene. A dark brown solid was obtained. m/z=110 (M+H).

Step 4-amino-5-methyl-2-[7-(3,3,4,4,4-pentafluorobutyl)imidazo[1,5-b]pyridazin-5-yl]-5-phenyl-5,7-dihydro-6H-pyrrolo[2,3-d]pyrimidin-6-one The indicated compound was prepared from the amidine intermediate derived from Step C and Intermediate 1 using the procedure described in Example 105 $^1$H NMR (500 MHz, DMSO-d$_6$): δ 11.02 (1H, s), 9.02 (1H, dd, J=9.2, 1.7 Hz), 8.44 (1H, dd, J=1.7, 4.1 Hz), 7.84 (1H, d, J=5.1 Hz), 7.33-7.26 (4H, m), 6.98 (1H, m), 6.4 (2H, broad s), 3.34-3.29 (2H, m, overlapping with DMSO), 2.86-2.83 (2H, m), 1.76 (3H, s). m/z=503.9 (M+H).

EXAMPLE 108

4-Amino-5-Methyl-5-(3-Methyl-1,2,4-Oxadiazol-5-yl)-2-[3-(3,3,4,4,4-Pentafluorobutyl)Imidazo[1,5-A]Pyridin-1-yl]-5,7-Dihydro-6H-Pyrrolo[2,3-D]Pyrimidin-6-One

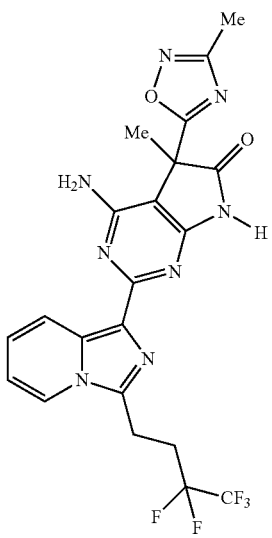 [SMILES: Cc1noc(C2(C)C(=O)Nc3nc(-c4nc(CCC(F)(F)C(F)(F)F)n5ccccc45)nc(N)c32)n1]

The indicated compound was prepared from the amidine intermediate derived from 2-(aminomethyl)pyridine and Intermediate 5 using the procedure described in Example 105. The racemic material was resolved by preparative HPLC using OD-H column to give the indicated compound (fast isomer). $^1$H NMR (DMSO-$d_6$, 500 MHz) δ 11.40 (1H, s), 8.66 (1H, d, J=9.2 Hz), 8.36 (1H, d, J=7.1 Hz), 7.06 (1H, dd, J=9.2, 6.4 Hz), 6.86 (1H, t, J=6.7 Hz), 6.67 (2H, s), 3.35-3.32 (2H, m, overlapping with DMSO), 2.93-3.86 (3H, m), 2.32 (3H, s), 1.86 (3H, s). m/z=509 (M+H).

EXAMPLE 109

4-Amino-2-[6-Fluoro-3-(3,3,4,4,4-Pentafluorobutyl)Imidazo[1,5-A]Pyridin-1-yl]-5-Methyl-5-(3-Methyl-1,2,4-Oxadiazol-5-yl)-5,7-Dihydro-6H-Pyrrolo[2,3-D]Pyrimidin-6-One

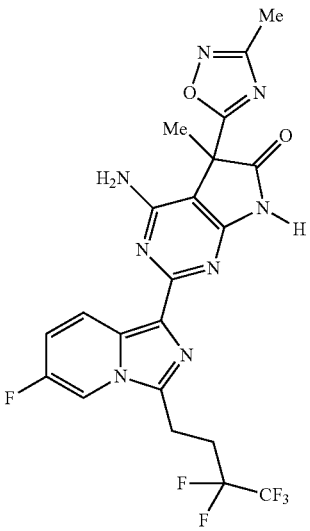 [SMILES: Cc1noc(C2(C)C(=O)Nc3nc(-c4nc(CCC(F)(F)C(F)(F)F)n5cc(F)ccc45)nc(N)c32)n1]

The indicated compound was prepared from the amidine derived from Example 106 Step C and Intermediate 5 using the procedure described in Example 105. The racemic material was resolved by preparative HPLC using AD-H column to give the indicated (fast isomer). $^1$H NMR (DMSO-$d_6$, 500 MHz) δ 11.44 (1H, s), 8.72 (1H, dd, J=10.0, 5.4 Hz), 8.64 (1H, d, J=4.9 Hz), 7.18-7.14 (1H, m), 6.73 (2H, s), 3.32-3.29 (2H, m, overlapping with DMSO), 2.92-2.81 (2H, m), 2.32 (3H, s), 1.86 (3H, s). m/z=527 (M+H).

EXAMPLE 110

4-Amino-2-[6-Chloro-3-(3,3,4,4,4-Pentafluorobutyl)Imidazo[1,5-A]Pyridin-1-yl]-5-Methyl-5-(3-Methyl-1,2,4-Oxadiazol-5-yl)-5,7-Dihydro-6H-Pyrrolo[2,3-D]Pyrimidin-6-One

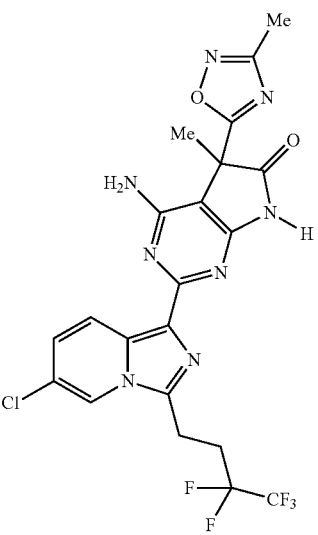 [SMILES: Cc1noc(C2(C)C(=O)Nc3nc(-c4nc(CCC(F)(F)C(F)(F)F)n5cc(Cl)ccc45)nc(N)c32)n1]

The indicated compound was prepared from the amidine derived from Example 105 Step J and Intermediate 5 using the procedure described in Example 105. The racemic material was resolved by preparative SFC using OJ column to give the indicated compound (slow isomer). $^1$H NMR (DMSO-$d_6$, 500 MHz) δ 11.47 (1H, s), 8.71 (1H, s) 8.68 (1H, d, J=9.0 Hz), 7.10 (1H, d, J=9.7 Hz), 6.77 (2H, s), 3.38-3.32 (2H, m, overlapping with DMSO), 2.93-2.83 (2H, m), 2.34 (3H, s), 1.88 (3H, s), m/z=543 (M+H).

EXAMPLE 111

4-Amino-2-[6-Chloro-3-(3,3,4,4,4-Pentafluorobutyl)
Imidazo[1,5-A]Pyridin-1-yl]-5-Methyl-5-(5-Methyl-
1,3-Oxazol-2-yl)-5,7-Dihydro-6H-Pyrrolo[2,3-D]
Pyrimidin-6-One

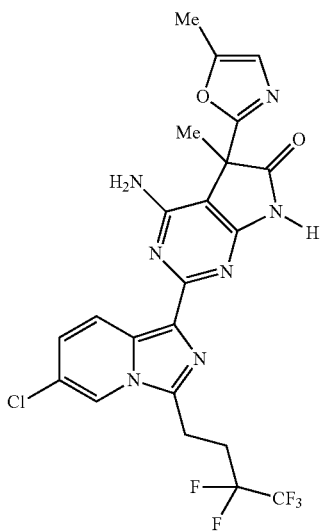 [SMILES: Cc1cnc(C2(C)C(=O)Nc3nc(-c4nc(CCC(F)(F)C(F)(F)F)n5cc(Cl)ccc45)nc(N)c32)o1]

The indicated compound was prepared from the amidine derived from Example 105 Step J and Intermediate 6 using the procedure described in Example 105. The racemic material was resolved by SFC using OD column to give the indicated compound (fast isomer). $^1$H NMR (DMSO-$d_6$, 500 MHz) δ 11.25 (1H, s), 8.68 (2H, d, J=8.8 Hz), 7.07 (1H, d, J=10.0 Hz), 6.82 (1H, s), 6.45 (2H, s), 3.34-3.30 (2H, m, overlapping with DMSO), 2.92-2.82 (2H, m), 2.26 (3H, s), 1.79 (3H, s). m/z=542 (M+H).

EXAMPLE 112

4-Amino-2-[6-Chloro-3-(3,3,4,4,4-Pentafluorobutyl)
Imidazo[1,5-A]Pyridin-1-yl]-5-Methyl-5-(2-Methyl-
1,3-Oxazol-4-yl)-5,7-Dihydro-6H-Pyrrolo[2,3-D]
Pyrimidin-6-One

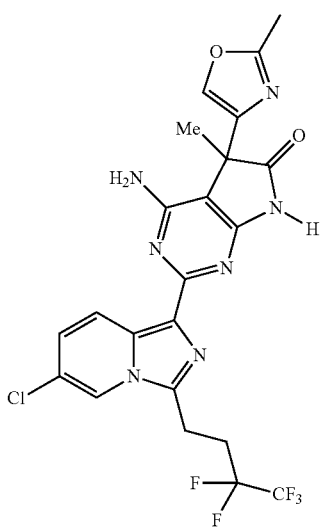 [SMILES: Cc1nc(C2(C)C(=O)Nc3nc(-c4nc(CCC(F)(F)C(F)(F)F)n5cc(Cl)ccc45)nc(N)c32)co1]

The indicated compound was prepared from the amidine derived from Example 105 Step J and Intermediate 7 using the procedure described in Example 105. The racemic material was resolved by preparative SFC using AD column to give the indicated compound (fast isomer). $^1$H NMR (DMSO-$d_6$, 500 MHz) δ 11.10 (1H, s), 8.67 (2H, t, J=4.2 Hz), 7.86 (1H, s), 7.06 (1H, d, J=9.9 Hz), 6.46 (2H, s), 3.34-3.29 (2H, m, overlapping with DMSO), 2.92-2.84 (2H, m), 2.36 (3H, s), 1.64 (3H, s). m/z=542 (M+H).

Using essentially the same procedure described in Examples 105 to 112, the following compounds in Table 8 were made.

TABLE 8

| EXAMPLE | R$^1$ | R$^2$ | R$^3$ | m/z (M + H) |
|---|---|---|---|---|
| 113 | H | 2-F Ph | Ph | 465.1 |
| 114 | H | 2-F Ph | 4-pyridyl | 466.0 |
| 115 | Cl | 2-F Ph | 3-methyl-1,2,4-oxadiazol-5-yl | 505 |
| 116 | H | 2,3-diF Ph | Ph | 483.0 |
| 117 | F | 2,3-diF Ph | Ph | 501 |
| 118 | H | 2,3-diF Ph | 4-F Ph | 501.2 |
| 119 | F | 2,3-diF Ph | 4-F Ph | 519.2 |
| 120 | H | 2,3-diF Ph | pyrazinyl | 485 |
| 121 | F | 2,3-diF Ph | pyrazinyl | 502.9 |
| 122 | H | 2,3,6-triF Ph | Ph | 501.1 |
| 123 | F | 2,3,6-triF Ph | Ph | 519 |
| 124 | Cl | 2,3,6-triF Ph | Ph | 535 |
| 125 | F | CH$_2$CF$_3$ | Ph | 470.8 |
| 126 | Cl | CH$_2$CF$_3$ | Ph | 486.8 |
| 127 | H | CH$_2$CH$_2$CF$_3$ | Ph | 467.3 |
| 128 | F | CH$_2$CH$_2$CF$_3$ | Ph | 485.1 |
| 129 | Cl | CH$_2$CH$_2$CF$_3$ | Ph | 500.7 |
| 130 | Cl | CH$_2$CH$_2$CF$_3$ | 4-F Ph | 518.9 |
| 131 | Cl | CH$_2$CH$_2$CF$_3$ | 2-pyridyl | 502 |

TABLE 8-continued

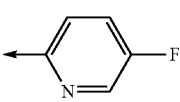

| EXAMPLE | R¹ | R² | R³ | m/z (M + H) |
|---|---|---|---|---|
| 132 | Cl | CH₂CH₂CF₃ | 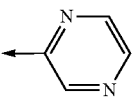 (2-pyridyl, 5-F) | 520 |
| 133 | Cl | CH₂CH₂CF₃ | 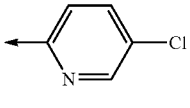 (pyrazinyl) | 503 |
| 134 | H | CH₂CF₂CF₃ | Ph | 502.8 |
| 135 | F | CH₂CF₂CF₃ | Ph | 520.9 |
| 136 | Cl | CH₂CF₂CF₃ | Ph | 536.9 |
| 137 | H | CH₂CF₂CF₃ | 2-F Ph | 521.1 |
| 138 | H | CH₂CF₂CF₃ | 3-F Ph | 521 |
| 139 | H | CH₂CF₂CF₃ | 4-F Ph | 521.0 |
| 140 | H | CH₂CF₂CF₃ | 3,5-diF Ph | 539 |
| 141 | H | CH₂CF₂CF₃ | 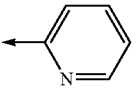 (2-pyridyl, 5-Cl) | 538.0 |
| 142 | F | CH₂CF₂CF₃ | 2-F Ph | 539.1 |
| 143 | F | CH₂CF₂CF₃ | 3-F Ph | 539.1 |
| 144 | F | CH₂CF₂CF₃ | 3,5-diF Ph | 557.1 |
| 145 | F | CH₂CF₂CF₃ | 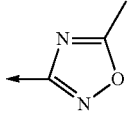 (2-pyridyl) | 522.1 |
| 146 | F | CH₂CF₂CF₃ | 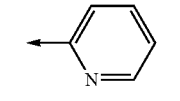 (5-methyl-1,2,4-oxadiazol-3-yl) | 527.1 |
| 147 | F | CH₂CF₂CF₃ | CO₂Et | 517.1 |
| 148 | Cl | CH₂CF₂CF₃ | 2-F Ph | 555 |
| 149 | Cl | CH₂CF₂CF₃ | 3-F Ph | 555 |
| 150 | Cl | CH₂CF₂CF₃ | 3,5-diF Ph | 573 |
| 151 | Cl | CH₂CF₂CF₃ | 4-Cl Ph | 570.9 |
| 152 | Cl | CH₂CF₂CF₃ | 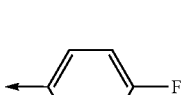 (2-pyridyl) | 538 |

TABLE 8-continued

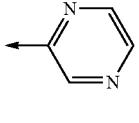

| EXAMPLE | R¹ | R² | R³ | m/z (M + H) |
|---|---|---|---|---|
| 153 | Cl | CH₂CF₂CF₃ | 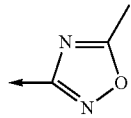 (2-pyridyl, 5-F) | 556 |
| 154 | Cl | CH₂CF₂CF₃ | 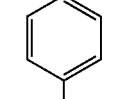 (pyrazinyl) | 538.9 |
| 155 | Cl | CH₂CF₂CF₃ | 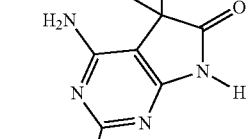 (5-methyl-1,2,4-oxadiazol-3-yl) | 543.1 |
| 156 | | | 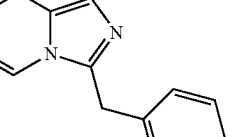 | 484.3 |

EXAMPLE 157

Ethyl 4-Amino-2-[6-Chloro-1-(3,3,4,4,4-Pentafluorobutyl)-1H-Indazol-3-yl]-5-Methyl-6-Oxo-6,7-Dihydro-5H-Pyrrolo[2,3-D]Pyrimidine-5-Carboxylate

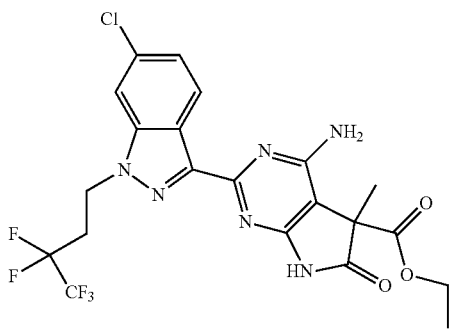 [SMILES: CCOC(=O)C1(C)C(=O)Nc2nc(-c3nn(CCC(F)(F)C(F)(F)F)c4cc(Cl)ccc34)nc(N)c21]

6-chloro-1-(3,3,4,4,4-pentafluorobutyl)-1H-indazole-3-carboximidamide, as described in Step E of Example 58, (13.5 g, 39.6 mmol), potassium bicarbonate (7.93 g, 79 mmol) and Intermediate 22 (10.38 g, 43.6 mmol) were dissolved in 2-propanol (150 mL) and heated at 80° C. for a total of 7 hours. The reaction solution was diluted with water and allowed to stir overnight. The reaction mixture, which was now a slurry, was filtered. The filtered product was washed with water and dried under a vacuum with a nitrogen sweep to give the title compound. The racemic product can be resolved by chiral SFC chromatography using a Chiralcel OJ or Chiralpak AD column. $^1$H NMR (400 MHz, CH$_3$CN-d$_3$): δ 8.64 (d, J=8.73 Hz, 1H); 7.70 (s, 1H); 7.26 (dd, J=8.72, 1.73 Hz, 1H); 5.62 (s, 2H); 4.76 (t, J=7.11 Hz, 2H); 4.17 (q, J=7.10 Hz, 2H); 2.93-2.73 (m, 2H); 1.66 (s, 3H); 1.17 (t, J=7.11 Hz, 3H). m/z=533.1 (M+H).

EXAMPLE 158

Ethyl 4-Amino-5-Methyl-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carboxylate

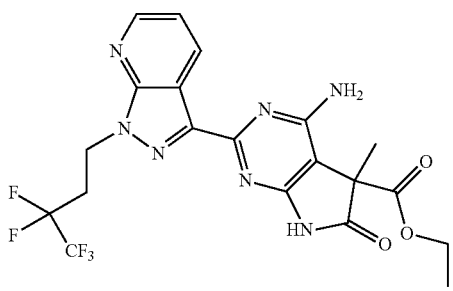 [SMILES: CCOC(=O)C1(C)C(=O)Nc2nc(-c3nn(CCC(F)(F)C(F)(F)F)c4ncccc34)nc(N)c21]

Step A: 1H-pyrazolo[3,4-b]pyridine

A solution of 2-chloropyridine-3-carbaldehyde (20 g, 141 mmol) and hydrazine monohydrate (60% in water, 113 g, 2.1 mol) in 140 mL water was heated at 100° C. for 72 hours. The reaction mixture was cooled to room temperature and diluted with 200 mL of EtOAc. The aqueous layer was separated and extracted with EtOAc (3×). The combined organics were dried over MgSO$_4$, filtered and concentrated in vacuo to give a light orange solid which was crystallized from hexanes to give the title compound as an off-white solid. $^1$H NMR (400 MHz, CH$_3$CN-d$_3$): δ 11.56 (s, 1H); 8.51 (dd, J=4.52, 1.56 Hz, 1H); 8.17 (dd, J=8.05, 1.58 Hz, 1H); 8.05 (s, 1H); 7.17 (dd, J=8.05, 4.51 Hz, 1H).

Step B: 3-iodo-1H-pyrazolo[3,4-b]pyridine

A solution of the intermediate from Step A above (14.3 g, 120 mmol) and N-iodosuccinimide (28.4 g, 126 mmol) in acetonitrile (210 mL) was heated at 75° C. After 17 hours, N-iodosuccinimide (5.4 g, 24 mmol) was added and the reaction solution stirred at 75° C. for an additional 1.5 hours. The reaction solution was cooled to room temperature and diluted with water. The slurry was concentrated in vacuo to remove most of the acetonitrile. The solid was collected, washed with water, and dried under a vacuum with a nitrogen sweep for 17 hours to give the title compound. $^1$H NMR (400 MHz, CH$_3$CN-d$_3$): δ 11.85 (s, 1H); 8.55 (dd, J=4.53, 1.53 Hz, 1H); 7.87 (dd, J=8.11, 1.53 Hz, 1H); 7.24 (dd, J=8.11, 4.51 Hz, 1H). m/z=246.1 (M+H).

Step C: 1H-pyrazolo[3,4-b]pyridine-3-carbonitrile

A DMF (180 mL) solution containing the intermediate from Step B above (24.1 g, 98 mmol), zinc cyanide (6.93 g, 59.0 mmol), 1,1'-bis(diphenylphosphino)ferrocene (4.36 g, 7.87 mmol) and tris(dibenzylideneacetone)dipalladium (3.60 g, 3.93 mmol) was heated at 120° C. for 1.5 hours. The solution was cooled to room temperature and diluted with water. The precipitated product was collected and dried under vacuum with a nitrogen sweep to give the title compound. $^1$H NMR (400 MHz, CH$_3$CN-d$_3$): δ 12.42 (s, 1H); 8.67 (dd, J=4.48, 1.53 Hz, 1H); 8.29 (dd, J=8.22, 1.53 Hz, 1H); 7.40 (dd, J=8.23, 4.48 Hz, 1H).

Step D: 1-(3,3,4,4,4-pentafluorobutyl)-1H-pyrazolo[3,4-b]pyridine-3-carbonitrile An acetonitrile solution (150 mL) containing the intermediate from Step C above (10.5 g, 43.7 mmol), potassium carbonate (30.2 g, 219 mmol) and 1,1,1,2,2-pentafluoro-4-iodobutane (23.95 g, 87 mmol) was heated at 75° C. for 48 hours. The reaction solution was cooled to room temperature and diluted with EtOAc. The solution was washed with water, brine and concentrated in vacuo. The residue was purified by silica gel chromatography using a hexanes/EtOAc gradient to give the title compound. $^1$H NMR (400 MHz, CH$_3$CN-d$_3$): δ 8.71 (dd, J=4.47, 1.51 Hz, 1H); 8.31 (dd, J=8.22, 1.52 Hz, 1H); 7.44 (dd, J=8.24, 4.48 Hz, 1H); 4.92 (t, J=6.98 Hz, 3H); 3.00-2.82 (m, 2H). m/z=291.0 (M+H).

Step E: 1-(3,3,4,4,4-pentafluorobutyl)-1H-pyrazolo[3,4-b]pyridine-3-carboximidamide Trimethylaluminum (2.0M in toluene, 60 mL, 120 mmol) was added dropwise to a suspension of ammonium chloride (6.42 g, 120 mmol) in 180 mL toluene cooled to 0° C. The solution was then stirred at room temperature for 3.5 hours. This solution (0.5M, 146 mL, 72.9 mmol) was then added to the intermediate from Step D above (4.6 g, 15.9 mmol) and then heated at 110° C. for 2.5 hours. The solution was then cooled to room temperature and carefully poured to silica gel (70 g) and methanol (750 mL). After stirring overnight the suspension was filtered and the filtered solid washed with methanol. The filtrate was concentrated in vacuo to give the title compound which was used in the next step without further purification. m/z=308.2 (M+H).

Step F: ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate A t-butanol (40 mL) solution containing the intermediate from Step E above (1.6 g, 5.21 mmol), potassium bicarbonate (1.4 g, 10.4 mmol) and Intermediate 22 (1.43 g, 6.0 mmol) was heated at 85° C. for 5 hours. The reaction solution was cooled to room temperature and diluted with EtOAc. The solution was washed with water then brine and dried over MgSO$_4$. The solution was filtered, concentrated in vacuo and the residue purified by silica gel chromatography using a hexanes/EtOAc gradient to give the title compound. $^1$H NMR (400 MHz, CH$_3$CN-d$_3$): δ 9.15 (s, 1H); 8.97 (d, J=8.14 Hz, 1H); 8.59 (d, J=4.20 Hz, 1H); 7.31 (dd, J=7.97, 4.52 Hz, 1H); 5.64 (s, 2H); 4.91 (t, J=7.15 Hz, 2H); 4.17 (q, J=7.16 Hz, 2H); 2.97-2.81 (m, 2H); 1.66 (s, 3H); 1.71 (t, J=7.2 Hz, 3H). m/z=500.1 (M+H).

EXAMPLE 159

4-Amino-2-[6-Chloro-1-(3,3,4,4,4-Pentafluorobutyl)-1H-Indazol-3-yl]-5-Methyl-6-Oxo-6,7-Dihydro-5H-Pyrrolo[2,3-D]Pyrimidine-5-Carboxamide

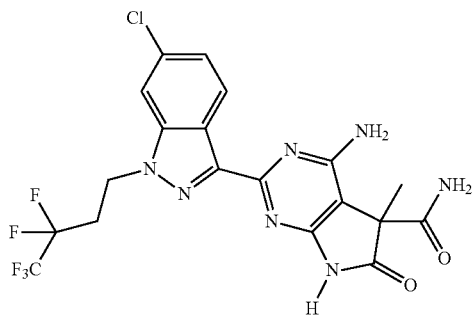 [SMILES: CC1(C(N)=O)C(=O)Nc2nc(-c3nn(CCC(F)(F)C(F)(F)F)c4cc(Cl)ccc34)nc(N)c21]

Ammonia (2.0M in MeOH, 11 mL, 22 mmol) was added to ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxylate, as prepared by the procedure described in Example 157, (150 mg, 0.289 mmol, single enantiomer from SFC separation on Chiralpak AD column). The resultant mixture was heated at 50° C. for 16 hours. The reaction solution was then concentrated in vacuo, and the residue purified by preparative TLC using 5% MeOH in DCM (with 0.5% NH$_4$OH) as the eluent to give the indicated compound. $^1$H NMR (500 MHz, DMSO-d$_6$): δ 8.66 (d, J=8.7 Hz, 1H); 8.02 (d, J=1.4 Hz, 1H); 7.45 (br s, 1H); 7.27 (dd, J=8.7, 1.7 Hz, 1H); 7.19 (br s, 1H); 6.79 (br s, 2H); 4.82 (t, J=6.8 Hz, 2H); 2.95-2.85 (m, 2H); 1.56 (s, 3H). m/z=504.1 (M+H).

EXAMPLE 160

4-Amino-2-[6-Chloro-1-(3,3,4,4,4-Pentafluorobutyl)-1H-Indazol-3-yl]-N-Cyclopropyl-5-Methyl-6-Oxo-6,7-Dihydro-5H-Pyrrolo[2,3-D]Pyrimidine-5-Carboxamide

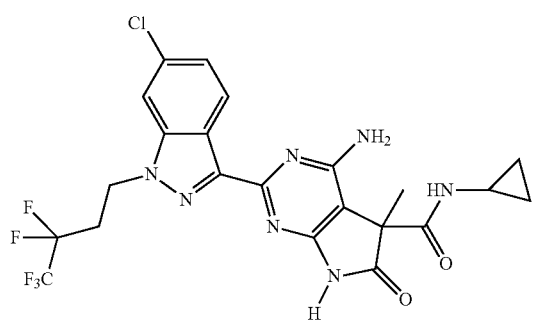 [SMILES: CC1(C(=O)NC2CC2)C(=O)Nc2nc(-c3nn(CCC(F)(F)C(F)(F)F)c4cc(Cl)ccc34)nc(N)c21]

Cyclopropylamine (486 mg, 8.52 mmol) and 0.5 mL anhydrous methanol was added to ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-c]pyrimidine-5-carboxylate, as prepared by the procedure described in Example 157 (34 mg, 0.066 mmol, single enantiomer from SFC separation on Chiralpak AD column). The resultant mixture was heated at 50° C. for 16 hours. The reaction solution was then concentrated in vacuo, and the residue purified by preparative TLC using 5% MeOH in DCM (with 0.5% NH$_4$OH) as eluent to give the indicated product. $^1$H NMR (500 MHz, DMSO-d$_6$): δ 11.22 (br s, 1H); 8.69 (d, J=8.7 Hz, 1H); 8.04 (s, 1H); 7.64 (d, J=3.9 Hz, 1H); 7.29 (d, J=8.8 Hz, 1H); 6.78 (br 5, 2H); 4.84 (t, J=6.7 Hz, 2H); 2.97-2.87 (m, 2H); 2.70-2.64 (m, 1H); 1.57 (s, 3H); 0.64-0.59 (m, 2H); 0.52-0.45 (m, 2H). m/z=544.1 (M+H).

EXAMPLE 161

4-Amino-5-Methyl-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carboxamide

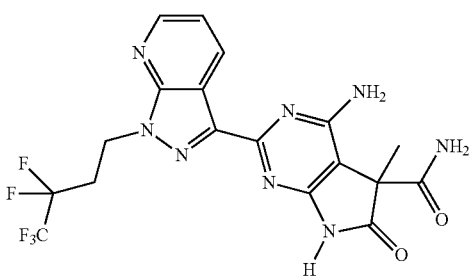 [SMILES: CC1(C(N)=O)C(=O)Nc2nc(-c3nn(CCC(F)(F)C(F)(F)F)c4ncccc34)nc(N)c21]

A 2 M solution of ammonia in MeOH (28.6 mL, 57.3 mmol) was added to ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate, as prepared by the procedure described in Example 158, (220 mg, 0.441 mmol) and the resultant mixture heated at 50° C. for 16 hours. The reaction mixture was concentrated in vacuo and the residue purified by silica gel column chromatography using a DCM/MeOH (with 0.5% NH₄OH) gradient. Chiral separation by SFC using a Chiralpak AD column provided both enantiomers of the title compound. ¹H NMR (500 MHz, DMSO-d₆): δ 11.27 (1H, s), 9.02 (1H, dd, J=8.06, 1.62 Hz), 8.64 (1H, dd, J=4.50, 1.63 Hz), 7.45 (1H, s), 7.38 (1H, dd, J=8.07, 4.49 Hz), 7.19 (1H, s), 6.82 (2H, s), 4.88 (2H, t, J=6.80 Hz), 3.04-2.90 (2H, m), 1.57 (3H, s). m/z=471.1 (M+H).

EXAMPLE 162

4-Amino-5-Cyclopropyl-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carboxamide

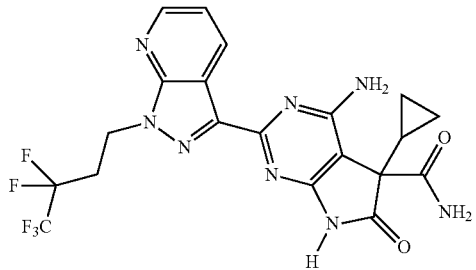 [SMILES: NC(=O)C1(C2CC2)C(=O)Nc2nc(-c3nn(CCC(F)(F)C(F)(F)F)c4ncccc34)nc(N)c21]

The title compound was prepared from Intermediate 27 following the procedure described in Example 161. ¹H NMR (500 MHz, CH₃OH-d₄): δ 9.00 (dd, J=8.08, 1.64 Hz, 1H); 8.60 (dd, J=4.54, 1.63 Hz, 1H); 7.34 (dd, J=8.09, 4.52 Hz, 1H); 4.94 (t, J=7.30 Hz, 3H); 3.03-2.89 (m, 3H); 1.83-1.75 (m, 1H); 0.65-0.53 (m, 4H).). m/z=497.0 (M+H).

EXAMPLE 163

4-Amino-5-Cyclopropyl-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carbonitrile

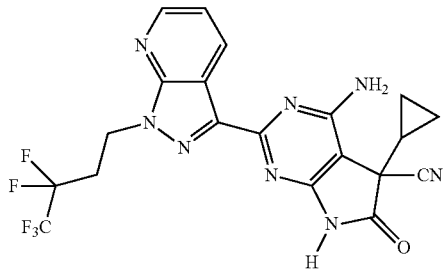 [SMILES: N#CC1(C2CC2)C(=O)Nc2nc(-c3nn(CCC(F)(F)C(F)(F)F)c4ncccc34)nc(N)c21]

4-amino-5-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, as described in Example 162, (565 mg, 1.201 mmol) was taken up in pyridine (6 mL) and the solution cooled to 0° C. Phosphorous oxychloride (0.896 ml, 9.61 mmol) was then added dropwise and the reaction mixture was warmed to room temperature. After 15 minutes, the pyridine solvent was concentrated in vacuo and the residue taken up in EtOAc. The mixture was then washed with water, brine and dried over sodium sulfate. The residue was purified by silica gel column chromatography using a hexanes/EtOAc gradient to give the title compound, Chiral separation by SFC provided both enantiomers of the title compound. ¹H NMR (500 MHz, DMSO-d₆): δ 9.07 (1H, d, J=8.07 Hz), 8.69 (1H, d, J=4.42 Hz), 7.44 (1H, dd, J=8.08, 4.48 Hz), 7.16 (2H, s), 4.93 (2H, t, J=6.82 Hz), 3.08-2.95 (2H, m), 1.80-1.73 (1H, m), 0.93-0.88 (1H, m), 0.65 (2H, d, J=8.31 Hz), 0.55-0.48 (1H, m). m/z=479.1 (M+H).

EXAMPLE 164

4-Amino-N-Cyclopropyl-5-Methyl-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carboxamide

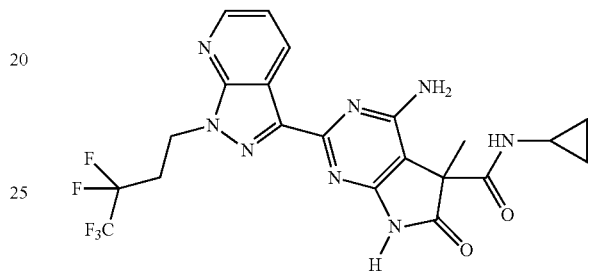

Cyclopropylamine (10.71 mL, 155 mmol) was added to ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate, as prepared by the procedure described in Example 158, (594 mg, 1.189 mmol) and the resultant mixture heated at 50° C. for 16 hours. The mixture was concentrated in vacuo and the residue purified by silica gel column chromatography using a hexanes/EtOAc gradient. Chiral separation using SFC on a Chiralpak AD-H column provided both enantiomers of the title compound, ¹H NMR (500 MHz, DMSO-d₆): δ 9.02 (1H, d, J=8.09 Hz), 8.63 (1H, d, J=4.45 Hz), 7.63 (1H, d, J=4.01 Hz), 7.38 (1H, dd, J=8.08, 4.48 Hz), 6.75 (2H, s), 4.87 (2H, t, J=6.77 Hz), 3.03-2.90 (2H, m), 2.68-2.62 (1H, m), 1.56 (3H, s), 0.63-0.54 (2H, m), 0.51-0.44 (2H, m). m/z=511.2 (M+H).

EXAMPLE 165

4-Amino-2-[6-Chloro-1-(3,3,4,4,4-Pentafluorobutyl)-1H-Indazol-3-yl]-5-Methyl-6-Oxo-N-Phenyl-6,7-Dihydro-5H-Pyrrolo[2,3-D]Pyrimidine-5-Carboxamide

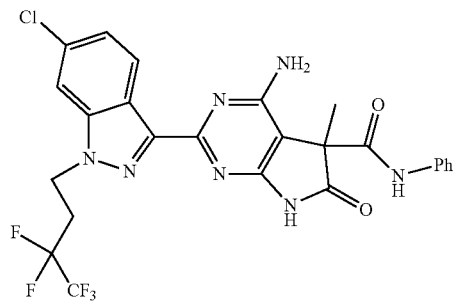 [SMILES: CC1(C(=O)Nc2ccccc2)C(=O)Nc2nc(-c3nn(CCC(F)(F)C(F)(F)F)c4cc(Cl)ccc34)nc(N)c21]

Trimethylaluminum (2.0 M in toluene, 1.2 mL, 2.4 mmol) was added to a toluene (8 mL) solution of aniline (248 mg, 2.66 mmol). After stirring at room temperature for 2 hours, solid ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxylate, as described in Example 157, (250 mg, 0.469 mmol) was added. The reaction solution was stirred at 50° C. for 30 minutes and then at room temperature overnight. Sodium potassium tartrate (0.5M aqueous, 25 mL) and EtOAc (25 mL) were added and the mixture stirred vigorously for 30 minutes. The phases were separated and the organic phase was washed with water (2×) and brine. The organic phase was then dried over MgSO$_4$, filtered and concentrated in vacuo. The residue was purified by silica gel chromatography using a hexanes/EtOAc gradient to give the indicated product. Chiral separation using SFC on a Chiralpak AD-H column provided both enantiomers of the title compound. $^1$H NMR (400 MHz, CH$_3$CN-d$_3$): δ 9.19 (s, 1H); 8.55 (d, J=8.69 Hz, 1H); 7.64 (s, 1H); 7.55 (d, J=8.01 Hz, 2H); 7.32 (t, J=7.77 Hz, 2H); 7.20-7.10 (m, 2H); 6.45 (s, 2H); 4.72 (t, J=7.10 Hz, 2H); 2.85-2.69 (m, 2H); 1.79 (s, 3H). m/z=580.2 (M+H).

EXAMPLE 166

Ethyl (4-Amino-2-(6-Chloro-1-(3,3,4,4,4-Pentafluorobutyl)-1H-Indazol-3-yl)-5-Methyl-6-Oxo-6,7-Dihydro-5H-Pyrrolo[2,3-D]Pyrimidin-5-yl)Carbamate

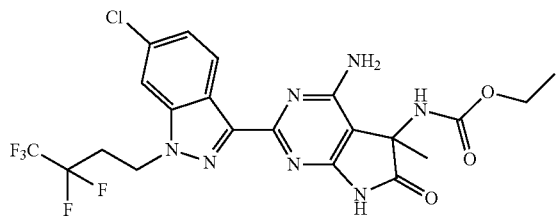 [SMILES: CCOC(=O)NC1(C)C(=O)Nc2nc(-c3nn(CCC(F)(F)C(F)(F)F)c4cc(Cl)ccc34)nc(N)c21]

Step A: 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carbohydrazide A methanol (9.5 mL) solution of ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxylate, as described in Example 157, (1.02 g, 1.91 mmol) and hydrazine (3.13 g, 96 mmol) was heated at 50° C. After 1.5 hours the solution was concentrated in vacuo. The crude reaction mixture was dissolved in methanol and concentrated in vacuo again. The remaining material was lyophilized from water and acetonitrile to give the title compound as a yellow solid which was used without further purification. m/z=519.0 (M+H).

Step B: 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carbonyl azide t-Butyl nitrite (0.34 mL, 2.89 mmol) was added dropwise to a THF (3.5 mL) solution containing the intermediate from Step A above (300 mg, 0.578 mmol) and TFA (50 μL, 0.636 mmol) cooled to 0° C. After 50 min. the solution was carefully concentrated in vacuo (temperature <30° C.) to give the title compound as a solid which was used without further purification. m/z 502.0 (M−N$_2$+H).

Step C: ethyl (4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)carbamate The acyl azide from Step B above (37.1 mg, 0.070 mmol) was dissolved in ethanol (2 mL, 34.3 mmol) and refluxed for 4 hours. The solution was concentrated in vacuo and the residue purified by silica gel column chromatography using a hexanes/EtOAc gradient. Chiral separation using SFC on a Chiralpak AD column provided both enantiomers of the title compound. $^1$H NMR (500 MHz, CD$_3$OD): δ 8.60 (d, J=4 Hz, 1H); 7.71 (s, 1H); 7.23 (d, J=3.6 Hz, 1H); 4.79 (t, J=2.4 Hz, 2H); 4.03 (m, 2H); 2.93 (m, 2H); 1.61 (s, 3H); 1.21 (m, 3H). m/z=548.0 (M+H).

EXAMPLE 167

4-Amino-2-[6-Chloro-1-(3,3,4,4,4-Pentafluorobutyl)-1H-Indazol-3-yl]-5-(4,5-Dimethyl-1,3-Thiazol-2-yl)-5-Methyl-5,7-Dihydro-6H-Pyrrolo[2,3-D]Pyrimidin-6-One

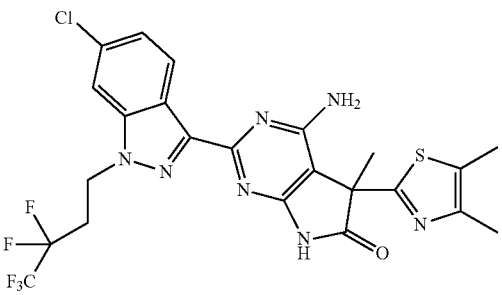 [SMILES: Cc1nc(C2(C)C(=O)Nc3nc(-c4nn(CCC(F)(F)C(F)(F)F)c5cc(Cl)ccc45)nc(N)c32)sc1C]

Step A: 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carbothioamide To a solution of 4-amino-2-[6-chloro-1-(3,3,4,4,4-pentafluorobutyl)-1H-indazol-3-yl]-5-methyl-6-oxo-6,7-dihydro-5H-pyrrolo[2,3-c]pyrimidine-5-carboxamide, as described in Example 159, (220 mg, 0.437 mmol) in toluene (6 mL), was added Lawesson's reagent (265 mg, 0.655 mmol). Acetonitrile was added as a co-solvent to dissolve the starting material. The resulting mixture was heated at 90° C. overnight. The solvent was then concentrated in vacuo. The residue was purified by silica gel column chromatography using a hexanes/EtOAc gradient to give the title product. $^1$H NMR (500 MHz, CH$_3$OH-d$_4$): δ 8.55 (d, J=8.7 Hz, 1H); 7.89 (s, 1H); 7.38 (d, J=8.7 Hz, 1H); 4.94-4.85 (m, 2H); 3.07-2.91 (m, 2H); 1.91 (s, 3H). m/z=519.9 (M+H).

Step B: 4-amino-2-[6-chloro-1-(3,3,4,4,4-pentafluorobutyl)-1H-indazol-3-yl]-5-(4,5-dimethyl-1,3-thiazol-2-yl)-5-methyl-5,7-dihydro-6H-pyrrolo[2,3-d]pyrimidin-6-one To a solution of the intermediate from Step A above (11 mg, 0.021 mmol) in ethanol (423 μl), was added 3-bromo-2-butanone (32.0 mg, 0.212 mmol). The mixture was stirred at 80° C. overnight. The solvent was then removed in vacuo. The residue was purified by preparative TLC using hexanes/EtOAc (1/1) as the eluent to give the indicated compound. Chiral separation using SFC on a Chiralpak AD column provided both enantiomers of the title compound. $^1$H NMR (500

MHz, CH₃OH-d₄): δ 8.59 (d, J=8.7 Hz, 1H); 7.86 (s, 1H); 7.36 (d, J=8.7 Hz, 1H); 4.92-4.82 (m, 2H); 3.08-2.88 (m, 2H); 2.38 (s, 3H); 2.34 (s, 3H); 1.94 (s, 3H). m/z=572.0 (M+H).

EXAMPLE 168

4-Amino-5-Methyl-2-[1-(3,3,4,4,4-Pentafluorobutyl)-1H-Pyrazolo[3,4-B]Pyridin-3-yl]-5-(1,3,4-Thiadiazol-2-yl)-5,7-Dihydro-6H-Pyrrolo[2,3-D]Pyrimidin-6-One

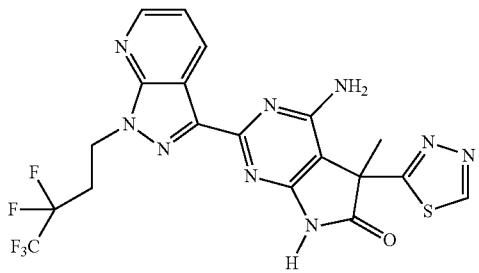 [SMILES: CC1(c2nncs2)C(=O)Nc2nc(-c3nn(CCC(F)(F)C(F)(F)F)c4ncccc34)nc(N)c21]

Step A: 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbohydrazide Hydrazine (2 mL, 63.7 mmol) was added to ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate, as prepared by the procedure described in Example 158, (400 mg, 0.761 mmol) and the reaction mixture was heated to 80° C. for 30 min. The reaction was then cooled to room temperature and concentrated in vacuo. Excess hydrazine was azeotropically removed by treatment with acetonitrile (3×4 mL). The product was lyophilized from water/acetonitrile overnight to give the title compound as a pale yellow solid which was used in the next step without further purification. m/z=486.01 (M+H).

Step B: 4-amino-N'-formyl-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbohydrazide Formic acid (3 mL, 78 mmol) was added to an acetonitrile solution (3 mL) of the intermediate from Step A (200 mg, 0.371 mmol). The reaction mixture was heated at 80° C. for 1.5 hours in a screw cap vial. The mixture was cooled, concentrated in vacuo and the residue diluted with EtOAc. The solution was then washed with saturated aqueous sodium bicarbonate, water and brine. The organic phase was dried over magnesium sulfate, filtered and concentrated in vacuo to give the title compound as a pale yellow solid which was used in the next step without further purification. m/z=513.97 (M+H).

Step C: 4-amino-5-methyl-2-[1-(3,3,4,4,4-pentafluorobutyl)-1H-pyrazolo[3,4-b]pyridin-3-yl]-5-(1,3,4-thiadiazol-2-yl)-5,7-dihydro-6H-pyrrolo[2,3-d]pyrimidin-6-one Lawesson's reagent (133 mg, 0.328 mmol) was added to a toluene (5 mL) solution of the intermediate from Step B (170 mg, 0.298 mmol). THF (0.5 mL) was added to improve solubility and the reaction was heated to 100° C. for 1 hour in a screw cap vial. The reaction was then cooled and concentrated in vacuo. The crude product was purified by silica gel column chromatography using a hexanes/EtOAc gradient to give the title compound. Chiral separation using SFC on a Chiralcel OD column provided both enantiomers of the title compound. ¹H NMR (600 MHz, CD₃OD): δ 9.45 (s, 1H); 9.04 (dd, J=7.8, 1.2 Hz, 1H); 8.60 (dd, J=4.2, 1.2 Hz, 1H); 7.36 (dd, J=7.8, 4.2 Hz, 1H); 4.94 (t, J=8.4 Hz, 2H); 4.56 (bs, 2H), 3.01-2.92 (m, 2H); 1.98 (s, 3H). m/z=511.95 (M+H).

EXAMPLE 169

4-Amino-5-Methyl-5-(5-Methyl-1,3,4-Oxadiazol-2-yl)-2-[1-(3,3,4,4,4-Pentafluorobutyl)-1H-Pyrazolo[3,4-B]Pyridin-3-yl]-5,7-Dihydro-6H-Pyrrolo[2,3-D]Pyrimidin-6-One

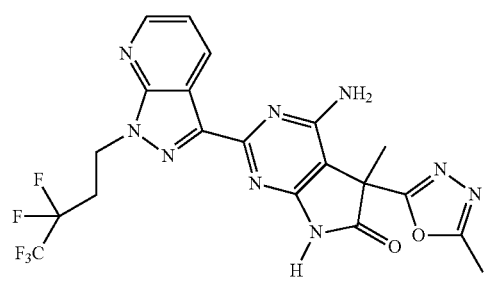 [SMILES: Cc1nnc(C2(C)C(=O)Nc3nc(-c4nn(CCC(F)(F)C(F)(F)F)c5ncccc45)nc(N)c32)o1]

Step A: N-acetyl-4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbohydrazide To a THF solution (7 mL) of the intermediate from Step A in Example 168 (325 mg, 0.67 mmol) was added 1-acetylimidazole (369 mg, 3.35 mmol). The resultant mixture was stirred at ambient temperature for 16 hours then purified by silica gel column chromatography using a DCM/MeOH (with 0.5% NH₄OH) gradient to give the title product. m/z=528.0 (M+H).

Step B: 4-amino-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one To the intermediate from Step A (144 mg, 0.273 mmol) was added approximately 15 mL of polyphosphoric acid and the resultant mixture heated at 125° C. for 5 hours. The reaction mixture was poured into a stirring mixture of aqueous pH 7 buffer solution (100 mL) and EtOAc (100 mL). The layers were separated and the aqueous phase was basified by adding solid K₂CO₃ portion-wise and was extracted once again with EtOAc. The combined organic extracts were washed sequentially with aqueous saturated NaHCO₃ solution, brine, then dried over MgSO₄, filtered, and concentrated in vacuo. The residue was purified by silica gel column chromatography using a hexanes/EtOAc gradient to provide the title product. Chiral separation using SFC on an OD-H column provided both enantiomers of the title compound. ¹H NMR (500 MHz, DMSO-d₆): δ 11.48 (1H, s), 9.02 (1H, dd, J=8.07, 1.57 Hz), 8.64 (1H, dd, J=4.50, 1.58 Hz), 7.39 (1H, dd, J=8.08, 4.49

Hz), 6.90 (2H, s), 4.89 (3H, t, J=6.81 Hz), 3.04-2.91 (3H, m), 1.85 (4H, s). m/z=510.1 (M+H).

EXAMPLE 170

4-Amino-5-Methyl-2-[1-(3,3,4,4,4-Pentafluorobutyl)-1H-Pyrazolo[3,4-B]Pyridin-3-yl]-5-Pyrimidin-2-yl-5,7-Dihydro-6H-Pyrrolo[2,3-D]Pyrimidin-6-One

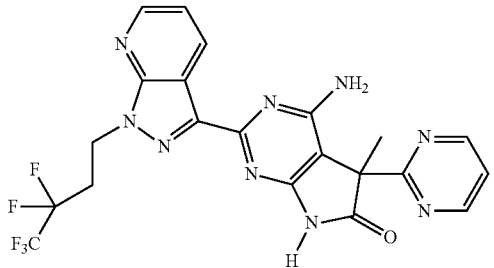 [SMILES: CC1(c2ncccn2)C(=O)Nc2nc(-c3nn(CCC(F)(F)C(F)(F)F)c4ncccc34)nc(N)c21]

A MeOH (2 mL) solution of Intermediate 18 (50 mg, 0.163 mmol, single enantiomer from chiral SFC separation), sodium bicarbonate (14 mg, 0.163 mmol) and 1-(3,3,4,4,4-pentafluorobutyl)-1H-pyrazolo[3,4-b]pyridine-3-carboximidamide, as described in Step E of Example 158 (52 mg, 0.212 mmol) was heated in a microwave reactor to 135° C. for 45 minutes. The solution was cooled to room temperature and the MeOH removed under reduced pressure. The residue was taken up in EtOAc and washed with water, brine and dried over Na$_2$SO$_4$. The solution was filtered, concentrated in vacuo and the residue purified by silica gel column chromatography using a DCM/MeOH (with NH$_4$OH) gradient to give the title compound. $^1$H NMR (500 MHz, DMSO-d$_6$): δ 11.27 (1H, s), 8.99 (1H, d, J=8.06 Hz), 8.81 (2H, d, J=4.88 Hz), 8.63 (1H, d, J=4.48 Hz), 7.46 (1H, t, J=4.89 Hz), 7.36 (1H, dd, J=8.06, 4.51 Hz), 6.45 (2H, s), 4.87 (2H, t, J=6.81 Hz), 3.03-2.91 (2H, m), 1.84 (3H, s). m/z=506.2 (M+H).

EXAMPLE 171

4-Amino-2-[6-Chloro-1-(3,3,4,4,4-Pentafluorobutyl)-1H-Indazol-3-yl]-5-Methyl-5-[5-Oxo-4-(Propan-2-yl)-4,5-Dihydro-1,3,4-Oxadiazol-2-yl]-5,7-Dihydro-6H-Pyrrolo[2,3-D]Pyrimidin-6-One

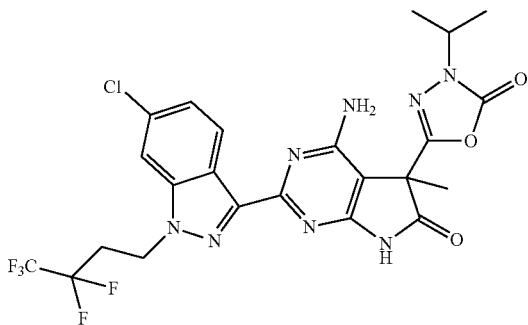 [SMILES: CC(C)n1nc(C2(C)C(=O)Nc3nc(-c4nn(CCC(F)(F)C(F)(F)F)c5cc(Cl)ccc45)nc(N)c32)oc1=O]

Step A: 4-amino-2-[6-chloro-1-(3,3,4,4,4-pentafluorobutyl)-1H-indazol-3-yl]-5-methyl-5-(5-oxo-4,5-dihydro-1,3,4-oxadiazol-2-yl)-5,7-dihydro-6H-pyrrolo[2,3-d]pyrimidin-6-one 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carbohydrazide, as described in Step A of Example 166 (1150 mg, 2.217 mmol) and 1,1-carbonyldiimidazole (603 mg, 3.71 mmol) in 15 mL of CH$_2$Cl$_2$ were stirred for 8 hours at room temperature. Water (15 mL) was added to the reaction and the mixture was extracted with EtOAc (3×). The combined organic layer was dried over Na$_2$SO$_4$ and evaporated under reduced pressure to give the title product. $^1$H NMR (500 MHz, CD$_3$COCD$_3$) δ 1.72 (s, 3H); 2.76 (m, 2H); 4.6 (t, J=7.1 Hz, 2H); 6.87 (br, 2H), 7.03 (d, J=8.7 Hz, 1H): 7.43 (s, 1H); 8.27 (d, J=8.7 Hz, 1H); 11.2 (s, 1H). m/z=544.99 (M+H).

Step B: 4-amino-2-[6-chloro-1-(3,3,4,4,4-pentafluorobutyl)-1H-indazol-3-yl]-5-methyl-5-[5-oxo-4-(propan-2-yl)-4,5-dihydro-1,3,4-oxadiazol-2-yl]-5,7-dihydro-6H-pyrrolo[2,3-d]pyrimidin-6-one To the intermediate from Step A above (120 mg, 0.22 mmol) and finely powdered potassium carbonate (36.9 mg, 0.264 mmol) in DMF (3 mL), was added 2-iodopropane (35.9 mg, 0.21 mmol) and the reaction was stirred for 7 hours at room temperature. Water (4 mL) and ethyl acetate (15 mL) were then added to the reaction mixture. The water layer was extracted with ethyl acetate (3×). The combined organic layer was dried over Na$_2$SO$_4$ and evaporated under reduced pressure. The residue was purified by reverse phase HPLC to give the indicated compound as a white solid. Chiral separation using SFC on a Chiralcel OJ column provided both enantiomers of the title compound. $^1$H NMR (500 MHz, CDCl$_3$) δ 1.31 (d, J=6.4 Hz, 3H); 1.33 (d, J=6.4 Hz, 3H); 1.77 (s, 3H); 2.84 (t, J=7.8 Hz, 2H); 4.36 (t, J=6.6 Hz, 1H); 4.78 (t, J=7.6 Hz, 2H); 5.34 (s, 2H); 7.27 (d, J=8.7 Hz, 1H); 7.49 (s, 1H); 8.51 (d, J=8.7 Hz, 1H). m/z=587.13 (M+H).

EXAMPLE 172

4-Amino-2-[6-Chloro-1-(3,3,4,4,4-Pentafluorobutyl)-1H-Indazol-3-yl]-5-Methyl-5-[4-(Propan-2-yl)-5-Thioxo-4,5-Dihydro-1,3,4-Oxadiazol-2-yl]-5,7-Dihydro-6H-Pyrrolo[2,3-D]Pyrimidin-6-One

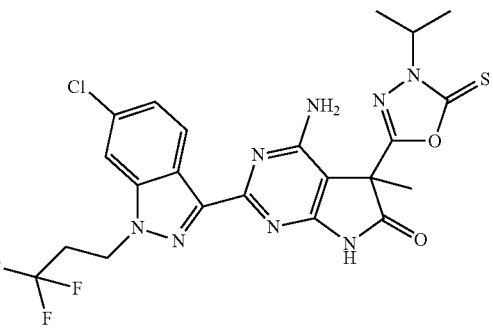

Step A: 4-amino-2-[6-chloro-1-(3,3,4,4,4-pentafluorobutyl)-1H-indazol-3-yl]-5-methyl-5-(5-thioxo-4,5-dihydro-1,3,4-oxadiazol-2-yl)-5,7-dihydro-6H-pyrrolo[2,3-d]pyrimidin-6-one Thiophosgene (264 mg, 2.23 mmol) was added to a DCM (6 mL), THF (4 mL) solution of 4-amino-2-[6-chloro-1-(3,3,4,4,4-pentafluorobutyl)-1H-indazol-3-yl]-5-methyl-6-oxo-6,7-dihydro-5H-pyrrolo[2,3-A]pyrimidine-5-carbohydrazide, as described in Step A of Example 166 (1050 mg, 2.03 mmol) at −78° C. The solution was then stirred at 0° C. for 1.5 h. The reaction mixture was then evaporated under reduced pressure. The residue was purified by reverse phase HPLC to give the product as a white solid. $^1$NMR (500 MHz, CD$_3$COCD$_3$) δ 2.037 (s, 3H); 3.12 (m, 2H); 4.95 (t, J=7.1 Hz, 2H); 7.08 (br, 2H); 7.30 (d, J=8.8 Hz, 1H); 7.94 (s, 1H); 8.67 (d, J=8.8 Hz, 1H). m/z=561 (M+H).

Step B: 4-amino-2-[6-chloro-1-(3,3,4,4,4-pentafluorobutyl)-1H-indazol-3-yl]-5-methyl-5-[4-(propan-2-yl)-5-thioxo-4,5-dihydro-1,3,4-oxadiazol-2-yl]-5,7-dihydro-6H-pyrrolo[2,3-d]pyrimidin-6-one The indicated compound was prepared from the intermediate from Step A above, according to the procedure described in Step B in Example 171. Chiral separation using SFC on a Chiralpak AD column provided both enantiomers of the title compound. $^1$NMR (500 MHz, CDCl$_3$) δ 1.43 (s, 3H); 1.45 (s, 3H); 1.91 (s, 3H); 2.61 (m, 2H); 3.85 (m, 1H); 4.61 (t, J=6.4 Hz, 2H); 5.08 (s, 2H); 7.16 (d, J=8.1 Hz, 1H); 7.36 (s, 1H); 8.51 (d, J=8.1 Hz, 1H). m/z=603.03 (M+H).

EXAMPLE 173

4-Amino-5-(1-Ethyl-1H-1,2,3-Triazol-4-yl)-5-Methyl-2-[1-(3,3,4,4,4-Pentafluorobutyl)-1H-Pyrazolo[3,4-B]Pyridin-3-yl]-5,7-Dihydro-6H-Pyrrolo[2,3-D]Pyrimidin-6-One

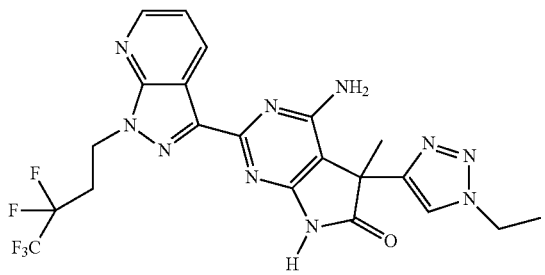 [SMILES: CCn1cc(C2(C)C(=O)Nc3nc(-c4nn(CCC(F)(F)C(F)(F)F)c5ncccc45)nc(N)c32)nn1]

Ethyl azide was prepared by adding iodoethane (59.1 μl, 0.731 mmol) and sodium azide (43.2 mg, 0.665 mmol) to DMF (2.8 mL, 0.08M) in a 4 mL vial wrapped in aluminum foil. After stirring for 12 hours, 4-amino-5-ethynyl-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one (Example 219) (52.7 mg, 0.266 mmol) was added to the ethyl azide DMF solution followed quickly by the addition of copper(II) sulfate (14.14 mg, 0.089 mmol), sodium ascorbate (53 mg, 0.27 mmol) and water (1.5 mL). The reaction was stirred at 40° C. for 24 h. The reaction was partitioned between EtOAc and 5% aqueous ammonium chloride solution. The aqueous layer was extracted with EtOAc. The combined organic layers were dried (sodium sulfate) and concentrated in vacuo. Purification by silica gel column chromatography using hexanes/EtOAc gradient afforded the indicated product as a white solid. Chiral separation using SFC on a Chiralpak IC column provided both enantiomers of the title compound. $^1$H NMR (500 MHz, CHCl$_3$-d): δ 8.92 (s, 1H); 8.85 (d, J=8.09 Hz, 1H); 8.58 (d, J=4.37 Hz, 1H); 7.62 (s, 1H); 7.21 (dd, J=8.05, 4.50 Hz, 1H); 6.85-6.18 (m, 2H); 4.96 (t, J=7.72 Hz, 2H); 4.39 (q, J=7.38 Hz, 2H); 2.90-2.76 (m, 2H); 1.87 (s, 3H); 1.56 (t, J=7.40 Hz, 3H).). m/z=523.1 (M+H).

EXAMPLE 174

4-Amino-5-[(Cyclopropylmethyl)Amino]-5-Methyl-2-[1-(3,3,4,4,4-Pentafluorobutyl)-1H-Pyrazolo[3,4-B]Pyridin-3-yl]-5,7-Dihydro-6H-Pyrrolo[2,3-D]Pyrimidin-6-One

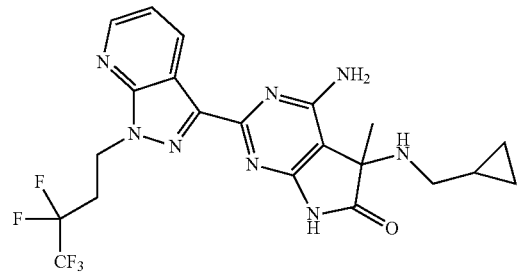 [SMILES: CC1(NCC2CC2)C(=O)Nc2nc(-c3nn(CCC(F)(F)C(F)(F)F)c4ncccc34)nc(N)c21]

Step A: tert-butyl {4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidin-5-yl}carbamate The title compound was prepared using 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbohydrazide, as described in Step A of Example 168 using the procedure described in Example 166 (substituting ethanol with t-butanol). m/z=543.2 (M+H).

Step B: 4,5-diamino-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one The intermediate from Step A (111 mg, 0.205 mmol) was dissolved in DCM (2.0 mL) and trifluoroacetic acid (0.39 mL, 5.12 mmol). The solution was stirred overnight at room temperature. The reaction was then diluted with EtOAc and washed with 1N NaOH aq. (twice) and brine. The solution was then dried over MgSO$_4$, filtered and concentrated in vacuo. The residue was purified by silica gel column chromatography using a MeOH/EtOAc gradient to give the indicated product. m/z=443.1 (M+H).

Step C: 4-amino-5-[(cyclopropylmethyl)amino]-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one To the intermediate from Step B (20 mg, 0.045 mmol) in MeOH (45.2 μl) and DCM (45.2 μl) was added cyclopropanecarbaldehyde (3.17 mg, 0.045 mmol) followed by sodium triacetoxyborohydride (28.7 mg, 0.136 mmol). The reaction was stirred for 3 h at room temperature and was quenched with aqueous NaHCO$_3$. The solution was extracted with EtOAc. The organic layer was dried (sodium sulfate), concentrated in vacuo and purified by silica gel column chromatography to afford the title product as a white solid. $^1$H NMR (500 MHz, CHCl$_3$-d): δ 9.20 (s, 1H); 8.77 (d, J=8.07 Hz, 1H); 8.56 (dd, J=4.53, 1.58 Hz, 1H); 7.13 (dd, J=8.08, 4.50 Hz, 1H); 5.55 (s, 2H); 4.95-4.88 (m, 3H); 2.88-2.74 (m, 2H); 2.27 (dd, J=11.46, 6.00 Hz, 1H); 2.20-1.94 (m, 1H); 1.54 (s, 3H); 0.87-0.80 (m, 1H); 0.48-0.37 (m, 2H); 0.05-0.00 (m, 2H). m/z=497.1 (M+H).

EXAMPLE 175

{4-Amino-2-[6-Chloro-1-(3,3,4,4,4-Pentafluorobutyl)-1H-Indazol-3-yl]-5-Methyl-6-Oxo-6,7-Dihydro-5H-Pyrrolo[2,3-D]Pyrimidin-5-yl}Acetonitrile

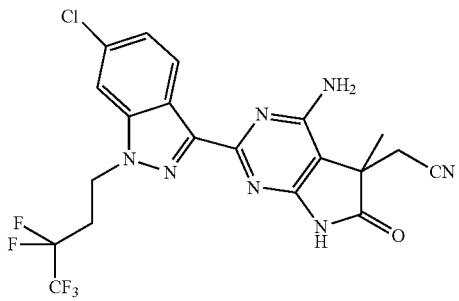 [SMILES: CC1(CC#N)C(=O)Nc2nc(-c3nn(CCC(F)(F)C(F)(F)F)c4cc(Cl)ccc34)nc(N)c21]

Step A: 4-amino-2-[6-chloro-1-(3,3,4,4,4-pentafluorobutyl)-1H-indazol-3-yl]-5-methyl-5,7-dihydro-6H-pyrrolo[2,3-d]pyrimidin-6-one The indicated compound was prepared from Intermediate 24 and the intermediate from Step E in Example 58 using the procedure described in Example 157. m/z=461.1 (M+H).

Step B: tert-butyl 4-amino-2-[6-chloro-1-(3,3,4,4,4-pentafluorobutyl)-1H-indazol-3-yl]-5-methyl-6-oxo-5,6-dihydro-7H-pyrrolo[2,3-d]pyrimidine-7-carboxylate To a solution of the intermediate from Step A above (219 mg, 0.475 mmol) in THF at room temperature was added DMAP (58.1 mg, 0.475 mmol), followed by the dropwise addition of di-tert-butyl dicarbonate (110 µl, 0.475 mmol) as a solution in THF. After stirring at room temperature for 1.5 hours, saturated aqueous NH$_4$Cl was added and the reaction was partitioned between EtOAc and water. The organic layer was dried (sodium sulfate), concentrated in vacuo and purified by silica gel column chromatography using a hexanes/EtOAc gradient to afford the product as a white solid. ln/z=559.14 (M−H).

Step C {4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}acetonitrile A solution of the intermediate from Step B above (102 mg, 0.182 mmol) stirred in THF (3566 µl) was added 2-tert-butyl-1,1,3,3-tetramethylguanidine (34.2 µl, 0.182 mmol) followed by 2-bromoacetonitrile (19.02 µl, 0.273 mmol). After stirring for 5 minutes at room temperature, saturated aqueous NH$_4$Cl was added. The reaction mixture reaction was then partitioned between EtOAc and water. The organic layer was dried (sodium sulfate), filtered and concentrated in vacuo. The crude material was taken up in DCM (1 mL) and TFA (280 µl, 3.64 mmol) was added. After 3 hours the reaction was quenched with aq. NaHCO$_3$ and partitioned between water and EtOAc. The organic layer was dried, concentrated in vacuo and purified by silica gel column chromatography using a hexanes/EtOAc gradient to afford the product as a white solid. Chiral separation using SFC provided both enantiomers of the title compound. $^1$H NMR (500 MHz, CHCl$_3$-d): δ 8.45 (d, J=8.72 Hz, 1H); 7.43 (s, 1H); 7.18 (dd, J=8.75, 1.62 Hz, 1H); 5.48 (s, 2H); 4.71 (t, J=7.69 Hz, 2H); 2.99 (d, J=16.98 Hz, 1H); 2.81-2.68 (m, 2H); 2.67 (d, J=16.98 Hz, 1H); 1.68 (s, 3H). m/z=500.0 (M+H).

EXAMPLE 176

4-Amino-2-(6-Chloro-1-(3,3,4,4,4-Pentafluorobutyl)-1H-Pyrazolo[3,4-B]Pyridin-3-yl)-N-Cyclopropyl-5-Methyl-6-Oxo-6,7-Dihydro-5H-Pyrrolo[2,3-D]Pyrimidine-5-Carboxamide

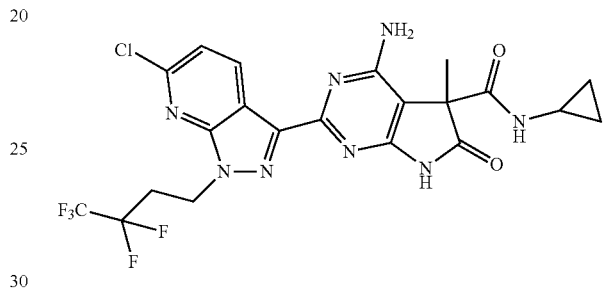

Step A: 3-cyano-1-(3,3,4,4,4-pentafluorobutyl)-1H-pyrazolo[3,4-b]pyridine 7-oxide 1-(3,3,4,4,4-pentafluorobutyl)-1H-pyrazolo[3,4-b]pyridine-3-carbonitrile, as described in Step D of Example 158 (1.818 g, 6.26 mmol) and 3-chloroperbenzoic acid (7.1 g, 31.68 mmol, 77%) in acetic acid (20 mL) were stirred at 75° C. for 6 hours. The reaction was then evaporated under reduced pressure to remove acetic acid. To the residue was added a mixture of hexane/ethyl acetate (2/1, 200 mL total) and the pH adjusted to 7.0~7.5 with aq. K$_2$CO$_3$ at 0° C. The water layer was extracted with hexane/ethyl acetate (2/1, 2×60 mL). The combined organic layer was dried over MgSO$_4$ and evaporated under reduced pressure. The residue was purified by silica gel column chromatography using hexanes/ethyl acetate eluent to give the desired product as a white solid. $^1$H NMR (500 MHz, CDCl$_3$): δ 2.86 (m, 2H); 5.44 (t, J=7.3 Hz, 2H); 7.31 (t, J=8.2 Hz, 1H); 7.80 (d, J=8.4 Hz, 1H); 8.38 (d, J=5.1 Hz, 1H). m/z=307.02 (M+H).

Step B: 6-chloro-1-(3,3,4,4,4-pentafluorobutyl)-1H-pyrazolo[3,4-b]pyridine-3-carbonitrile To the intermediate from Step A above (225 mg, 0.735 mmol) was added POCl$_3$ (2.8 g, 18.3 mmol) and the mixture was stirred at 75° C. for 9 hours. The reaction mixture was then concentrated in vacuo to remove POCl$_3$. To the residue was added hexane/ethyl acetate (2/1, 50 mL) and the pH adjusted to 7.5~8.0 with aqueous K$_2$CO$_3$ at 0° C. The water layer was extracted with the hexane/ethyl acetate (2/1, 2×20 mL). The combined organic layer was dried over Na$_2$SO$_4$ and evaporated under reduced pressure. The residue was purified by silica gel column chromatography using hexane/ethyl acetate eluent to give the product as a white solid. $^1$H NMR (500 MHz, CDCl$_3$): δ 2.86 (m, 2H); 4.90 (t, J=8.4 Hz, 2H); 7.42 (d, J=8.4 Hz, 1H); 8.17 (d, J=8.4 Hz, 1H), m/z=325.04 (M+H).

Step C: 6-chloro-1-(3,3,4,4,4-pentafluorobutyl)-1H-pyrazolo[3,4-b]pyridine-3-carboximidamide The title compound was prepared from the intermediate from Step B above using the procedure described in Step E of Example 158. m/z=341.94 (M+H).

Step D: ethyl 4-amino-2-(6-chloro-1-(3,3,4,4,4-pentafluorobutyl)-1H-pyrazolo[3,4-b]pyridin-3-yl)-5-methyl-6-oxo-6,7-dihydro-5H-pyrrolo[2,3-d]pyrimidine-5-carboxylate The title compound was prepared from the intermediate from Step C above and Intermediate 22 using the procedure described in Step F of Example 158. $^1$H NMR (500 MHz, CDCl$_3$): δ 1.27 (t, J=7.1 Hz, 3H); 1.79 (s, 3H); 2.84 (m, 2H); 4.27 (t, J=7.1 Hz, 2H); 4.93 (t, J=7.7 Hz, 2H); 5.50 (s, 2H); 7.22 (d, J=8.4 Hz, 1H); 8.76 (d, J=8.5 Hz, 1H); 8.80 (br, 1H), m/z=534.08 (M+H).

Step E: 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide The title compound was prepared from the intermediate from Step D above according to the procedure described in Example 160. Chiral separation using SFC on a Chiralcel OD column provided both enantiomers of the title compound. $^1$NMR (500 MHz, CDCl$_3$): δ 0.58 (m, 2H); 0.84 (M, 2H); 1.80 (s, 3H); 2.77 (m, 1H); 2.86 (m, 2H); 4.91 (m, 2H); 7.25 (d, J=8.3 Hz, 1H); 7.29 (s, 1H); 8.78 (d, J=8.4 Hz, 1H); 9.31 (br, 1H). m/z=545.15 (M+H).

EXAMPLE 177

4-Amino-2-(6-Cyano-1-(3,3,4,4,4-Pentafluorobutyl)-1H-Pyrazolo[3,4-B]Pyridin-3-yl)-N-Cyclopropyl-5-Methyl-6-Oxo-6,7-Dihydro-5H-Pyrrolo[2,3-D]Pyrimidine-5-Carboxamide

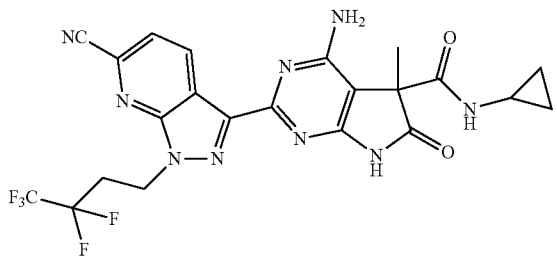 [SMILES: CC1(C(=O)NC2CC2)C(=O)Nc2nc(-c3nn(CCC(F)(F)C(F)(F)F)c4nc(C#N)ccc34)nc(N)c21]

A DMF (4 mL) solution containing 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide, as described in Example 176, (149 mg, 0.273 mmol), zinc cyanide (19.3 mg, 0.164 mmol), 1,1'-bis(diphenylphosphino)ferrocene (15.16 mg, 0.027 mmol), and tris(dibenzylideneacetone)dipalladium (0) (12.52 mg, 0.014 mmol) was degassed for 1 hour at rt. The reaction mixture was then stirred for 15 hours at 130° C. The reaction mixture was then cooled and ethyl acetate (30 mL) and water (10 mL) were added. The water layer was extracted with ethyl acetate (3×20 mL). The combined organic layer was dried over Na$_2$SO$_4$ and evaporated under reduced pressure. The residue was purified by reverse phase HPLC to afford the indicated product. Chiral separation using SFC on a Chiralcel OD column provided both enantiomers of the title compound. $^1$NMR (500 MHz, CD$_3$COCD$_3$): δ 0.56 (m, 2H); 0.71 (M, 2H); 1.73 (s, 3H); 2.77 (m, 1H); 3.06 (m, 2H); 5.02 (t, J=7.0 Hz, 2H); 7.00 (br, 2H); 7.52 (br, 1H); 7.84 (d, J=8.2 Hz, 1H); 9.28 (d, J=8.2 Hz, 1H). m/z=536.1 (M+H).

EXAMPLE 178

4-Amino-N-Cyclopropyl-2-(6-Methoxy-1-(3,3,4,4,4-Pentafluorobutyl)-1H-Pyrazolo[3,4-B]Pyridin-3-yl)-5-Methyl-6-Oxo-6,7-Dihydro-5H-Pyrrolo[2,3-D]Pyrimidine-5-Carboxamide

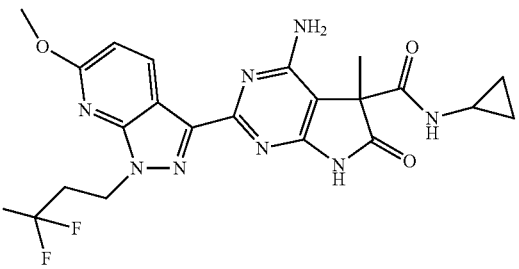

A methanol (1.5 mL, anhydrous) solution containing 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide, as described in Example 176, (62 mg, 0.114 mmol) and sodium methoxide (0.21 ml, 0.91 mmol, 25% in methanol) was stirred for 10 hours at 60° C. The reaction mixture was cooled and adjusted to pH 7.0 with 2N HCl aq. at 0° C. The residue was purified by reverse phase HPLC to afford the indicated product. Chiral separation using SFC on a Chiralcel OJ column provided both enantiomers of the title compound. $^1$H NMR (500 MHz, CD$_3$COCD$_3$): δ 0.61 (m, 2H); 0.77 (M, 2H); 1.83 (s, 3H); 2.85 (m, 1H); 3.04 (m, 2H); 4.05 (s, 3H); 4.88 (m, 2H); 6.78 (d, J=8.7 Hz, 2H); 7.72 (br, 1H); 7.84 (d, J=8.6 Hz, 1H); 9.13 (d, J=8.6 Hz, 1H). m/z=541.21 (M+H).

EXAMPLE 179

4-Amino-N-Cyclopropyl-5-Methyl-2-(6-Methyl-1-(3,3,4,4,4-Pentafluorobutyl)-1H-Pyrazolo[3,4-B]Pyridin-3-yl)-6-Oxo-6,7-Dihydro-5H-Pyrrolo[2,3-D]Pyrimidine-5-Carboxamide

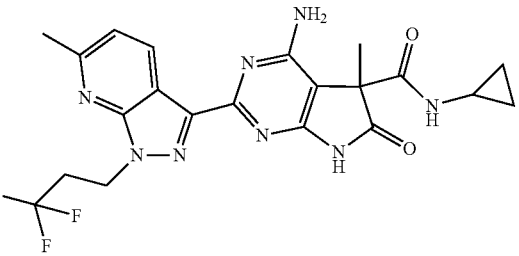

Methylmagnesium bromide (0.42 ml, 0.584 mmol, 1.4 M in THF) was added to a THF (1.2 ml) and NMP (0.3 ml) solution containing 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide, as described in Example 176, (53 mg, 0.097 mmol) and iron(111) acetylacetonate (34.4 mg, 0.097 mmol). After stirring at rt for 30 min. the reaction mixture was adjusted to pH 7 with 1N HCl at 0° C. The reaction mixture was filtered through a plug of Celite™ (diatomaceous earth) and the filtrate was washed with ethyl acetate (30 mL). The combined organic fractions were evaporated under reduced pressure. The residue was purified by reverse phase HPLC to afford the indicated product. Chiral separation using SFC on a Chiralcel OJ column provided both enantiomers of the title compound. $^1$H NMR (500 MHz, CD$_3$COCD$_3$): δ 0.58 (m, 2H); 0.73 (M, 2H); 1.78 (s, 3H); 2.68 (s, 3H), 2.80 (m, 1H); 3.10 (m, 2H); 4.94 (t, J=7.1 Hz, 2H); 7.26 (d, J=8.2 Hz, 2H); 7.52 (br, 1H); 7.79 (br, 1H); 8.74 (d, J=8.2 Hz, 1H). m/z=525.17 (M+H).

EXAMPLE 180

4-Amino-5-[1-(Cyclopropylmethyl)-1H-1,2,3-Triazol-4-yl]-5-Methyl-2-[1-(3,3,3-Trifluoropropyl)-1H-Pyrazolo[3,4-B]Pyridin-3-yl]-5,7-Dihydro-6H-Pyrrolo[2,3-D]Pyrimidin-6-One

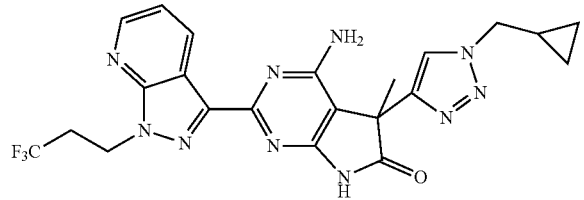 [SMILES: CC1(c2cn(CC3CC3)nn2)C(=O)Nc2nc(-c3nn(CCC(F)(F)F)c4ncccc34)nc(N)c21]

Step A: 1-(3,3,3-trifluoropropyl)-1H-pyrazolo[3,4-b]pyridine-3-carbonitrile 1H-pyrazolo[3,4-b]pyridine-3-carbonitrile, as described in Step C of Example 158 (30 g, 208 mmol), 3-bromo-1,1,1-trifluoropropane (44.5 mL, 416 mmol) and potassium carbonate (95 g, 687 mmol) were combined in a flask with acetonitrile (300 mL) and stirred at 40° C. After 5 h, the reaction was cooled to rt and EtOAc and water were added. The layers were separated and the aqueous layer was washed two times with EtOAc. The combined organics were dried (Na$_2$SO$_4$) and filtered. The solvent was removed under reduced pressure and the material was used without further purification. $^1$H NMR (500 MHz, DMSO-d$_6$): δ 8.77 (d, J=4.50 Hz, 1H); 8.46 (d, J=8.23 Hz, 1H); 7.51 (dd, J=8.22, 4.47 Hz, 1H); 4.86 (t, J=6.66 Hz, 2H); 3.10-2.98 (m, 2H). m/z=241.1 (M+H).

Step B: 1-(3,3,3-trifluoropropyl)-1H-pyrazolo[3,4-b]pyridine-3-carboximidamide

To the intermediate from Step A above (44.4 g, 185 mmol) in MeOH (16 mL) at rt was added sodium methoxide (13.98 g, 259 mmol). After stirring for 3 hours, acetic acid (42.3 mL, 739 mmol) and ammonium chloride (12.85 g, 240 mmol) were added to the reaction. The resulting slurry was heated to 65° C. and stirred for 4 hours. The reaction was then cooled to rt and quenched with EtOAc and saturated aqueous NaHCO$_3$. The aqueous layer was removed and back extracted with EtOAc (4×). The combined organic layers were washed with 20% brine and dried over Na$_2$SO$_4$, filtered and the solvent removed under vacuum. EtOAc was added and the precipitated product was filtered and washed with methyl tert-butyl ether. The solid was dried at rt under vacuum oven overnight and the material used without further purification. $^1$H NMR (500 MHz, CH$_3$OH-d$_4$): δ 8.74 (d, J=4.57 Hz, 1H); 8.52 (d, J=8.32 Hz, 1H); 7.51 (dd, J=8.31, 4.44 Hz, 1H); 4.96 (t, J=6.91 Hz, 3H); 3.08-2.97 (m, 2H). m/z=258.3 (M+H).

Step C: 4-amino-5-ethynyl-5-methyl-2-[1-(3,3,3-trifluoropropyl)-1H-pyrazolo[3,4-b]pyridin-3-yl]-5,7-dihydro-6H-pyrrolo[2,3-d]pyrimidin-6-one The intermediate from Step B above (750 mg, 2.92 mmol), Intermediate 25 (555 mg, 2.92 mmol) and potassium bicarbonate (613 mg, 6.12 mmol) were combined in a flask followed by the addition of t-BuOH (7.3 mL). The reaction was heated to 80° C. and stirred for 16 hours. The reaction was quenched with saturated aqueous ammonium chloride and diluted with water and EtOAc. The organic layer was separated and dried (sodium sulfate). Purification by silica gel column chromatography using a hexanes/EtOAc gradient afforded the product as an off-white solid. $^1$H NMR (500 MHz, CHCl$_3$-d): δ 8.85 (d, J=7.91 Hz, 1H); 8.60 (d, J=4.48 Hz, 1H); 7.26 (s, 1H); 5.18 (s, 2H); 4.92 (t, J=7.59 Hz, 2H); 2.96-2.84 (m, 2H); 2.51 (s, 1H); 1.78 (s, 3H). m/z=402.1 (M+H).

Step D: 4-amino-5-[1-(cyclopropylmethyl)-1H-1,2,3-triazol-4-yl]-5-methyl-2-[1-(3,3,3-trifluoropropyl)-1H-pyrazolo[3,4-b]pyridin-3-yl]-5,7-dihydro-6H-pyrrolo[2,3-d]pyrimidin-6-one To (bromomethyl)cyclopropane (150 mg, 0.822 mmol) in DMF (2492 µl) was added sodium azide (50.2 mg, 0.772 mmol) in a 4 mL vial wrapped in aluminum foil. The solution was left to stir for 16 hours at rt. To the azide solution was added water (1.5 mL), the intermediate from Step C (100 mg, 0.249 mmol), copper(II) sulfate (15.91 mg, 0.100 mmol) and sodium ascorbate (49.4 mg, 0.249 mmol). The solution was heated to 40° C. and stirred for an additional 24 h. The reaction was then filtered through a pad of Celite™ (diatomaceous earth) and partitioned between EtOAc and water. The organic layer was separated, dried (sodium sulfate) and concentrated in vacuo under vacuum. Purification by silica gel column chromatography using a hexanes/EtOAc gradient afforded the product as a white solid. Chiral separation using SFC provided both enantiomers of the title compound. $^1$H NMR (500 MHz, CHCl$_2$-d): δ 8.86 (dd, J=8.06, 1.59 Hz, 1H); 8.58 (dd, J=4.52, 1.57 Hz, 1H); 7.71 (s, 1H); 7.22 (dd, J=8.08, 4.50 Hz, 1H); 4.90 (dd, J=9.19, 6.28 Hz, 2H); 4.25-4.13 (m, 2H); 2.95-2.83 (m, 2H); 1.88 (s, 3H); 1.33-1.24 (m, 1H); 0.73-0.68 (m, 2H); 0.45-0.41 (m, 2H). m/z=499.1 (M+H).

EXAMPLE 181

4-Amino-N-Cyclopropyl-5-Methyl-6-Oxo-2-[1-(3,3,3-Trifluoropropyl)-1H-Pyrazolo[3,4-B]Pyridin-3-yl]-6,7-Dihydro-5H-Pyrrolo[2,3-D]Pyrimidine-5-Carboxamide

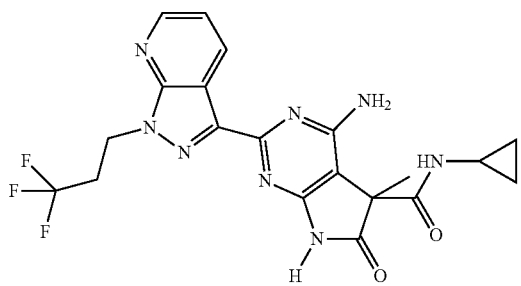 [SMILES: CC1(C(=O)NC2CC2)C(=O)Nc2nc(-c3nn(CCC(F)(F)F)c4ncccc34)nc(N)c21]

Step A: ethyl 4-amino-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxylate The title compound was prepared from 1-(3,3,3-trifluoropropyl)-1H-pyrazolo[3,4-b]pyridine-3-carboximidamide, as described in Step B of Example 180 using the procedures described in Example 158. m/z=450.1 (M+H).

Step. B: 4-amino-N-cyclopropyl-5-methyl-6-oxo-2-[1-(3,3,3-trifluoropropyl-1H-pyrazolo[3,4-b]pyridin-3-yl]-6,7-dihydro-5H-pyrrolo[2,3-d]pyrimidine-5-carboxamide To the intermediate from Step A above (165 mg, 0.367 mmol) was added cyclopropylamine (3.31 mL, 47.7 mmol) and the resultant mixture heated to 50° C. for 16 hours. The reaction mixture was concentrated in vacuo and the residue purified by silica gel column chromatography using a DCM/MeOH (with 0.5% NH$_4$OH) gradient. Chiral separation using SFC on a Chiralcel OJ-H column provided both enantiomers of the title compound. $^1$H NMR (500 MHz, DMSO-d$_6$): δ 11.23 (1H, s), 9.02 (1H, dd, J=8.08, 1.55 Hz), 8.62 (1H, dd, J=4.50, 1.57 Hz), 7.64 (1H, d, J=4.05 Hz), 7.37 (1H, dd, J=8.08, 4.49 Hz), 6.76 (2H, s), 4.81 (2H, t, J=6.60 Hz), 3.06-2.94 (2H, m), 2.67-2.60 (1H, m), 1.55 (3H, s), 0.62-0.53 (2H, m), 0.50-0.41 (2H, m). m/z=461.3 (M+H).

EXAMPLE 182

4-Amino-5-Methyl-6-Oxo-N-(Pyridin-3-yl)-2-[1-(3,3,3-Trifluoropropyl)-1H-Pyrazolo[3,4-B]Pyridin-3-yl]-6,7-Dihydro-5H-Pyrrolo[2,3-D]Pyrimidine-5-Carboxamide

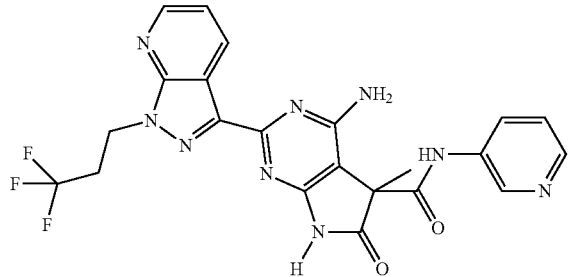 [SMILES: CC1(C(=O)Nc2cccnc2)C(=O)Nc2nc(-c3nn(CCC(F)(F)F)c4ncccc34)nc(N)c21]

Step A: 4-amino-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carbohydrazide The title compound was prepared from ethyl 4-amino-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxylate, as described in Step A of Example 181 using the procedure described in Step A of Example 168. m/z=436.1 (M+H).

Step B: 4-amino-5-methyl-6-oxo-N-(pyridin-3-yl)-2-[1-(3,3,3-trifluoropropyl)-1H-pyrazolo[3,4-b]pyridin-3-yl]-6,7-dihydro-5H-pyrrolo[2,3-d]pyrimidine-5-carboxamide To a THF solution (2 mL) of the intermediate from Step A (227 mg, 0.521 mmol) at 0° C. was added trifluoroacetic acid (0.044 mL, 0.574 mmol) and tert-butyl nitrite (0.186 mL, 1.564 mmol). After stirring at 0° C. for 30 minutes, the mixture was concentrated in vacuo, ensuring that the temperature was maintained below 40° C. The residue was suspended in acetonitrile (3 mL), cooled to 0° C., and 3-aminopyridine (245 mg, 2.61 mmol) was added in one portion. The resultant mixture was heated to 40° C. for one hour, and then stirred at ambient temperature for 16 hours. The mixture was concentrated in vacuo, suspended in EtOAc and washed sequentially with water (4×), saturated aqueous ammonium chloride solution (2×), and brine. The organic layer was dried over MgSO$_4$, filtered, and concentrated in vacuo. Purification by silica gel column chromatography using DCM/MeOH (with 0.5% NH$_4$OH) gradient provided the title compound. Chiral separation using SFC on a Chiralpak IC column provided both enantiomers of the title compound, $^1$H NMR (500 MHz, DMSO-d$_6$): δ 9.53 (1H, s), 9.05 (1H, dd, J=8.08, 1.58 Hz), 8.77 (1H, d, J=2.48 Hz), 8.63 (1H, dd, J=4.47, 1.58 Hz), 8.28 (1H, d, J=4.69 Hz), 8.00 (1H, d, J=8.47 Hz), 7.36 (2H, ddd, J=21.65, 8.21, 4.57 Hz), 6.86 (2H, s), 4.85-4.77 (2H, m), 3.06-2.95 (2H, m), 1.72 (3H, s). m/z=498.2 (M+H).

EXAMPLE 183

4-Amino-2-[6-Chloro-1-(3,3,3-Trifluoropropyl)-1H-Pyrazolo[3,4-B]Pyridin-3-yl]-N-Cyclopropyl-5-Methyl-6-Oxo-6,7-Dihydro-5H-Pyrrolo[2,3-D]Pyrimidine-5-Carboxamide

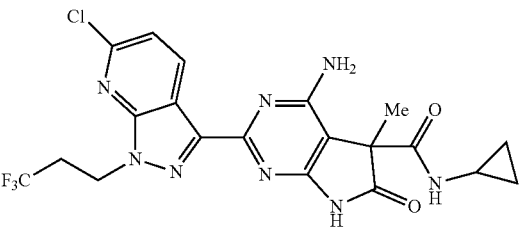 [SMILES: CC1(C(=O)NC2CC2)C(=O)Nc2nc(-c3nn(CCC(F)(F)F)c4nc(Cl)ccc34)nc(N)c21]

Step A: 1-(3,3,3-trifluoropropyl)-1H-pyrazolo[3,4-b]pyridine-3-carbonitrile 7-oxide The title compound was prepared from 1-(3,3,3-trifluoropropyl)-1H-pyrazolo[3,4-b]pyridine-3-carbonitrile, as described in Step A of Example 180 according to the procedure described in Step A of Example 176. m/z=257.0 (M+H).

Step B: 6-chloro-1-(3,33-trifluoropropyl)-1H-pyrazolo[3,4-b]pyridine-3-carbonitrile The title compound was prepared from the intermediate from Step A above according to the procedure described Step B of Example 176. m/z=275.0 (M+H).

Step C: 6-chloro-1-(3,3,3-trifluoropropyl)-1H-pyrazolo[3,4-b]pyridine-3-carboximidamide The title compound was prepared from the intermediate from Step B above according to the procedure described for Step E of Example 158. m/z=292.2 (M+H).

Step D: Ethyl 4-amino-2-[6-chloro-1-(3,3,3-trifluoropropyl)-1H-pyrazolo[3,4-b]pyridin-3-yl]-5-methyl-6-oxo-6,7-dihydro-5H-pyrrolo[2,3-d]pyrimidine-5-carboxylate The title compound was prepared from the intermediate from Step C above according to the procedure described for Step F of Example 158. m/z=484.0 (M+H).

Step E: 4-amino-2-[6-chloro-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide The title compound was prepared from the intermediate from Step D above according to the procedure described for Example 160. $^1$NMR (500 MHz, CD$_3$COCD$_3$): δ 8.99 (d, J=8.2 Hz, 1H); 7.50 (br, 1H); 7.34 (d, J=8.2 Hz, 2H); 7.08 (br, 2H); 4.88 (t, J=7.0 Hz, 2H); 3.10 (m, 2H); 2.80 (m, 1H); 1.75 (s, 3H); 0.72 (m, 2H) 0.56 (m, 2H). m/z=495.0 (M+H).

EXAMPLE 184

4-Amino-N-Cyclopropyl-5-Methyl-2-[6-Methyl-1-(3,3,3-Trifluoropropyl)-1H-Pyrazolo[3,4-B]Pyridin-3-yl]-6-Oxo-6,7-Dihydro-5H-Pyrrolo[2,3-D]Pyrimidine-5-Carboxamide

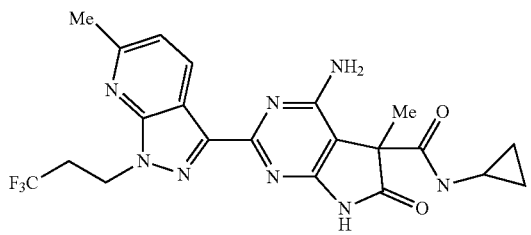 [SMILES: Cc1ccc2c(-c3nc(N)c4c(n3)NC(=O)C4(C)C(=O)NC3CC3)nn(CCC(F)(F)F)c2n1]

Methyl magnesium bromide (2.08 mL, 2.91 mmol, 1.4 M in THF) was added to 4-amino-2-[6-chloro-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, as described in Example 183, (240 mg, 0.485 mmol) and iron(111) acetylacetonate (171 mg, 0.485 mmol) in THF (2.8 mL) and NMP (0.7 mL). The solution was then stirred for 30 min. at rt. The reaction mixture was adjusted to pH 7.0 with 1N HCl at 0° C. The reaction mixture was filtered through a plug of Celite™ (diatomaceous earth) and the filtrate was washed with EtOAc (30 mL). The combined organic fractions were evaporated under reduced pressure. The residue was purified by reverse phase HPLC to afford the product as a white solid. Chiral separation using SFC provided both enantiomers of the title compound. $^1$H NMR (500 MHz, CD$_3$COCD$_3$): δ 8.87 (d, J=8.2 Hz, 1H); 7.53 (br, 1H); 7.22 (d, J=8.2 Hz, 2H); 7.10 (br, 1H); 4.89 (t, J=7.0 Hz, 2H); 3.06 (m, 2H); 2.79 (m, 1H); 2.67 (s, 3H); 1.73 (s, 3H); 0.72 (m, 2H); 0.56 (m, 2H). m/z=475.1 (M+H).

EXAMPLE 185

4-Amino-N-Cyclopropyl-2-[6-Methoxy-1-(3,3,3-Trifluoropropyl)-1H-Pyrazolo[3,4-B]Pyridin-3-yl]-5-Methyl-6-Oxo-6,7-Dihydro-5H-Pyrrolo[2,3-D]Pyrimidine-5-Carboxamide

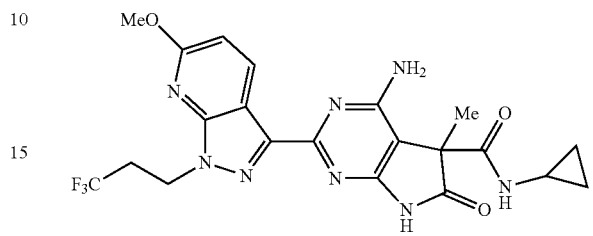

The title compound was prepared from 4-amino-2-[6-chloro-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, as described in Example 183, according to the procedure described for Example 178. $^1$H NMR (500 MHz, CD$_3$COCD$_3$): δ 8.80 (d, J=8.6 Hz, 2H); 7.65 (br, 1H); 6.96 (br, 2H); 6.70 (d, J=8.6 Hz, 1H); 4.80 (m, 2H); 4.03 (s, 3H); 3.02 (m, 2H); 2.78 (m, 1H); 1.70 (s, 3H); 0.72 (m, 2H); 0.54 (m, 2H). m/z=491.0 (M+H).

EXAMPLE 186

5-Methyl-4-(Methylamino)-2-[1-(3,3,4,4,4-Pentafluorobutyl)-1H-Pyrazolo[3,4-B]Pyridin-3-yl]-5-Phenyl-5,7-Dihydro-6H-Pyrrolo[2,3-D]Pyrimidin-6-One

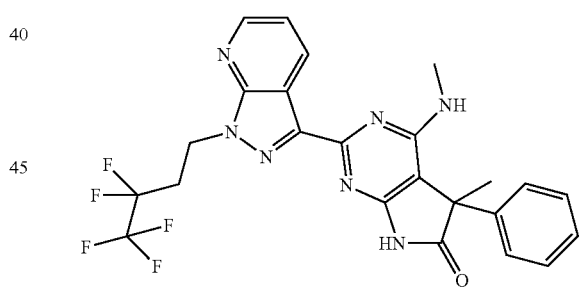

Step A: 4-bromo-5-methyl-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one 4-amino-5-methyl-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one (Example 84) (294 mg, 0.584 mmol), tert-butyl nitrite (0.104 mL, 0.876 mmol), copper (II) bromide (157 mg, 0.701 mmol) and 1,2-dichloroethane (10 mL) were mixed in a sealed tube and heated at 65° C. for 5 h. The crude reaction mixture was partitioned between water and DCM. The separated aqueous phase was back extracted with EtOAc. The combined organic extracts were concentrated in vacuo. The residue was purified by reverse phase HPLC to give the title product, as a solid. m/z=567.1 (M+H).

Step B: -methyl-4-(methylamino)-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one The intermediate from Step A above (100 mg, 0.176 mmol), methylamine (0.881 mL, 1.763 mmo, 2 M in THF) and THF (2 mL) were sealed in a microwave tube and subject to microwave irradiation at 140° C. for 2 h. The reaction mixture was partitioned between brine and EtOAc. The combined organic extracts were dried ($Na_2SO_4$), filtered and concentrated in vacuo. The residue was purified by reverse phase HPLC to give the title product, as a solid. $^1$H NMR (500 MHz, $CD_3OD$) δ 9.01 (dd, J=8.1, 1.6 Hz, 1H); 8.6 (dd, J=4.5, 1.6 Hz, 1H); 7.39-7.32 (m, 5H); 7.32-7.27 (m, 1H); 4.96 (t, J=7.3 Hz, 3H); 3.07 (s, 3H); 3.05-2.91 (m, 2H); 1.88 (s, 3H). m/z=518.1 (M+H).

EXAMPLE 187

N-Cyclopropyl-5-Methyl-4-(Methylamino)-6-Oxo-2-[1-(3,3,4,4,4-Pentafluorobutyl)-1H-Pyrazolo[3,4-B]Pyridin-3-yl]-6,7-Dihydro-5H-Pyrrolo[2,3-D]Pyrimidine-5-Carboxamide

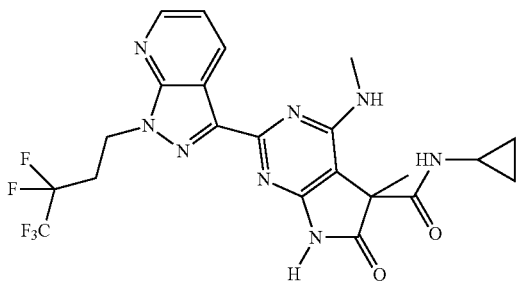 [SMILES: CNc1nc(-c2nn(CCC(F)(F)C(F)(F)F)c3ncccc23)nc2c1C(C)(C(=O)NC1CC1)C(=O)N2]

Step A: ethyl 4-bromo-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate, as prepared by the procedure described in Example 158, (615 mg, 1.231 mmol), tert-butyl nitrite (0.220 mL, 1.847 mmol), copper (II) bromide (330 mg, 1.478 mmol) and 1,2-dichloroethane (20 mL) were mixed in a sealed tube and heated at 65° C. for 2 h. The reaction mixture was partitioned between water and DCM. The separated aqueous phase was back extracted with EtOAc. The combined organic extracts were concentrated in vacuo. The residue was purified by reverse phase preparative HPLC to afford the title product, as a solid. m/z=563.1 (M+H).

Step B: ethyl 5-methyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate The intermediate from Step A above (190 mg, 0.337 mmol), methylamine (2M in THF) (0.843 mL, 1.687 mmol) and THF (2 mL) were sealed in a microwave tube and subjected to microwave irradiation at 150° C. for 3 h. The reaction mixture was partitioned between brine and EtOAc. The combined organic extracts were dried ($Na_2SO_4$), filtered and concentrated in vacuo to afford a dark solid. The residue was purified by reverse phase preparative HPLC to give the title product, as a solid. $^1$H NMR (500 MHz, DMSO-$d_6$): δ 11.35 (s, 1H); 8.87 (d, J=8.1 Hz, 1H); 8.64-8.62 (m, 1H); 7.39 (dd, J=8.1, 4.5 Hz, 1H); 6.61 (d, J=4.9 Hz, 1H); 4.88 (t, J=6.8 Hz, 2H); 4.12-4.07 (m, 2H); 3.04-2.90 (m, 5H); 1.61 (s, 3H); 1.09 (t, J=7.1 Hz, 3H). m/z=514.1 (M+H).

Step C: N-cyclopropyl-5-methyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide The intermediate from Step B above (65 mg, 0.127 mmol) and cyclopropylamine (0.088 mL, 1.266 mmol) in MeOH (1 mL) were sealed in a microwave tube and heated at 80° C. for 2 days.

The reaction mixture was concentrated in vacuo. The resulting crude material was partitioned between brine and EtOAc. The combined organic extracts were dried ($Na_2SO_4$), filtered and concentrated in vacuo. The residue was purified by reverse phase HPLC to afford the title compound. Chiral separation using SFC on a Chiralpak AD column provided both enantiomers of the title compound. $^1$H NMR (500 MHz, $CD_3OD$): δ 8.97 (dd, J=8.1, 1.6 Hz, 1H); 8.60 (dd, J=4.5, 1.6 Hz, 1H); 7.35 (dd, J=8.1, 4.5 Hz, 1H); 4.93 (t, J=1.4 Hz, 2H); 3.18 (s, 3H); 3.02-2.89 (m, 2H); 2.69 (tt, J=7.2, 3.9 Hz, 1H); 1.69 (s, 3H); 0.78-0.69 (m, 2H); 0.58-0.49 (m, 2H). m/z=525.1 (M+H).

EXAMPLE 188

2-[6-Chloro-1-(3,3,4,4,4-Pentafluorobutyl)-1H-Indazol-3-yl]-5-Methyl-4-(Methylamino)-5-Phenyl-5,7-Dihydro-6H-Pyrrolo[2,3-D]Pyrimidin-6-One

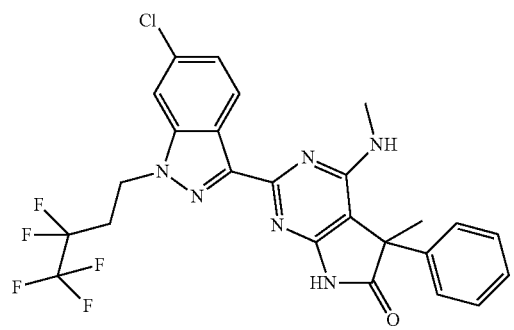 [SMILES: CNc1nc(-c2nn(CCC(F)(F)C(F)(F)F)c3cc(Cl)ccc23)nc2c1C(C)(c1ccccc1)C(=O)N2]

Step A: 4-brom-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one, as described in Example 58, (450 mg, 0.838 mmol), text-butyl nitrite (0.199 mL, 1.676 mmol), copper (II) bromide (225 mg, 1.006 mmol) and 1,2-dichloroethane (8.5 mL) were mixed in a sealed tube and heated at 65° C. overnight. The reaction mixture was partitioned between water and DCM. The combined organic extracts were dried ($Na_2SO_4$), filtered and concentrated in vacuo to afford a dark mixture. The residue was purified by reverse phase HPLC to afford the title product, as a solid. m/z=599.9 (M+H).

Step B: 2-[6-chloro-1-(3,3,4,4,4-pentafluorobutyl)-1H-indazol-3-yl]-5-methyl-4-ethylamino)-5-phenyl-5,7-dihydro-6H-pyrrolo[2,3-d]pyrimidin-6-one The intermediate from Step A above (35 mg, 0.058 mmol), methylamine (0.058 mL, 0.117 mmol, 2M in THF) and THF (0.5 mL) were stirred in a sealed tube at 50° C. for 1.5 h, then at 65° C. overnight. The reaction mixture was subjected to microwave irradiation at 150° C. for 2 h, The reaction mixture was partitioned between brine and EtOAc. The combined organic extracts were dried ($Na_2SO_4$), filtered and concentrated in vacuo. The residue was purified by reverse phase HPLC to afford the indicated product, as a solid. $^1$H NMR (500 MHz, $CD_3OD$): δ 8.64 (d, J=8.7 Hz, 1H); 7.77 (d, J=1.6 Hz, 1H); 7.38-7.31 (m, 4H); 7.32-7.28 (m, 2H); 4.82 (d, 7.1 Hz, 2H); 3.07 (s, 3H); 3.00-2.88 (m, 2H); 1.88 (s, 3H). m/z=551.0 (WE).

EXAMPLE 189

5-Methyl-4-(Methylamino)-5-(5-Methyl-1,3,4-Oxadiazol-2-yl)-2-[1-(3,3,4,4,4-Pentafluorobutyl)-1H-Pyrazolo [3,4-B]Pyridin-3-yl]-5,7-Dihydro-6H-Pyrrolo[2,3-D]Pyrimidin-6-One

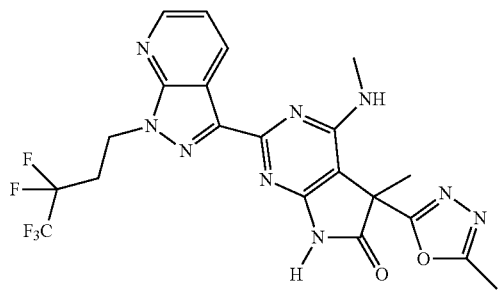 [SMILES: CNc1nc(-c2nn(CCC(F)(F)C(F)(F)F)c3ncccc23)nc2c1C(C)(c1nnc(C)o1)C(=O)N2]

Step A: 4-bromo-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one To a 1,2-dichloroethane (3 mL) solution of 4-amino-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, as described in Example 169, (144 mg, 0.283 mmol) in a screw-cap vial was added $CuBr_2$ (126 mg, 0.565 mmol) and tert-butyl nitrite (0.067 mL, 0.565 mmol). The vial was purged with nitrogen, capped, and heated at 65° C. for 45 minutes. An additional amount of $CuBr_2$ (126 mg, 0.565 mmol) and tert-butyl nitrite (0.067 mL, 0.565 mmol) was added and the reaction solution was heated for 1 hour. The reaction mixture was cooled, diluted with DCM and washed with a 0.1 M aqueous ethylenediaminetetraacetic acid solution. The aqueous layer was back-extracted with EtOAc and the organic layers were combined, dried over $MgSO_4$, filtered, and concentrated in vacuo. Purification by preparative TLC using 5% MeOH in DCM (with 0.5% $NH_4OH$) as eluent provided the title compound. m/z=574.0 (M+H).

Step B: 5-methyl-4-(methylamino)-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one To a THF solution (9 mL) of the intermediate from Step A above (116 mg, 0.202 mmol) was added a 2 M methanol solution of methylamine (0.809 mL, 1.619 mmol) and the resultant mixture heated at 140° C. under microwave irradiation for 1 hour. Purification by silica gel column chromatography using DCM/MeOH (with 0.5% $NH_4OH$) gradient provided the title compound. Chiral separation using SFC on a Chiralcel OD column provided both enantiomers of the title compound. $^1$H NMR (500 MHz, DMSO-$d_6$): δ 11.52 (1H, s), 8.90-8.86 (1H, m), 8.66-8.64 (1H, m), 7.42 (1H, dd, J=8.08, 4.49 Hz), 6.77 (1H, d, J=5.11 Hz), 4.90 (2H, t, J=6.81 Hz), 3.05-2.92 (5H, m), 1.86 (3H, s). $^1$H NMR δ (ppm) (DMSO-$d_6$ with added $D_2O$): 8.86 (1H, d, J=8.14 Hz), 8.60 (1H, d, J=4.35 Hz), 7.40 (1H, dd, J=8.09, 4.54 Hz), 4.88 (2H, t, J=6.46 Hz), 2.99-2.85 (5H, m), 2.45 (3H, s), 1.81 (3H, s). m/z=524.1 (M+H).

EXAMPLE 190

4-Amino-5-Methyl-2-[1-(3,3,4,4,4-Pentafluorobutyl)Imidazo[1,5-A]Pyridin-3-yl]-5-Phenyl-5,7-Dihydro-6H-Pyrrolo[2,3-D]Pyrimidin-6-One

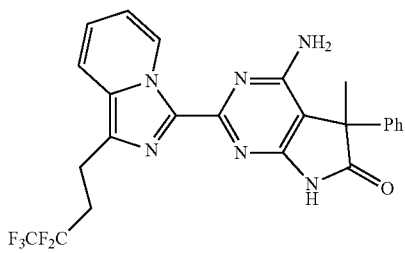

Step A: 4,4,5,5,5-pentafluoro-N-methoxy-N-methyl-pentanamide

Triethylamine (1.082 mL, 7.81 mmol) was added to a stirred solution of 4,4,5,5,5-pentafluoropentanoic acid (1.00 g, 5.21 mmol), N,O-dimethylhydroxylamine hydrochloride (0.559 g, 5.73 mmol), and 1-(3-dimethylaminopropyl)-3-ethylcarbodiimide hydrochloride (0.998 g, 5.21 mmol) in dry DCM (5.35 mL) at 25° C. under $N_2$. The reaction was stirred at 25° C. overnight. The reaction was diluted with $CH_2Cl_2$ (60 mL) and washed consecutively with 1N aq. HCl (2x), satd aq. $NaHCO_3$, dried ($Na_2SO_4$) and concentrated in vacuo to give the desired product, as a colorless liquid. $^1$H NMR (500 MHz, $CHCl_3$-d): δ 3.72 (s, 3H); 3.21 (s, 3H); 2.74 (t, J=7.8 Hz, 2H); 2.51-2.37 (m, 2H). m/z=236.2 (M+H).

Step B: 4,4,5,5,5-pentafluoro-1-(pyridin-2-yl)pentan-1-one

Isopropylmagnesium chloride (2 M in THF) (1.960 mL, 3.92 mmol) was added to a stirred solution of 2-bromopyridine (0.392 mL, 4.11 mmol) in dry THF (3.73 mL) at 25° C. under N₂. After 2 h at 25° C. a solution of 4,4,5,5,5-pentafluoro-N-methoxy-N-methylpentanamide (0.8781 g, 3.73 mmol) in dry THF (1.866 mL) was added via cannula and the resulting mixture was stirred at 25° C. overnight. Another 0.2 eq. of Grignard reagent was generated by same procedure as above and added to reaction via cannula and the reaction was stirred for 1 h. Another 0.6 eq. of Grignard reagent was generated by same procedure as above and added to reaction via cannula and the reaction was stirred for 1 h. The reaction was quenched by the addition of saturated aq. NH₄Cl and the resulting mixture was extracted with EtOAc (3×). The combined extracts were dried (Na₂SO₄) and concentrated in vacuo to give the crude product. This was purified by silica gel chromatography using a hexanes/EtOAc gradient to afford the desired product, as an oil. ¹H NMR (500 MHz, CHCl₃-d): δ 8.69 (d, J=4.8 Hz, 1H); 8.05 (d, J=7.9 Hz, 1H); 7.85 (dt, J=9.1, 3.7 Hz, 1H); 7.48 (d, J=7.7 Hz, 1H); 3.56 (t, J=7.8 Hz, 2H); 2.56-2.50 (m, 2H). m/z=254.0 (M+H).

Step C: 4,4,5,5,5-pentafluoro-1-(pyridin-2-yl)pentan-1-amine

Hydroxylamine (0.216 mL, 3.53 mmol) was added to a solution of 4,4,5,5,5-pentafluoro-1-(pyridin-2-yl)pentan-1-one (0.894 g, 3.53 mmol) in MeOH (10.87 mL) and the resulting solution was stirred at 25° C. for 5 h. Another 1 eq. hydroxylamine was added and the reaction was stirred overnight. Another 2 eq hydroxylamine was added and the reaction was stirred overnight. The reaction mixture was concentrated in vacuo and the resulting residue was diluted with EtOAc and the resulting organic phase was washed with water and brine, then dried (Na₂SO₄) and concentrated in vacuo to give the crude oxime, as a colorless solid. This was redissolved in TFA (6.52 mL) and cooled to 0° C. Zinc (1.155 g, 17.66 mmol) was added in one portion. After 3 h at 0° C. the reaction mixture was poured into a mixture of ice and 5 N aq. NaOH. The pH was adjusted to pH 10. The mixture was extracted with DCM (3×). The combined organic extracts were dried (Na₂SO₄) and concentrated in vacuo to give the desired amine product. m/z=255.1 (M+H).

Step D: methyl oxo{[4,4,5,5,5-pentafluoro-1-(pyridin-2-yl)pentyl]amino}acetate

Triethylamine (0.607 mL, 4.38 mmol) and methyl oxalyl chloride (0.322 mL, 3.50 mmol) were added sequentially to a solution of 4,4,5,5,5-pentafluoro-1-(pyridin-2-yl)pentan-1-amine (0.7424 g, 2.92 mmol) in dry DCM (10.82 mL) at 0° C. The reaction was allowed to warm to 25° C. and stirred for 3 h. The reaction mixture was diluted with DCM and washed with saturated aq. NaHCO₃. The organic layer was dried (Na₂SO₄) and concentrated in vacuo to give the crude product. This was purified by silica gel chromatography using a hexanes/EtOAc gradient to afford the desired product, as a colorless oil. m/z=341.0 (M+H).

Step E: methyl 1-(3,3,4,4,4-pentafluorobutyl)imidazo[1,5-A]pyridine-3-carboxylate Phosphoryl chloride (1.428 mL, 15.36 mmol) was added to a stirred solution of the intermediate from Step D (0.6534 g, 1.920 mmol) in dry ClCH₂CH₂Cl (14.44 mL). The resulting solution was heated at 120° C. overnight. Another 8 eq. POCl₃ was added and the reaction was heated at 120° C. for 2 days. The reaction was cooled to room temperature and concentrated in vacuo. The reaction was diluted with water and EtOAc and basified by the careful addition of saturated aq. NaHCO₃ until not further effervescence was observed. The layers were separated and the aqueous layer was further extracted with EtOAc (2×). The organic layer was washed with brine, dried (Na₂SO₄) and concentrated in vacuo to give the crude product. This was purified by silica gel chromatography using a hexanes/EtOAc gradient to afford the desired product, as a colorless solid. ¹H NMR (500 MHz, CHCl₃-d) δ 9.31 (d, J=7.2 Hz, 1H); 7.59 (d, J=9.1 Hz, 1H); 7.08 (dd, J=9.0, 6.6 Hz, 1H); 6.96-6.90 (m, 1H); 4.03 (s, 3H); 3.25-3.19 (m, 2H); 2.66-2.52 (m, 2H). m/z=323.0 (M+H).

Step F: 1-(3,3,4,4,4-pentafluorobutyl)imidazo[1,5-A]pyridine-3-carboximidamide

A solution of the intermediate from Step E (0.5277 g, 1.638 mmol) in dry toluene (19.97 mL) was added dropwise via cannula to a stirred solution of amino(chloro)methylaluminum (0.5 M in toluene, 28.7 mL, 14.33 mmol) at 107° C. The mixture was heated at 107° C. for 3 h. The reaction mixture was cooled to room temperature, silica gel, and MeOH were added and the mixture was stirred for 30 min. The reaction mixture was filtered through a plug of Celite™ (diatomaceous earth), washed through with 2M NH₃ in MeOH and the filtrate was concentrated in vacuo to give the crude product. A mixture of the crude product and 7N NH₃ in MeOH (20 mL) was heated in a sealed screw cap vial at 85° C. for 6 h. The solvent was removed in vacuo and the resulting residue was purified by silica gel column chromatography using a MeOH/DCM/hexanes eluent to afford desired product, as a yellow solid. ¹H NMR (500 MHz, CH₃OH-d₄) δ 9.25 (d, J=7.3 Hz, 1H); 7.54 (d, J=9.2 Hz, 1H); 6.89-6.84 (m, 1H); 6.74 (t, J=6.9 Hz, 1H); 3.18-3.04 (m, 2H); 2.65-2.51 (m, 2H). m/z=307.1 (M+H).

Step G: 4-amino-5-methyl-2-[1-(3,3,4,4,4-pentafluorobutyl)imidazo[1,5-A]pyridin-3-yl]-5-phenyl-5,7-dihydro-6H-pyrrolo[2,3-d]pyrimidin-6-one The title compound was prepared from the intermediate from Step F and Intermediate 1 (single enantiomer) using the procedure described in Example 58.

¹H NMR (500 MHz, CH₃OH-d₄): δ 9.95 (d, J=7.4 Hz, 1H); 7.67 (d, J=9.1 Hz, 1H); 7.37-7.32 (m, 4H); 7.32-7.26 (m, 1H); 6.99 (dd, J=9.1, 6.4 Hz, 1H); 6.85 (t, J=6.9 Hz, 1H); 3.33-3.29 (m, 2H); 2.73-2.59 (m, 2H); 1.87 (s, 3H). m/z=503.1 (M+H).

EXAMPLE 191

4-Amino-5-Methyl-2-[8-(3,3,4,4,4-Pentafluorobutyl) Imidazo[1,5-A]Pyrimidin-6-yl]-5-Phenyl-5,7-Dihydro-6H-Pyrrolo[2,3-D]Pyrimidin-6-One

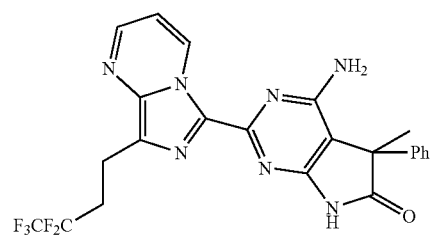

Step A: 2-amino-5,5,6,6,6-pentafluorohexanenitrile

A solution of 1,1,1,2,2-pentafluoro-4-iodobutane (2.00 g, 7.30 mmol) in $CH_2Cl_2$ (5.99 mL), potassium hydroxide (11 N aq.) (11.95 mL, 131 mmol) and benzyltriethylammonium chloride (0.166 g, 0.730 mmol) were added to a stirred solution of N-(diphenylmethylene)aminoacetonitrile (1.608 g, 730 mmol) in DCM (6 mL) at 25° C. The resulting two-phase mixture was stirred at 25° C. for 4 days. The organic phase was separated, dried ($Na_2SO_4$) and concentrated in vacuo. The resulting residue was mixed with $Et_2O$ (72 mL) and 1N aq. HCl (72 mL) and stirred at room temperature for 2 days. The aqueous layer was separated and made alkaline with 5N aq. NaOH solution and the resulting oil was taken up in DCM. The organic phase was dried ($Na_2SO_4$) and concentrated in vacuo to afford the desired product, as an oil. $^1$H NMR (500 MHz, $CHCl_3$-d): δ 3.75 (br s, 1H); 2.41-2.17 (m, 2H); 2.11-4.97 (m, 2H); 1.50 (br s, 2H). m/z=203.2 (M+H).

Step B: 2-ethoxy-1-(methylsulfanyl)-2-oxoethaniminium tetrafluoroborate

Trimethyloxonium tetrafluoroborate (0.833 g, 5.63 mmol) was added to a stirred solution of ethyl thiooxamate (0.50 g, 3.75 mmol) in dry DCM (19.97 mL) at −5° C. under $N_2$. The reaction was sealed and kept at −20° C. in the freezer overnight. The solvent was removed in vacuo and the resulting orange residue was carried forward to the next step as is. m/z=148.2 (M+H).

Step C: ethyl 5-amino-4-(3,3,4,4,4-pentafluorobutyl)-1H-imidazole-2-carboxylate A solution of 2-amino-5,5,6,6,6-pentafluorohexanenitrile (0.5722 g, 2.83 mmol) and 2-ethoxy-1-(methylsulfanyl)-2-oxoethaniminium tetrafluoroborate (0.808 g, 3.45 mmol) in dry 1,4-dioxane (5.2 mL) was stirred at 25° C. under $N_2$ for 6 days. The solution was concentrated in vacuo. The resulting residue was purified by silica gel chromatography using DCM/MeOH gradient to afford the desired product, as an orange oil. $^1$H NMR (500 MHz, $CHCl_3$-d): δ 4.36 (q, J=7.1 Hz, 2H); 2.85 (br s, 2H); 2.41-2.16 (m, 3H); 2.11-1.94 (m, 1H); 1.35 (t, J=7.1 Hz, 3H). m/z 302.2 (M+H).

Step D: ethyl 8-(3,3,4,4,4-pentafluorobutyl)imidazo[1,5-A]pyrimidine-6-carboxylate A solution of the intermediate from Step C (0.4356 g, 1.446 mmol) and 1,1,3,3-tetramethoxypropane (1.572 mL, 9.54 mmol) in dry EtOH (11.39 mL) was heated by microwave irradiation at 160° C. for 6 h. Another 3.3 eq. 1,1,3,3-tetramethoxypropane was added and the reaction was subjected to microwave irradiation at 160° C. for 6 h. Another 3.3 eq 1,1,3,3-tetramethoxypropane was added and the reaction was subjected to microwave irradiation at 160° C. for 3 h. The reaction mixture was concentrated in vacuo and the resulting crude product was purified by silica gel chromatography using a hexanes/EtOAc gradient to afford the desired product, as a yellow solid. $^1$H NMR (500 MHz, $CHCl_3$-d) δ 9.48 (dd, J=1.77, 0.4 Hz, 1H); 8.38 (dd, J=3.8, 1.8 Hz, 1H); 6.91 (dd, J=7.3, 3.8 Hz, 1H); 4.53 (q, J=7.1 Hz, 2H); 3.41-3.35 (m, 2H); 2.70-2.56 (m, 2H); 1.48 (t, J=7.1 Hz, 3H). m/z=337.9 (M+H).

Step E: 8-(3,3,4,4,4-pentafluorobutyl)imidazo[1,5-A]pyrimidine-6-carboxamide A solution of the intermediate from Step D (0.3684 g, 1.092 mmol) and ammonia (11.70 mL, 82 mmol, 7 N in MeOH) was heated at 50° C. under $N_2$ in a screw cap vial for 24 h. The reaction mixture was concentrated in vacuo to remove the excess amine to afford the desired product, as a yellow solid. m/z=309.1 (M+H).

Step F: 8-(3,3,4,4,4-pentafluorobutyl)imidazo[1,5-A]pyrimidine-6-carbonitrile A solution of the intermediate from Step E in phosphoryl chloride (9.43 mL, 101 mmol) was heated at 105° C. for 30 min. The majority of the phosphoryl chloride was removed in vacuo. The crude product was partitioned between saturated aq. $NaHCO_3$ and EtOAc. The aqueous layer was separated and further extracted with EtOAc (2×). The combined extracts were dried ($Na_2SO_4$) and concentrated in vacuo to give the desired product, as a yellow solid. $^1$H NMR (600 MHz, $CHCl_3$-d) δ 8.47 (dd, J=7.1, 1.6 Hz, 1H); 8.41 (dd, J=3.8, 1.7 Hz, 1H); 6.98 (dd, J=7.1, 3.8 Hz, 1H); 3.35-3.31 (m, 2H); 2.68-2.57 (m, 2H). m/z=291.1 (M+H).

Step G: 8-(3,3,4,4,4-pentafluorobutyl)imidazo[1,5-A]pyrimidine-6-carboximidamide A solution of amino(chloro)methylaluminum (0.5 M in toluene, 18.13 mL, 9.06 mmol) was added quickly to a stirred solution of the intermediate from Step F (0.3006 g, 1.036 mmol) in toluene (12.63 mL) and the mixture was heated at 107° C. overnight. The reaction mixture was cooled to room temperature, MeOH was added and the mixture was stirred for 30 min. The reaction mixture was filtered through a plug of Celite™ (diatomaceous earth), washed through with 2M $NH_3$ in MeOH and the filtrate was concentrated in vacuo to give the crude product. This was purified by flash chromatography using a DCM/MeOH (2 N $NH_3$ in MeOH) gradient to afford the desired product, as a yellow solid. m/z=308.0 (M+H).

Step H: 4-amino-5-methyl-2-[8-(3,3,4,4,4-pentafluorobutyl)imidazo[1,5-A]pyrimidin-6-yl]-5-phenyl-5,7-dihydro-6H-pyrrolo[2,3-d]pyrimidin-6-one The title compound was prepared from the intermediate from Step G and Intermediate 1 (single enantiomer) as described in Example 58.
$^1$H NMR (500 MHz, $CH_3OH$-$d_4$) δ 10.16 (d, J=7.4 Hz, 1H); 8.28 (d, J=3.5 Hz, 1H); 7.37-7.33 (m, 4H); 7.29 (t, J=4.9 Hz, 1H); 6.90 (dd, J=7.4, 3.7 Hz, 1H); 3.37-3.31 (m, 2H); 2.77-2.63 (m, 2H); 1.87 (s, 3H). m/z=503.9 (M+H).

Using essentially the same procedures described in the previous Examples, the following compounds in Table 9 to Table 13 were made.

TABLE 9

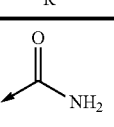

| EXAMPLE | IUPAC | X | R¹ | R² | R³ | m/z (M + H) |
|---|---|---|---|---|---|---|
| 192 | 4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide | CH | F | $CH_2CF_2CF_3$ | 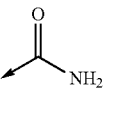 | 488.0 |
| 193 | 4-amino-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide | CH | H | $CH_2CF_2CF_3$ | 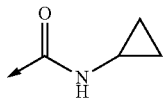 | 470.1 |
| 194 | 4-amino-N-cyclopropyl-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide | CH | H | $CH_2CF_2CF_3$ | 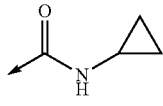 | 510.2 |
| 195 | 4-amino-N-cyclopropyl-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide | CH | F | $CH_2CF_2CF_3$ | 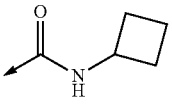 | 528.1 |
| 196 | 4-amino-2-[6-chloro-1-(3,3,4,4,4-pentafluorobutyl)-1H-indazol-3-yl]-N-cyclobutyl-5-methyl-6-oxo-6,7-difluoro-5H-pyrrolo[2,3-d]pyrimidine-5-carboxamide | CH | Cl | $CH_2CF_2CF_3$ | 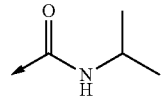 | 558.2 |
| 197 | 4-amino-5-methyl-N-(1-methylethyl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | N | H | $CH_2CF_2CF_3$ | 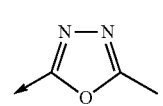 | 513.2 |
| 198 | 4-amino-2-[6-chloro-1-(3,3,3-trifluoropropyl)-1H-indazol-3-yl]-5-methyl-5-(5-methyl-1,3,4-oxadiazol-2-yl)-5,7-dihydro-6H-pyrrolo[2,3-d]pyrimidin-6-one | CH | Cl | $CH_2CF_3$ | 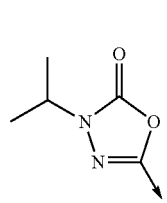 | 493.2 |
| 199 | 4-amino-5-methyl-5-[4-(1-methylethyl)-5-oxo-4,5-dihydro-1,3,4-oxadiazol-2-yl]-2-[1-(3,3,4,4,4-pentafluorobutyl)-1H-pyrazolo[3,4-d]pyridin-3-yl]-5,7-dihydro-6H-pyrrolo[2,3-d]pyrimidin-6-one | N | H | $CH_2CF_2CF_3$ | | 554 |

TABLE 9-continued

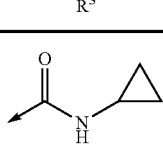

| EXAMPLE | IUPAC | X | R¹ | R² | R³ | m/z (M + H) |
|---|---|---|---|---|---|---|
| 200 | 4-amino-N-cyclopropyl-5-methyl-6-oxo-2-{1-[2-(trifluoromethoxy)ethyl]-1H-pyrazolo[3,4-6]pyridin-3-yl}-6,7-dihydro-5H-pyrrolo[2,3-d]pyrimidine-5-carboxamide | N | H | $CH_2OCF_3$ | 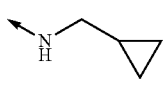 | 477.4 |
| 201 | 4,5-diamino-2-[6-chloro-1-(3,3,4,4,4-pentafluorobutyl)-1H-indazol-3-yl]-5-methyl-5,7-dihydro-6H-pyrrolo[2,3-d]pyrimidin-6-one | CH | Cl | $CH_2CF_2CF_3$ | $NH_2$ | 474.0 M − H |
| 202 | 4-amino-2-[6-chloro-1-(3,3,4,4,4-pentafluorobutyl)-1H-indazol-3-yl]-5-[(cyclopropylmethyl)amino]-5-methyl-5,7-dihydro-6H-pyrrolo[2,3-d]pyrimidin-6-one | CH | Cl | $CH_2CF_2CF_3$ | 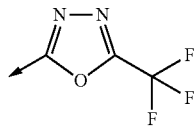 | 530.1 |
| 203 | 4-amino-5-methyl-2-[1-(3,3,4,4,4-pentafluorobutyl)-1H-pyrazolo[3,4-d]pyridin-3-yl]-5-[5-(trifluoromethyl)-1,3,4-oxadiazol-2-yl]-5,7-dihydro-6H-pyrrolo[2,3-d]pyrimidin-6-one | N | H | $CH_2CF_2CF_3$ | 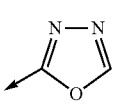 | 564.2 |
| 204 | 4-amino-5-methyl-5-(1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ | 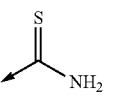 | 496.2 |
| 205 | 4-amino-5-methyl-6-oxo-2-[1-(3,3,4,4,4-pentafluorobutyl)-1H-pyrazolo[3,4-6]pyridin-3-yl]-6,7-dihydro-5H-pyrrolo[2,3-d]pyrimidine-5-carbothioamide | N | H | $CH_2CF_2CF_3$ | 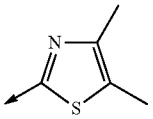 | 487.1 |
| 206 | 4-amino-5-(4,5-dimethyl-1,3-thiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ | | 539.1 |

TABLE 9-continued

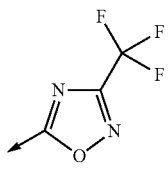

| EXAMPLE | IUPAC | X | R¹ | R² | R³ | m/z (M + H) |
|---------|-------|---|-----|-----|-----|-------------|
| 207 | 4-amino-5-methyl-2-[1-(3,3,4,4,4-pentafluorobutyl)-1H-pyrazolo[3,4-b]pyridin-3-yl]-5-[3-(trifluoromethyl)-1,2,4-oxadiazol-5-yl]-5,7-dihydro-6H-pyrrolo[2,3-d]pyrimidin-6-one | N | H | $CH_2CF_2CF_3$ | 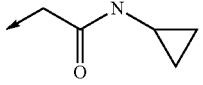 | 564 |
| 208 | 2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-N-cyclopropylacetamide | CH | Cl | $CH_2CF_2CF_3$ | 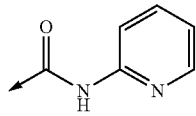 | 558.1 |
| 209 | 4-amino-5-methyl-6-oxo-N-pyridin-2-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide | N | H | $CH_2OCF_3$ | 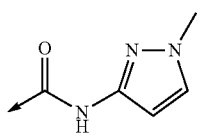 | 514.4 |
| 210 | 4-amino-5-methyl-N-(1-methyl-1H-pyrazol-3-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide | N | H | $CH_2OCF_3$ | 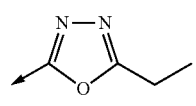 | 517.4 |
| 211 | 4-amino-5-(5-ethyl-1,3,4-oxadiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ | 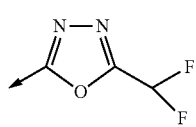 | 524.1 |
| 212 | 4-amino-5-[5-(difluoromethyl)-1,3,4-oxadiazol-2-yl]-5-methyl-2-[1-(3,3,4,4,4-pentafluorobutyl)-1H-pyrazolo[3,4-b]pyridin-3-yl]-5,7-dihydro-6H-pyrrolo(2,3-d]pyrimidin-6-one | N | H | $CH_2CF_2CF_3$ | 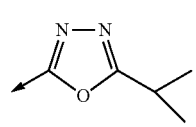 | 546.2 |
| 213 | 4-amino-5-methyl-5-[5-(1-methylethyl)-1,3,4-oxadiazol-2-yl]-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ | | 538.1 |

TABLE 9-continued

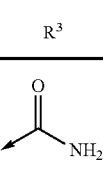

| EXAMPLE | IUPAC | X | R¹ | R² | R³ | m/z (M + H) |
|---|---|---|---|---|---|---|
| 214 | 4-amino-2-[6-chloro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide | N | Cl | $CH_2CF_2CF_3$ | 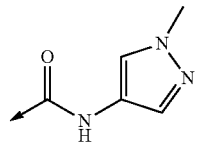 | 505 |
| 215 | 4-amino-5-methyl-N-(1-methyl-1H-pyrazol-4-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide | N | H | $CH_2OCF_3$ | 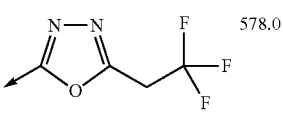 | 517.2 |
| 216 | 4-amino-5-methyl-2-[1-(3,3,4,4,4-pentafluorobutyl)-1H-pyrazolo[3,4-b]pyridin-3-yl]-5-[5-(2,2,2-trifluoroethyl)-1,3,4-oxadiazol-2-yl]-5,7-dihydro-6H-pyrrolo[2,3-d]pyrimidin-6-one | N | H | $CH_2CF_2CF_3$ | 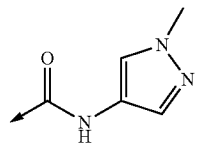 | 578.0 |
| 217 | 4-amino-2-[6-chloro-1-(3,3,4,4,4-pentafluorobutyl)-1H-indazol-3-yl]-5-methyl-N-(1-methyl-1H-pyrazol-4-yl)-6-oxo-6,7-dihydro-5H-pyrrolo[2,3-d]pyrimidine-5-carboxamide | CH | Cl | $CH_2CF_2CF_3$ | 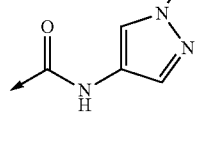 | 584.9 |
| 218 | 4-amino-5-methyl-N-(1-methyl-1H-pyrazol-3-yl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | N | H | $CH_2CF_2CF_3$ |  | 551.4 |
| 219 | 4-amino-5-ethynyl-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ |  | 452.1 |
| 220 | 4-amino-2-[6-methoxy-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide | N | MeO | $CH_2CF_2CF_3$ | (same amide as 214) | 501.2 |

TABLE 9-continued

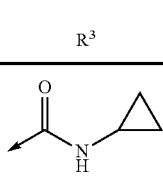

| EXAMPLE | IUPAC | X | R¹ | R² | R³ | m/z (M + H) |
|---|---|---|---|---|---|---|
| 221 | 4-amino-2-[6-cyano-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide | N | CN | $CH_2CF_3$ | 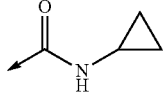 | 486 |
| 222 | 4-amino-N-cyclopropyl-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | N | H | $CH_2CF_2CF_3$ |  | 475.1 |
| 223 | 4-amino-N-cyclopropyl-2-[6-cyclopropyl-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide | N | 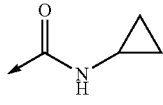 | $CH_2CF_2CF_3$ |  | 551 |
| 224 | 4-amino-N-cyclopropyl-2-[6-cyclopropyl-1-(3,3,3-trifluoropropyl)-1H-pyrazolo[3,4-b]pyridin-3-yl]-5-methyl-6-oxo-6,7-dihydro-5H-pyrrolo[2,3-d]pyrimidine-5-carboxamide | N | 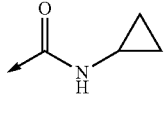 | $CH_2CF_3$ | 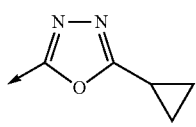 | 501 |
| 225 | 4-amino-5-(5-cyclopropyl-1,3,4-oxadiazol-2-yl)-5-methyl-2-[1-(4,4,4-trifluorobutyl)-1H-pyrazolo[3,4-b]pyridin-3-yl]-5,7-dihydro-6H-pyrrolo[2,3-d]pyrimidin-6-one | N | H | $CH_2CH_2CF_3$ | 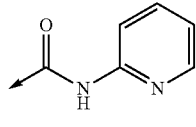 | 500 |
| 226 | 4-amino-5-methyl-6-oxo-N-pyridin-2-yl-2-[1-(4,4,4-trifluorobutyl)-1H-pyrazolo[3,4-b]pyridin-3-yl]-6,7-dihydro-5H-pyrrrolo[2,3-d]pyrimidine-5-carboxamide | N | H | $CH_2CH_2CF_3$ |  | 512.2 |

TABLE 9-continued

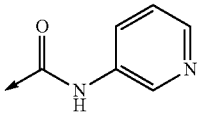

| EXAMPLE | IUPAC | X | R¹ | R² | R³ | m/z (M + H) |
|---|---|---|---|---|---|---|
| 227 | 4-amino-5-methyl-6-oxo-N-pyridin-3-y]-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | N | H | $CH_2CH_2CF_3$ | 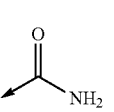 | 512.2 |
| 228 | 4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | N | H | $CH_2CH_2CF_3$ | 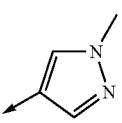 | 435 |
| 229 | 4-amino-2-[6-chloro-1-(3,3,4,4,4-pentafluorobutyl)-1H-indazol-3-yl]-5-methyl-5-(1-methyl-1H-pyrazol-4-yl)-5,7-dihydro-6H-pyrrolo[2,3-d]pyrimidin-6-one | CH | Cl | $CH_2CF_2CF_3$ | 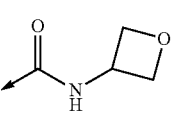 | 541.0 |
| 230 | 4-amino-2-[6-chloro-1-(3,3,4,4,4-pentafluorobutyl)-1H-pyrazolo[3,4-b]pyridin-3-yl]-5-methyl-N-oxetan-3-yl-6-oxo-6,7-dihydro-5H-pyrrolo[2,3-d]pyrimidine-5-carboxamide | N | Cl | $CH_2CF_2CF_3$ | 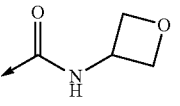 | 561.03 |
| 231 | 4-amino-5-methyl-N-oxetan-3-yl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | N | H | $CH_2CF_2CF_3$ | 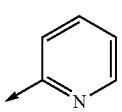 | 527 |
| 232 | 4-amino-5-methyl-5-pyridin-2-yl-2-[1-(3,3,3-trifluoropropyl)-1H-pyrazolo[3,4-b]pyridin-3-yl]-5,7-dihydro-6H-pyrrolo[2,3-d]pyrimidin-6-one | N | H | $CH_2CF_3$ | 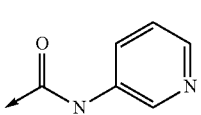 | 455.08 |
| 233 | 4-amino-5-methyl-6-oxo-N-pyridin-3-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide | N | H | $CH_2OCF_3$ |  | 514.3 |

145 146

TABLE 9-continued

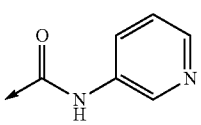

| EXAMPLE | IUPAC | X | R¹ | R² | R³ | m/z (M + H) |
|---|---|---|---|---|---|---|
| 234 | 4-amino-5-methyl-6-oxo-2-[1-(3,3,4,4,4-pentafluorobutyl)-1H-pyrazolo[3,4-b]pyridin-3-yl]-N-pyridin-3-yl-6,7-dihydro-5H-pyrrolo[2,3-d]pyrimidine-5-carboxamide | N | H | $CH_2CF_2CF_3$ | 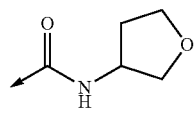 | 548.2 |
| 235 | 4-amino-5-methyl-6-oxo-2-[1-(3,3,4,4,4-pentafluorobutyl)-1H-pyrazolo[3,4-b]pyridin-3-yl]-N-(tetrahydrofuran-3-yl)-6,7-dihydro-5H-pyrrolo[2,3-d]pyrimidine-5-carboxamide | N | H | $CH_2CF_2CF_3$ | 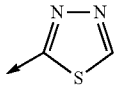 | 541.1 |
| 236 | 4-amino-5-methyl-5-(1,3,4-thiadiazol-2-yl)-2-[1-(4,4,4-trifluorobutyl)-1H-pyrazolo[3,4-b]pyridin-3-yl]-5,7-dihydro-6H-pyrrolo[2,3-d]pyrimidin-6-one | N | H | $CH_2CF_2CF_3$ | 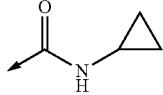 | 476.1 |
| 237 | 4-amino-N-cyclopropyl-5-methyl-6-oxo-2-[1-(3,3,4,4-tetrafluorobutyl)-1H-pyrazolo[3,4-b]pyridin-3-yl]-6,7-dihydro-5H-pyrrolo[2,3-d]pyrimidine-5-carboxamide | N | H | $CH_2CF_2CHF_3$ | 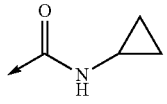 | 493.2 |
| 238 | 4-amino-N-cyclopropyl-2-[1-(3,3-difluoropropyl)-1H-pyrazolo[3,4-b]pyridin-3-yl]-5-methyl-6-oxo-6,7-dihydro-5H-pyrrolo[2,3-d]pyrimidine-5-carboxamide | N | H | $CH_2CHF_2$ | | 443.3 |
| 239 | 4-amino-5-methyl-2-[6-methyl-1-(3,3,4,4,4-pentafluorobutyl)-1H-pyrazolo[3,4-b]pyridin-3-yl]-6-oxo-N-(tetrahydro-2H-pyran-4-yl)-6,7-dihydro-5H-pyrrolo[2,3-d]pyrimidine-5-carboxamide | N | Me | $CH_2CF_2CF_3$ | 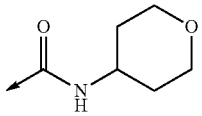 | 569.1 |
| 240 | 4-amino-N-cyclopropyl-2-[1-(3,3-difluorobutyl)-1H-pyrazolo[3,4-b]pyridin-3-yl]-5-methyl-6-oxo-6,7-dihydro-5H-pyrrolo[2,3-d]pyrimidine-5-carboxamide | N | H | $CH_2CF_2CF_3$ | 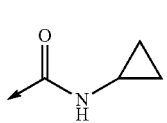 | 457.0 |

TABLE 10

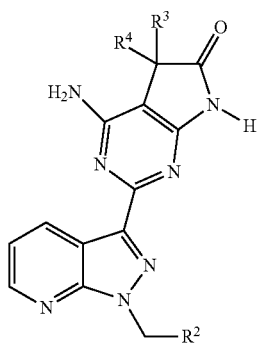

| EXAMPLE | IUPAC | R² | R³ | R⁴ | m/z (M + H) |
|---|---|---|---|---|---|
| 241 | 4-amino-5-ethyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | $CH_2CF_2CF_3$ | C(=O)NH₂ | Et | 485.1 |
| 242 | 4-amino-N,5-dicyclopropyl-6-oxo-2-[1-(3,3,4,4,4-pentafluorobutyl)-1H-pyrazolo(3,4-b]pyridin-3-yl]-6,7-dihydro-5H-pyrrolo[2,3-d]pyrimidine-5-carboxamide | $CH_2CF_2CF_3$ | C(=O)NH-cyclopropyl | cyclopropyl | 537.1 |
| 243 | 4-amino-5-cyclopentyl-N-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | $CH_2CF_2CF_3$ | C(=O)NH-cyclopropyl | cyclopentyl | 565.1 |
| 244 | 4-amino-5-(1-methylethyl)-6-oxo-2-(1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | $CH_2CF_2CF_3$ | C(=O)NH₂ | iPr | 499.1 |
| 245 | 4-amino-N,5-dicyclopropyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide | $CH_2CF_3$ | C(=O)NH-cyclopropyl | cyclopropyl | 487.0 |

TABLE 10-continued

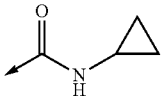

| EXAMPLE | IUPAC | R² | R³ | R⁴ | m/z (M + H) |
|---|---|---|---|---|---|
| 246 | 4-amino-N,5-dicyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | CH₂CH₂CF₃ |  |  | 501.1 |
| 247 | 4-amino-5-cyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | CH₂CF₂CF₃ |  |  | 461.1 |

TABLE 11

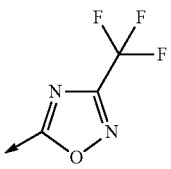

| EXAMPLE | IUPAC | X | R¹ | R² | R³ | m/z (M + H) |
|---|---|---|---|---|---|---|
| 248 | 4-amino-2-[6-fluoro-3-(4,4,4-trifluorobutyl)imidazo[1,5-a]pyridin-1-yl]-5-methyl-5-[3-(trifluoromethyl)-1,2,4-oxadiazol-5-yl]-5,7-dihydro-6H-pyrrolo[2,3-d]pyrimidin-6-one | CH | F | CH₂CH₂CF₃ |  | 545 |

TABLE 11-continued

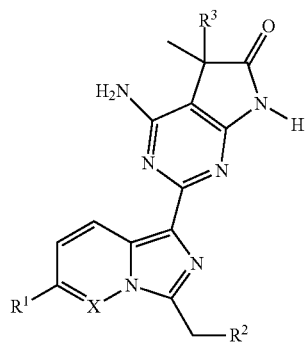

| EXAMPLE | IUPAC | X | R¹ | R² | R³ | m/z (M + H) |
|---|---|---|---|---|---|---|
| 249 | 4-amino-2-[6-chloro-3-(4,4,4-trifluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one | CH | Cl | CH₂CH₂CF₃ | 5-methyl-1,2,4-oxadiazol-3-yl | 507.1 |
| 250 | 4-amino-2-[6-chloro-3-(3,3,4,4,4-pentafluorobutyl)imidazo[1,5-a]pyridin-1-yl]-H-cyclopropyl-5-methyl-6-oxo-6,7-dihydro-5H-pyrrolo[2,3-d]pyrimidine-5-carboxamide | CH | Cl | CH₂CF₂CF₃ | C(O)NH-cyclopropyl | 544 |
| 251 | 4-amino-H-cyclopropyl-5-methyl-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide | N | H | CH₂CF₂CF₃ | C(O)NH-cyclopropyl | 511.4 |
| 252 | 4-amino-H-cyclopropyl-2-[6-fluoro-3-(3,3,4,4,4-pentafluorobutyl)imidazo[1,5-a]pyridin-1-yl]-5-methyl-6-oxo-6,7-dihydro-5H-pyrrolo[2,3-d]pyrimidine-5-carboxamide | CH | F | CH₂CF₂CF₃ | C(O)NH-cyclopropyl | 528.4 |
| 253 | 4-amino-2-[6-fluoro-3-(3,3,4,4,4-pentafluorobutyl)imidazo[1,5-a]pyridin-1-yl]-5-methyl-6-oxo-H-pyridin-3-yl-6,7-dihydro-5H-pyrrolo[2,3-d]pyrimidine-5-carboxamide | CH | F | CH₂CF₂CF₃ | C(O)NH-pyridin-3-yl | 565 |
| 254 | 4-amino-5-methyl-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide | N | H | CH₂CF₂CF₃ | C(O)NH₂ | 471.3 |
| 255 | 4-amino-5-(5-cyclopropyl-1,3,4-oxadiazol-2-yl)-5-methyl-2-[7-(3,3,4,4,4-pentafluorobutyl)imidazo[1,5-b]pyridazin-5-yl]-5,7-dihydro-6H-pyrrolo[2,3-d]pyrimidin-6-one | N | H | CH₂CF₂CF₃ | 5-cyclopropyl-1,3,4-oxadiazol-2-yl | 536.4 |
| 256 | 4-amino-H-cyclopropyl-5-methyl-6-oxo-2-[7-(3,3,3-trifluoropropyl)imidazo[1,5-b]pyridazin-5-yl]-6,7-dihydro-5H-pyrrolo[2,3-d]pyrimidine-5-carboxamide | N | H | CH₂CF₃ | C(O)NH-cyclopropyl | 461.3 |

TABLE 12

| EXAMPLE | IUPAC | A | R² | R³ | R⁴ | m/z (M + H) |
|---|---|---|---|---|---|---|
| 257 | 2-[6-chloro-1-(3,3,4,4,4-pentafluorobutyl)-1H-indazol-3-yl]-N-cyclopropyl-5-methyl-4-(methylamino)-6-oxo-6,7-dihydro-5H-pyrrolo[2,3-d]pyrimidine-5-carboxamide | 6-chloro-indazol-3-yl | CH₂CF₂CF₃ | C(=O)NH-cyclopropyl | Me | 558.1 |
| 258 | 2-[6-chloro-1-(3,3,4,4,4-pentafluorobutyl)-1H-indazol-3-yl]-N,5-dimethyl-4-(methylamino)-6-oxo-6,7-dihydro-5H-pyrrolo[2,3-d]pyrimidine-5-carboxamide | 6-chloro-indazol-3-yl | CH₂CF₂CF₃ | C(=O)NHMe | Me | 532.1 |
| 259 | N,5-dimethyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | pyrazolo[3,4-b]pyridin-3-yl | CH₂CF₂CF₃ | C(=O)NHMe | Me | 499.2 |
| 260 | N-cyclopropyl-5-methyl-4-(methylamino)-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide | imidazo[1,5-b]pyridazin-5-yl | CH₂CF₂CF₃ | C(=O)NH-cyclopropyl | Me | 525.3 |
| 261 | 5-(5-cyclopropyl-1,3,4-oxadiazol-2-yl)-5-methyl-4-(methylamino)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one | pyrazolo[3,4-b]pyridin-3-yl | CH₂CF₂CF₃ | 5-cyclopropyl-1,3,4-oxadiazol-2-yl | Me | 550.1 |
| 262 | N,5-dicyclopropyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide | pyrazolo[3,4-b]pyridin-3-yl | CH₂CF₂CF₃ | C(=O)NH-cyclopropyl | cyclopropyl | 551.1 |

TABLE 12-continued

[Structure: pyrrolo[2,3-d]pyrimidine core with R³, R⁴, NHMe, and A-CH(H)(H)-R² substituents]

| EXAMPLE | IUPAC | A | R² | R³ | R⁴ | m/z (M + H) |
|---|---|---|---|---|---|---|
| 263 | N-cyclopropyl-5-methyl-4-(methylamino)-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide | pyrazolo[3,4-b]pyridin-3-yl (attached at *, N1 at **) | $CH_2CF_3$ | C(O)NH-cyclopropyl | Me | 475.1 |
| 264 | N-cyclopropyl-5-methyl-4-(methylamino)-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide | pyrazolo[3,4-b]pyridin-3-yl (attached at *, N1 at **) | $CH_2CH_2CF_3$ | C(O)NH-cyclopropyl | Me | 489.2 |

TABLE 13

[Structure: pyrrolo[2,3-d]pyrimidine core with R³, Me, H₂N, and A-CH₂-CH₂-CF₂-CF₃ chain]

| EXAMPLE | IUPAC | A | R³ | m/z (M + H) |
|---|---|---|---|---|
| 265 | 4-amino-2-[5-chloro-3-(3,3,4,4,4-pentafluorobutyl)-1H-indazol-1-yl]-N,N,5-trimethyl-6-oxo-6,7-dihydro-5H-pyrrolo[2,3-d]pyrimidine-5-carboxamide | 5-chloro-indazol-1-yl (N1 at *, C3 at **) | C(O)N(Me)₂ | 532.1 |

TABLE 13-continued

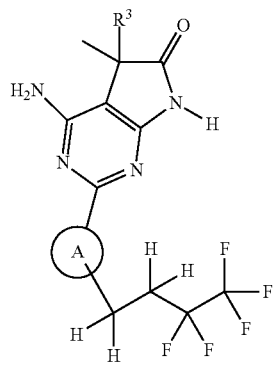

| EXAMPLE | IUPAC | A | R³ | m/z (M + H) |
|---|---|---|---|---|
| 266 | 4-amino-N-cyclopropyl-5-methyl-6-oxo-2-[3-(3,3,4,4,4-pentafluorobutyl)-1H-pyrazolo[4,3-b]pyridin-1-yl]-6,7-dihydro-5H-pyrrolo[2,3-d]pyrimidine-5-carboxamide | pyrazolo[4,3-b]pyridinyl | C(=O)NH-cyclopropyl | 511.2 |
| 267 | 4-amino-2-[5-chloro-1-(3,3,4,4,4-pentafluorobutyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide | 5-chloro-pyrazolo[3,4-b]pyridinyl | C(=O)NH-cyclopropyl | 544.2 |
| 268 | 4-amino-2-[5-chloro-1-(3,3,4,4,4-pentafluorobutyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide | 5-chloro-pyrazolo[3,4-b]pyridinyl | C(=O)NH-cyclopropyl | 545.3 |
| 269 | 4-amino-2-[5-chloro-1-(3,3,4,4,4-pentafluorobutyl)-1H-pyrazolo[3,4-b]pyridin-3-yl]-5-methyl-5-(5-methyl-1,3,4-oxadiazol-2-yl)-5,7-dihydro-6H-pyrrolo[2,3-d]pyrimidin-6-one | 5-chloro-pyrazolo[3,4-b]pyridinyl | 5-methyl-1,3,4-oxadiazol-2-yl | 544.3 |
| 270 | 4-amino-5-methyl-6-oxo-2-[1-(3,3,4,4,4-pentafluorobutyl)imidazo[1,5-a]pyridin-3-yl]-6,7-dihydro-5H-pyrrolo[2,3-d]pyrimidine-5-carboxamide | imidazo[1,5-a]pyridinyl | C(=O)NH₂ | 470.0 |

Example Data

208  ¹H NMR (500 MHz, CH₃OH-d₄): δ 8.64 (d, J = 8.69 Hz, 1 H); 7.73 (s, 1 H); 7.25 (d, J = 8.70 Hz, 1 H); 4.80 (t, J = 7.11 Hz, 2 H); 4.63 (s, 1 H); 3.01-2.84 (m, 4 H); 2.77 (d, J = 15.29 Hz, 1 H); 2.47 (s, 1 H); 1.45 (s, 3 H); 0.60 (s, 2 H); 0.43-0.38 (m, 1 H); 0.30-0.25 (m, 1 H).

-continued

Example Data

| | |
|---|---|
| 214 | $^1$H NMR (500 MHz, Acetone-$d_6$): δ 9.01 (d, J = 8.29 Hz, 1 H); 7.36 (d, J = 8.37 Hz, 1 H); 4.96-4.90 (m, 2 H); 3.12-2.98 (m, 2 H); 1.78 (s, 3 H). |
| 224 | $^1$H NMR (500 MHz, Acetone-$d_6$): δ 8.77 (d, J = 8.24 Hz, 1 H); 7.48 (s, 1 H); 7.22 (d, J = 8.25 Hz, 1 H); 7.06 (s, 2 H); 4.87-4.76 (m, 2 H); 3.06-2.94 (m, 2 H); 2.80-2.73 (m, 1 H); 2.29-2.22 (m, 1 H); 1.72 (s, 3 H); 1.17-1.13 (m, 2 H); 1.08-1.03 (m, 2 H); 0.75-0.65 (m, 2 H); 0.58-0.48 (m, 2 H). |
| 229 | $^1$H NMR (500 MHz, CHCl$_3$-d): δ 8.33 (d, J = 8.68 Hz, 1 H); 7.39 (s, 1 H); 7.36-7.33 (m, 2 H); 6.98 (d, J = 8.72 Hz, 1 H); 5.00 (s, 2 H); 4.64-4.55 (m, 2 H); 3.85 (s, 3 H); 2.77-2.63 (m, 2 H); 1.77 (s, 3 H). |
| 233 | $^1$H NMR (500 MHz, DMSO-$d_6$): δ 11.43 (s, 1H), 9.05 (d, J = 7.8 Hz, 1H), 8.76 (s, 1H), 8.62 (d, J = 4.3 Hz, 1H), 8.27 (d, J = 4.3 Hz, 1H), 7.99 (d, J = 8.0 Hz, 1H), 7.34 (m, 2H), 6.84 (bs, 2H), 4.88 (t, J = 4.9Hz, 2H), 4.6 (t, J = 4.9 Hz, 2H), 1.71 (s, 3H). |
| 241 | $^1$H NMR (500 MHz, CH$_3$OH-$d_4$): δ 8.99 (d, J = 7.92 Hz, 1 H); 8.58 (s, 1 H); 7.43-7.20 (m, 1 H); 4.93 (t, J = 7.26 Hz, 2 H); 3.01-2.88 (m, 2 H); 2.43-2.35 (m, 1 H); 2.29-2.22 (m, 1 H); 0.81 (t, J = 7.33 Hz, 3 H). |
| 244 | $^1$H NMR (500 MHz, CH$_3$OH-$d_4$): δ 9.04 (dd, J = 8.08, 1.66 Hz, 1 H); 8.62 (dd, J = 4.54, 1.64 Hz, 1 H); 7.36 (dd, J = 8.10, 4.51 Hz, 1 H); 4.95 (t, J = 7.25 Hz, 3 H); 3.03-2.90 (m, 3 H); 2.88-2.81 (m, 1 H); 1.18 (d, J = 6.72 Hz, 3 H); 0.91 (d, J = 6.89 Hz, 3 H). |
| 245 | $^1$H NMR (500 MHz, CHCl$_3$-d): δ 8.77 (1 H, d, J = 8.06 Hz), 8.55 (1 H, d, J = 4.47 Hz), 7.70-7.68 (1 H, m), 7.14 (1 H, dd, J = 8.06, 4.50 Hz), 6.28 (2 H, s), 4.92-4.78 (2 H, m), 2.92-2.79 (2 H, m), 2.76-2.69 (1 H, m), 1.69-1.61 (1 H, m), 0.83-0.66 (3 H, m), 0.60-0.43 (5 H, m). |
| 262 | $^1$H NMR (500 MHz, CHCl$_3$-d): δ 8.93 (1 H, dd, J = 8.04, 1.59 Hz), 8.61 (1 H, dd, J = 4.52, 1.57 Hz), 8.28-8.23 (1 H, m), 7.77 (1 H, d, J = 3.29 Hz), 5.03-4.84 (2 H, m), 3.22 (3 H, d, J = 4.73 Hz), 2.90-2.77 (2 H, m), 2.76-2.70 (1 H, m), 1.69-1.61 (1 H, m), 0.85-0.74 (2 H, m), 0.65-0.46 (6 H, m). |

Biological Assays

Cell-based sGC Functional Assay (CASA Assay)
Rationale sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods

A CHO-K1 cell line stably expressing the sGC α up heterodimer was generated using a standard transfection protocol. CHO-K1 cells were transfected with plasmids pIREShy-ghsGCα1 and pIRESneo-hsGCβ1 simultaneously using FUGENE reagent. Clones that stably express both subunits were selected with hygromycin and neomycin for weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. On the day of the assay, cells were harvested in EBSS Assay Buffer (EAB) containing 5 mM MgCl$_2$, 10 mM HEPES (4-(2-hydroxyethyl)piperazine-1-ethanesulfonic acid) and 0.05% BSA (bovine serum albumin) and cell density was adjusted to 2×10$^6$/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 1%. Cells were incubated with compounds in the presence and absence of 10 μM of 1H-(1,2,4)oxadiazolo(4,3-a) quinoxalin-1-one (ODQ) for 1 hr at 37° C. At the end of the incubation period, the reaction was terminated and the cells were lysed. The level of intracellular cGMP was determined using an HTRF-based assay kit (Cis-Bio, 62GM2PEC), which detects the displacement of a fluorescence labeled cGMP from its specific antibody. The amount of cGMP was plotted against compound concentration in PRISM software and the IP and maximum fold induction over DMSO control were derived from the plot.

The compounds of the instant invention had inflection points (IP) less than or equal to 10 μM and a maximum fold induction over DMSO control of at least 4-fold in the cell based assay described above (without ODQ incubation), and more particularly less than or equal to about 200 nM/equal to or greater than about 20-fold. Preferred compounds had an IP of less than or equal to about 100 nM and a maximum fold induction over DMSO control of at least 50-fold.

Cell-based assay results (without ODQ incubation) for the following representative compounds are provided. Data are listed as inflection points (IP) and the maximal fold induction over DMSO control:

| Example # | IUPAC Name | IP (nM) | Maximum fold induction over DMSO control |
|---|---|---|---|
| 2 | 4-amino-2-[5-chloro-3-(3,3,4,4,4-pentafluorobutyl)-1H-indazol-1-yl]-5-methyl-5-phenyl-5,7-dihydro-6H-pyrrolo[2,3-d]pyrimidin-6-one | 114 | 133 |
| 26 | 4-amino-2-[5-fluoro-3-(3,3,4,4,4-pentafluorobutyl)-1H-indazol-1-yl]-5-methyl-5-phenyl-5,7-dihydro-6H-pyrrolo[2,3-d]pyrimidin-6-one | 212 | 156 |
| 58 | 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one | 50 | 225 |
| 9 | 4-amino-2-[6-chloro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one | 143 | 187 |

| Example # | IUPAC Name | IP (nM) | Maximum fold induction over DMSO control |
|---|---|---|---|
| 70 | 4-amino-2-[6-fluoro-1-(3,3,4,4,4-pentafluorobutyl)-1H-indazol-3-yl]-5-methyl-5-phenyl-5,7-dihydro-6H-pyrrolo[2,3-d]pyrimidin-6-one | 46 | 126 |
| 105 | 4-amino-2-[6-chloro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one | 258 | 150 |
| 136 | 4-amino-2-[6-chloro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one | 139 | 52 |

Acute Efficacy in Spontaneously Hypertensive Rats (SHR)

Spontaneously hypertensive rats (SHR, male, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following representative compounds are provided.

Category A=SBP in SHRs<25 mmHg
Category B=SBP in SHRs 25-40 mmHg
Category C=SBP in SHRs>40 mmHg

| Example number | Dose P.O. mpk | Category |
|---|---|---|
| 159 | 0.3 | B |
| 160 | 0.3 | C |
| 161 | 0.3 | B |
| 162 | 0.3 | B |
| 163 | 0.3 | C |
| 164 | 0.3 | C |
| 165 | 0.3 | B |
| 166 | 0.3 | A |
| 167 | 0.3 | B |
| 168 | 0.3 | A |
| 169 | 0.3 | C |
| 170 | 1 | C |
| 171 | 0.3 | C |
| 172 | 0.3 | A |
| 173 | 0.3 | C |
| 174 | 0.3 | B |
| 175 | 0.3 | B |
| 176 | 0.1 | C |
| 178 | 0.1 | A |
| 179 | 0.1 | B |
| 180 | 0.3 | A |
| 181 | 0.3 | B |
| 182 | 1 | B |
| 183 | 0.3 | C |
| 184 | 0.3 | A |
| 185 | 1.0 | C |
| 186 | 0.3 | B |
| 187 | 0.3 | B |
| 188 | 0.3 | B |
| 189 | 0.3 | C |
| 190 | 0.3 | B |
| 191 | 0.3 | B |
| 192 | 0.3 | B |
| 193 | 0.3 | C |
| 194 | 0.3 | C |
| 195 | 0.3 | C |
| 196 | 0.3 | B |
| 197 | 0.3 | B |
| 198 | 0.3 | B |
| 199 | 0.3 | B |
| 200 | 0.3 | C |
| 201 | 0.3 | A |
| 202 | 0.3 | C |
| 203 | 0.3 | C |
| 204 | 0.3 | B |
| 205 | 1 | C |
| 206 | 0.3 | C |
| 207 | 0.3 | C |
| 208 | 1 | A |
| 209 | 1 | B |
| 210 | 0.3 | B |
| 211 | 0.3 | C |
| 212 | 0.1 | B |
| 213 | 0.3 | C |
| 214 | 0.1 | A |
| 215 | 0.3 | B |
| 216 | 0.1 | A |
| 217 | 0.3 | C |
| 218 | 1 | C |
| 219 | 0.3 | C |
| 220 | 1 | B |
| 221 | 1 | C |
| 222 | 0.3 | C |
| 223 | 0.3 | B |
| 224 | 1 | B |
| 225 | 0.3 | C |
| 226 | 0.3 | B |
| 227 | 0.3 | B |
| 228 | 0.3 | A |
| 229 | 1 | C |
| 230 | 0.1 | A |
| 231 | 0.3 | C |
| 232 | 0.3 | B |
| 233 | 0.3 | B |
| 234 | 0.3 | C |
| 235 | 0.3 | B |
| 236 | 0.3 | B |
| 237 | 0.1 | B |
| 238 | 0.3 | B |
| 239 | 0.3 | A |
| 241 | 1 | B |
| 242 | 0.3 | B |
| 243 | 1 | B |
| 244 | 0.3 | C |
| 245 | 0.3 | C |
| 246 | 0.3 | C |
| 247 | 1 | C |
| 248 | 0.3 | B |
| 249 | 1 | A |
| 250 | 1 | C |
| 251 | 0.3 | C |
| 252 | 0.3 | B |
| 253 | 0.3 | A |
| 254 | 1 | B |
| 255 | 0.3 | B |

163
-continued

| Example number | Dose P.O. mpk | Category |
|---|---|---|
| 256 | 0.3 | B |
| 257 | 0.3 | A |
| 258 | 0.3 | A |
| 259 | 0.3 | A |
| 260 | 0.3 | B |
| 261 | 0.3 | C |
| 262 | 0.3 | A |
| 263 | 0.3 | A |
| 264 | 0.3 | B |
| 265 | 1 | C |
| 266 | 0.3 | C |
| 267 | 0.3 | B |
| 268 | 0.1 | B |
| 269 | 0.3 | C |
| 270 | 0.3 | A |

BP Lowering Data for Preferred Compounds

| Example number | Dose mpk | Maximum SBP reduction mmHg |
|---|---|---|
| 159 | 0.3 | 38 ± 6 |
| 160 | 0.3 | 77 ± 10 |
| 162 | 0.3 | 26 ± 7 |
| 168 | 0.3 | 19 ± 9 |
| 169 | 0.3 | 52 ± 5 |
| 170 | 1.0 | 65 ± 13 |
| 173 | 0.3 | 66 ± 6 |
| 180 | 0.3 | 18 ± 5 |
| 181 | 0.3 | 49 ± 2 |
| 182 | 1.0 | 46 ± 11 |
| 184 | 0.3 | 19 ± 5 |
| 185 | 1.0 | 43 ± 7 |

What is claimed is:

1. A compound having structural Formula I, or a pharmaceutically acceptable salt thereof:

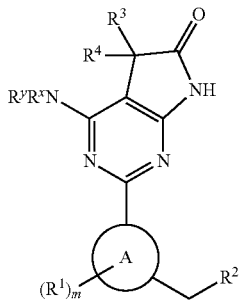

I or a pharmaceutically acceptable salt thereof, wherein

is a heteroaryl selected from

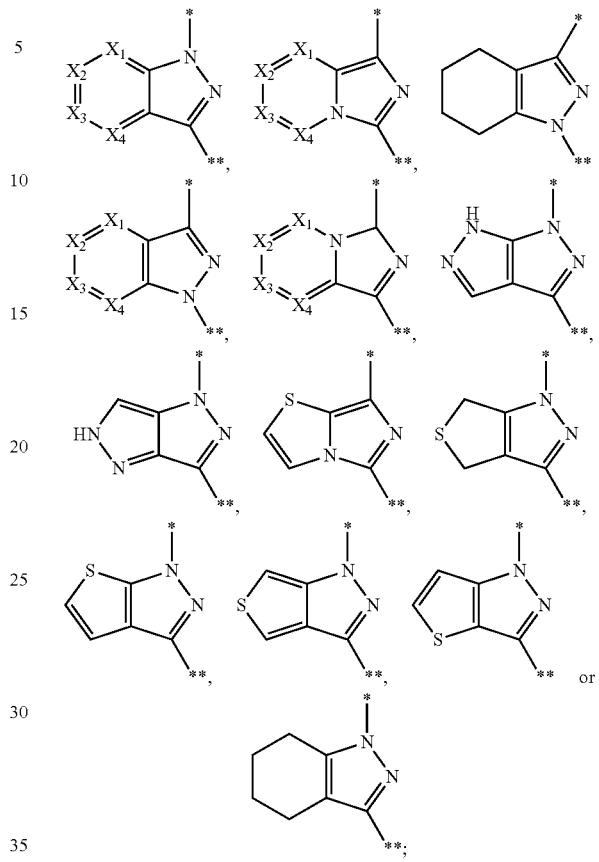

where * indicates attachment to the pyrimidinyl ring and ** indicates attachment to the —$CH_2$—$R^2$ of structural Formula I;

Each $X^1$, $X^2$, $X^3$ and $X^4$ is independently N or CH, provided that no more than two of $X^1$, $X^2$, $X^3$ and $X^4$ is N;

Each $R^x$ and $R^y$ are independently H, $C_{3-10}$ cycloalkyl, or —$C_1$-$C_6$ alkyl;

Each $R^1$ is independently —H, halo, OR, —$C_1$-$C_6$ alkyl, aryl, heterocyclyl, heteroaryl, —$C_{3-10}$ cycloalkyl, —CN, —$NR^aC(O)R^b$, or —$C(O)NR^aR^b$, said aryl, heteroaryl, and cycloalkyl optionally being substituted with one to three substituents selected from halo, —$C_1$-$C_6$ alkyl, —OR, —CN, and —$CF_3$;

$R^2$ is —$(CR^d_2)_tC_1$-$C_6$ alkyl, —$C_2$-$C_6$ alkenyl, —$C_2$-$C_6$ alkynyl, —$(CR^d_2)_tOR$, —$(CR^d_2)_tSR$, —$(CR^d_2)_tCF_3$, —$(CR^d_2)_tC_{3-10}$cycloalkyl, —$(CR^d_2)_t$-aryl, —$(CR^d_2)_t$-heterocyclyl or —$(CR^d_2)_t$heteroaryl, said alkyl, cycloalkyl, aryl, heterocyclyl and heteroaryl being optionally substituted with one to three substituents selected from halo, —$C_1$-$C_6$ alkyl, —$CF_3$, —CN or —OR;

$R^3$ is $(CR^d_2)_t$-aryl, —$(CR^d_2)_t$-heteroaryl, —$(CR^d_2)_t$-heterocyclyl, —$(CR^d_2)_t$-$C_{3-10}$cycloalkyl, —$(CR^d_2)_t$CN, —$(CR^d_2)_t$—$C(O)NR^aR^b$, —$(CR^d_2)_t NR^aC(O)R^b$, —$(CR^d_2)_t$—$C(S)NR^aR^b$, —$(CR^d_2)_t$—$C(O)OR^a$, —$(CR^d_2)_t$—$NR^aC(O)OR^a$, —$(CR^d_2)_t$—$NR^aR^b$, or —$OR^a$, said, aryl, heteroaryl or heterocyclyl are optionally substituted with from one to three substituents selected from $R^5$;

$R^4$ is —$C_1$-$C_6$ alkyl, $C_{3-10}$cycloalkyl, halo or $CF_3$;

Each $R^5$ is independently halo, OR, CN, —$(CR^d_2)_tCF_3$, $S(O)_pR^d$, —$(CR^d_2)_tC_{3-10}$cycloalkyl, or —$C_1$-$C_6$ alkyl, said alkyl and cycloalkyl being optionally substituted with one to three substituents selected from halo or OR;

Each $R^6$ is independently halo, —$C_1$-$C_6$ alkyl, OR, CN, $CF_3$, aryl or heteroaryl, where said alkyl, aryl or heteroaryl are optionally substituted with halo, $C_1$-$C_6$ alkyl or $CF_3$;

Each R is independently —H, —$C_1$-$C_6$ alkyl, —$CF_3$, or aryl;

Each $R^a$ and $R^b$ are independently —H, —$C_1$-$C_6$ alkyl, aryl, heteroaryl, heterocyclyl, or —$(CH_2)_{0-3}$—$C_{3-10}$ cycloalkyl, wherein said alkyl, heteroaryl, heterocyclyl, and cycloalkyl are optionally substituted with one to three substituents selected from $R^6$;

optionally, when $R^a$ and $R^b$ are —$C_1$-$C_6$ alkyl and are attached to the same nitrogen atom, $R^a$ and $R^b$ may be cyclized to form a $C_3$-$C_6$ cycloalkyl ring;

Each $R^d$ is independently —$C_1$-$C_6$ alkyl, —$CF_3$, or aryl;

Each $R^d$ is independently H, halo, —$CF_3$ or —$C_1$-$C_6$ alkyl;

m is an integer selected from 1, 2, or 3;

p is an integer independently selected from 0, 1 or 2; and t is an integer independently selected from 0, 1, 2, 3, or 4.

2. The compound according to claim 1, wherein

is a heteroaryl selected from

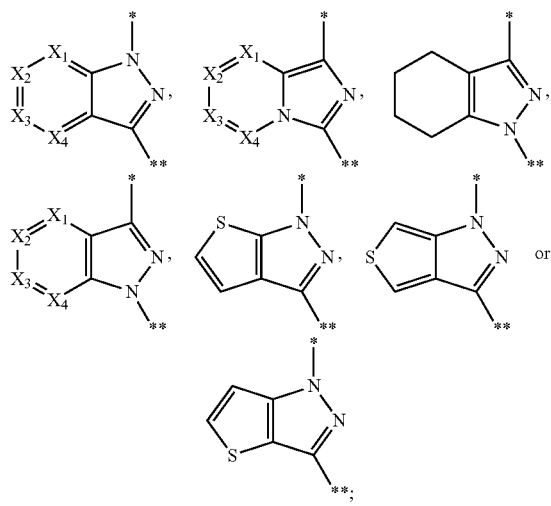

where * indicates attachment to the pyrimidinyl ring and ** indicates attachment to the —$CH_2$—$R^2$ of structural Formula I;

$X^1$, $X^2$, $X^3$ and $X^4$ are independently selected from N or CH, provided that no more than one of $X^1$, $X^2$, $X^3$ and $X^4$ is N;

or a pharmaceutically acceptable salt thereof.

3. The compound according to claim 1, wherein $R^3$ is aryl, heteroaryl, heterocyclyl, CN, —C(O)$NR^aR^b$, —$NR^a$C(O)$R^b$, —C(O)$OR^a$, or —$OR^a$, said aryl, heteroaryl or heterocyclyl are optionally substituted with from one to three substituents selected from halo, OR, CN, S(O)$_p$$R^c$, or —$C_1$-$C_6$ alkyl, said alkyl being optionally substituted with one to three substituents selected from halo or OR;

or a pharmaceutically acceptable salt thereof.

4. The compound according to claim 1 having structural Formula III:

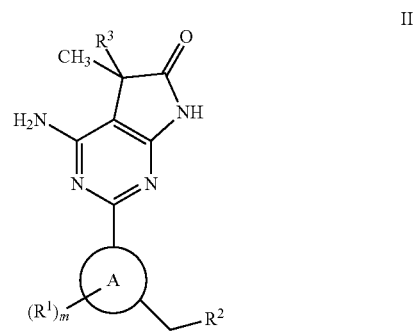

or a pharmaceutically acceptable salt thereof, wherein $X^4$ is CH or N;

Each R is independently —H, —$C_1$-$C_6$ alkyl, —$CF_3$, or aryl;

Each $R^a$ is independently —H or —$C_1$-$C_6$ alkyl;

Each $R^b$ is independently —H, —$C_1$-$C_6$ alkyl, —$C_{3-10}$ cycloalkyl or heteroaryl, wherein said alkyl, cycloalkyl and heteroaryl are optionally substituted with one to three substituents selected $R^6$;

Each $R^d$ is independently —$C_1$-$C_6$ alkyl, —$CF_3$, or aryl;

Each $R^d$ is independently H, halo, —$CF_3$ or —$C_1$-$C_6$ alkyl;

Each $R^1$ is independently —H, OR, CN, halo or —$C_1$-$C_6$ alkyl;

$R^2$ is —$(CR^d{}_2)_t C_1$-$C_6$ alkyl, —$(CR^d{}_2)_t CF_3$, —$(CR^d{}_2)_t$—$C_{3-10}$cycloalkyl, or —$(CR^d{}_2)_t$aryl, said alkyl, cycloalkyl and aryl being optionally substituted with one to three substituents selected from halo, —$C_1$-$C_6$ alkyl and —$CF_3$;

$R^3$ is aryl, heteroaryl, heterocyclyl, CN, —C(O)$NR^aR^b$, —$NR^a$C(O)$R^b$, —C(O)$OR^a$, or —$OR^a$, said aryl, heteroaryl or heterocyclyl are optionally substituted with from one to three substituent selected $R^5$;

$R^4$ is —$CH_3$ or $C_{3-10}$cycloalkyl;

Each $R^5$ is independently halo, OR, CN, S(O)$_p$$R^d$, or —$C_1$-$C_6$ alkyl, said alkyl being optionally substituted with one to three substituents selected from halo or OR;

Each $R^6$ is independently halo, —$C_1$-$C_6$ alkyl, OR, CN, $CF_3$, aryl or heteroaryl, where said alkyl, aryl or heteroaryl are optionally substituted with halo, $C_1$-$C_6$ alkyl or $CF_3$;

m is an integer selected from 1, 2, or 3;

p is an integer independently selected from 0, 1 or 2; and t is an integer independently selected from 0, 1, 2, 3, or 4.

5. The compound according to claim 1, which is

| 1 | 4-amino-2-[5-chloro-3-(3,3,3-trifluoropropyl)-1H-indazol-1-yl]-5-methyl-5-phenyl-5,7-dihydro-6H-pyrrolo[2,3-d]pyrimidin-6-one, |
|---|---|
| 2 | 4-amino-2-[5-chloro-3-(3,3,4,4,4-pentafluorobutyl)-1H-indazol-1-yl]-5-methyl-5-phenyl-5,7-dihydro-6H-pyrrolo[2,3-d]pyrimidin-6-one, |

-continued

| | |
|---|---|
| 3 | 4-amino-2-[5-chloro-3-(2,3,6-trifluorobenzyl)-1H-indazol-1-yl]-5-methyl-5-phenyl-5,7-dihydro-6H-pyrrolo[2,3-d]pyrimidin-6-one, |
| 4 | 4-amino-2-[5-chloro-3-(3,3,4,4,4-pentafluorobutyl)-1H-indazol-1-yl]-5-methyl-5-(3-methyl-1,2,4-oxadiazol-5-yl)-5,7-dihydro-6H-pyrrolo[2,3-d]pyrimidin-6-one, |
| 5 | 4-amino-2-[3-(2-fluorobenzyl)-1H-indazol-1-yl]-5-methyl-5-phenyl-5,7-dihydro-6H-pyrrolo[2,3-d]pyrimidin-6-one, |
| 6 | 4-amino-2-[5-chloro-3-(2-fluorobenzyl)-1H-indazol-1-yl]-5-methyl-5-phenyl-5,7-dihydro-6H-pyrrolo[2,3-d]pyrimidin-6-one, |
| 7 | 4-amino-2-[5-chloro-3-(2-fluorobenzyl)-1H-indazol-1-yl]-5-methyl-5-(pyridin-3-yl)-5,7-dihydro-6H-pyrrolo[2,3-d]pyrimidin-6-one, |
| 8 | 4-amino-2-[5-chloro-3-(2-fluorobenzyl)-1H-indazol-1-yl]-5-methyl-5-(pyridin-4-yl)-5,7-dihydro-6H-pyrrolo[2,3-d]pyrimidin-6-one, |
| 9 | 4-amino-2-[5-chloro-3-(2,3-difluorobenzyl)-1H-indazol-1-yl]-5-methyl-5-phenyl-5,7-dihydro-6H-pyrrolo[2,3-d]pyrimidin-6-one, |
| 10 | 4-amino-2-[5-chloro-3-(2,3-difluorobenzyl)-1H-indazol-1-yl]-5-methyl-5-(pyridin-3-yl)-5,7-dihydro-6H-pyrrolo[2,3-d]pyrimidin-6-one, |
| 11 | 4-amino-2-[5-chloro-3-(2,3-difluorobenzyl)-1H-indazol-1-yl]-5-methyl-5-(pyridin-4-yl)-5,7-dihydro-6H-pyrrolo[2,3-d]pyrimidin-6-one, |
| 12 | 4-amino-5-methyl-5-phenyl-2-[3-(2,3,6-trifluorobenzyl)-1H-indazol-1-yl]-5,7-dihydro-6H-pyrrolo[2,3-d]pyrimidin-6-one, |
| 13 | 4-amino-2-[5-chloro-3-(2-phenylethyl)-1H-indazol-1-yl]-5-methyl-5-phenyl-5,7-dihydro-6H-pyrrolo[2,3-d]pyrimidin-6-one, |
| 14 | 4-amino-5-methyl-5-phenyl-2-[3-(3,3,3-trifluoropropyl)-1H-indazol-1-yl]-5,7-dihydro-6H-pyrrolo[2,3-d]pyrimidin-6-one, |
| 15 | 4-amino-2-[5-fluoro-3-(3,3,3-trifluoropropyl)-1H-indazol-1-yl]-5-methyl-5-phenyl-5,7-dihydro-6H-pyrrolo[2,3-d]pyrimidin-6-one, |
| 16 | 4-amino-2-[5-chloro-3-(3,3,3-trifluoropropyl)-1H-indazol-1-yl]-5-(4-fluorophenyl)-5-methyl-5,7-dihydro-6H-pyrrolo[2,3-d]pyrimidin-6-one, |
| 17 | 4-amino-2-[5-chloro-3-(3,3,3-trifluoropropyl)-1H-indazol-1-yl]-5-methyl-5-(pyridin-2-yl)-5,7-dihydro-6H-pyrrolo[2,3-d]pyrimidin-6-one, |
| 18 | 4-amino-2-[5-chloro-3-(3,3,3-trifluoropropyl)-1H-indazol-1-yl]-5-methyl-5-(pyridin-3-yl)-5,7-dihydro-6H-pyrrolo[2,3-d]pyrimidin-6-one, |
| 19 | 4-amino-2-[5-chloro-3-(3,3,3-trifluoropropyl)-1H-indazol-1-yl]-5-methyl-5-(pyridin-4-yl)-5,7-dihydro-6H-pyrrolo[2,3-d]pyrimidin-6-one, |
| 20 | 4-amino-2-[5-chloro-3-(3,3,3-trifluoropropyl)-1H-indazol-1-yl]-5-methyl-5-(pyrazin-2-yl)-5,7-dihydro-6H-pyrrolo[2,3-d]pyrimidin-6-one, |
| 21 | 4-amino-2-[5-chloro-3-(3,3,3-trifluoro-2-methylpropyl)-1H-indazol-1-yl]-5-methyl-5-phenyl-5,7-dihydro-6H-pyrrolo[2,3-d]pyrimidin-6-one, |
| 22 | 4-amino-5-methyl-2-[3-(3,3,4,4,4-pentafluorobutyl)-1H-indazol-1-yl]-5-phenyl-5,7-dihydro-6H-pyrrolo[2,3-d]pyrimidin-6-one, |
| 23 | 4-amino-5-(2-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one, |
| 24 | 4-amino-5-(3-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one, |
| 25 | 4-amino-5-(4-fluorophenyl)-5-methyl-2-[3-(3,3,4,4,4-pentafluorobutyl)-1H-indazol-1-yl]-5,7-dihydro-6H-pyrrolo[2,3-d]pyrimidin-6-one, |
| 26 | 4-amino-2-[5-fluoro-3-(3,3,4,4,4-pentafluorobutyl)-1H-indazol-1-yl]-5-methyl-5-phenyl-5,7-dihydro-6H-pyrrolo[2,3-d]pyrimidin-6-one, |
| 27 | 4-amino-2-[5-fluoro-3-(3,3,4,4,4-pentafluorobutyl)-1H-indazol-1-yl]-5-(2-fluorophenyl)-5-methyl-5,7-dihydro-6H-pyrrolo[2,3-d]pyrimidin-6-one, |
| 28 | 4-amino-2-[5-chloro-3-(3,3,4,4,4-pentafluorobutyl)-1H-indazol-1-yl]-5-(2-fluorophenyl)-5-methyl-5,7-dihydro-6H-pyrrolo[2,3-d]pyrimidin-6-one, |
| 29 | 4-amino-2-[5-chloro-3-(3,3,4,4,4-pentafluorobutyl)-1H-indazol-1-yl]-5-(3-fluorophenyl)-5-methyl-5,7-dihydro-6H-pyrrolo[2,3-d]pyrimidin-6-one, |
| 30 | 4-amino-2-[5-chloro-3-(3,3,4,4,4-pentafluorobutyl)-1H-indazol-1-yl]-5-(4-fluorophenyl)-5-methyl-5,7-dihydro-6H-pyrrolo[2,3-d]pyrimidin-6-one, |
| 31 | 4-amino-2-[5-chloro-3-(3,3,4,4,4-pentafluorobutyl)-1H-indazol-1-yl]-5-(3,5-difluorophenyl)-5-methyl-5,7-dihydro-6H-pyrrolo[2,3-d]pyrimidin-6-one, |
| 32 | 4-amino-5-(4-chlorophenyl)-5-methyl-2-[3-(3,3,4,4,4-pentafluorobutyl)-1H-indazol-1-yl]-5,7-dihydro-6H-pyrrolo[2,3-d]pyrimidin-6-one, |
| 33 | 4-amino-2-[5-chloro-3-(3,3,4,4,4-pentafluorobutyl)-1H-indazol-1-yl]-5-(4-chlorophenyl)-5-methyl-5,7-dihydro-6H-pyrrolo[2,3-d]pyrimidin-6-one, |
| 34 | 4-amino-5-(4-bromophenyl)-2-[5-chloro-3-(3,3,4,4,4-pentafluorobutyl)-1H-indazol-1-yl]-5-methyl-5,7-dihydro-6H-pyrrolo[2,3-d]pyrimidin-6-one, |
| 35 | 4-{4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidin-5-yl}benzonitrile, |
| 36 | 4-amino-5-(4-hydroxyphenyl)-5-methyl-2-[3-(3,3,4,4,4-pentafluorobutyl)-1H-indazol-1-yl]-5,7-dihydro-6H-pyrrolo[2,3-d]pyrimidin-6-one, |
| 37 | 4-amino-2-[5-chloro-3-(3,3,4,4,4-pentafluorobutyl)-1H-indazol-1-yl]-5-methyl-5-[4-(methylsulfonyl)phenyl]-5,7-dihydro-6H-pyrrolo[2,3-d]pyrimidin-6-one, |
| 38 | 4-amino-5-methyl-2-[3-(3,3,4,4,4-pentafluorobutyl)-1H-indazol-1-yl]-5-(pyridin-2-yl)-5,7-dihydro-6H-pyrrolo[2,3-d]pyrimidin-6-one, |
| 39 | 4-amino-2-[5-fluoro-3-(3,3,4,4,4-pentafluorobutyl)-1H-indazol-1-yl]-5-methyl-5-(pyridin-2-yl)-5,7-dihydro-6H-pyrrolo[2,3-d]pyrimidin-6-one, |
| 40 | 4-amino-2-[5-chloro-3-(3,3,4,4,4-pentafluorobutyl)-1H-indazol-1-yl]-5-methyl-5-(pyridin-2-yl)-5,7-dihydro-6H-pyrrolo[2,3-d]pyrimidin-6-one, |

-continued

| | |
|---|---|
| 41 | 4-amino-2-[5-chloro-3-(3,3,4,4,4-pentafluorobutyl)-1H-indazol-1-yl]-5-(5-fluoropyridin-2-yl)-5-methyl-5,7-dihydro-6H-pyrrolo[2,3-d]pyrimidin-6-one, |
| 42 | 4-amino-5-(5-chloropyridin-2-yl)-5-methyl-2-[3-(3,3,4,4,4-pentafluorobutyl)-1H-indazol-1-yl]-5,7-dihydro-6H-pyrrolo[2,3-d]pyrimidin-6-one, |
| 43 | 4-amino-2-[5-chloro-3-(3,3,4,4,4-pentafluorobutyl)-1H-indazol-1-yl]-5-(5-chloropyridin-2-yl)-5-methyl-5,7-dihydro-6H-pyrrolo[2,3-d]pyrimidin-6-one, |
| 44 | 4-amino-2-[5-chloro-3-(3,3,4,4,4-pentafluorobutyl)-1H-indazol-1-yl]-5-methyl-5-(pyrazin-2-yl)-5,7-dihydro-6H-pyrrolo[2,3-d]pyrimidin-6-one, |
| 45 | 4-amino-2-[5-chloro-3-(3,3,4,4,4-pentafluorobutyl)-1H-indazol-1-yl]-5-methyl-5-(5-methyl-1,2,4-oxadiazol-3-yl)-5,7-dihydro-6H-pyrrolo[2,3-d]pyrimidin-6-one, |
| 46 | 4-amino-2-[5-fluoro-3-(3,3,4,4,4-pentafluorobutyl)-1H-indazol-1-yl]-5-methyl-5-(3-methyl-1,2,4-oxadiazol-5-yl)-5,7-dihydro-6H-pyrrolo[2,3-d]pyrimidin-6-one, |
| 47 | 4-amino-2-[5-chloro-3-(4,4,5,5,5-pentafluoropentyl)-1H-indazol-1-yl]-5-methyl-5-phenyl-5,7-dihydro-6H-pyrrolo[2,3-d]pyrimidin-6-one, |
| 48 | 4-amino-2-[5-chloro-3-(3,3,4,4,5,5,5-heptafluoropentyl)-1H-indazol-1-yl]-5-methyl-5-phenyl-5,7-dihydro-6H-pyrrolo[2,3-d]pyrimidin-6-one, |
| 49 | methyl 4-amino-2-[5-chloro-3-(3,3,3-trifluoropropyl)-1H-indazol-1-yl]-5-methyl-6-oxo-6,7-dihydro-5H-pyrrolo[2,3-d]pyrimidine-5-carboxylate, |
| 50 | ethyl 4-amino-2-[5-chloro-3-(3,3,3-trifluoropropyl)-1H-indazol-1-yl]-5-methyl-6-oxo-6,7-dihydro-5H-pyrrolo[2,3-d]pyrimidine-5-carboxylate, |
| 51 | methyl 4-amino-2-[5-fluoro-3-(3,3,4,4,4-pentafluorobutyl)-1H-indazol-1-yl]-5-methyl-6-oxo-6,7-dihydro-5H-pyrrolo[2,3-d]pyrimidine-5-carboxylate, |
| 52 | methyl 4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carboxylate, |
| 53 | 4-amino-2-[5-chloro-3-(3,3,3-trifluoropropyl)-1H-thieno[2,3-c]pyrazol-1-yl]-5-methyl-5-phenyl-5,7-dihydro-6H-pyrrolo[2,3-d]pyrimidin-6-one, |
| 54 | 4-amino-5-methyl-5-phenyl-2-[3-(2,3,6-trifluorobenzyl)-1H-thieno[3,4-c]pyrazol-1-yl]-5,7-dihydro-6H-pyrrolo[2,3-d]pyrimidin-6-one, |
| 55 | 4-amino-2-[3-(2,3-difluorobenzyl)-1H-pyrazolo[4,3-b]pyridin-1-yl]-5-methyl-5-phenyl-5,7-dihydro-6H-pyrrolo[2,3-d]pyrimidin-6-one, |
| 56 | 4-amino-5-methyl-5-phenyl-2-[3-(3,3,3-trifluoropropyl)-1H-pyrazolo[4,3-b]pyridin-1-yl]-5,7-dihydro-6H-pyrrolo[2,3-d]pyrimidin-6-one, |
| 57 | 4-amino-5-methyl-2-[3-(3,3,4,4,4-pentafluorobutyl)-1H-pyrazolo[4,3-b]pyridin-1-yl]-5-phenyl-5,7-dihydro-6H-pyrrolo[2,3-d]pyrimidin-6-one, |
| 58 | 4-amino-2-[6-chloro-1-(3,3,4,4,4-pentafluorobutyl)-1H-indazol-3-yl]-5-methyl-5-phenyl-5,7-dihydro-6H-pyrrolo[2,3-d]pyrimidin-6-one, |
| 59 | 4-amino-2-[6-chloro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one, |
| 60 | 4-amino-5-methyl-5-phenyl-2-[1-(2,2,2-trifluoroethyl)-1H-indazol-3-yl]-5,7-dihydro-6H-pyrrolo[2,3-d]pyrimidin-6-one, |
| 61 | 4-amino-2-[1-(2-methoxyethyl)-1H-indazol-3-yl]-5-methyl-5-phenyl-5,7-dihydro-6H-pyrrolo[2,3-d]pyrimidin-6-one, |
| 62 | 4-amino-2-[1-(ethoxymethyl)-1H-indazol-3-yl]-5-methyl-5-phenyl-5,7-dihydro-6H-pyrrolo[2,3-d]pyrimidin-6-one, |
| 63 | 4-amino-5-methyl-2-[1-(2,2,3,3,3-pentafluoropropyl)-1H-indazol-3-yl]-5-phenyl-5,7-dihydro-6H-pyrrolo[2,3-d]pyrimidin-6-one, |
| 64 | 4-amino-2-{1-[(2,2-difluorocyclopropyl)methyl]-1H-indazol-3-yl}-5-methyl-5-phenyl-5,7-dihydro-6H-pyrrolo[2,3-d]pyrimidin-6-one, |
| 65 | 4-amino-5-methyl-5-phenyl-2-[1-(3,3,3-trifluoropropyl)-1H-indazol-3-yl]-5,7-dihydro-6H-pyrrolo[2,3-d]pyrimidin-6-one, |
| 66 | 4-amino-2-[6-chloro-1-(3,3,3-trifluoropropyl)-1H-indazol-3-yl]-5-methyl-5-phenyl-5,7-dihydro-6H-pyrrolo[2,3-d]pyrimidin-6-one, |
| 67 | 4-amino-2-[6-chloro-1-(3,3,3-trifluoropropyl)-1H-indazol-3-yl]-5-methyl-5-(3-methyl-1,2,4-oxadiazol-5-yl)-5,7-dihydro-6H-pyrrolo[2,3-d]pyrimidin-6-one, |
| 68 | methyl 4-amino-2-[6-chloro-1-(3,3,3-trifluoropropyl)-1H-indazol-3-yl]-5-methyl-6-oxo-6,7-dihydro-5H-pyrrolo[2,3-d]pyrimidine-5-carboxylate, |
| 69 | 4-amino-5-methyl-2-[1-(3,3,4,4,4-pentafluorobutyl)-1H-indazol-3-yl]-5-phenyl-5,7-dihydro-6H-pyrrolo[2,3-d]pyrimidin-6-one, |
| 70 | 4-amino-2-[6-fluoro-1-(3,3,4,4,4-pentafluorobutyl)-1H-indazol-3-yl]-5-methyl-5-phenyl-5,7-dihydro-6H-pyrrolo[2,3-d]pyrimidin-6-one, |
| 71 | 4-amino-2-[6-bromo-1-(3,3,4,4,4-pentafluorobutyl)-1H-indazol-3-yl]-5-methyl-5-phenyl-5,7-dihydro-6H-pyrrolo[2,3-d]pyrimidin-6-one, |
| 72 | 4-amino-5-(2-fluorophenyl)-5-methyl-2-[1-(3,3,4,4,4-pentafluorobutyl)-1H-indazol-3-yl]-5,7-dihydro-6H-pyrrolo[2,3-d]pyrimidin-6-one, |
| 73 | 4-amino-2-[6-fluoro-1-(3,3,4,4,4-pentafluorobutyl)-1H-indazol-3-yl]-5-(2-fluorophenyl)-5-methyl-5,7-dihydro-6H-pyrrolo[2,3-d]pyrimidin-6-one, |
| 74 | 4-amino-2-[6-chloro-1-(3,3,4,4,4-pentafluorobutyl)-1H-indazol-3-yl]-5-(2-fluorophenyl)-5-methyl-5,7-dihydro-6H-pyrrolo[2,3-d]pyrimidin-6-one, |
| 75 | 4-amino-5-(4-chlorophenyl)-5-methyl-2-[1-(3,3,4,4,4-pentafluorobutyl)-1H-indazol-3-yl]-5,7-dihydro-6H-pyrrolo[2,3-d]pyrimidin-6-one, |
| 76 | 4-amino-2-[6-chloro-1-(3,3,4,4,4-pentafluorobutyl)-1H-indazol-3-yl]-5-(4-chlorophenyl)-5-methyl-5,7-dihydro-6H-pyrrolo[2,3-d]pyrimidin-6-one, |
| 77 | 4-amino-5-(4-bromophenyl)-2-[6-chloro-1-(3,3,4,4,4-pentafluorobutyl)-1H-indazol-3-yl]-5-methyl-5,7-dihydro-6H-pyrrolo[2,3-d]pyrimidin-6-one, |

| | |
|---|---|
| 78 | 4-amino-2-[6-chloro-1-(3,3,4,4,4-pentafluorobutyl)-1H-indazol-3-yl]-5-methyl-5-[4-(methylsulfonyl)phenyl]-5,7-dihydro-6H-pyrrolo[2,3-d]pyrimidin-6-one, |
| 79 | 4-amino-5-methyl-2-[1-(3,3,4,4,4-pentafluorobutyl)-1H-indazol-3-yl]-5-(pyridin-2-yl)-5,7-dihydro-6H-pyrrolo[2,3-d]pyrimidin-6-one, |
| 80 | 4-amino-2-[6-chloro-1-(3,3,4,4,4-pentafluorobutyl)-1H-indazol-3-yl]-5-methyl-5-(pyridin-2-yl)-5,7-dihydro-6H-pyrrolo[2,3-d]pyrimidin-6-one, |
| 81 | 4-amino-2-[6-chloro-1-(3,3,4,4,4-pentafluorobutyl)-1H-indazol-3-yl]-5-methyl-5-(pyrimidin-2-yl)-5,7-dihydro-6H-pyrrolo[2,3-d]pyrimidin-6-one, |
| 82 | 4-amino-2-[6-chloro-1-(3,3,4,4,4-pentafluorobutyl)-1H-indazol-3-yl]-5-methyl-5-(5-methyl-1,3-oxazol-2-yl)-5,7-dihydro-6H-pyrrolo[2,3-d]pyrimidin-6-one, |
| 83 | 4-amino-2-[6-fluoro-1-(3,3,4,4,4-pentafluorobutyl)-1H-indazol-3-yl]-5-methyl-5-(3-methyl-1,2,4-oxadiazol-5-yl)-5,7-dihydro-6H-pyrrolo[2,3-d]pyrimidin-6-one, |
| 84 | 4-amino-5-methyl-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one, |
| 85 | 4-amino-2-[5-chloro-3-(3,3,4,4,4-pentafluorobutyl)-1H-indazol-1-yl]-5-methyl-5-(5-methyl-1,3,4-thiadiazol-2-yl)-5,7-dihydro-6H-pyrrolo[2,3-d]pyrimidin-6-one, |
| 86 | 4-amino-2-[5-chloro-3-(3,3,4,4,4-pentafluorobutyl)-1H-indazol-1-yl]-5-methyl-5-(5-methyl-1,3,4-oxadiazol-2-yl)-5,7-dihydro-6H-pyrrolo[2,3-d]pyrimidin-6-one, |
| 87 | 4-amino-5-methyl-6-oxo-2-[3-(3,3,4,4,4-pentafluorobutyl)-1H-indazol-1-yl]-6,7-dihydro-5H-pyrrolo[2,3-d]pyrimidine-5-carboxamide, |
| 88 | 4-amino-2-[5-chloro-3-(3,3,4,4,4-pentafluorobutyl)-1H-indazol-1-yl]-5-methyl-6-oxo-6,7-dihydro-5H-pyrrolo[2,3-d]pyrimidine-5-carboxamide, |
| 89 | 4-amino-2-[5-fluoro-3-(3,3,4,4,4-pentafluorobutyl)-1H-indazol-1-yl]-N,5-dimethyl-6-oxo-6,7-dihydro-5H-pyrrolo[2,3-d]pyrimidine-5-carboxamide, |
| 90 | 4-amino-2-[5-chloro-3-(3,3,4,4,4-pentafluorobutyl)-1H-indazol-1-yl]-N,5-dimethyl-6-oxo-6,7-dihydro-5H-pyrrolo[2,3-d]pyrimidine-5-carboxamide, |
| 91 | 4-amino-2-[5-chloro-3-(3,3,4,4,4-pentafluorobutyl)-1H-indazol-1-yl]-N-ethyl-5-methyl-6-oxo-6,7-dihydro-5H-pyrrolo[2,3-d]pyrimidine-5-carboxamide, |
| 92 | 4-amino-2-[5-chloro-3-(3,3,4,4,4-pentafluorobutyl)-1H-indazol-1-yl]-5-methyl-N-[(1-methyl-1H-pyrazol-3-yl)methyl]-6-oxo-6,7-dihydro-5H-pyrrolo[2,3-d]pyrimidine-5-carboxamide, |
| 93 | 4-amino-5-methyl-5-(4-methyl-5-oxo-4,5-dihydro-1,3,4-oxadiazol-2-yl)-2-[3-(3,3,4,4,4-pentafluorobutyl)-1H-indazol-1-yl]-5,7-dihydro-6H-pyrrolo[2,3-d]pyrimidin-6-one, |
| 94 | 4-amino-2-[5-chloro-3-(3,3,4,4,4-pentafluorobutyl)-1H-indazol-1-yl]-5-methyl-5-(1,3,4-thiadiazol-2-yl)-5,7-dihydro-6H-pyrrolo[2,3-d]pyrimidin-6-one, |
| 95 | 4-amino-2-[6-chloro-1-(3,3,4,4,4-pentafluorobutyl)-1H-indazol-3-yl]-N,5-dimethyl-6-oxo-6,7-dihydro-5H-pyrrolo[2,3-d]pyrimidine-5-carboxamide, |
| 96 | 4-amino-2-[6-chloro-1-(3,3,4,4,4-pentafluorobutyl)-1H-indazol-3-yl]-5-methyl-5-(4-methyl-5-oxo-4,5-dihydro-1,3,4-oxadiazol-2-yl)-5,7-dihydro-6H-pyrrolo[2,3-d]pyrimidin-6-one, |
| 97 | 4-amino-2-[6-chloro-1-(3,3,4,4,4-pentafluorobutyl)-1H-indazol-3-yl]-5-methyl-5-(5-methyl-1,3,4-thiadiazol-2-yl)-5,7-dihydro-6H-pyrrolo[2,3-d]pyrimidin-6-one, |
| 98 | 4-amino-2-[6-chloro-1-(3,3,4,4,4-pentafluorobutyl)-1H-indazol-3-yl]-5-methyl-5-(5-methyl-1,3,4-oxadiazol-2-yl)-5,7-dihydro-6H-pyrrolo[2,3-d]pyrimidin-6-one, |
| 99 | 4-amino-5-methyl-5-phenyl-2-[3-(2,3,6-trifluorobenzyl)-4,6-dihydro-1H-thieno[3,4-c]pyrazol-1-yl]-5,7-dihydro-6H-pyrrolo[2,3-d]pyrimidin-6-one, |
| 100 | 4-amino-5-methyl-2-[1-(3,3,4,4,4-pentafluorobutyl)-4,5,6,7-tetrahydro-1H-indazol-3-yl]-5-phenyl-5,7-dihydro-6H-pyrrolo[2,3-d]pyrimidin-6-one, |
| 101 | 4-amino-5-(2-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one, |
| 102 | 4-amino-5-(3-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one, |
| 103 | 4-amino-5-(4-fluorophenyl)-5-methyl-2-[3-(3,3,4,4,4-pentafluorobutyl)-4,5,6,7-tetrahydro-1H-indazol-1-yl]-5,7-dihydro-6H-pyrrolo[2,3-d]pyrimidin-6-one, |
| 104 | 4-amino-5-methyl-5-phenyl-2-[1-(3,3,3-trifluoropropyl)-4,5,6,7-tetrahydro-1H-indazol-3-yl]-5,7-dihydro-6H-pyrrolo[2,3-d]pyrimidin-6-one, |
| 105 | 4-amino-2-[6-chloro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one, |
| 106 | 4-amino-2-[6-fluoro-3-(3,3,4,4,4-pentafluorobutyl)imidazo[1,5-a]pyridin-1-yl]-5-(4-fluorophenyl)-5-methyl-5,7-dihydro-6H-pyrrolo[2,3-d]pyrimidin-6-one, |
| 107 | 4-amino-5-methyl-2-[7-(3,3,4,4,4-pentafluorobutyl)imidazo[1,5-b]pyridazin-5-yl]-5-phenyl-5,7-dihydro-6H-pyrrolo[2,3-d]pyrimidin-6-one, |

| | |
|---|---|
| 108 | 4-amino-5-methyl-5-(3-methyl-1,2,4-oxadiazol-5-yl)-2-[3-(3,3,4,4,4-pentafluorobutyl)imidazo[1,5-a]pyridin-1-yl]-5,7-dihydro-6H-pyrrolo[2,3-d]pyrimidin-6-one, |
| 109 | 4-amino-2-[6-fluoro-3-(3,3,4,4,4-pentafluorobutyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one, |
| 110 | 4-amino-2-[6-chloro-3-(3,3,4,4,4-pentafluorobutyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one, |
| 111 | 4-amino-2-[6-chloro-3-(3,3,4,4,4-pentafluorobutyl)imidazo[1,5-a]pyridin-1-yl]-5-methyl-5-(5-methyl-1,3-oxazol-2-yl)-5,7-dihydro-6H-pyrrolo[2,3-d]pyrimidin-6-one, |
| 112 | 4-amino-2-[6-chloro-3-(3,3,4,4,4-pentafluorobutyl)imidazo[1,5-a]pyridin-1-yl]-5-methyl-5-(2-methyl-1,3-oxazol-4-yl)-5,7-dihydro-6H-pyrrolo[2,3-d]pyrimidin-6-one, |
| 113 | 4-amino-2-[3-(2-fluorobenzyl)imidazo[1,5-a]pyridin-1-yl]-5-methyl-5-phenyl-5,7-dihydro-6H-pyrrolo[2,3-d]pyrimidin-6-one, |
| 114 | 4-amino-2-[3-(2-fluorobenzyl)imidazo[1,5-a]pyridin-1-yl]-5-methyl-5-(pyridin-4-yl)-5,7-dihydro-6H-pyrrolo[2,3-d]pyrimidin-6-one, |
| 115 | 4-amino-2-[6-chloro-3-(2-fluorobenzyl)imidazo[1,5-a]pyridin-1-yl]-5-methyl-5-(3-methyl-1,2,4-oxadiazol-5-yl)-5,7-dihydro-6H-pyrrolo[2,3-d]pyrimidin-6-one, |
| 116 | 4-amino-2-[3-(2,3-difluorobenzyl)imidazo[1,5-a]pyridin-1-yl]-5-methyl-5-phenyl-5,7-dihydro-6H-pyrrolo[2,3-d]pyrimidin-6-one, |
| 117 | 4-amino-2-[3-(2,3-difluorobenzyl)-6-fluoroimidazo[1,5-a]pyridin-1-yl]-5-methyl-5-phenyl-5,7-dihydro-6H-pyrrolo[2,3-d]pyrimidin-6-one, |
| 118 | 4-amino-2-[3-(2,3-difluorobenzyl)imidazo[1,5-a]pyridin-1-yl]-5-(4-fluorophenyl)-5-methyl-5,7-dihydro-6H-pyrrolo[2,3-d]pyrimidin-6-one, |
| 119 | 4-amino-2-[3-(2,3-difluorobenzyl)-6-fluoroimidazo[1,5-a]pyridin-1-yl]-5-(4-fluorophenyl)-5-methyl-5,7-dihydro-6H-pyrrolo[2,3-d]pyrimidin-6-one, |
| 120 | 4-amino-2-[3-(2,3-difluorobenzyl)imidazo[1,5-a]pyridin-1-yl]-5-methyl-5-(pyrazin-2-yl)-5,7-dihydro-6H-pyrrolo[2,3-d]pyrimidin-6-one, |
| 121 | 4-amino-2-[3-(2,3-difluorobenzyl)-6-fluoroimidazo[1,5-a]pyridin-1-yl]-5-methyl-5-(pyrazin-2-yl)-5,7-dihydro-6H-pyrrolo[2,3-d]pyrimidin-6-one, |
| 122 | 4-amino-5-methyl-5-phenyl-2-[3-(2,3,6-trifluorobenzyl)imidazo[1,5-a]pyridin-1-yl]-5,7-dihydro-6H-pyrrolo[2,3-d]pyrimidin-6-one, |
| 123 | 4-amino-2-[6-fluoro-3-(2,3,6-trifluorobenzyl)imidazo[1,5-a]pyridin-1-yl]-5-methyl-5-phenyl-5,7-dihydro-6H-pyrrolo[2,3-d]pyrimidin-6-one, |
| 124 | 4-amino-2-[6-chloro-3-(2,3,6-trifluorobenzyl)imidazo[1,5-a]pyridin-1-yl]-5-methyl-5-phenyl-5,7-dihydro-6H-pyrrolo[2,3-d]pyrimidin-6-one, |
| 125 | 4-amino-2-[6-fluoro-3-(3,3,3-trifluoropropyl)imidazo[1,5-a]pyridin-1-yl]-5-methyl-5-phenyl-5,7-dihydro-6H-pyrrolo[2,3-d]pyrimidin-6-one, |
| 126 | 4-amino-2-[6-chloro-3-(3,3,3-trifluoropropyl)imidazo[1,5-a]pyridin-1-yl]-5-methyl-5-phenyl-5,7-dihydro-6H-pyrrolo[2,3-d]pyrimidin-6-one, |
| 127 | 4-amino-5-methyl-5-phenyl-2-[3-(4,4,4-trifluorobutyl)imidazo[1,5-a]pyridin-1-yl]-5,7-dihydro-6H-pyrrolo[2,3-d]pyrimidin-6-one, |
| 128 | 4-amino-2-[6-fluoro-3-(4,4,4-trifluorobutyl)imidazo[1,5-a]pyridin-1-yl]-5-methyl-5-phenyl-5,7-dihydro-6H-pyrrolo[2,3-d]pyrimidin-6-one, |
| 129 | 4-amino-2-[6-chloro-3-(4,4,4-trifluorobutyl)imidazo[1,5-a]pyridin-1-yl]-5-methyl-5-phenyl-5,7-dihydro-6H-pyrrolo[2,3-d]pyrimidin-6-one, |
| 130 | 4-amino-2-[6-chloro-3-(4,4,4-trifluorobutyl)imidazo[1,5-a]pyridin-1-yl]-5-(4-fluorophenyl)-5-methyl-5,7-dihydro-6H-pyrrolo[2,3-d]pyrimidin-6-one, |
| 131 | 4-amino-2-[6-chloro-3-(4,4,4-trifluorobutyl)imidazo[1,5-a]pyridin-1-yl]-5-methyl-5-(pyridin-2-yl)-5,7-dihydro-6H-pyrrolo[2,3-d]pyrimidin-6-one, |
| 132 | 4-amino-2-[6-chloro-3-(4,4,4-trifluorobutyl)imidazo[1,5-a]pyridin-1-yl]-5-(5-fluoropyridin-2-yl)-5-methyl-5,7-dihydro-6H-pyrrolo[2,3-d]pyrimidin-6-one, |
| 133 | 4-amino-2-[6-chloro-3-(4,4,4-trifluorobutyl)imidazo[1,5-a]pyridin-1-yl]-5-methyl-5-(pyrazin-2-yl)-5,7-dihydro-6H-pyrrolo[2,3-d]pyrimidin-6-one, |
| 134 | 4-amino-5-methyl-2-[3-(3,3,4,4,4-pentafluorobutyl)imidazo[1,5-a]pyridin-1-yl]-5-phenyl-5,7-dihydro-6H-pyrrolo[2,3-d]pyrimidin-6-one, |
| 135 | 4-amino-2-[6-fluoro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one, |
| 136 | 4-amino-2-[6-chloro-3-(3,3,4,4,4-pentafluorobutyl)imidazo[1,5-a]pyridin-1-yl]-5-methyl-5-phenyl-5,7-dihydro-6H-pyrrolo[2,3-d]pyrimidin-6-one, |
| 137 | 4-amino-5-(2-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one, |
| 138 | 4-amino-5-(3-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one, |
| 139 | 4-amino-5-(4-fluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one, |
| 140 | 4-amino-5-(3,5-difluorophenyl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one, |

| | |
|---|---|
| 141 | 4-amino-5-(5-chloropyridin-2-yl)-5-methyl-2-[3-(3,3,4,4,4-pentafluorobutyl)imidazo[1,5-a]pyridin-1-yl]-5,7-dihydro-6H-pyrrolo[2,3-d]pyrimidin-6-one, |
| 142 | 4-amino-2-[6-fluoro-3-(3,3,4,4,4-pentafluorobutyl)imidazo[1,5-a]pyridin-1-yl]-5-(2-fluorophenyl)-5-methyl-5,7-dihydro-6H-pyrrolo[2,3-d]pyrimidin-6-one, |
| 143 | 4-amino-2-[6-fluoro-3-(3,3,4,4,4-pentafluorobutyl)imidazo[1,5-a]pyridin-1-yl]-5-(3-fluorophenyl)-5-methyl-5,7-dihydro-6H-pyrrolo[2,3-d]pyrimidin-6-one, |
| 144 | 4-amino-5-(3,5-difluorophenyl)-2-[6-fluoro-3-(3,3,4,4,4-pentafluorobutyl)imidazo[1,5-a]pyridin-1-yl]-5-methyl-5,7-dihydro-6H-pyrrolo[2,3-d]pyrimidin-6-one, |
| 145 | 4-amino-2-[6-fluoro-3-(3,3,4,4,4-pentafluorobutyl)imidazo[1,5-a]pyridin-1-yl]-5-methyl-5-(pyridin-2-yl)-5,7-dihydro-6H-pyrrolo[2,3-d]pyrimidin-6-one, |
| 146 | 4-amino-2-[6-fluoro-3-(3,3,4,4,4-pentafluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one, |
| 147 | ethyl 4-amino-2-[6-fluoro-3-(3,3,4,4,4-pentafluorobutyl)imidazo[1,5-a]pyridin-1-yl]-5-methyl-6-oxo-6,7-dihydro-5H-pyrrolo[2,3-d]pyrimidine-5-carboxylate, |
| 148 | 4-amino-2-[6-chloro-3-(3,3,4,4,4-pentafluorobutyl)imidazo[1,5-a]pyridin-1-yl]-5-(2-fluorophenyl)-5-methyl-5,7-dihydro-6H-pyrrolo[2,3-d]pyrimidin-6-one, |
| 149 | 4-amino-2-[6-chloro-3-(3,3,4,4,4-pentafluorobutyl)imidazo[1,5-a]pyridin-1-yl]-5-(3-fluorophenyl)-5-methyl-5,7-dihydro-6H-pyrrolo[2,3-d]pyrimidin-6-one, |
| 150 | 4-amino-2-[6-chloro-3-(3,3,4,4,4-pentafluorobutyl)imidazo[1,5-a]pyridin-1-yl]-5-(3,5-difluorophenyl)-5-methyl-5,7-dihydro-6H-pyrrolo[2,3-d]pyrimidin-6-one, |
| 151 | 4-amino-2-[6-chloro-3-(3,3,4,4,4-pentafluorobutyl)imidazo[1,5-a]pyridin-1-yl]-5-(4-chlorophenyl)-5-methyl-5,7-dihydro-6H-pyrrolo[2,3-d]pyrimidin-6-one, |
| 152 | 4-amino-2-[6-chloro-3-(3,3,4,4,4-pentafluorobutyl)imidazo[1,5-a]pyridin-1-yl]-5-methyl-5-(pyridin-2-yl)-5,7-dihydro-6H-pyrrolo[2,3-d]pyrimidin-6-one, |
| 153 | 4-amino-2-[6-chloro-3-(3,3,4,4,4-pentafluorobutyl)imidazo[1,5-a]pyridin-1-yl]-5-(5-fluoropyridin-2-yl)-5-methyl-5,7-dihydro-6H-pyrrolo[2,3-d]pyrimidin-6-one, |
| 154 | 4-amino-2-[6-chloro-3-(3,3,4,4,4-pentafluorobutyl)imidazo[1,5-a]pyridin-1-yl]-5-methyl-5-(pyrazin-2-yl)-5,7-dihydro-6H-pyrrolo[2,3-d]pyrimidin-6-one, |
| 155 | 4-amino-2-[6-chloro-3-(3,3,4,4,4-pentafluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one, |
| 156 | 4-amino-2-[3-(2,3-difluorobenzyl)imidazo[1,5-a]pyrazin-1-yl]-5-methyl-5-phenyl-5,7-dihydro-6H-pyrrolo[2,3-d]pyrimidin-6-one, |
| 157 | ethyl 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxylate, |
| 158 | ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate, |
| 159 | 4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide |
| 160 | 4-amino-2-[6-chloro-1-(3,3,4,4,4-pentafluorobutyl)-1H-indazol-3-yl]-N-cyclopropyl-5-methyl-6-oxo-6,7-dihydro-5H-pyrrolo[2,3-d]pyrimidine-5-carboxamide, |
| 161 | 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 162 | 4-amino-5-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 163 | 4-amino-5-cyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carbonitrile, |
| 164 | 4-amino-N-cyclopropyl-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 165 | 4-amino-2-[6-chloro-1-(3,3,4,4,4-pentafluorobutyl)-1H-indazol-3-yl]-5-methyl-6-oxo-N-phenyl-6,7-dihydro-5H-pyrrolo[2,3-d]pyrimidine-5-carboxamide, |
| 166 | ethyl (4-amino-2-(6-chloro-1-(3,3,4,4,4-pentafluorobutyl)-1H-indazol-3-yl)-5-methyl-6-oxo-6,7-dihydro-5H-pyrrolo[2,3-d]pyrimidin-5-yl)carbamate, |
| 167 | 4-amino-2-[6-chloro-1-(3,3,4,4,4-pentafluorobutyl)-1H-indazol-3-yl]-5-(4,5-dimethyl-1,3-thiazol-2-yl)-5-methyl-5,7-dihydro-6H-pyrrolo[2,3-d]pyrimidin-6-one, |
| 168 | 4-amino-5-methyl-2-[1-(3,3,4,4,4-pentafluorobutyl)-1H-pyrazolo[3,4-b]pyridin-3-yl]-5-(1,3,4-thiadiazol-2-yl)-5,7-dihydro-6H-pyrrolo[2,3-d]pyrimidin-6-one, |

| | -continued |
|---|---|
| 169 | 4-amino-5-methyl-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 170 | 4-amino-5-methyl-2-[1-(3,3,4,4,4-pentafluorobutyl)-1H-pyrazolo[3,4-b]pyridin-3-yl]-5-pyrimidin-2-yl-5,7-dihydro-6H-pyrrolo[2,3-d]pyrimidin-6-one, |
| 171 | 4-amino-2-[6-chloro-1-(3,3,4,4,4-pentafluorobutyl)-1H-indazol-3-yl]-5-methyl-5-[5-oxo-4-(propan-2-yl)-4,5-dihydro-1,3,4-oxadiazol-2-yl]-5,7-dihydro-6H-pyrrolo[2,3-d]pyrimidin-6-one, |
| 172 | 4-amino-2-[6-chloro-1-(3,3,4,4,4-pentafluorobutyl)-1H-indazol-3-yl]-5-methyl-5-[4-(propan-2-yl)-5-thioxo-4,5-dihydro-1,3,4-oxadiazol-2-yl]-5,7-dihydro-6H-pyrrolo[2,3-d]pyrimidin-6-one, |
| 173 | 4-amino-5-(1-ethyl-1H-1,2,3-triazol-4-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 174 | 4-amino-5-[(cyclopropylmethyl)amino]-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 175 | {4-amino-2-[6-chloro-1-(3,3,4,4,4-pentafluorobutyl)-1H-indazol-3-yl]-5-methyl-6-oxo-6,7-dihydro-5h-pyrrolo[2,3-d]pyrimidin-5-yl}acetonitrile, |
| 176 | 4-amino-2-(6-chloro-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide, |
| 177 | 4-amino-2-(6-cyano-1-(3,3,4,4,4-pentafluorobutyl)-1H-pyrazolo[3,4-b]pyridin-3-yl)-N-cyclopropyl-5-methyl-6-oxo-6,7-dihydro-5H-pyrrolo[2,3-d]pyrimidine-5-carboxamide, |
| 178 | 4-amino-N-cyclopropyl-2-(6-methoxy-1-(3,3,4,4,4-pentafluorobutyl)-1H-pyrazolo[3,4-b]pyridin-3-yl)-5-methyl-6-oxo-6,7-dihydro-5H-pyrrolo[2,3-d]pyrimidine-5-carboxamide, |
| 179 | 4-amino-N-cyclopropyl-5-methyl-2-(6-methyl-1-(3,3,4,4,4-pentafluorobutyl)-1H-pyrazolo[3,4-b]pyridin-3-yl)-6-oxo-6,7-dihydro-5H-pyrrolo[2,3-d]pyrimidine-5-carboxamide, |
| 180 | 4-amino-5-[1-(cyclopropylmethyl)-1H-1,2,3-triazol-4-YL]-5-methyl-2-[1-(3,3,3-trifluoropropyl)-1H-pyrazolo[3,4-b]pyridin-3-yl]-5,7-dihydro-6H-pyrrolo[2,3-d]pyrimidin-6-one, |
| 181 | 4-amino-N-cyclopropyl-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide, |
| 182 | 4-amino-5-methyl-6-oxo-N-(pyridin-3-yl)-2-[1-(3,3,3-trifluoropropyl)-1H-pyrazolo[3,4-b]pyridin-3-yl]-6,7-dihydro-5H-pyrrolo[2,3-d]pyrimidine-5-carboxamide, |
| 183 | 4-amino-2-[6-chloro-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, |
| 184 | 4-amino-N-cyclopropyll-5-methyl-2-[6-methyl-1-(3,3,3-trifluoropropyl)-1H-pyrazolo[3,4-b]pyridin-3-yl]-6-oxo-6,7-dihydro-5H-pyrrolo[2,3-d]pyrimidine-5-carboxamide, |
| 185 | 4-amino-N-cyclopropyl-2-[6-methoxy-1-(3,3,3-trifluoropropyl)-1H-pyrazolo[3,4-b]pyridin-3-yl]-5-methyl-6-oxo-6,7-dihydro-5H-pyrrolo[2,3-d]pyrimidine-5-carboxamide, |
| 186 | 5-methyl-4-(methylamino)-2-[1-(3,3,4,4,4-pentafluorobutyl)-1H-pyrazolo[3,4-b]pyridin-3-yl]-5-phenyl-5,7-dihydro-6H-pyrrolo[2,3-d]pyrimidin-6-one, |
| 187 | N-cyclopropyl-5-methyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 188 | 2-[6-chloro-1-(3,3,4,4,4-pentafluorobutyl)-1H-indazol-3-yl]-5-methyl-4-(methylamino)-5-phenyl-5,7-dihydro-6H-pyrrolo[2,3-d]pyrimidin-6-one, |
| 189 | 5-methyl-4-(methylamino)-5-(5-methyl-1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 190 | 4-amino-5-methyl-2-[1-(3,3,4,4,4-pentafluorobutyl)imidazo[1,5-a]pyridin-3-yl]-5-phenyl-5,7-dihydro-6H-pyrrolo[2,3-d]pyrimidin-6-one, |
| 191 | 4-amino-5-methyl-2-[8-(3,3,4,4,4-pentafluorobutyl)imidazo[1,5-a]pyrimidin-6-yl]-5-phenyl-5,7-dihydro-6H-pyrrolo[2,3-d]pyrimidin-6-one, |
| 192 | 4-amino-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide, |
| 193 | 4-amino-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide, |
| 194 | 4-amino-N-cyclopropyl-5-methyl-6-oxo-2-[1-(3,3,4,4,4-pentafluorobutyl)-1H-indazol-3-yl]-6,7-dihydro-5H-pyrrolo[2,3-d]pyrimidine-5-carboxamide, |
| 195 | 4-amino-N-cyclopropyl-2-[6-fluoro-1-(3,3,4,4,4-pentafluorobutyl)-1H-indazol-3-yl]-5-methyl-6-oxo-6,7-dihydro-5H-pyrrolo[2,3-d]pyrimidine-5-carboxamide, |
| 196 | 4-amino-2-[6-chloro-1-(3,3,4,4,4-pentafluorobutyl)-1H-indazol-3-yl]-N-cyclobutyl-5-methyl-6-oxo-6,7-dihydro-5H-pyrrolo[2,3-d]pyrimidine-5-carboxamide, |

| | |
|---|---|
| 197 | 4-amino-5-methyl-N-(1-methylethyl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 198 | 4-amino-2-[6-chloro-1-(3,3,3-trifluoropropyl)-1H-indazol-3-yl]-5-methyl-5-(5-methyl-1,3,4-oxadiazol-2-yl)-5,7-dihydro-6H-pyrrolo[2,3-d]pyrimidin-6-one, |
| 199 | 4-amino-5-methyl-5-[4-(1-methylethyl)-5-oxo-4,5-dihydro-1,3,4-oxadiazol-2-yl]-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 200 | 4-amino-N-cyclopropyl-5-methyl-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide, |
| 201 | 4,5-diamino-2-[6-chloro-1-(3,3,4,4,4-pentafluorobutyl)-1H-indazol-3-yl]-5-methyl-5,7-dihydro-6H-pyrrolo[2,3-d]pyrimidin-6-one, |
| 202 | 4-amino-2-[6-chloro-1-(3,3,4,4,4-pentafluorobutyl)-1H-indazol-3-yl]-5-[(cyclopropylmethyl)amino]-5-methyl-5,7-dihydro-6H-pyrrolo[2,3-d]pyrimidin-6-one, |
| 203 | 4-amino-5-methyl-2-[1-(3,3,4,4,4-pentafluorobutyl)-1H-pyrazolo[3,4-b]pyridin-3-yl]-5-[5-(trifluoromethyl)-1,3,4-oxadiazol-2-yl]-5,7-dihydro-6H-pyrrolo[2,3-d]pyrimidin-6-one, |
| 204 | 4-amino-5-methyl-5-(1,3,4-oxadiazol-2-yl)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 205 | 4-amino-5-methyl-6-oxo-2-[1-(3,3,4,4,4-pentafluorobutyl)-1H-pyrazolo[3,4-b]pyridin-3-yl]-6,7-dihydro-5H-pyrrrolo[2,3-d]pyrimidine-5-carbothioamide, |
| 206 | 4-amino-5-(4,5-dimethyl-1,3-thiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 207 | 4-amino-5-methyl-2-[1-(3,3,4,4,4-pentafluorobutyl)-1H-pyrazolo[3,4-b]pyridin-3-yl]-5-[3-(trifluoromethyl)-1,2,4-oxadiazol-5-yl]-5,7-dihydro-6H-pyrrolo[2,3-d]pyrimidin-6-one, |
| 208 | 2-{4-amino-2-[6-chloro-1-(3,3,4,4,4-pentafluorobutyl)-1H-indazol-3-yl]-5-methyl-6-oxo-6,7-dihydro-5H-pyrrolo[2,3-d]pyrimidin-5-yl}-N-cyclopropylacetamide, |
| 209 | 4-amino-5-methyl-6-oxo-N-pyridin-2-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide, |
| 210 | 4-amino-5-methyl-N-(1-methyl-1H-pyrazol-3-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide, |
| 211 | 4-amino-5-(5-ethyl-1,3,4-oxadiazol-2-yl)-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 212 | 4-amino-5-[5-(difluoromethyl)-1,3,4-oxadiazol-2-yl]-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 213 | 4-amino-5-methyl-5-[5-(1-methylethyl)-1,3,4-oxadiazol-2-yl]-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 214 | 4-amino-2-[6-chloro-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide, |
| 215 | 4-amino-5-methyl-N-(1-methyl-1H-pyrazol-4-yl)-6-oxo-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide, |
| 216 | 4-amino-5-methyl-2-[1-(3,3,4,4,4-pentafluorobutyl)-1H-pyrazolo[3,4-b]pyridin-3-yl]-5-[5-(2,2,2-trifluoroethyl)-1,3,4-oxadiazol-2-yl]-5,7-dihydro-6H-pyrrolo[2,3-d]pyrimidin-6-one, |
| 217 | 4-amino-2-[6-chloro-1-(3,3,4,4,4-pentafluorobutyl)-1H-indazol-3-yl]-5-methyl-N-(1-methyl-1H-pyrazol-4-yl)-6-oxo-6,7-dihydro-5H-pyrrolo[2,3-d]pyrimidine-5-carboxamide, |
| 218 | 4-amino-5-methyl-N-(1-methyl-1H-pyrazol-3-yl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 219 | 4-amino-5-ethynyl-5-methyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 220 | 4-amino-2-[6-methoxy-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide, |
| 221 | 4-amino-2-[6-cyano-1-(3,3,3-trifluoropropyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, |
| 222 | 4-amino-N-cyclopropyl-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 223 | 4-amino-N-cyclopropyl-2-[6-cyclopropyl-1-(3,3,4,4,4-pentafluorobutyl)-1H-pyrazolo[3,4-b]pyridin-3-yl]-5-methyl-6-oxo-6,7-dihydro-5H-pyrrolo[2,3-d]pyrimidine-5-carboxamide, |

-continued

| | |
|---|---|
| 224 | 4-amino-N-cyclopropyl-2-[6-cyclopropyl-1-(3,3,3-trifluoropropyl)-1H-pyrazolo[3,4-b]pyridin-3-yl]-5-methyl-6-oxo-6,7-dihydro-5H-pyrrolo[2,3-d]pyrimidine-5-carboxamide, |
| 225 | 4-amino-5-(5-cyclopropyl-1,3,4-oxadiazol-2-yl)-5-methyl-2-[1-(4,4,4-trifluorobutyl)-1H-pyrazolo[3,4-b]pyridin-3-yl]-5,7-dihydro-6H-pyrrolo[2,3-d]pyrimidin-6-one, |
| 226 | 4-amino-5-methyl-6-oxo-N-pyridin-2-yl-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 227 | 4-amino-5-methyl-6-oxo-N-pyridin-3-yl-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 228 | 4-amino-5-methyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 229 | 4-amino-2-[6-chloro-1-(3,3,4,4,4-pentafluorobutyl)-1H-indazol-3-yl]-5-methyl-5-(1-methyl-1H-pyrazol-4-yl)-5,7-dihydro-6H-pyrrolo[2,3-d]pyrimidin-6-one, |
| 230 | 4-amino-2-[6-chloro-1-(3,3,4,4,4-pentafluorobutyl)-1H-pyrazolo[3,4-b]pyridin-3-yl]-5-methyl-N-oxetan-3-yl-6-oxo-6,7-dihydro-5H-pyrrolo[2,3-d]pyrimidine-5-carboxamide, |
| 231 | 4-amino-5-methyl-N-oxetan-3-yl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 232 | 4-amino-5-methyl-5-pyridin-2-yl-2-[1-(3,3,3-trifluoropropyl)-1H-pyrazolo[3,4-b]pyridin-3-yl]-5,7-dihydro-6H-pyrrolo[2,3-d]pyrimidin-6-one, |
| 233 | 4-amino-5-methyl-6-oxo-N-pyridin-3-yl-2-{1-[2-(trifluoromethoxy)ethyl]-1H-pyrazolo[3,4-b]pyridin-3-yl}-6,7-dihydro-5H-pyrrolo[2,3-d]pyrimidine-5-carboxamide, |
| 234 | 4-amino-5-methyl-6-oxo-2-[1-(3,3,4,4,4-pentafluorobutyl)-1H-pyrazolo[3,4-b]pyridin-3-yl]-N-pyridin-3-yl-6,7-dihydro-5H-pyrrolo[2,3-d]pyrimidine-5-carboxamide, |
| 235 | 4-amino-5-methyl-6-oxo-2-[1-(3,3,4,4,4-pentafluorobutyl)-1H-pyrazolo[3,4-b]pyridin-3-yl]-N-(tetrahydrofuran-3-yl)-6,7-dihydro-5H-pyrrolo[2,3-d]pyrimidine-5-carboxamide, |
| 236 | 4-amino-5-methyl-5-(1,3,4-thiadiazol-2-yl)-2-[1-(4,4,4-trifluorobutyl)-1H-pyrazolo[3,4-b]pyridin-3-yl]-5,7-dihydro-6H-pyrrolo[2,3-d]pyrimidin-6-one, |
| 237 | 4-amino-N-cyclopropyl-5-methyl-6-oxo-2-[1-(3,3,4,4-tetrafluorobutyl)-1H-pyrazolo[3,4-b]pyridin-3-yl]-6,7-dihydro-5H-pyrrolo[2,3-d]pyrimidine-5-carboxamide, |
| 238 | 4-amino-N-cyclopropyl-2-[1-(3,3-difluoropropyl)-1H-pyrazolo[3,4-b]pyridin-3-yl]-5-methyl-6-oxo-6,7-dihydro-5H-pyrrolo[2,3-d]pyrimidine-5-carboxamide, |
| 239 | 4-amino-5-methyl-2-[6-methyl-1-(3,3,4,4,4-pentafluorobutyl)-1H-pyrazolo[3,4-b]pyridin-3-yl]-6-oxo-N-(tetrahydro-2H-pyran-4-yl)-6,7-dihdro-5H-pyrrolo[2,3-d]pyrimidine-5-carboxamide, |
| 240 | 4-amino-N-cyclopropyl-2-[1-(3,3-difluorobutyl)-1H-pyrazolo[3,4-b]pyridin-3-yl]-5-methyl-6-oxo-6,7-dihydro-5H-pyrrolo[2,3-d]pyrimidine-5-carboxamide, |
| 241 | 4-amino-5-ethyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 242 | 4-amino-N,5-dicyclopropyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 243 | 4-amino-5-cyclopentyl-N-cyclopropyl-6-oxo-2-[-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 244 | 4-amino-5-(1-methylethyl)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 245 | 4-amino-N,5-dicyclopropyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide, |
| 246 | 4-amino-N,5-dicyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 247 | 4-amino-5-cyclopropyl-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 248 | 4-amino-2-[6-fluoro-3-(4,4,4-trifluorobutyl)imidazo[1,5-a]pyridin-1-yl]-5-methyl-5-[3-(trifluoromethyl)-1,2,4-oxadiazol-5-yl]-5,7-dihydro-6H-pyrrolo[2,3-d]pyrimidin-6-one, |
| 249 | 4-amino-2-[6-chloro-3-(4,4,4-trifluorobutyl)imidazo[1,5-a]pyridin-1-yl]-5-methyl-5-(5-methyl-1,2,4-oxadiazol-3-yl)-5,7-dihydro-6H-pyrrolo[2,3-d]pyrimidin-6-one, |
| 250 | 4-amino-2-[6-chloro-3-(3,3,4,4,4-pentafluorobutyl)imidazo[1,5-a]pyridin-1-yl]-H-cyclopropyl-5-methyl-6-oxo-6,7-dihydro-5H-pyrrolo[2,3-d]pyrimidine-5-carboxamide, |
| 251 | 4-amino-H-cyclopropyl-5-methyl-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide, |

| | -continued |
|---|---|
| 252 | 4-amino-H-cyclopropyl-2-[6-fluoro-3-(3,3,4,4,4-pentafluorobutyl)imidazo[1,5-a]pyridin-1-yl]-5-methyl-6-oxo-6,7-dihydro-5H-pyrrolo[2,3-d]pyrimidine-5-carboxamide, |
| 253 | 4-amino-2-[6-fluoro-3-(3,3,4,4,4-pentafluorobutyl)imidazo[1,5-a]pyridin-1-yl]-5-methyl-6-oxo-H-pyridin-3-yl-6,7-dihydro-5H-pyrrolo[2,3-d]pyrimidine-5-carboxamide, |
| 254 | 4-amino-5-methyl-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide, |
| 255 | 4-amino-5-(5-cyclopropyl-1,3,4-oxadiazol-2-yl)-5-methyl-2-[7-(3,3,4,4,4-pentafluorobutyl)imidazo[1,5-b]pyridazin-5-yl]-5,7-dihydro-6H-pyrrolo[2,3-d]pyrimidin-6-one, |
| 256 | 4-amino-H-cyclopropyl-5-methyl-6-oxo-2-[7-(3,3,3-trifluoropropyl)imidazo[1,5-b]pyridazin-5-yl]-6,7-dihydro-5H-pyrrolo[2,3-d]pyrimidine-5-carboxamide, |
| 257 | 2-[6-chloro-1-(3,3,4,4,4-pentafluorobutyl)-1H-indazol-3-yl]-N-cyclopropyl-5-methyl-4-(methylamino)-6-oxo-6,7-dihydro-5H-pyrrolo[2,3-d]pyrimidine-5-carboxamide, |
| 258 | 2-[6-chloro-1-(3,3,4,4,4-pentafluorobutyl)-1H-indazol-3-yl]-N,5-dimethyl-4-(methylamino)-6-oxo-6,7-dihydro-5H-pyrrolo[2,3-d]pyrimidine-5-carboxamide, |
| 259 | N,5-dimethyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 260 | N-cyclopropyl-5-methyl-4-(methylamino)-6-oxo-2-[7-(3,3,4,4,4-pentafluorobutyl)imidazo[1,5-b]pyridazin-5-yl]-6,7-dihydro-5H-pyrrolo[2,3-d]pyrimidine-5-carboxamide, |
| 261 | 5-(5-cyclopropyl-1,3,4-oxadiazol-2-yl)-5-methyl-4-(methylamino)-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one, |
| 262 | N,5-dicyclopropyl-4-(methylamino)-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide, |
| 263 | N-cyclopropyl-5-methyl-4-(methylamino)-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide, |
| 264 | N-cyclopropyl-5-methyl-4-(methylamino)-6-oxo-2-[1-(4,4,4-trifluorobutyl)-1H-pyrazolo[3,4-b]pyridin-3-yl]-6,7-dihydro-5H-pyrrolo[2,3-d]pyrimidine-5-carboxamide, |
| 265 | 4-amino-2-[5-chloro-3-(3,3,4,4,4-pentafluorobutyl)-1H-indazol-1-yl]-N,N,5-trimethyl-6-oxo-6,7-dihydro-5H-pyrrolo[2,3-d]pyrimidine-5-carboxamide, |
| 266 | 4-amino-N-cyclopropyl-5-methyl-6-oxo-2-[3-(3,3,4,4,4-pentafluorobutyl)-1H-pyrazolo[4,3-b]pyridin-1-yl]-6,7-dihydro-5H-pyrrolo[2,3-d]pyrimidine-5-carboxamide, |
| 267 | 4-amino-2-[5-chloro-1-(3,3,4,4,4-pentafluorobutyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, |
| 268 | 4-amino-2-[5-chloro-1-(3,3,4,4,4-pentafluorobutyl)-1H-pyrazolo[3,4-b]pyridin-3-yl]-N-cyclopropyl-5-methyl-6-oxo-6,7-dihydro-5H-pyrrolo[2,3-d]pyrimidine-5-carboxamide, |
| 269 | 4-amino-2-[5-chloro-1-(3,3,4,4,4-pentafluorobutyl)-1H-pyrazolo[3,4-b]pyridin-3-yl]-5-methyl-5-(5-methyl-1,3,4-oxadiazol-2-yl)-5,7-dihydro-6H-pyrrolo[2,3-d]pyrimidin-6-one, |
| 270 | 4-amino-5-methyl-6-oxo-2-[1-(3,3,4,4,4-pentafluorobutyl)imidazo[1,5-a]pyridin-3-yl]-6,7-dihydro-5H-pyrrolo[2,3-d]pyrimidine-5-carboxamide, | or a pharmaceutically acceptable salt thereof.

6. A pharmaceutical composition comprised of the compound of claim 1, or a pharmaceutically acceptable salt thereof, and a pharmaceutically acceptable carrier.

7. The pharmaceutical composition of claim 6 comprising one or more pharmaceutically active agents in addition to the compound of claim 1, or a pharmaceutically acceptable salt thereof.

8. The pharmaceutical composition of claim 7 wherein the one or more additional active agents is selected from an angiotensin converting enzyme inhibitor, an angiotensin II receptor antagonist, a neutral endopeptidase inhibitor, an aldosterone antagonist, a renin inhibitor, an endothelin receptors antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent or a metabolic altering agent.

9. The compound of claim 1 or a pharmaceutically acceptable salt thereof that is

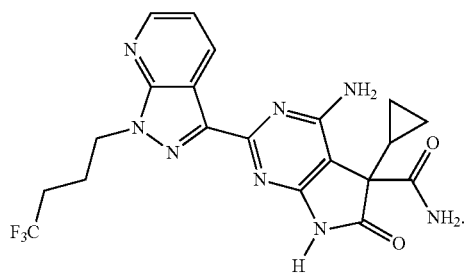 [SMILES: NC(=O)C1(C2CC2)C(=O)Nc2nc(-c3nn(CCCC(F)(F)F)c4ncccc34)nc(N)c21]

10. The compound of claim 9 that is

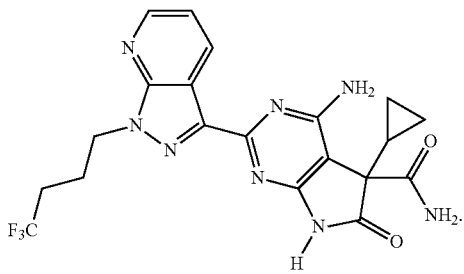 [SMILES: NC(=O)C1(C2CC2)C(=O)Nc2nc(-c3nn(CCCC(F)(F)F)c4ncccc34)nc(N)c21]

11. A pharmaceutical composition comprised of the compound of claim 9 or a pharmaceutically acceptable salt thereof, and a pharmaceutically acceptable carrier.

12. The compound of claim 1 or a pharmaceutically acceptable salt thereof that is

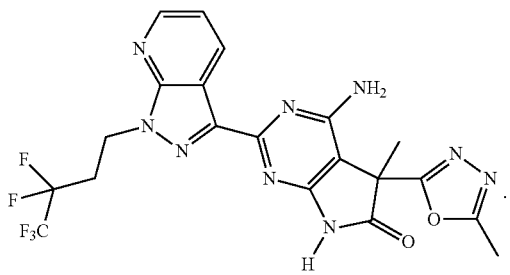 [SMILES: Cc1nnc(C2(C)C(=O)Nc3nc(-c4nn(CCC(F)(F)C(F)(F)F)c5ncccc45)nc(N)c32)o1]

13. The compound of claim 12 that is

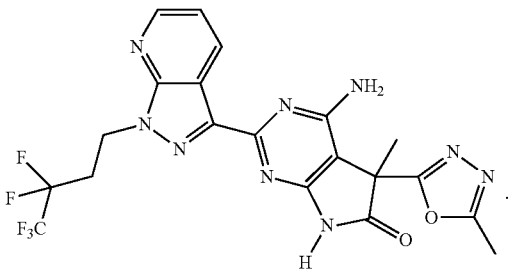 [SMILES: Cc1nnc(C2(C)C(=O)Nc3nc(-c4nn(CCC(F)(F)C(F)(F)F)c5ncccc45)nc(N)c32)o1]

14. A pharmaceutical composition comprised of the compound of claim 12 or a pharmaceutically acceptable salt thereof, and a pharmaceutically acceptable carrier.

15. The compound of claim 1 or a pharmaceutically acceptable salt thereof that is

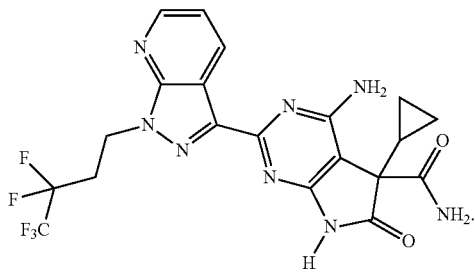 [SMILES: NC(=O)C1(C2CC2)C(=O)Nc2nc(-c3nn(CCC(F)(F)C(F)(F)F)c4ncccc34)nc(N)c21]

16. The compound of claim 15 that is

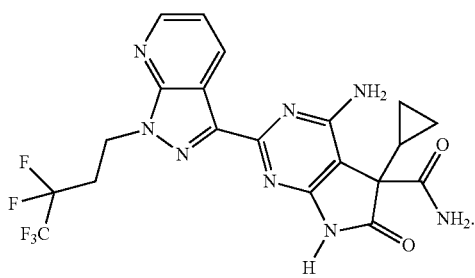 [SMILES: NC(=O)C1(C2CC2)C(=O)Nc2nc(-c3nn(CCC(F)(F)C(F)(F)F)c4ncccc34)nc(N)c21]

17. A pharmaceutical composition comprised of the compound of claim 15 or a pharmaceutically acceptable salt thereof, and a pharmaceutically acceptable carrier.

* * * * *